US012479862B2

(12) United States Patent
Lee et al.

(10) Patent No.: US 12,479,862 B2
(45) Date of Patent: Nov. 25, 2025

(54) HETEROCYCLIC COMPOUND AND ORGANIC LIGHT-EMITTING DEVICE COMPRISING SAME

(71) Applicant: LT MATERIALS CO., LTD., Yongin-si (KR)

(72) Inventors: Nam-Jin Lee, Yongin-si (KR); Yu-Jin Heo, Yongin-si (KR); Won-Jang Jeong, Yongin-si (KR); Dong-Jun Kim, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 832 days.

(21) Appl. No.: 17/606,550

(22) PCT Filed: Aug. 20, 2020

(86) PCT No.: PCT/KR2020/011087
§ 371 (c)(1),
(2) Date: Oct. 26, 2021

(87) PCT Pub. No.: WO2021/034118
PCT Pub. Date: Feb. 25, 2021

(65) Prior Publication Data

US 2022/0213120 A1 Jul. 7, 2022

(30) Foreign Application Priority Data

Aug. 21, 2019 (KR) ........................ 10-2019-0102562

(51) Int. Cl.
*C07D 519/00* (2006.01)
*C07D 491/147* (2006.01)
(Continued)

(52) U.S. Cl.
CPC ....... *C07D 519/00* (2013.01); *C07D 491/147* (2013.01); *C07D 495/14* (2013.01);
(Continued)

(58) Field of Classification Search
CPC ............ C07D 491/048; C07D 491/147; C07D 519/00; H10K 85/622; H10K 85/626; H10K 85/657; C09K 2211/1014
See application file for complete search history.

(56) References Cited

U.S. PATENT DOCUMENTS 4,356,429 A 10/1982 Tang
10,892,422 B2 1/2021 Hwang et al.
(Continued)

FOREIGN PATENT DOCUMENTS

JP 11-354281 A 12/1999
KR 10-2014-0093565 A 7/2014
(Continued)

OTHER PUBLICATIONS

International Search Report (PCT/IS/210) issued in PCT/KR2020/011087, dated Nov. 30, 2020.
(Continued)

*Primary Examiner* — Jenna N Chandhok
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

6 Claims, 3 Drawing Sheets

(51) Int. Cl.

*C07D 495/14* (2006.01)
*H10K 50/13* (2023.01)
*H10K 50/17* (2023.01)
*H10K 50/18* (2023.01)
*H10K 85/60* (2023.01)

(52) U.S. Cl.

CPC ......... *H10K 85/622* (2023.02); *H10K 85/626* (2023.02); *H10K 85/654* (2023.02); *H10K 85/6572* (2023.02); *H10K 50/13* (2023.02); *H10K 50/17* (2023.02); *H10K 50/171* (2023.02); *H10K 50/18* (2023.02)

(56) References Cited

U.S. PATENT DOCUMENTS

| | | | | |
|---|---|---|---|---|
| 2014/0203257 | A1* | 7/2014 | Hwang .................. | H10K 85/40 544/333 |
| 2016/0164002 | A1 | 6/2016 | Parham et al. | |
| 2017/0104165 | A1 | 4/2017 | Martynova et al. | |
| 2018/0375037 | A1 | 12/2018 | Chen et al. | |
| 2021/0151683 | A1* | 5/2021 | Sakaino .................... | G09F 9/30 |

FOREIGN PATENT DOCUMENTS

| | | |
|---|---|---|
| KR | 10-2015-0016252 A | 2/2015 |
| KR | 10-2015-0066157 A | 6/2015 |
| KR | 10-2016-0038006 A | 4/2016 |

OTHER PUBLICATIONS

Kuwabara et al., "Thermally Stable Multilayered Organic Electroluminescent Devices Using Novel Starburst Molecules, 4, 4', 4"-Tri(Ncarbazolyl)triphenylamine (TCTA) and 4,4',4"-Tris(3-methyiphenylphenyl-amino)triphenylamine (m-MTDATA), as Hole-Transport Materials," Advanced Materials, vol. 6, No. 9, 1994, pp. 677-679.

* cited by examiner

【FIG. 1】
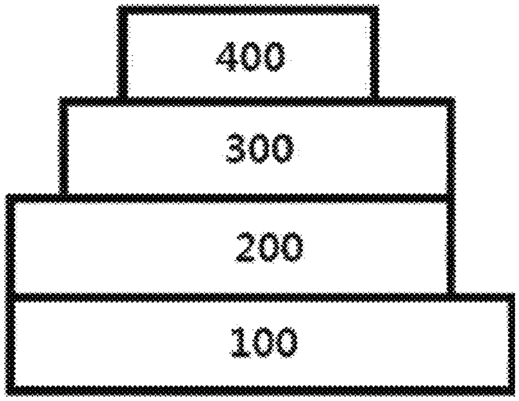
【FIG. 2】
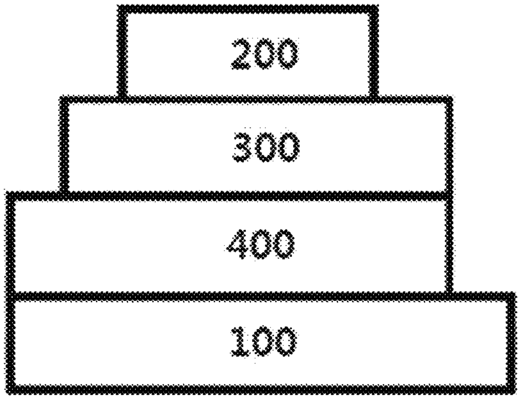

【FIG. 3】
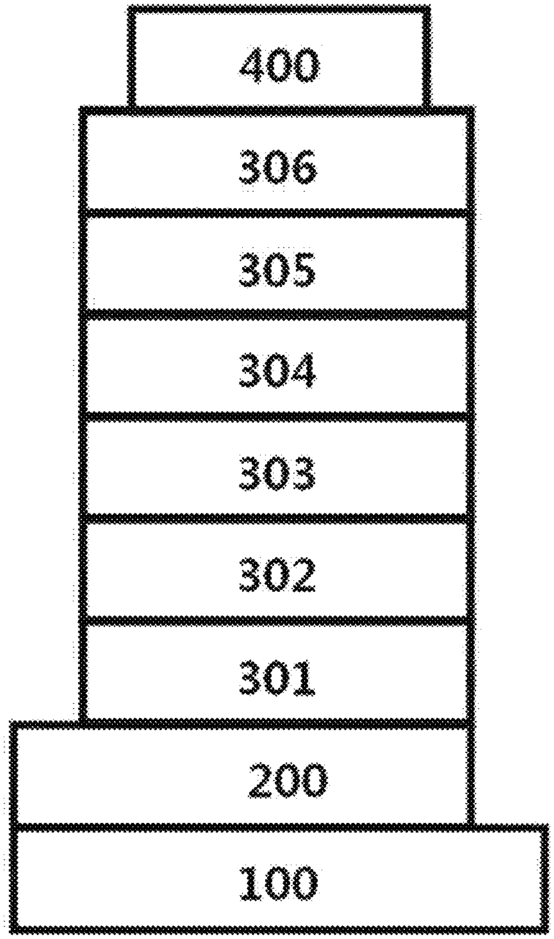

【FIG. 4】
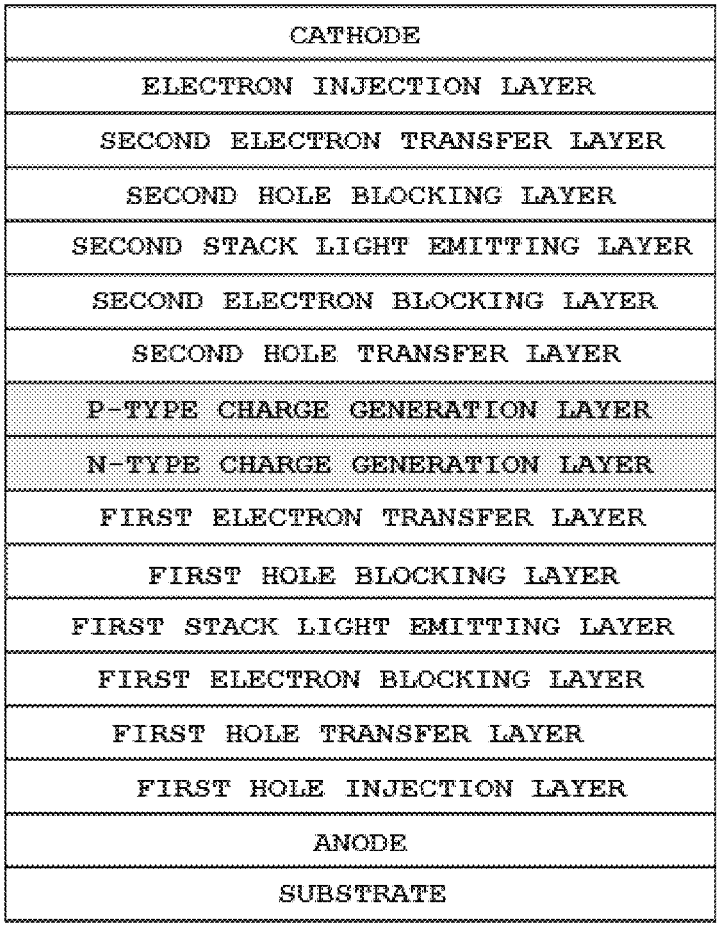

HETEROCYCLIC COMPOUND AND ORGANIC LIGHT-EMITTING DEVICE COMPRISING SAME

TECHNICAL FIELD

This application claims priority to and the benefits of Korean Patent Application No. 10-2019-0102562, filed with the Korean Intellectual Property Office on Aug. 21, 2019, the entire contents of which are incorporated herein by reference.

The present specification relates to a heterocyclic compound, and an organic light emitting device including the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents (Patent Document 1) U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

[Chemical Formula 1]

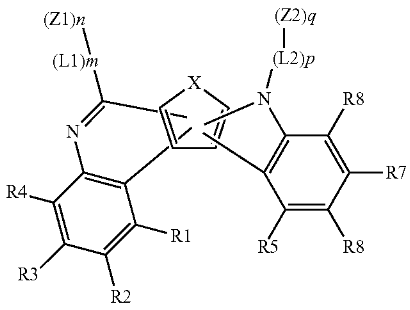

In Chemical Formula 1,

X is O; or S,

R1 to R8 are the same as or different from each other, and each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(═O)RR'; and —NR301R302, or two or more groups adjacent to each other bond to each other to form a substituted or unsubstituted C6 to C60 aromatic hydrocarbon ring or a substituted or unsubstituted C2 to C60 heteroring, L1 and L2 are a substituted or unsubstituted C6 to C60 arylene group; or a substituted or unsubstituted C2 to C60 heteroarylene group, Z1 and Z2 are hydrogen; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; or —P(═O)RR', R301 and R302 are the same as or different from each other, and each independently a substituted or unsubstituted C6 to C40 aryl group; or a substituted or unsubstituted C2 to C40 heteroaryl group, R, R' and R" are the same as or different from each other, and each independently hydrogen; a substituted or unsubstituted C1 to C40 alkyl group; or a substituted or unsubstituted C6 to C40 aryl group, m and p are an integer of 1 to 4, and when m is 2 or greater, the two or more L1s are the same as or different from each other, and when p is 2 or greater, the two or more L2s are the same as or different from each other, and n and q are an integer of 1 to 6, and when n is 2 or greater, the two or more Z1s are the same as or different from each other, and when q is 2 or greater, the two or more Z2s are the same as or different from each other.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a hole blocking material, a light emitting material, an electron transfer material, an electron injection material, a charge generation material or the like in an organic light emitting device. Particularly, the compound can be used as an electron transfer layer material, a hole blocking layer material or a charge generation layer material of an organic light emitting device.

When using the compound represented by Chemical Formula 1 in an organic material layer, a driving voltage of a device can be lowered, light efficiency can be enhanced, and lifetime properties of the device can be enhanced by thermal stability of the compound.

The compound represented by Chemical Formula 1 has a core form in which a quinoline group and an indole group are fused to a pyrrole group or thiophene group structure, and by adding a more electron-friendly heteroatom to the central skeleton of the core structure, a charge balance is enhanced in a light emitting layer through enhancing an electron transfer ability, and as a result, driving, lifetime and efficiency of a device are improved.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

Mode for Disclosure

Hereinafter, the present application will be described in detail.

In the present specification, a description of a certain part "including" certain constituents means capable of further comprising other constituents, and does not exclude other constituents unless particularly stated on the contrary.

In the present specification, a T1 value means an energy level value in a triplet state.

In the present specification, a term "substitution" means a hydrogen atom bonding to a carbon atom of a compound being changed to another substituent, and the position of substitution is not limited as long as it is a position at which the hydrogen atom is substituted, that is, a position at which a substituent is capable of substituting, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0% or a hydrogen content being 100%. In other words, an expression of "substituent X is hydrogen" does not exclude deuterium unlike a hydrogen content being 100% or a deuterium content being 0%, and therefore, may mean a state in which hydrogen and deuterium are mixed.

In one embodiment of the present application, deuterium is one of isotopes of hydrogen, is an element having deuteron formed with one proton and one neutron as a nucleus, and may be expressed as hydrogen-2, and the elemental symbol may also be written as D or $^2H$.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

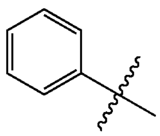 [SMILES: *c1ccccc1]

means that the total number of substituents that the phenyl group may have is 5 (T1 in the formula) and the number of deuterium among these is 1 (T2 in the formula). In other words, having a deuterium content of 20% in a phenyl group may be represented by the following structural formulae.

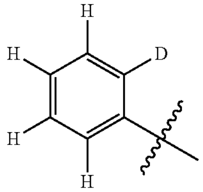
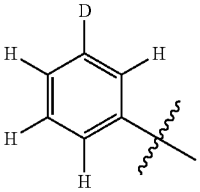
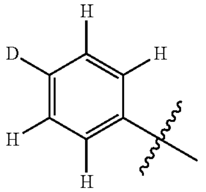
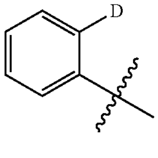
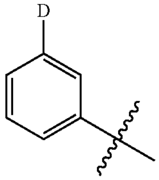
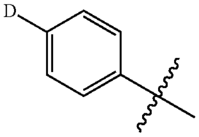

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises 0, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring group thereof, and the like, but are not limited thereto.

In the present specification, the phosphine oxide group is represented by —P(═O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR104R105R106. R104 to R106 are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted, the following structures and the like may be included, however, the structure is not limited thereto.

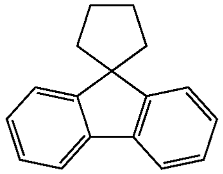 , 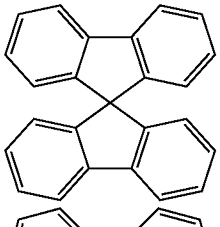 ,

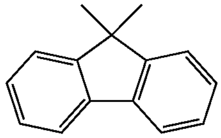 , 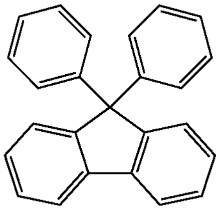 ,

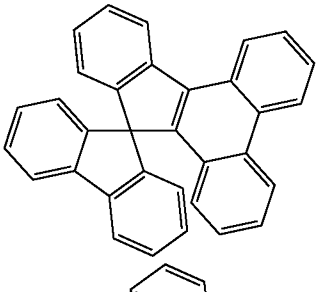 ,

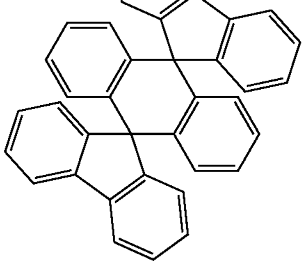

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group is represented by —N(R106) (R107), and R106 and R107 are the same as or different from each other and may be each independently a substituent formed with at least one of hydrogen; deuterium; a halogen group; an alkyl group; an alkenyl group; an alkoxy group; a cycloalkyl group; an aryl group; and a heteroaryl group. The amine group may be selected from the group consisting of —$NH_2$; a monoalkylamine group; a monoarylamine group; a monoheteroarylamine group; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

One embodiment of the present application provides a compound represented by Chemical Formula 1.

In one embodiment of the present application, Chemical Formula 1 may be represented by any one of the following Chemical Formula 2 to Chemical Formula 5.

[Chemical Formula 2]

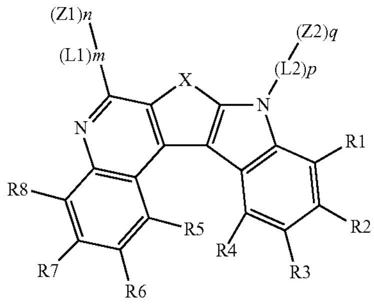

[Chemical Formula 3]

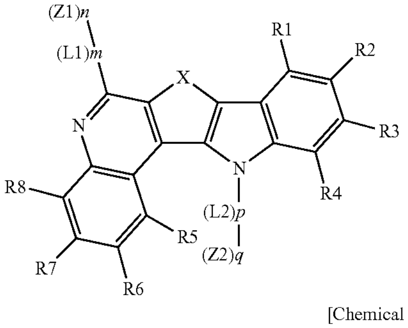

[Chemical Formula 4]

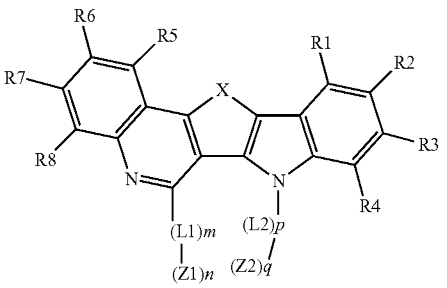

-continued

[Chemical Formula 5]

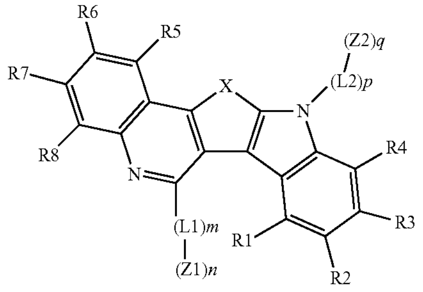

In Chemical Formulae 2 to 5,

X, R1 to R8, L1, L2, z1, Z2, m, n, p and q have the same definitions as in Chemical Formula 1.

In one embodiment of the present application, X may be O.

In one embodiment of the present application, X may be S.

In one embodiment of the present application, L1 and L2 may be a substituted or unsubstituted C6 to C60 arylene group; or a substituted or unsubstituted C2 to C60 heteroarylene group.

In another embodiment, L1 and L2 may be a substituted or unsubstituted C6 to C40 arylene group; or a substituted or unsubstituted C2 to C40 heteroarylene group.

In another embodiment, L1 and L2 may be a C6 to C40 arylene group; or a C2 to C40 heteroarylene group.

In another embodiment, L1 and L2 may be a C6 to C40 monocyclic or polycyclic arylene group; or a C2 to C40 monocyclic or polycyclic heteroarylene group.

In another embodiment, L1 and L2 may be a C6 to C40 monocyclic arylene group; or a C10 to C40 polycyclic arylene group.

In another embodiment, L1 and L2 may be a phenylene group; a biphenylene group; or an anthracene group.

In one embodiment of the present application, Z1 and Z2 may be hydrogen; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; or —P(═O)RR'.

In another embodiment, Z1 and Z2 may be hydrogen; a substituted or unsubstituted C1 to C60 alkyl group; a substituted or unsubstituted C6 to C60 aryl group; a substituted or unsubstituted C2 to C60 heteroaryl group; or —P(═O)RR'.

In another embodiment, Z1 and Z2 may be hydrogen; a substituted or unsubstituted C1 to C40 alkyl group; a substituted or unsubstituted C6 to C40 aryl group; a substituted or unsubstituted C2 to C40 heteroaryl group; or —P(═O)RR'.

In another embodiment, Z1 and Z2 may be hydrogen; a C6 to C40 aryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(═O)RR'.

In another embodiment, Z1 and Z2 may be hydrogen; a C6 to C40 monocyclic aryl group; a C10 to C40 polycyclic aryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(═O)RR'.

In another embodiment, Z1 and Z2 may be hydrogen; a phenyl group; a biphenyl group; an anthracenyl group; a triphenylenyl group; a pyridine group unsubstituted or substituted with a pyridine group; a phenanthroline group unsubstituted or substituted with a phenyl group; a benzimidazole group unsubstituted or substituted with an ethyl group; a pyrimidine group unsubstituted or substituted with one or more substituents selected from the group consisting of a phenyl group and a biphenyl group; or a triazine group unsubstituted or substituted with one or more substituents selected from the group consisting of a phenyl group, a biphenyl group and a naphthyl group.

In one embodiment of the present application, Z1 and Z2 may be further substituted with a C1 to C20 alkyl group; or a C6 to C20 aryl group.

In one embodiment of the present application, Z1 and Z2 may be further substituted with a methyl group; or a phenyl group.

In one embodiment of the present application, R1 to R8 are the same as or different from each other, and each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and —NR301R302, or two or more groups adjacent to each other may bond to each other to form a substituted or unsubstituted C6 to C60 aromatic hydrocarbon ring or a substituted or unsubstituted C2 to C60 heteroring.

In another embodiment, R1 to R8 are the same as or different from each other, and may be each independently selected from the group consisting of hydrogen; deuterium; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and —NR301R302.

In another embodiment, R1 to R8 are the same as or different from each other, and may be each independently selected from the group consisting of hydrogen; a substituted or unsubstituted C6 to C40 aryl group; a substituted or unsubstituted C2 to C40 heteroaryl group; and —P(=O)RR'.

In another embodiment, R1 to R8 are the same as or different from each other, and may be each independently selected from the group consisting of hydrogen; a C6 to C40 aryl group unsubstituted or substituted with one or more substituents selected from the group consisting of a C6 to C40 aryl group and a C2 to C40 heteroaryl group; a C2 to C40 heteroaryl group unsubstituted or substituted with one or more substituents selected from the group consisting of a C6 to C40 aryl group and a C2 to C40 heteroaryl group; and —P(=O)RR'.

In one embodiment of the present application, Chemical Formula 1 may be represented by any one of the following Chemical Formulae 6 to 10.

[Chemical Formula 6]

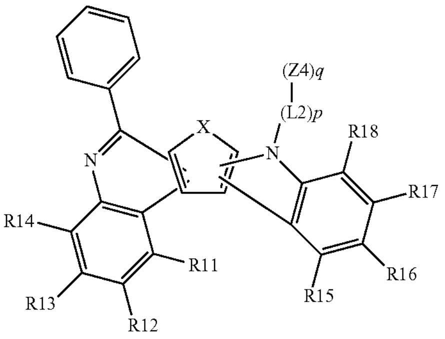

[Chemical Formula 7]

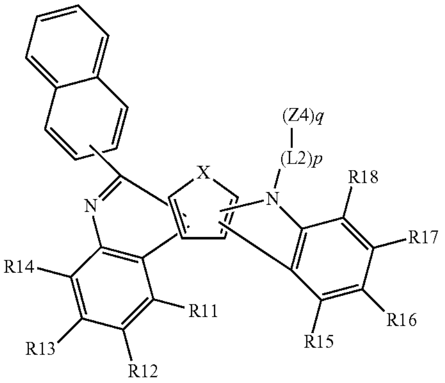

[Chemical Formula 8]

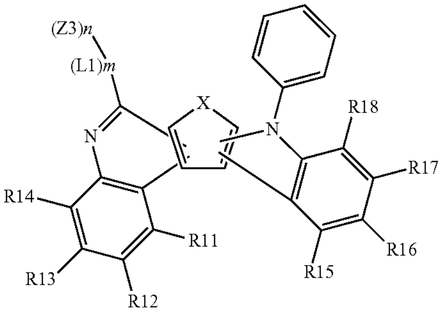

[Chemical Formula 9]

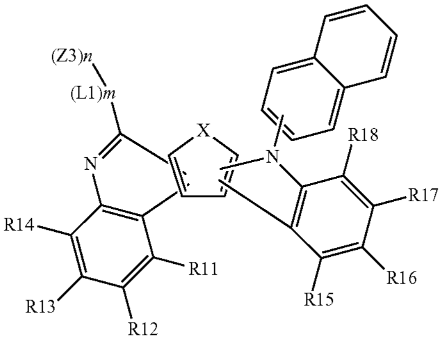

-continued

[Chemical Formula 10]

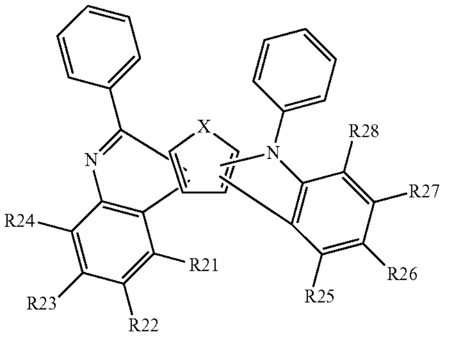

In Chemical Formulae 6 to 10,

X, L1, L2, p, q, m and n have the same definitions as in Chemical Formula 1,

Z3 and Z4 are the same as or different from each other, and each independently a substituted or unsubstituted C1 to C60 alkyl group; a substituted or unsubstituted C6 to C60 aryl group; a substituted or unsubstituted C2 to C60 heteroaryl group; —SiRR'R"; or —P(═O)RR', R11 to R18 and R21 to R28 are the same as or different from each other, and each independently hydrogen; a substituted or unsubstituted C1 to C60 alkyl group; a substituted or unsubstituted C6 to C60 aryl group; a substituted or unsubstituted C2 to C60 heteroaryl group; or —P(═O)RR', and R, R' and R" have the same definitions as in Chemical Formula 1.

In one embodiment of the present application, Z3 and Z4 are the same as or different from each other, and may be each independently a substituted or unsubstituted C1 to C60 alkyl group; a substituted or unsubstituted C6 to C60 aryl group; a substituted or unsubstituted C2 to C60 heteroaryl group; —SiRR'R"; or —P(═O)RR'.

In another embodiment, Z3 and Z4 are the same as or different from each other, and may be each independently a substituted or unsubstituted C1 to C40 alkyl group; a substituted or unsubstituted C6 to C40 aryl group; a substituted or unsubstituted C2 to C40 heteroaryl group; or —P(═O)RR'.

In another embodiment, Z3 and Z4 are the same as or different from each other, and may be each independently a C6 to C40 aryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(═O)RR'.

In another embodiment, Z3 and Z4 are the same as or different from each other, and may be each independently a C6 to C40 monocyclic aryl group; a C10 to C40 polycyclic aryl group; a C2 to C40 heteroaryl group unsubstituted or substituted with one or more substituents selected from the group consisting of a C1 to C20 alkyl group, a C6 to C40 aryl group and a C2 to C40 heteroaryl group; or —P(═O)RR'.

In another embodiment, Z3 and Z4 are the same as or different from each other, and may be each independently a phenyl group; a biphenyl group; an anthracenyl group; a triphenylenyl group; a pyridine group unsubstituted or substituted with a pyridine group; a phenanthroline group unsubstituted or substituted with a phenyl group; a benzimidazole group unsubstituted or substituted with an ethyl group; a pyrimidine group unsubstituted or substituted with one or more substituents selected from the group consisting of a phenyl group and a biphenyl group; or a triazine group unsubstituted or substituted with one or more substituents selected from the group consisting of a phenyl group, a biphenyl group and a naphthyl group.

In one embodiment of the present application, Z3 and Z4 may be further substituted with a C1 to C20 alkyl group; or a C6 to C20 aryl group.

In one embodiment of the present application, R11 to R18 may be hydrogen.

In one embodiment of the present application, at least one of R21 to R28 of Chemical Formula 10 may be represented by -(L3)r-(Z5)s, and the rest are hydrogen; a substituted or unsubstituted C6 to C60 aryl group; or a substituted or unsubstituted C2 to C60 heteroaryl group, L3 is a substituted or unsubstituted C6 to C60 arylene group; or a substituted or unsubstituted C2 to C60 heteroarylene group, Z5 is hydrogen; a halogen group; —CN; a substituted or unsubstituted C1 to C60 alkyl group; a substituted or unsubstituted C6 to C60 aryl group; a substituted or unsubstituted C2 to C60 heteroaryl group; —SiRR'R"; or —P(═O)RR', R, R' and R" are the same as or different from each other, and each independently hydrogen; a substituted or unsubstituted C1 to C40 alkyl group; or a substituted or unsubstituted C6 to C40 aryl group, r is an integer of 1 to 4, and s is an integer of 1 to 6.

In one embodiment of the present application, one of R21 to R28 of Chemical Formula 10 may be represented by -(L3)r-(Z5)s, and the rest may be hydrogen; a substituted or unsubstituted C6 to C60 aryl group; or a substituted or unsubstituted C2 to C60 heteroaryl group.

In one embodiment of the present application, R21 of R21 to R28 of Chemical Formula 10 may be represented by -(L3)r-(Z5)s, and the rest may be hydrogen.

In one embodiment of the present application, R22 of R21 to R28 of Chemical Formula 10 may be represented by -(L3)r-(Z5)s, and the rest may be hydrogen.

In one embodiment of the present application, R23 of R21 to R28 of Chemical Formula 10 may be represented by -(L3)r-(Z5)s, and the rest may be hydrogen.

In one embodiment of the present application, R24 of R21 to R28 of Chemical Formula 10 may be represented by -(L3)r-(Z5)s, and the rest may be hydrogen.

In one embodiment of the present application, R25 of R21 to R28 of Chemical Formula 10 may be represented by -(L3)r-(Z5)s, and the rest may be hydrogen.

In one embodiment of the present application, R26 of R21 to R28 of Chemical Formula 10 may be represented by -(L3)r-(Z5)s, and the rest may be hydrogen.

In one embodiment of the present application, R27 of R21 to R28 of Chemical Formula 10 may be represented by -(L3)r-(Z5)s, and the rest may be hydrogen.

In one embodiment of the present application, R28 of R21 to R28 of Chemical Formula 10 may be represented by -(L3)r-(Z5)s, and the rest may be hydrogen.

In one embodiment of the present application, L3 may be a substituted or unsubstituted C6 to C60 arylene group; or a substituted or unsubstituted C2 to C60 heteroarylene group.

In another embodiment, L3 may be a substituted or unsubstituted C6 to C40 arylene group; or a substituted or unsubstituted C2 to C40 heteroarylene group.

In another embodiment, L3 may be a C6 to C40 monocyclic arylene group; or a C10 to C40 polycyclic arylene group.

In another embodiment, L3 may be a phenylene group; a biphenylene group; or a naphthalene group.

In one embodiment of the present application, Z5 may be a substituted or unsubstituted C6 to C60 aryl group; or a substituted or unsubstituted C2 to C60 heteroaryl group.

In another embodiment, Z5 may be a substituted or unsubstituted C6 to C40 aryl group; or a substituted or unsubstituted C2 to C40 heteroaryl group.

In another embodiment, Z5 may be a C2 to C40 heteroaryl group unsubstituted or substituted with a C6 to C40 aryl group.

In another embodiment, Z5 may be a pyrimidine group unsubstituted or substituted with a phenyl group; or a triazine group unsubstituted or substituted with a phenyl group.

In one embodiment of the present application, Chemical Formula 1 may be represented by the following Chemical Formula 11 or 12.

[Chemical Formula 11]

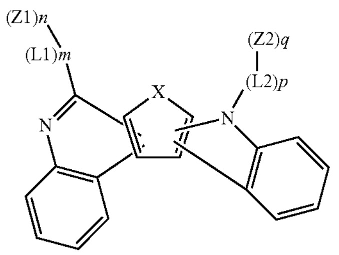

[Chemical Formuila 12]

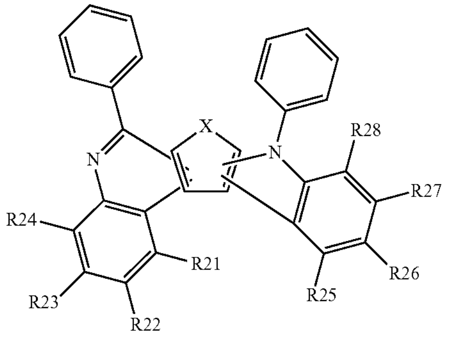

In Chemical Formula 11 and Chemical Formula 12,

X, L1, L2, Z1, Z2, m, n, p and q have the same definitions as in Chemical Formula 1, and R21 to R28 have the same definitions as in Chemical Formula 10.

In one embodiment of the present application, R, R' and R" are the same as or different from each other, and may be each independently hydrogen; a substituted or unsubstituted C1 to C40 alkyl group; or a substituted or unsubstituted C6 to C40 aryl group.

In another embodiment, R, R' and R" are the same as or different from each other, and may be each independently a substituted or unsubstituted C1 to C20 alkyl group; or a substituted or unsubstituted C6 to C20 aryl group.

In another embodiment, R, R' and R" are the same as or different from each other, and may be each independently a C1 to C20 alkyl group; or a C6 to C20 aryl group.

In another embodiment, R, R' and R" are the same as or different from each other, and may be each independently a C6 to C20 monocyclic aryl group.

In another embodiment, R, R' and R" may be a phenyl group.

In one embodiment of the present application, R301 and R302 are the same as or different from each other, and may be each independently a substituted or unsubstituted C6 to C40 aryl group; or a substituted or unsubstituted C2 to C40 heteroaryl group.

In another embodiment, R301 and R302 are the same as or different from each other, and may be each independently a phenyl group; a biphenyl group; a naphthyl group; a triphenylenyl group; a dimethylfluorenyl group; a diphenylfluorenyl group; a spirobifluorenyl group; a dibenzofuran group; a dibenzothiophene group; or a carbazole group.

In the heterocyclic compound provided in one embodiment of the present application, Chemical Formula 1 is represented by any one of the following compounds.

001

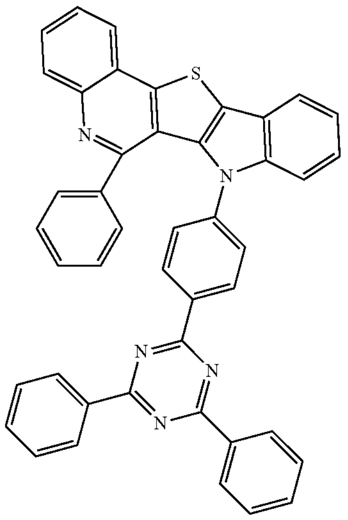

002

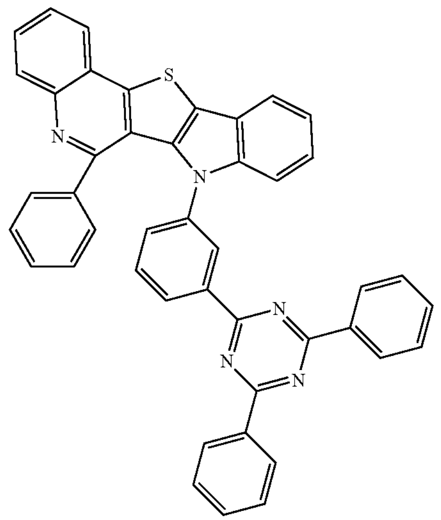

-continued
003
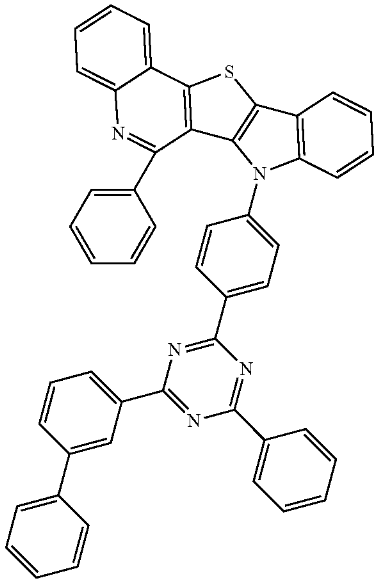
004
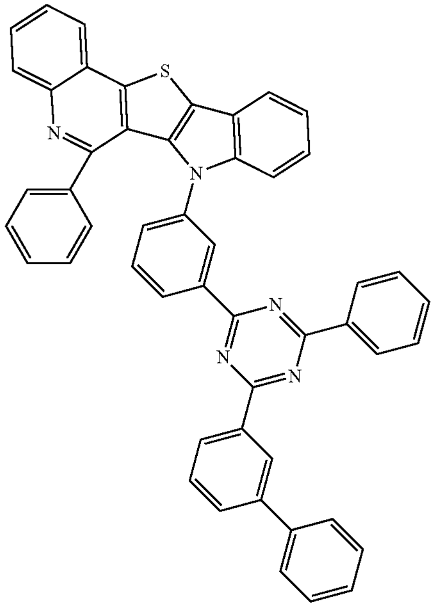
-continued
005
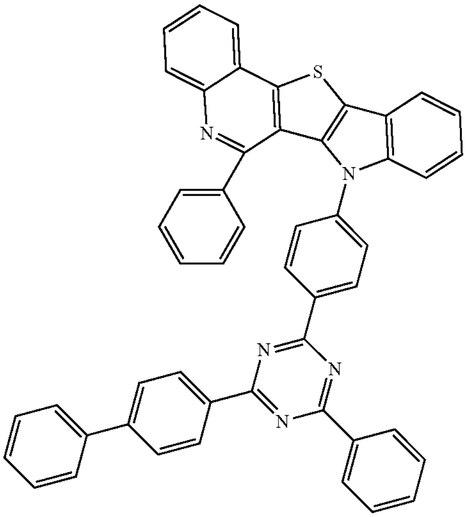
006
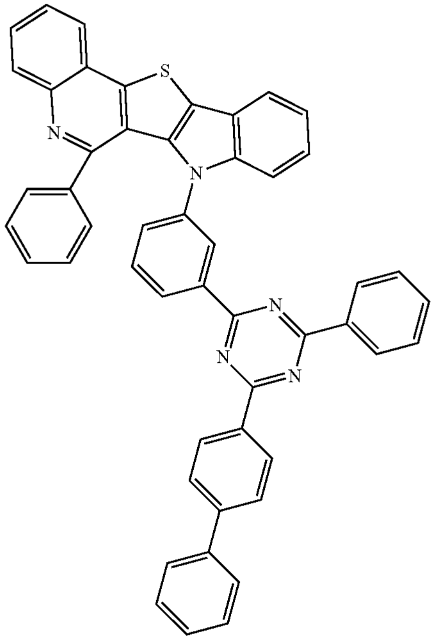

-continued
007
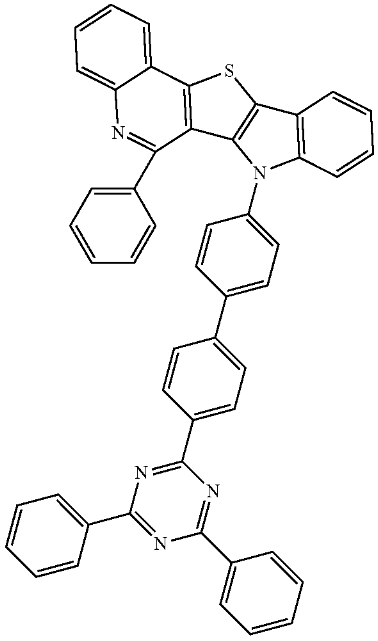
008
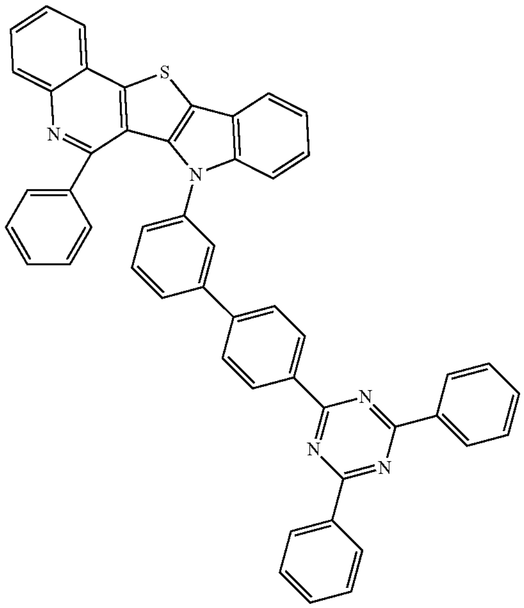
-continued
009
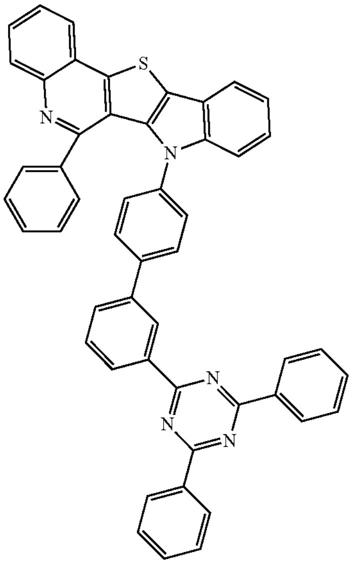
010
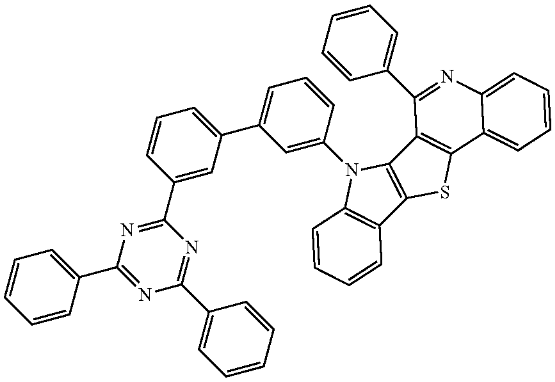
011
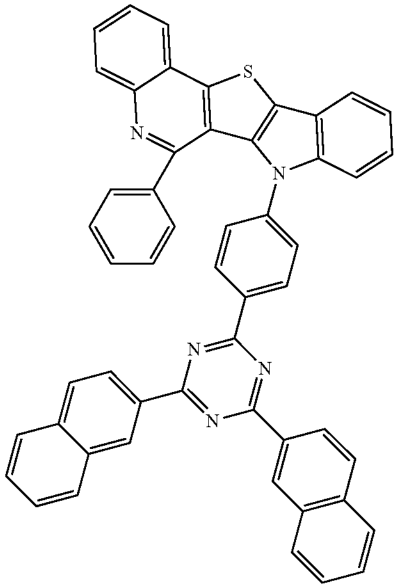

-continued
012
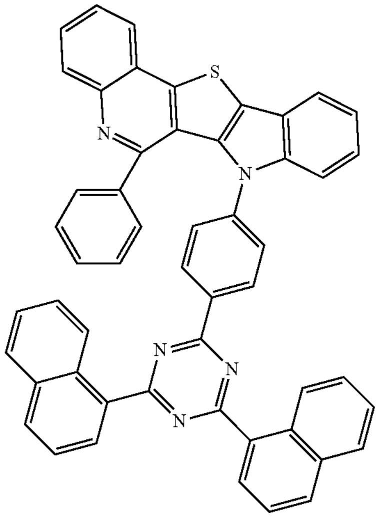
013
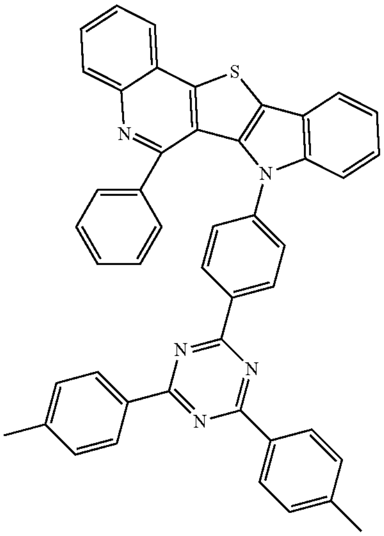
014
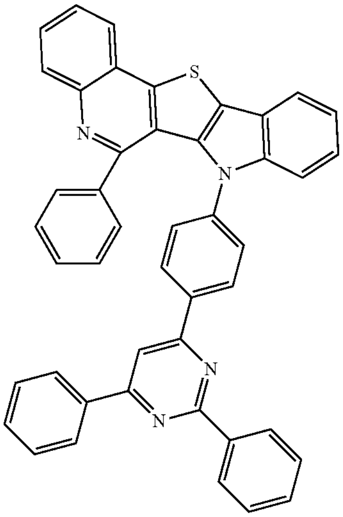
-continued
015
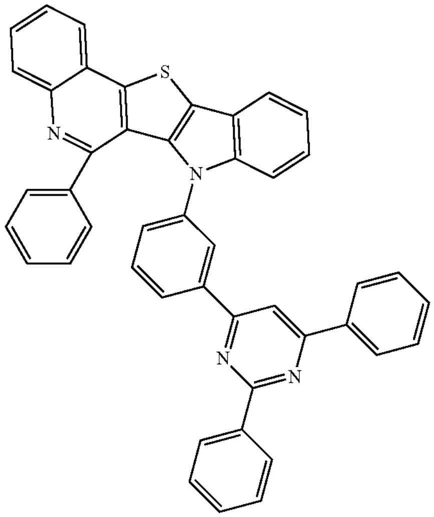
016
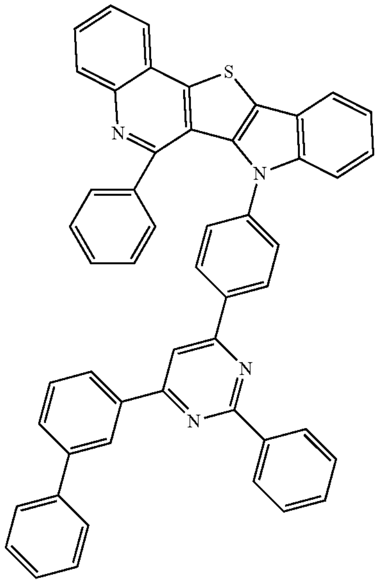

-continued
017
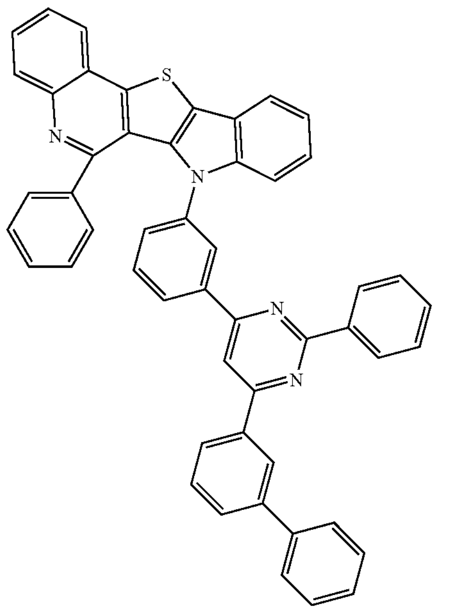
019
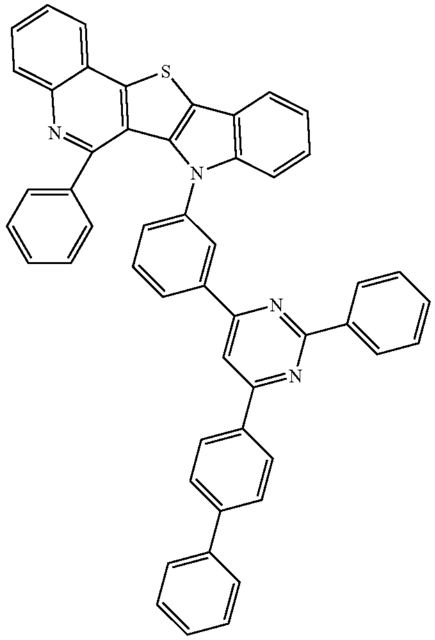
018
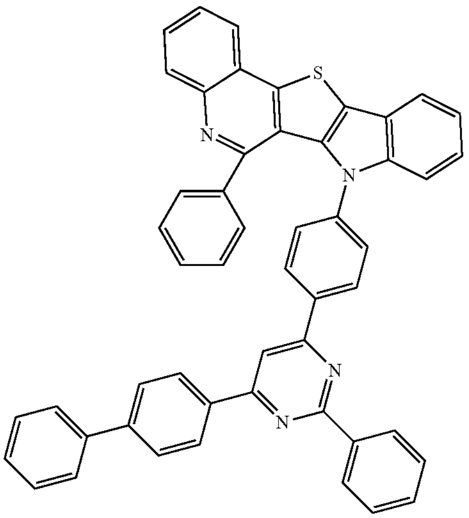
020
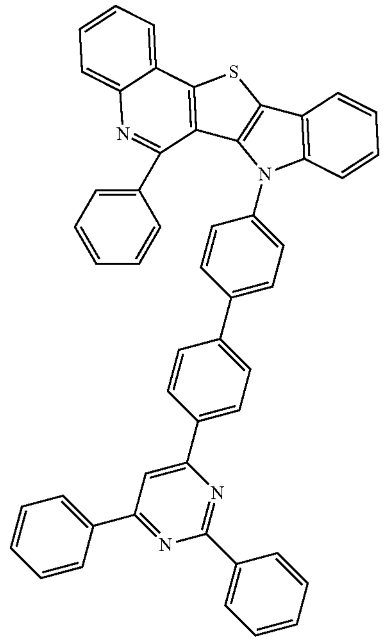

-continued
021
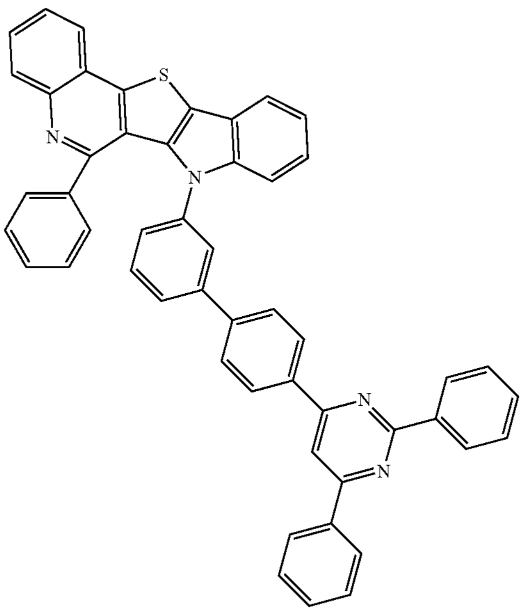
022
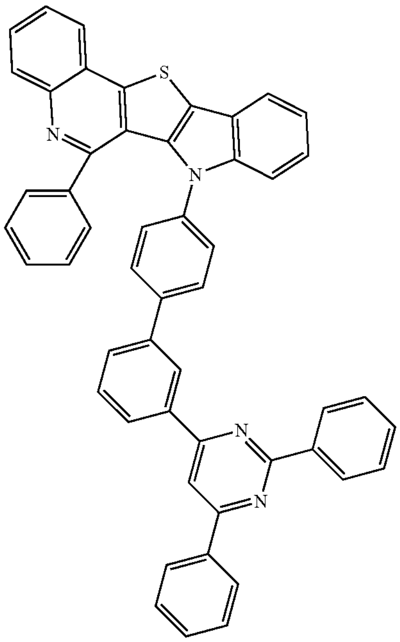
023
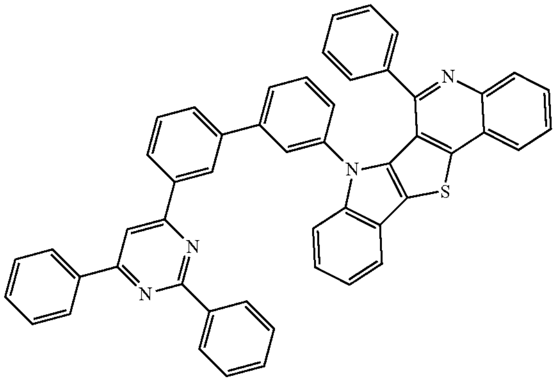
-continued
024
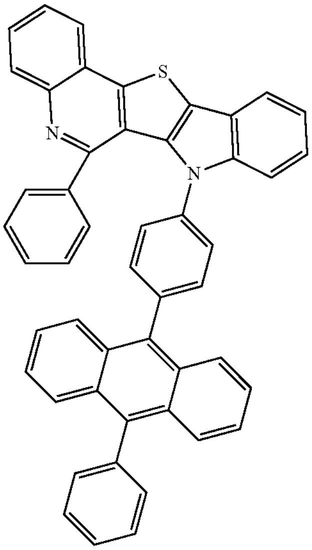
025
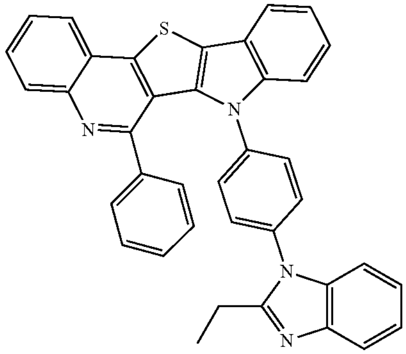
026
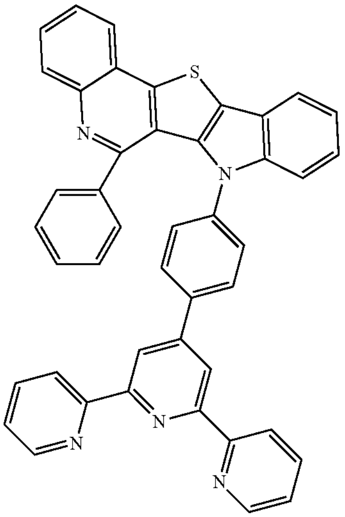

-continued
027
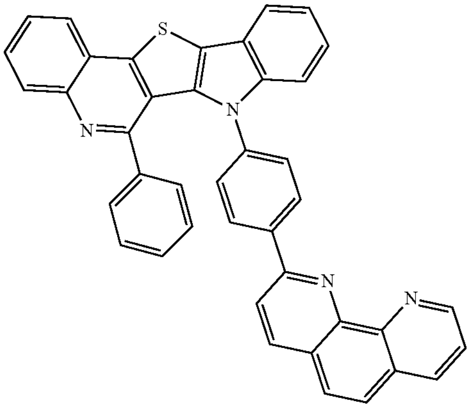
028
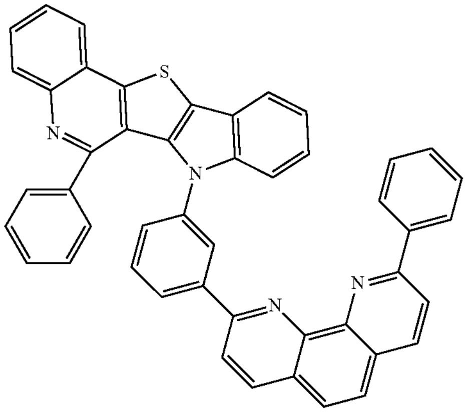
029
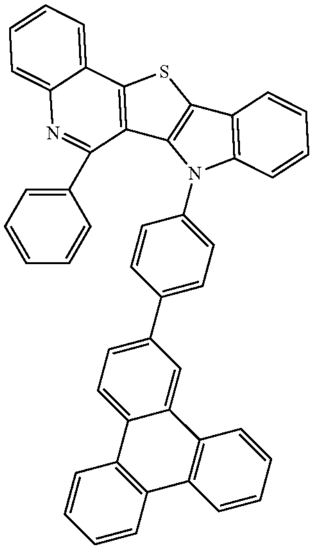
-continued
030
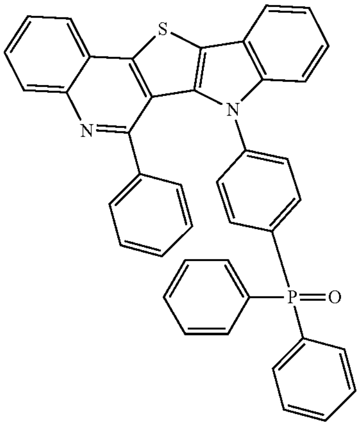
031
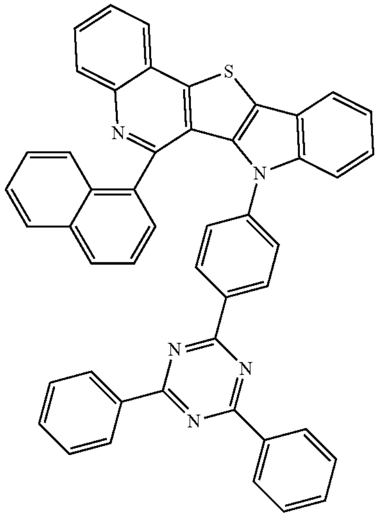
032
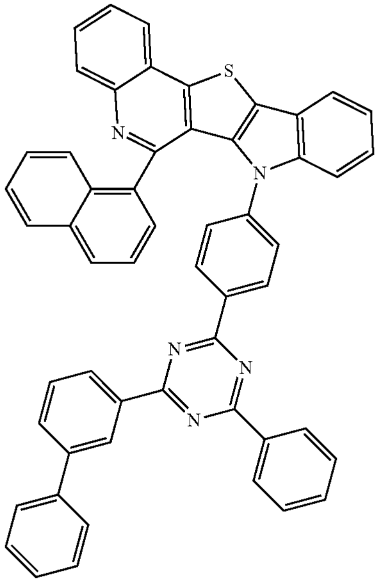

-continued
033
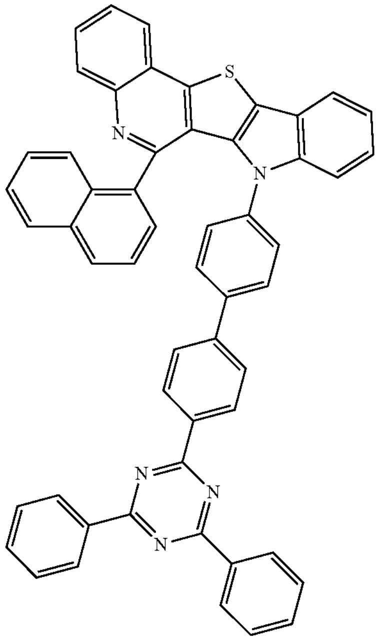
034
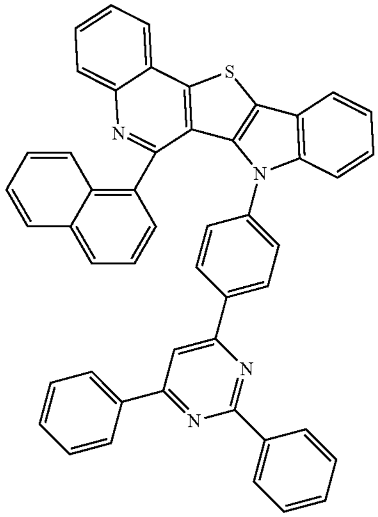
-continued
035
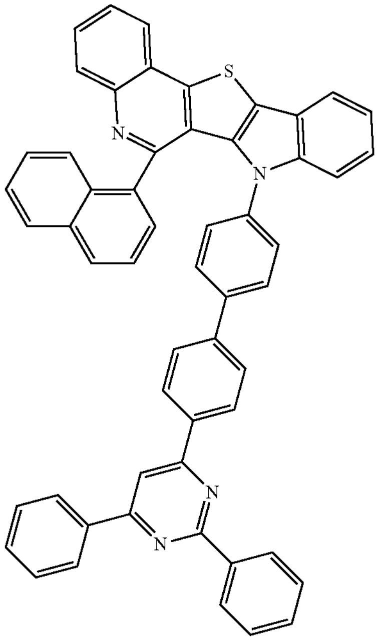
036
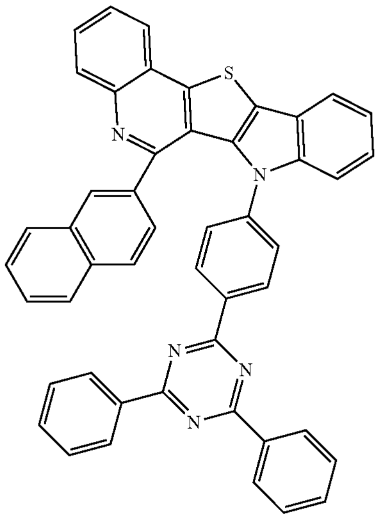

-continued
037
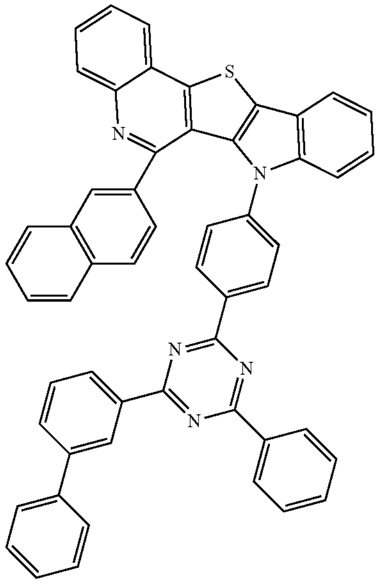
038
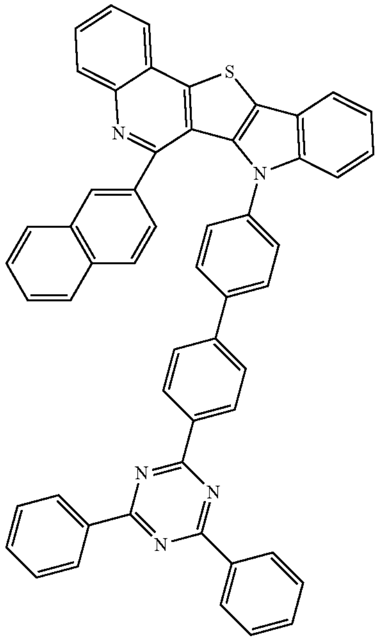
-continued
039
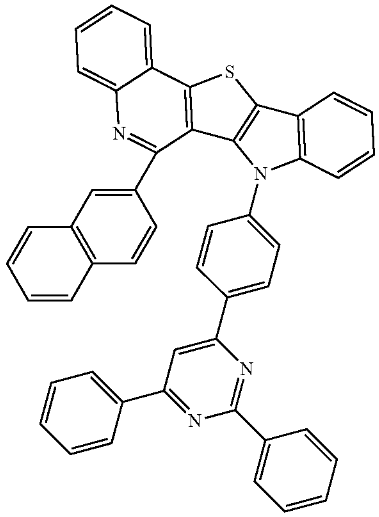
040
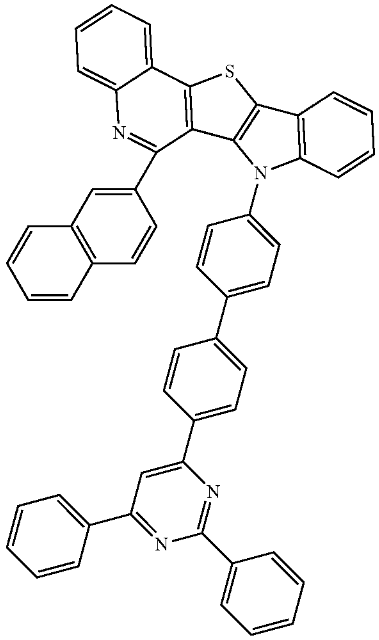

-continued
041
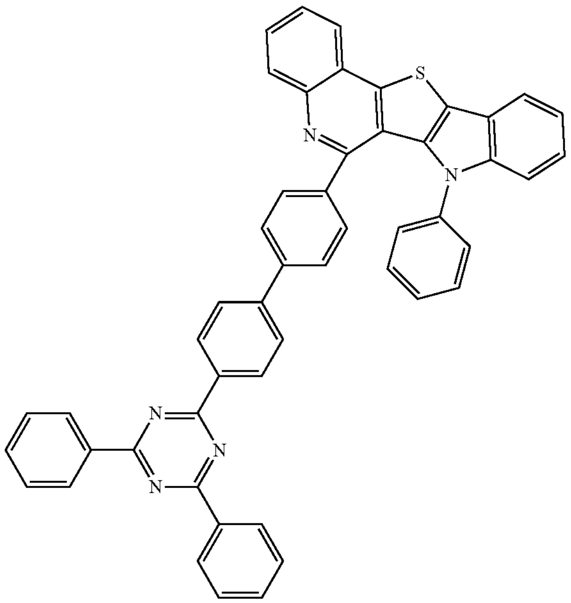
-continued
043
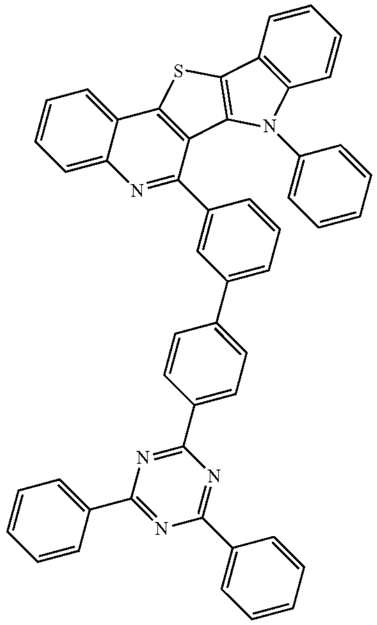
042
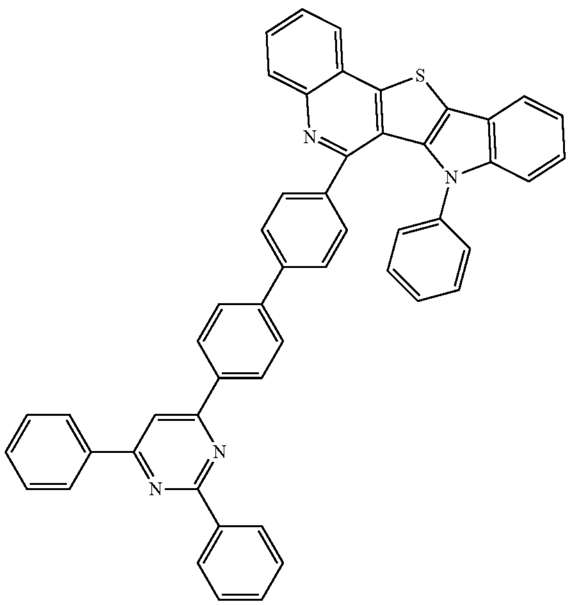
044
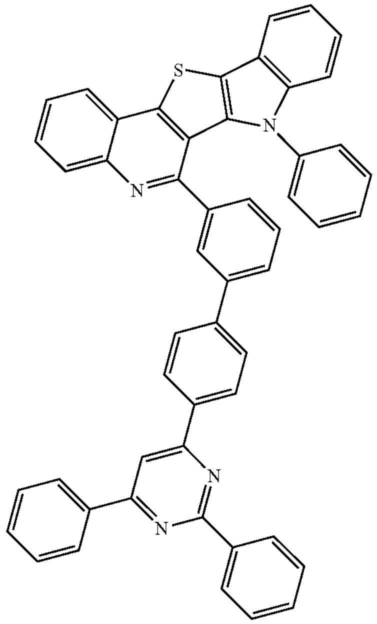

-continued
045
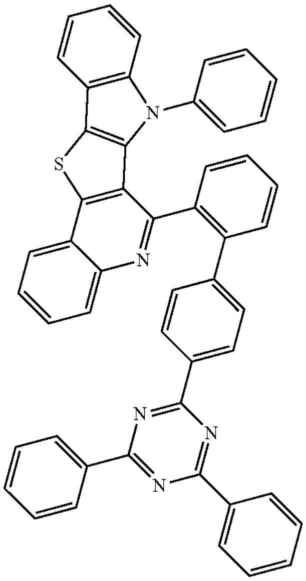
046
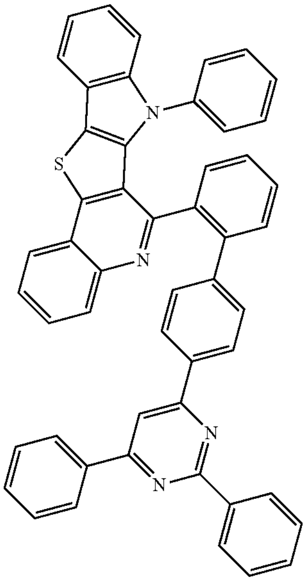
-continued
047
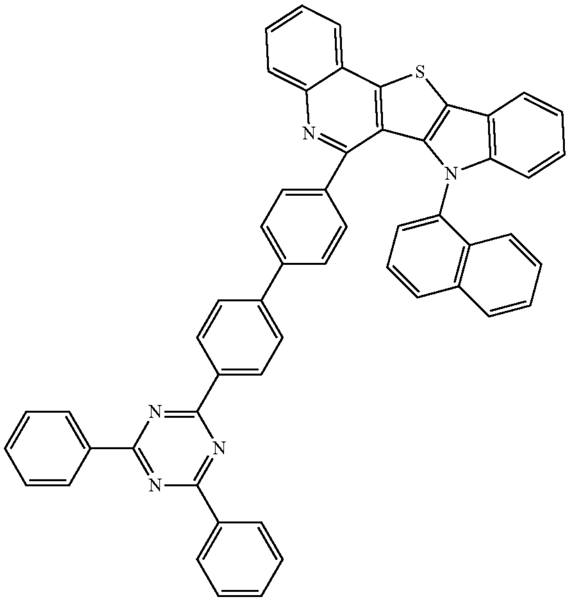
048
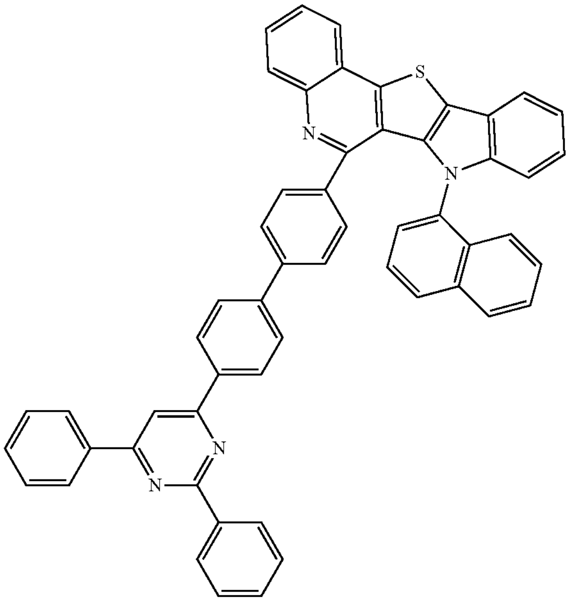

-continued
049
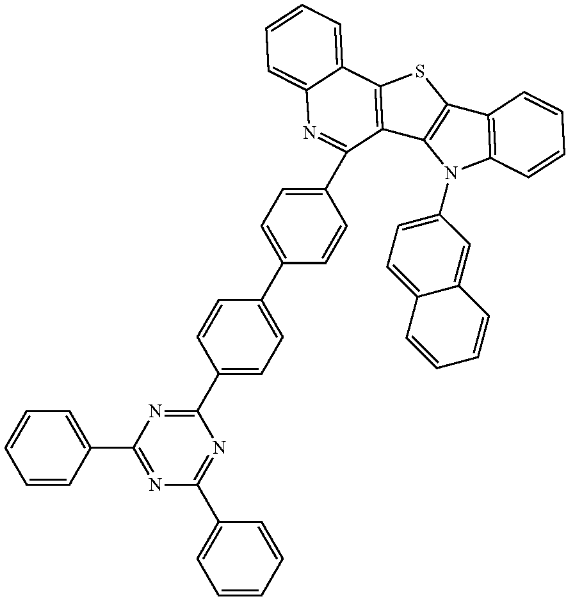
050
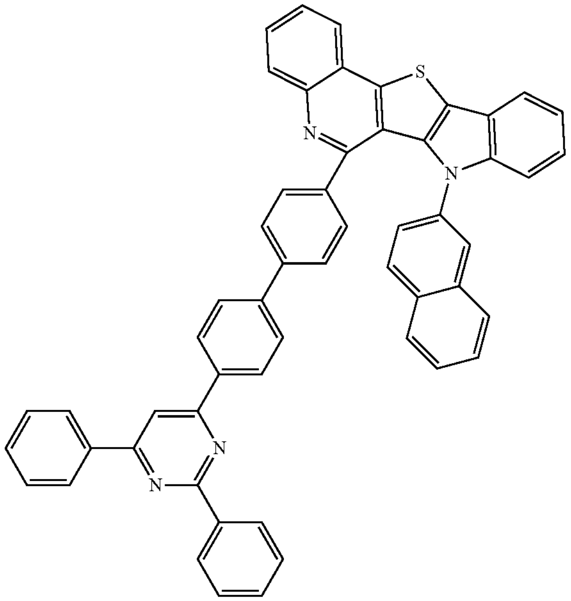
-continued
051
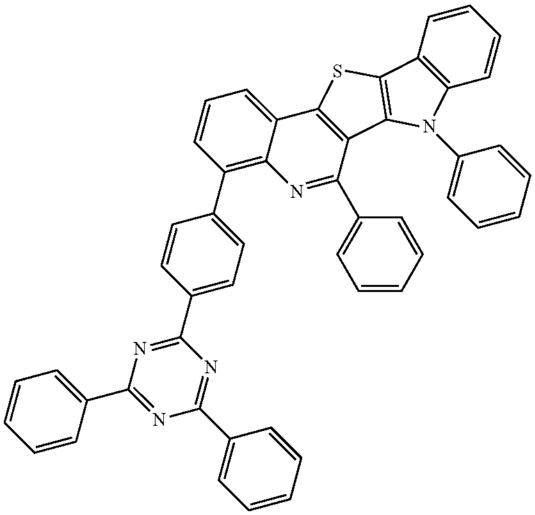
052
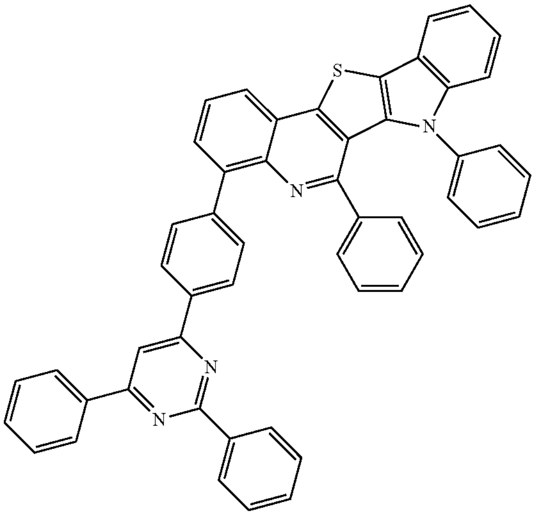

-continued
053
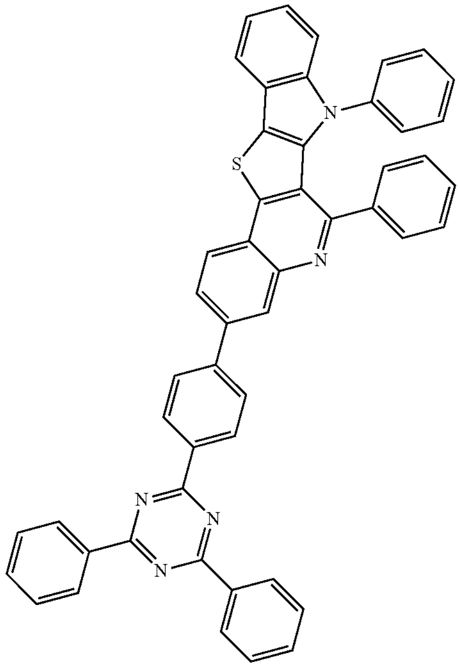
054
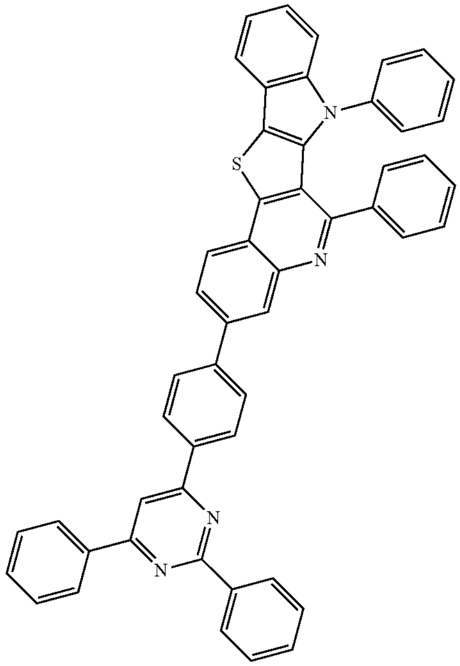
-continued
055
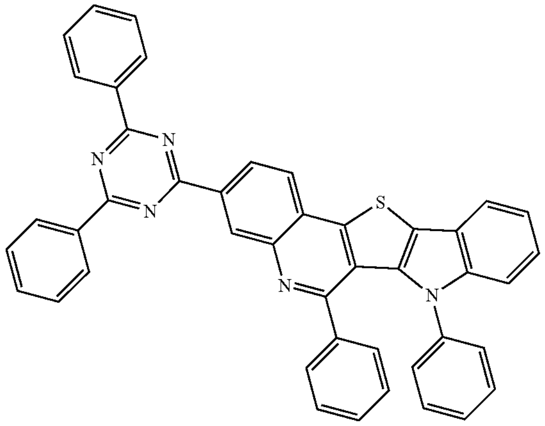
056
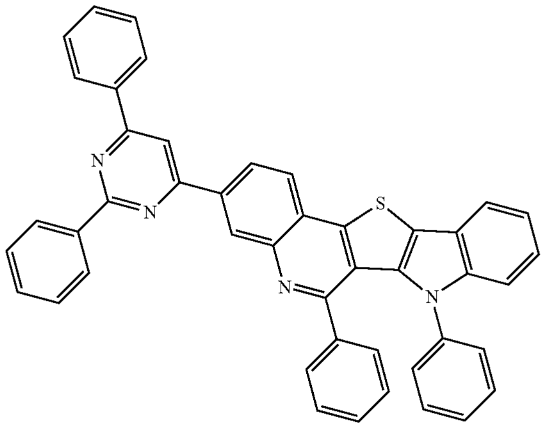
057
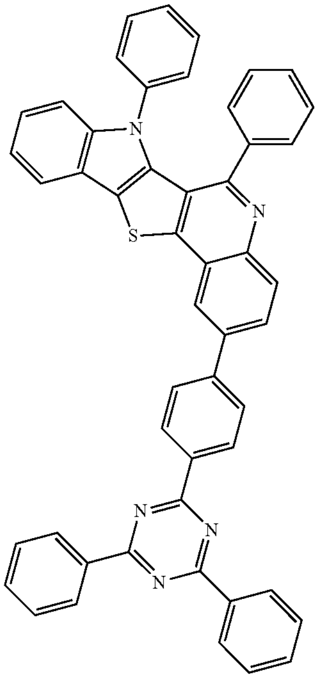

-continued
058
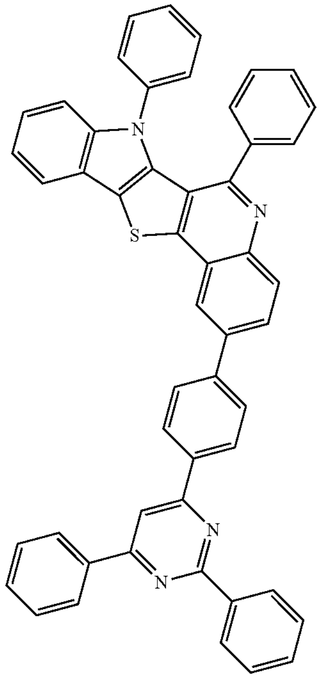
059
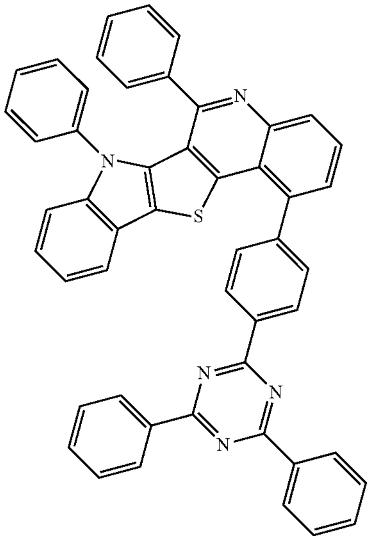
-continued
060
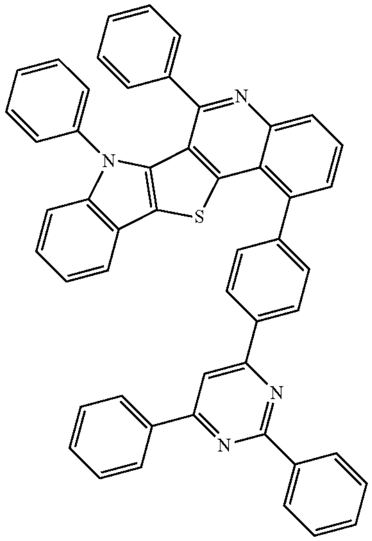
061
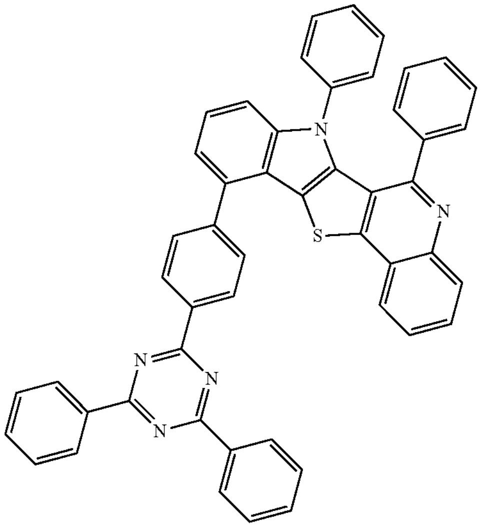
062
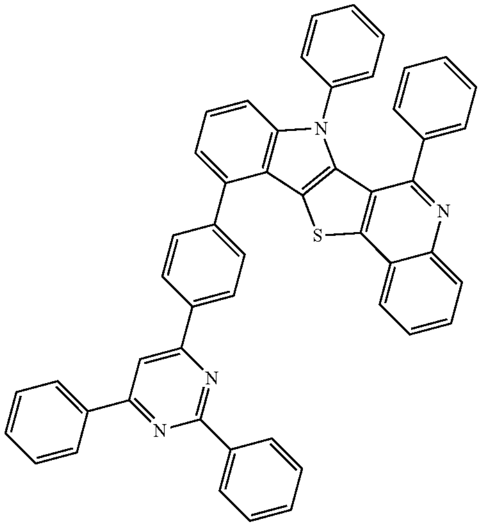

-continued
063
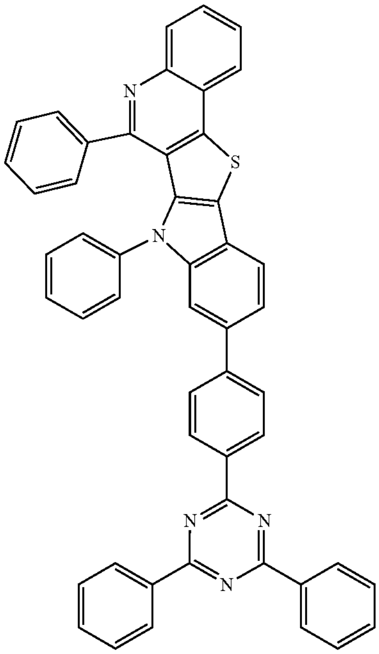
064
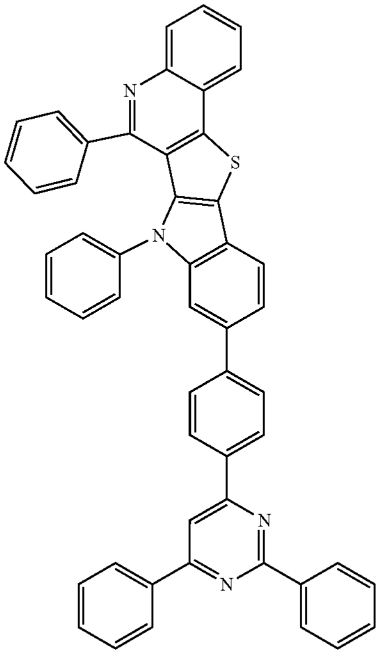
-continued
065
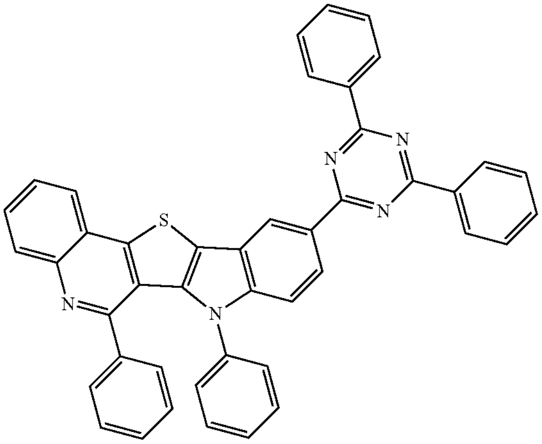
066
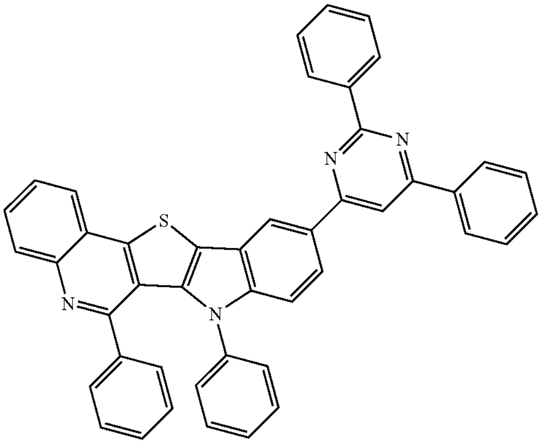
067
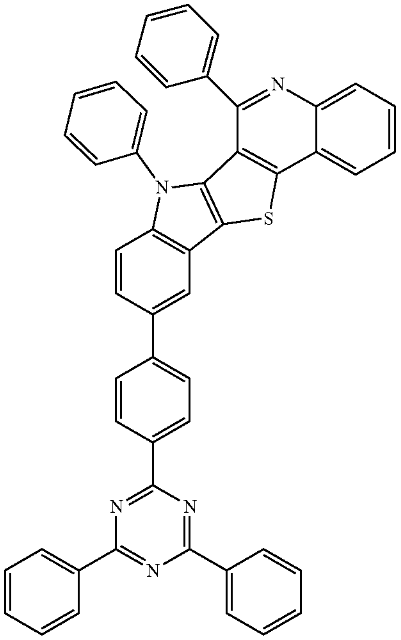

-continued
068
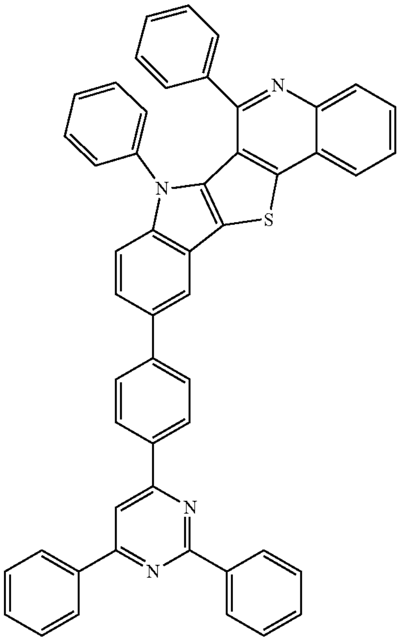
069
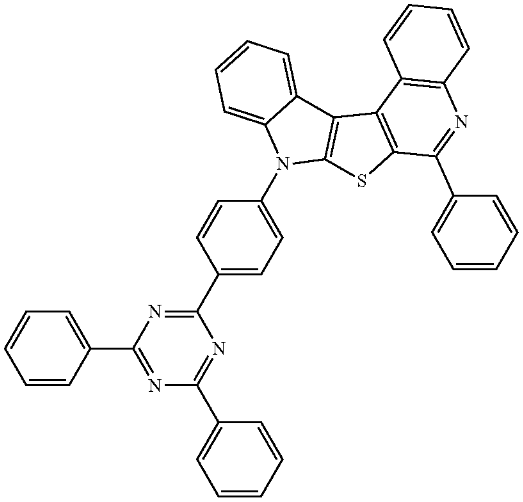
070
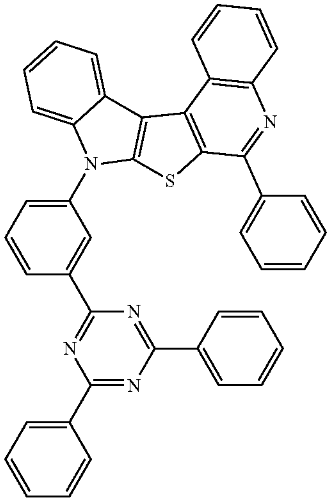
-continued
071
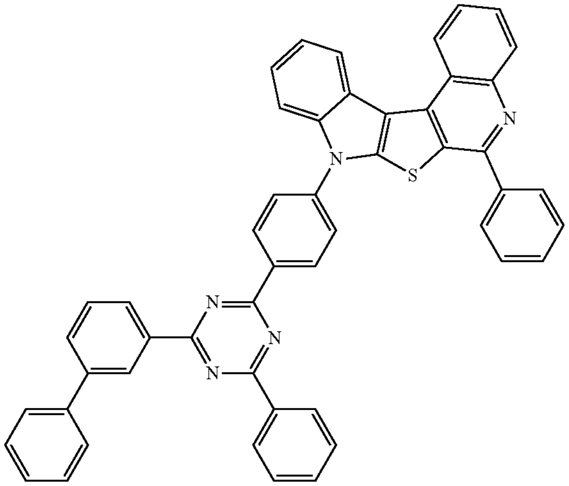
072
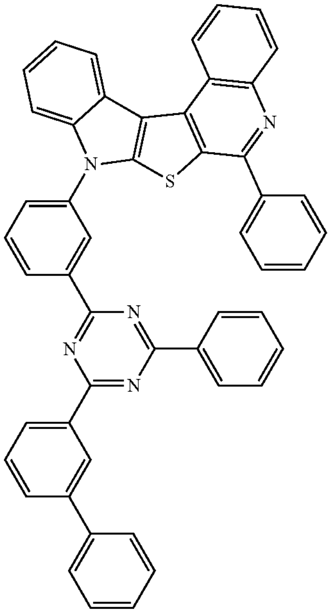
073
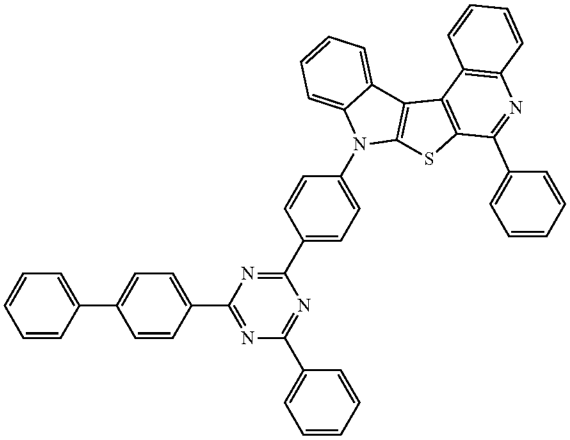

-continued
074
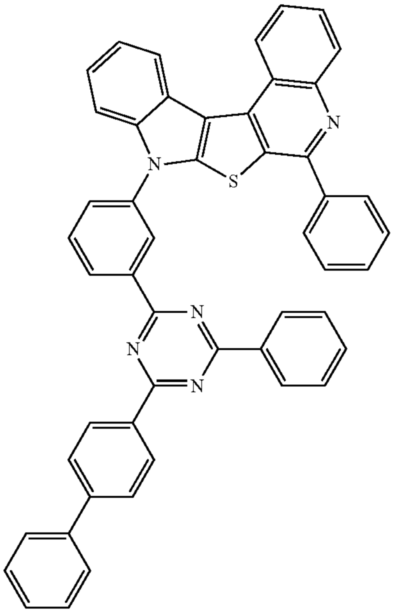
075
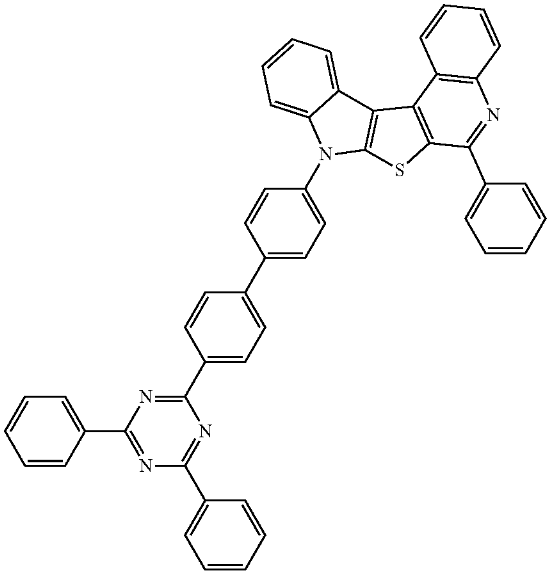
-continued
076
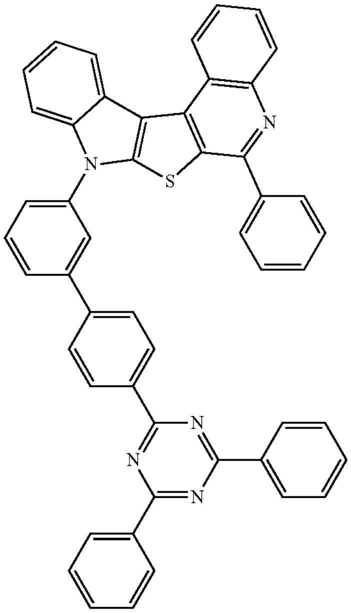
077
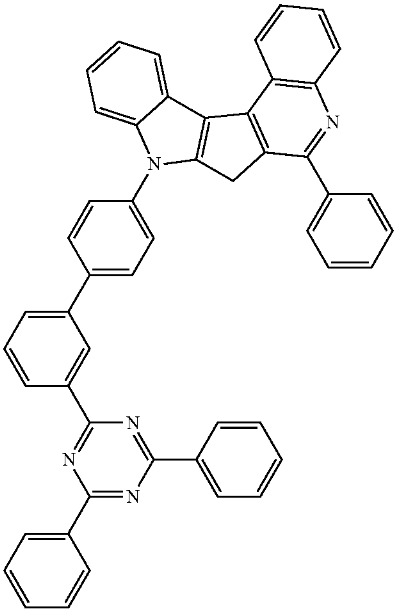

-continued
078
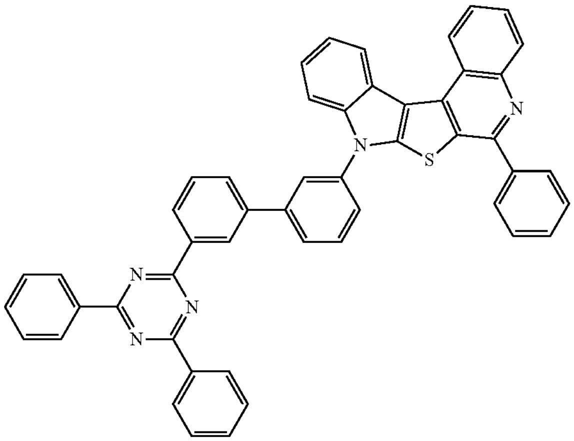
079
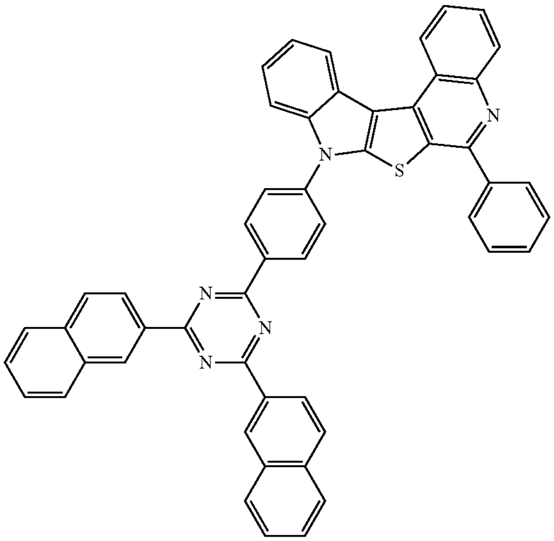
080
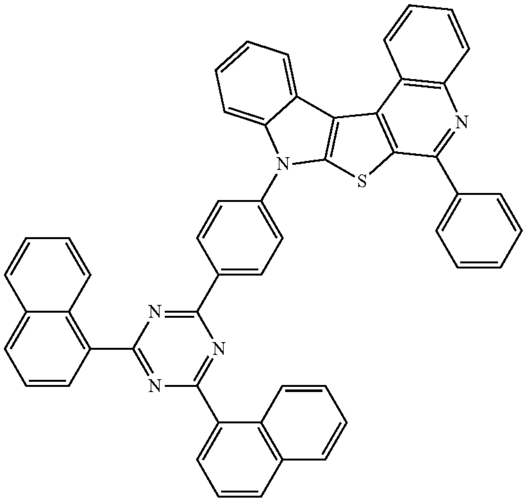
-continued
081
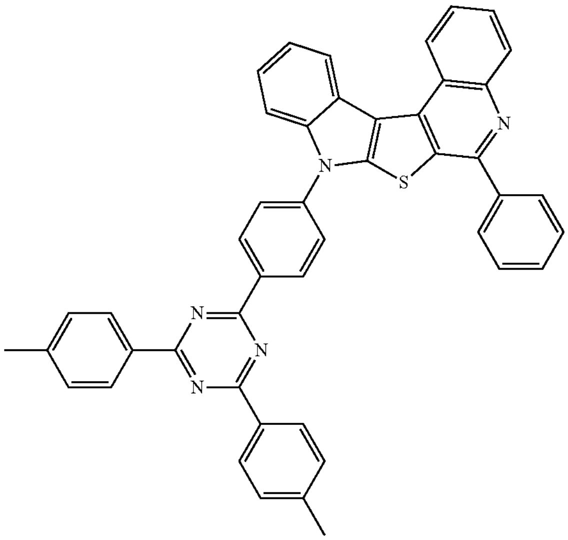
082
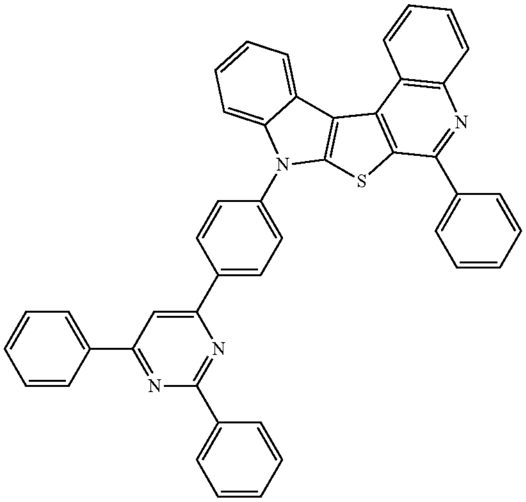
083
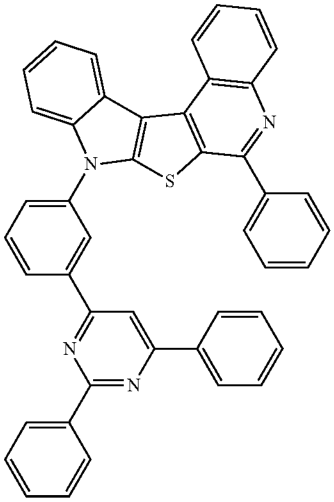

-continued
084
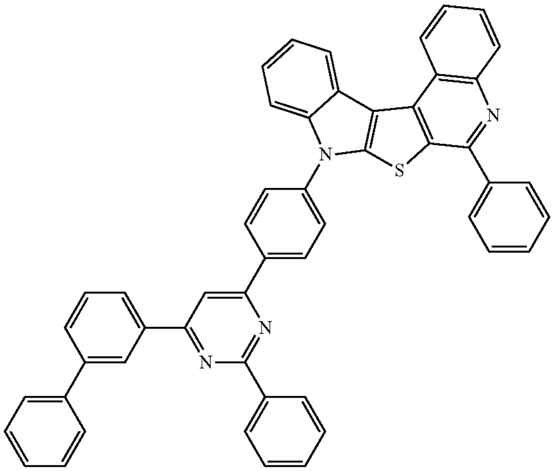
085
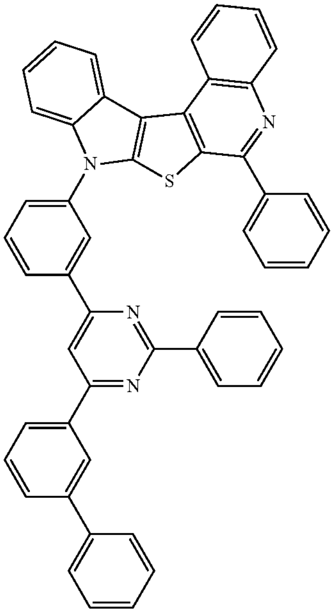
086
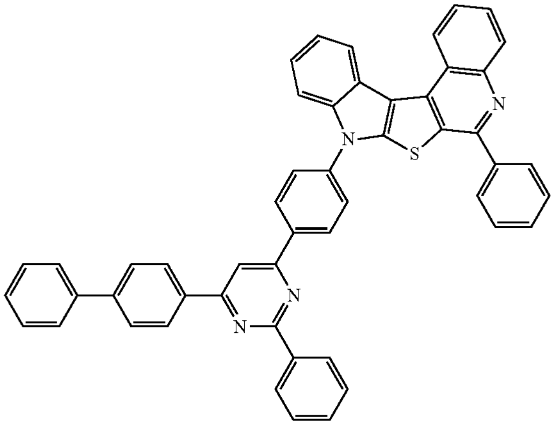
-continued
087
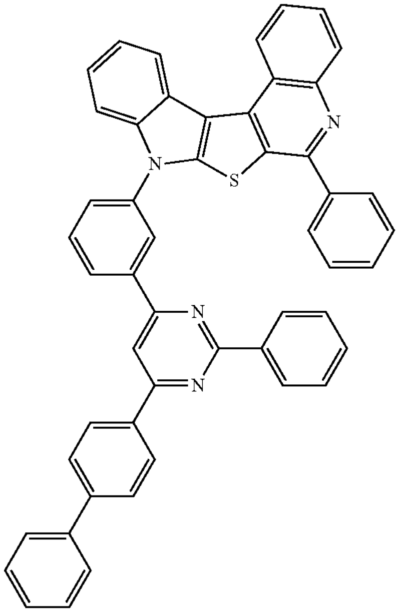
088
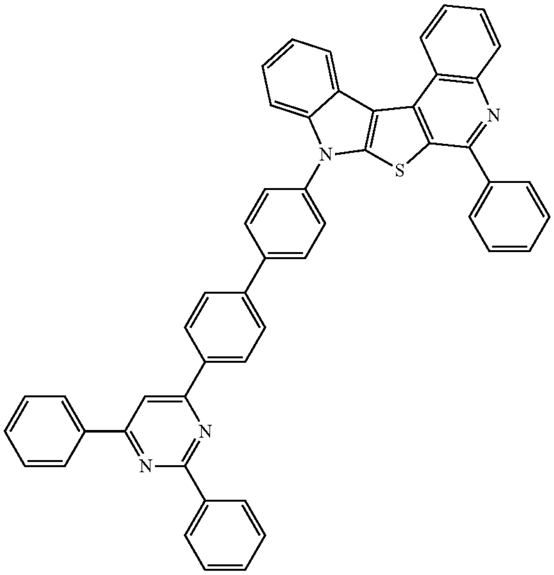

-continued
089
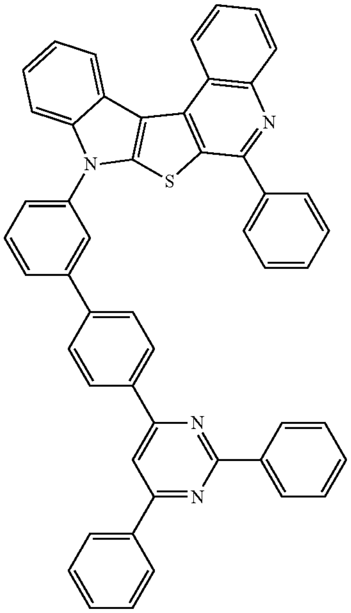
090
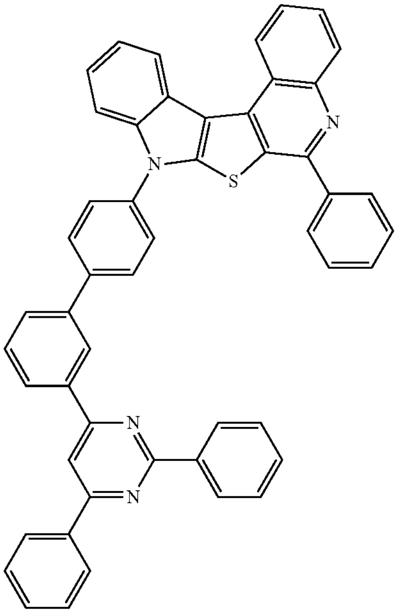
091
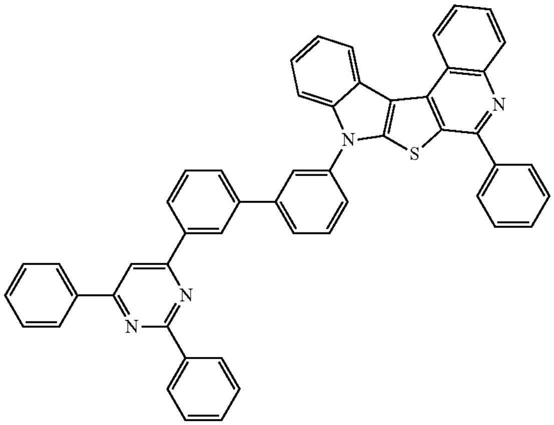
-continued
092
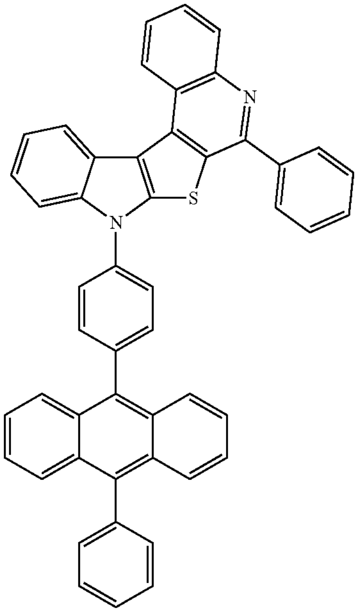
093
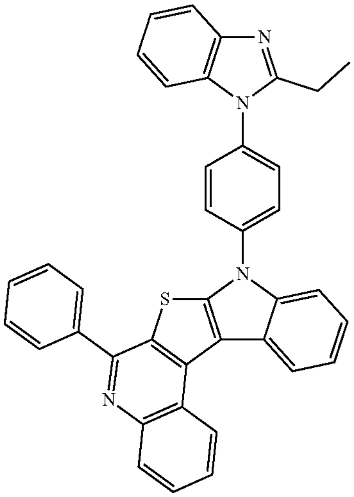
094
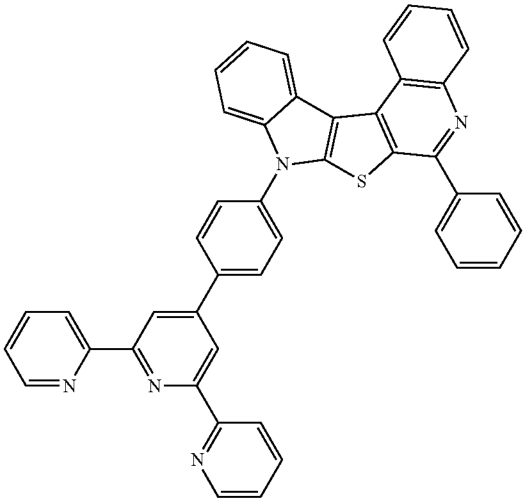

-continued
095
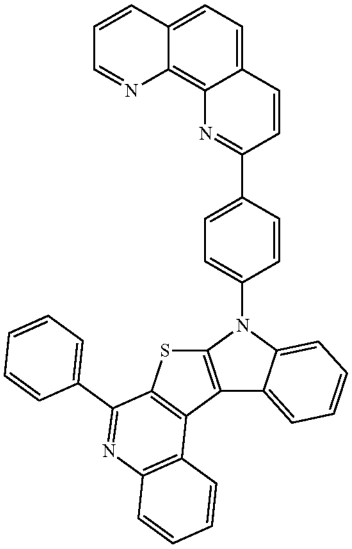
096
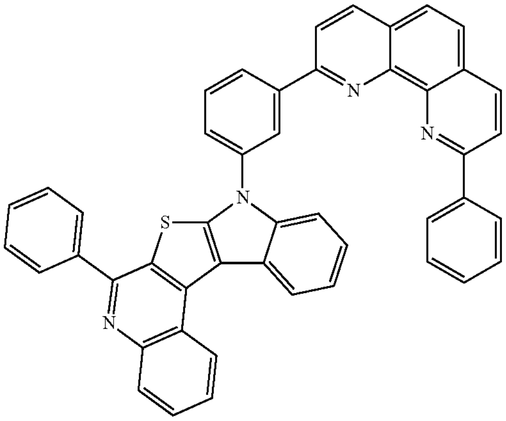
097
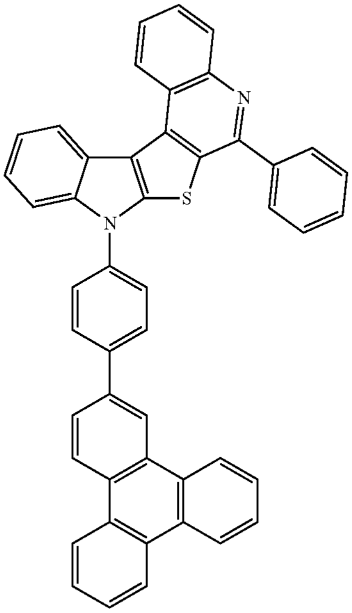
-continued
098
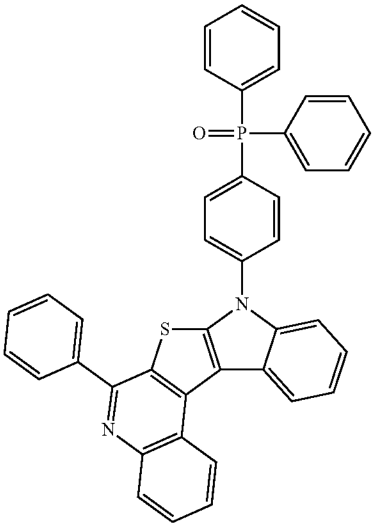
099
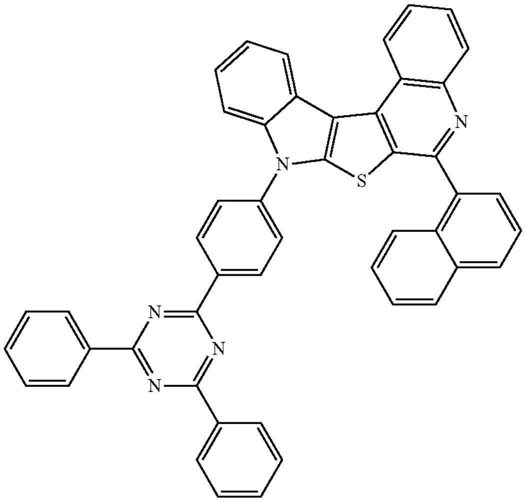
100
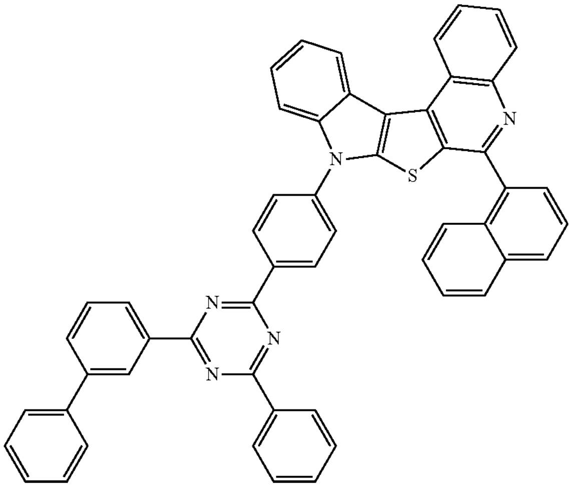

101
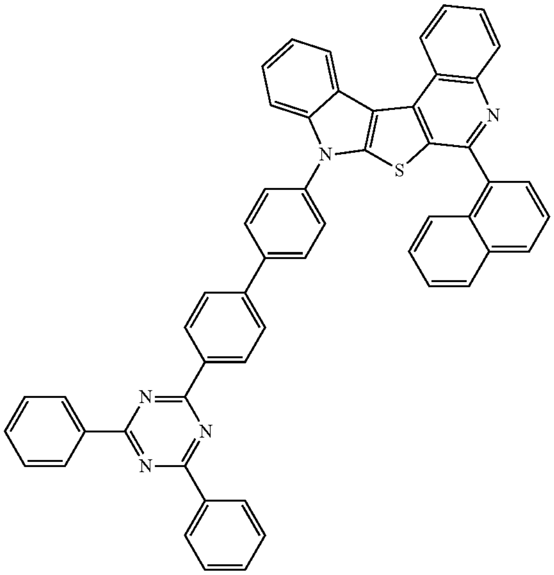
102
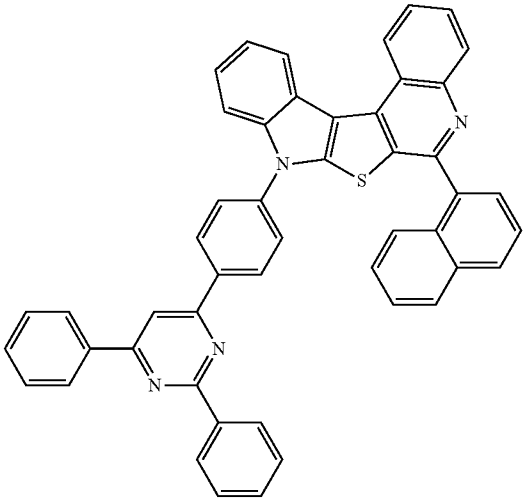
103
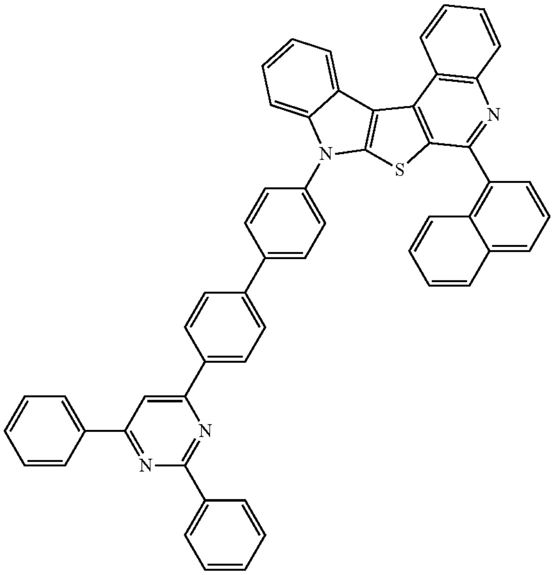
104
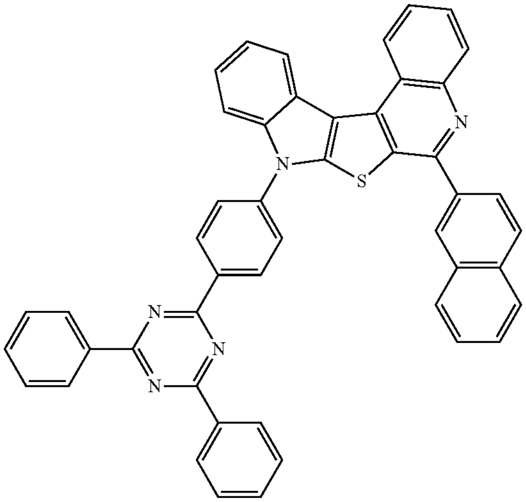
105
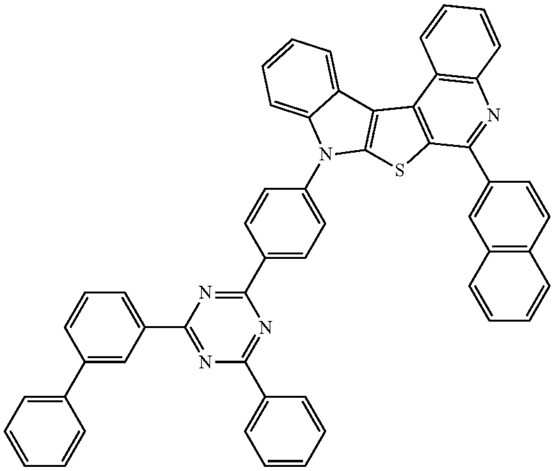

-continued
106
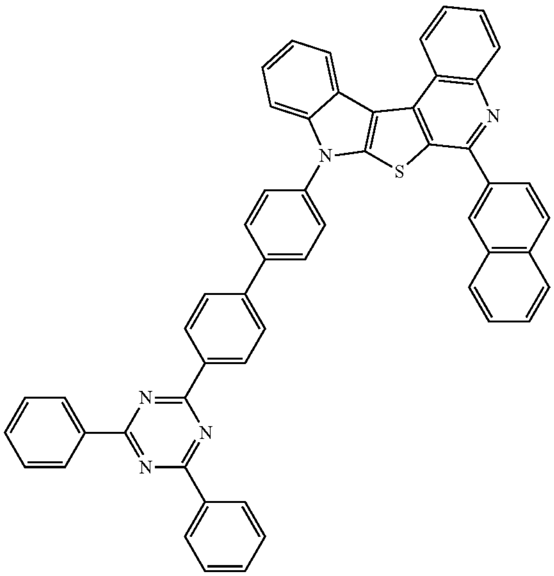
107
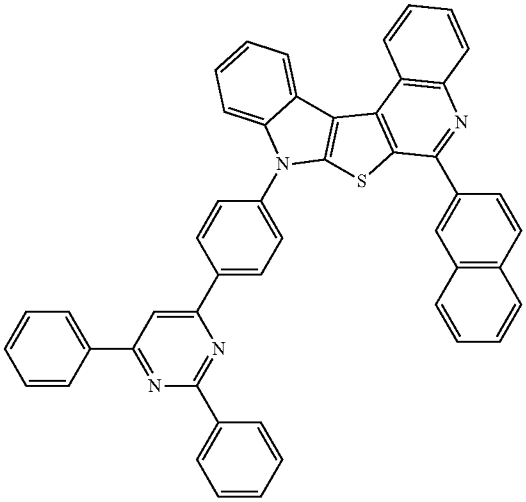
-continued
108
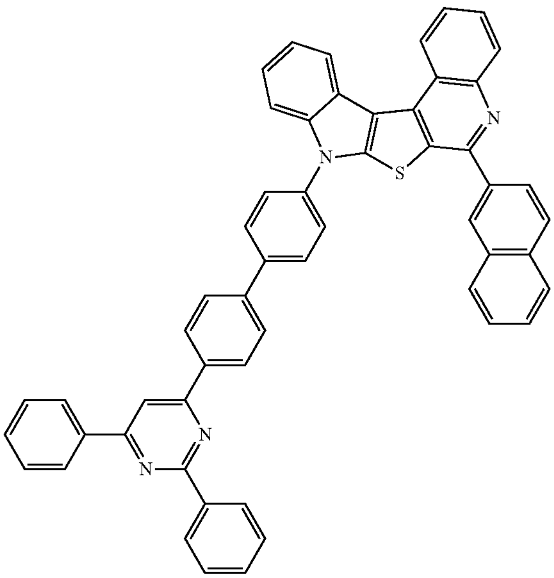
109
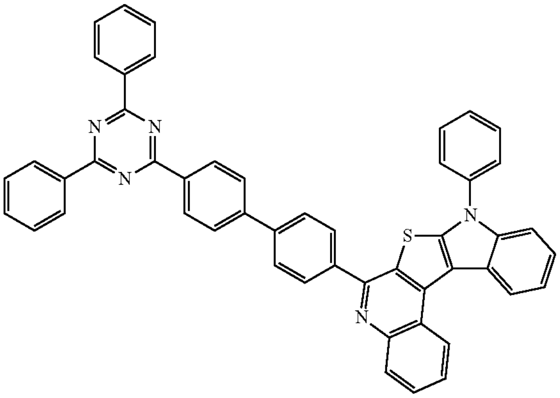
110
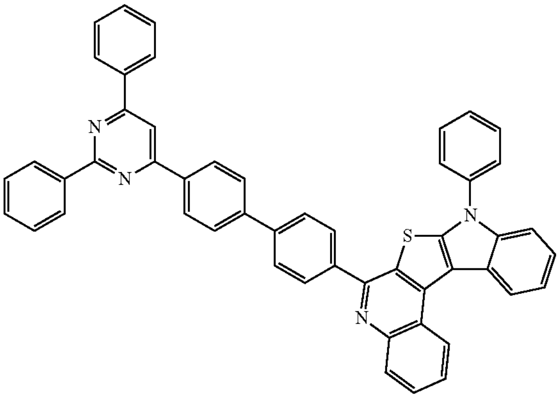

-continued
111
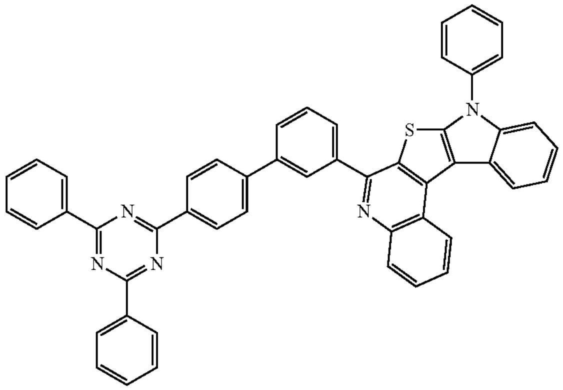
112
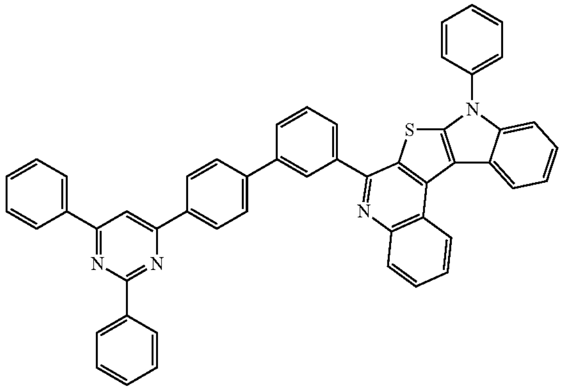
113
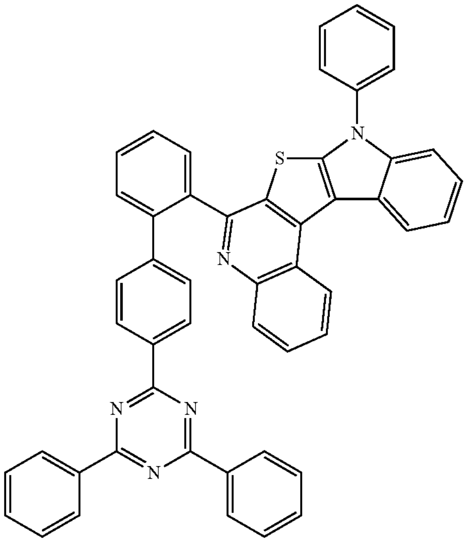
-continued
114
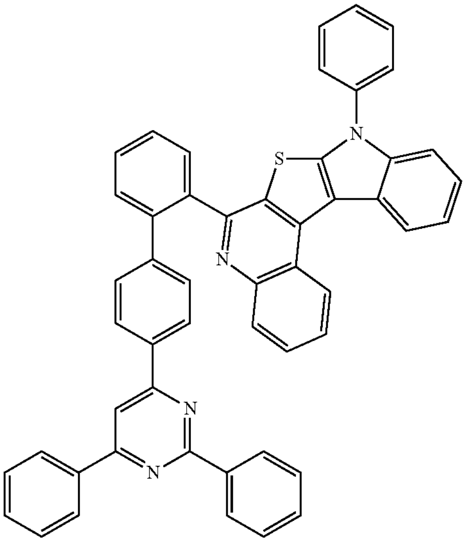
115
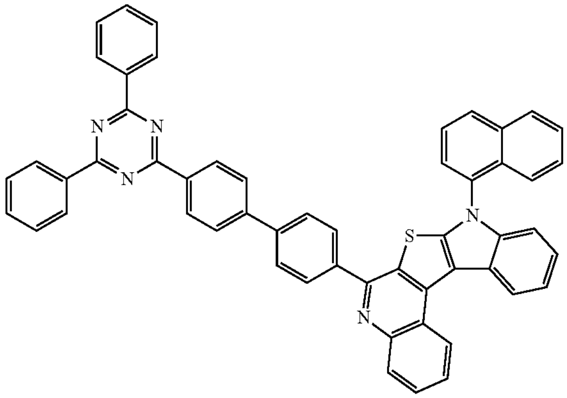
116
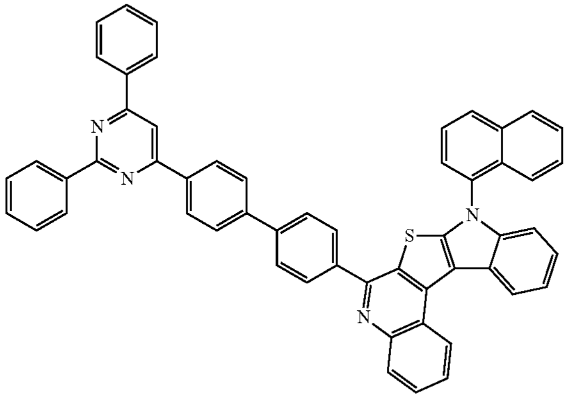

-continued
117
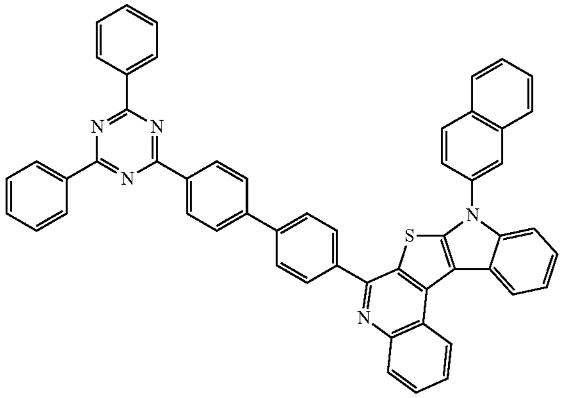
118
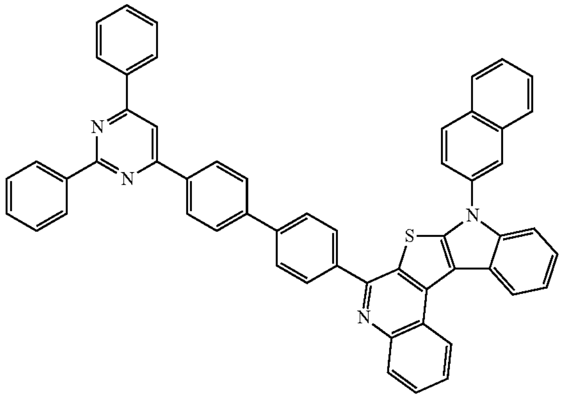
119
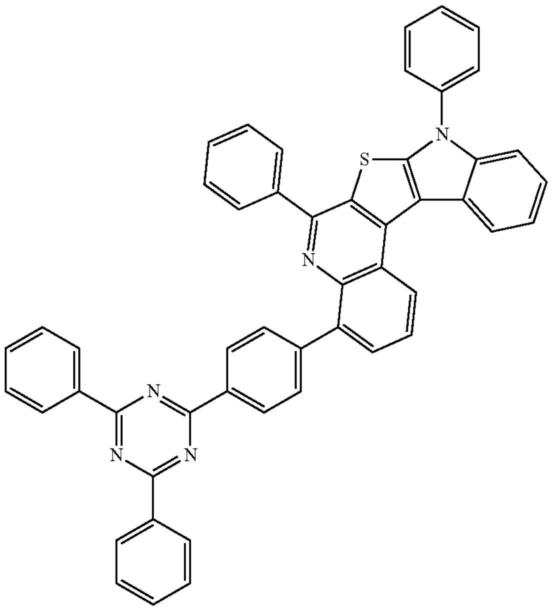
-continued
120
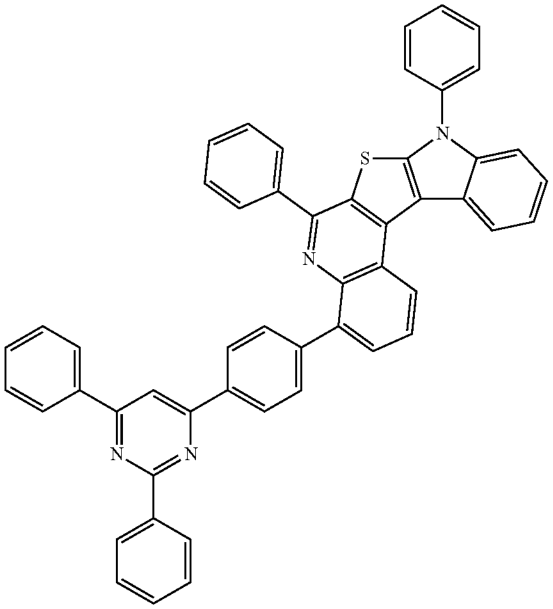
121
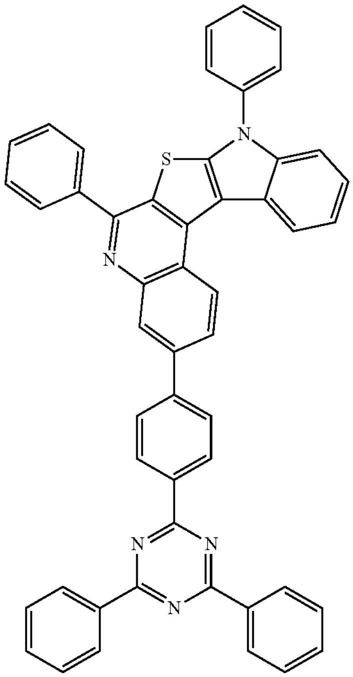

-continued
122
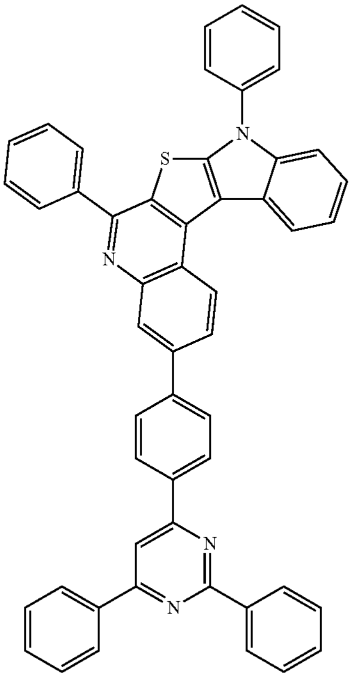
123
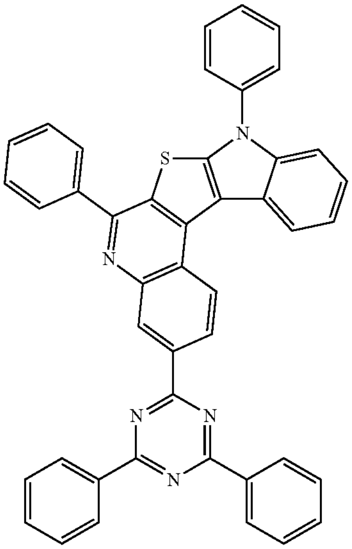
-continued
124
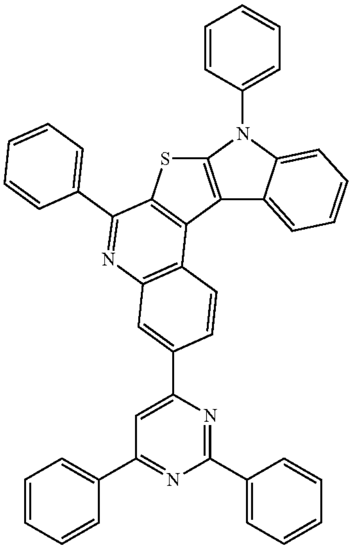
125
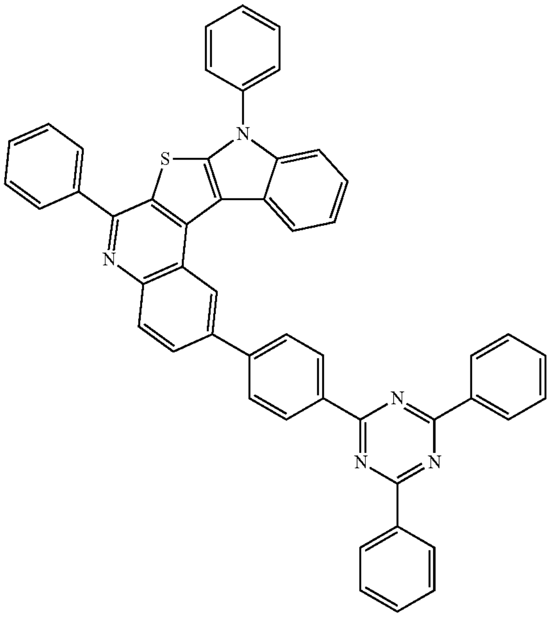

-continued
126
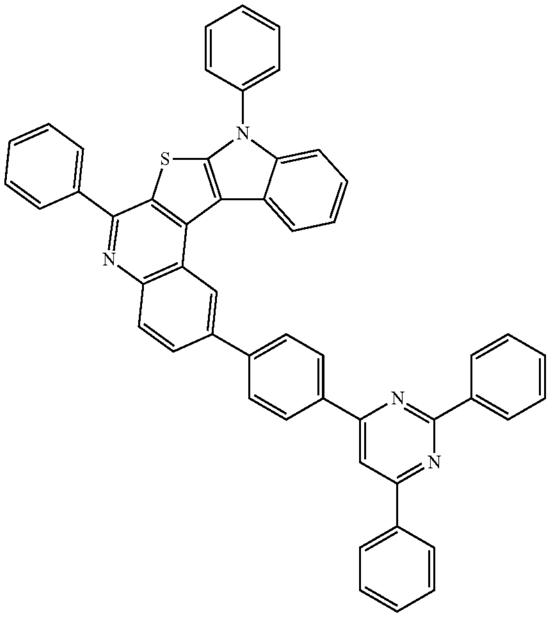
127
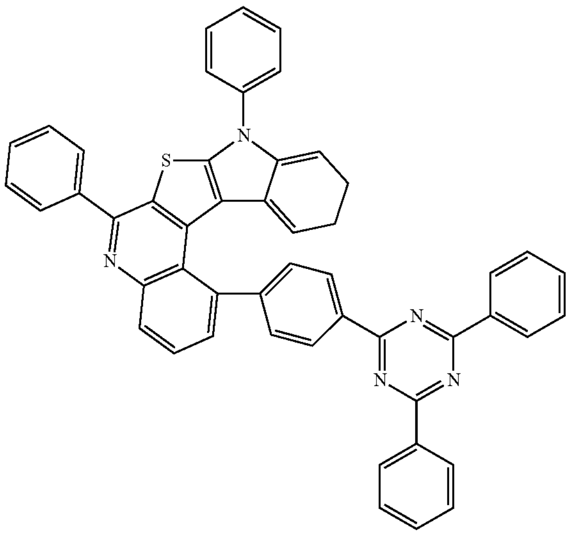
-continued
128
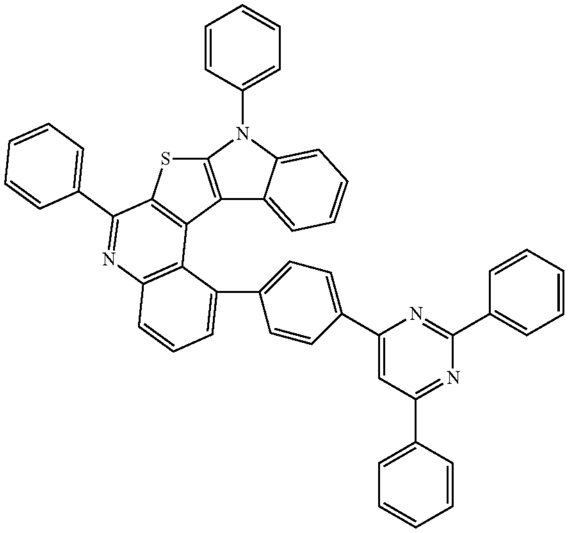
129
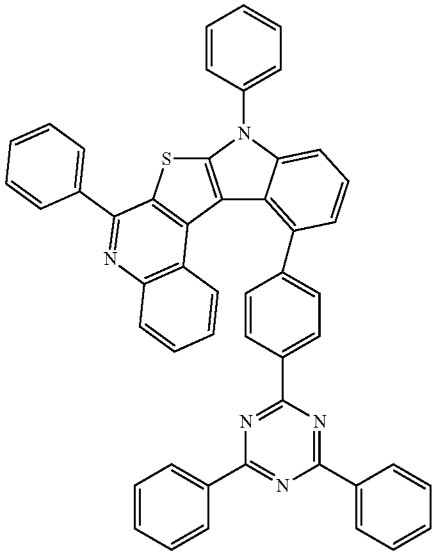
130
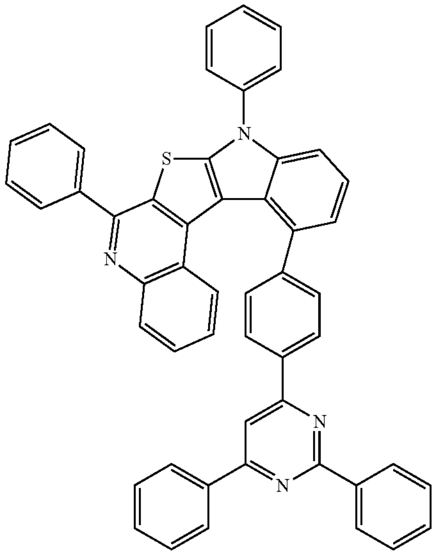

-continued
131
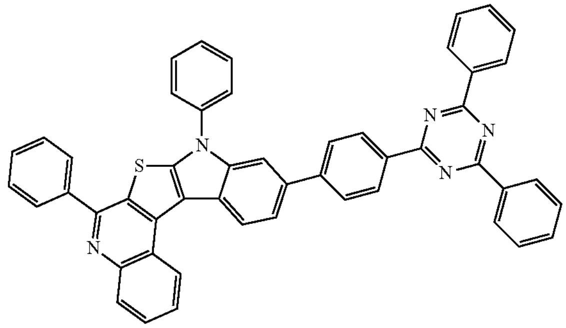
132
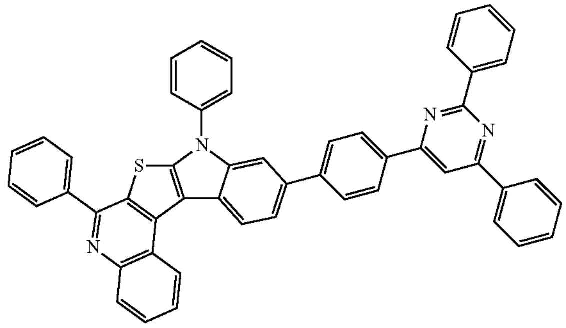
133
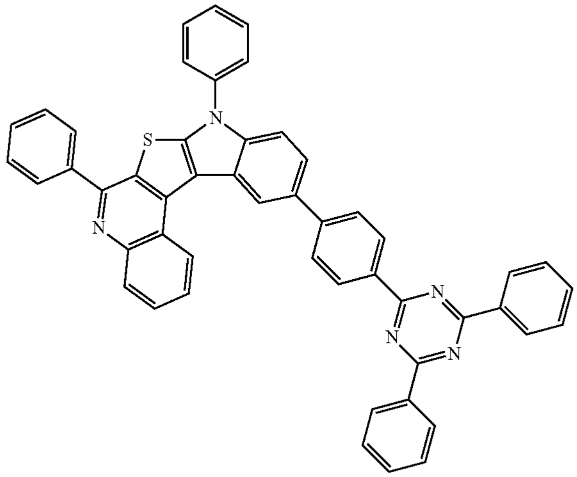
-continued
134
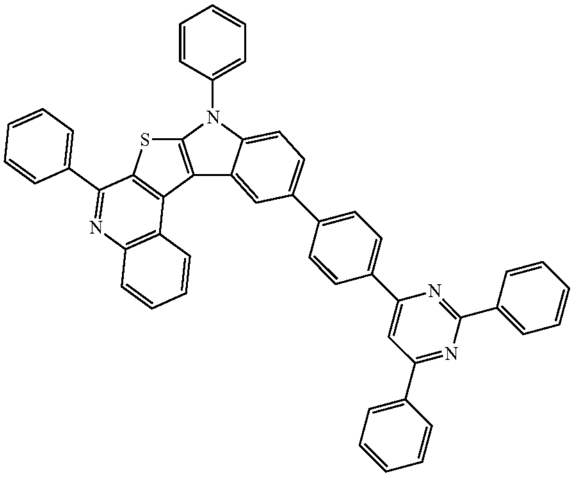
135
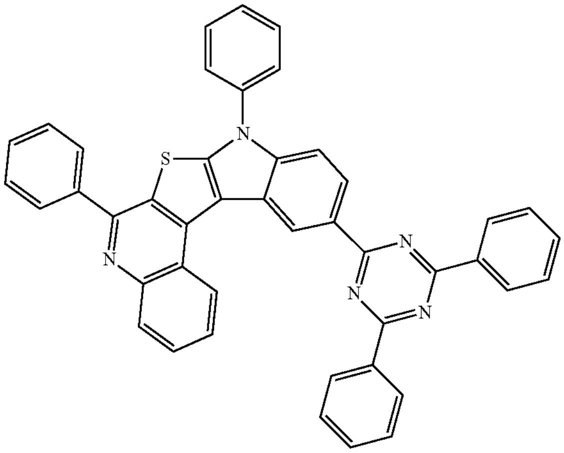
136
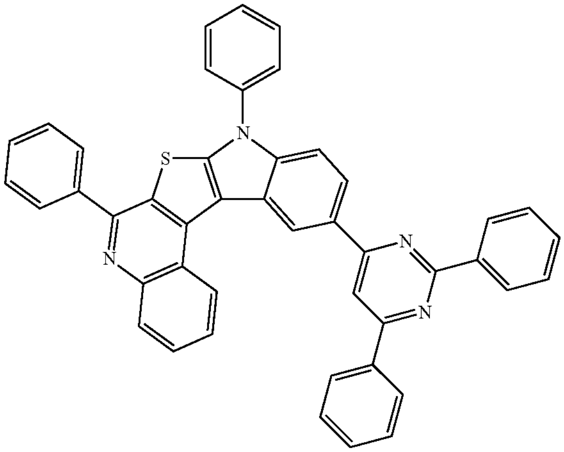

-continued
137
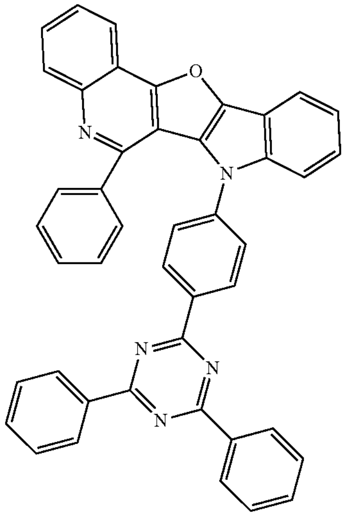
138
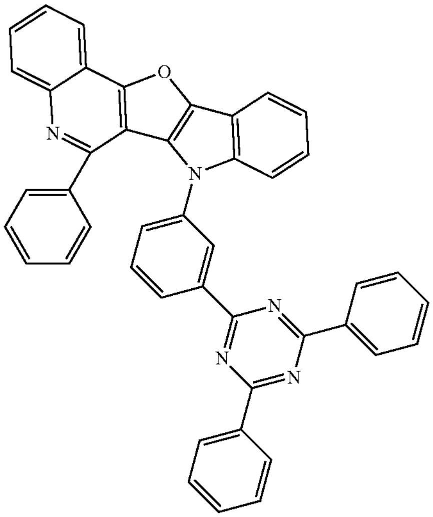
139
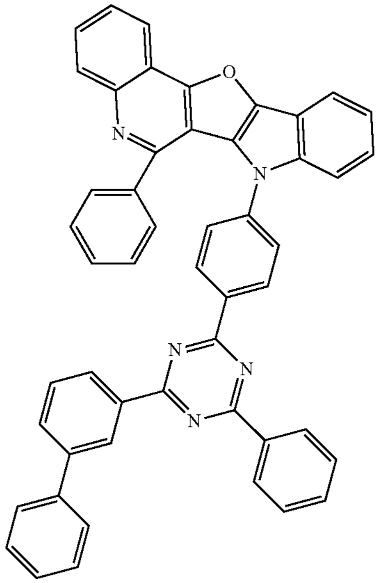
-continued
140
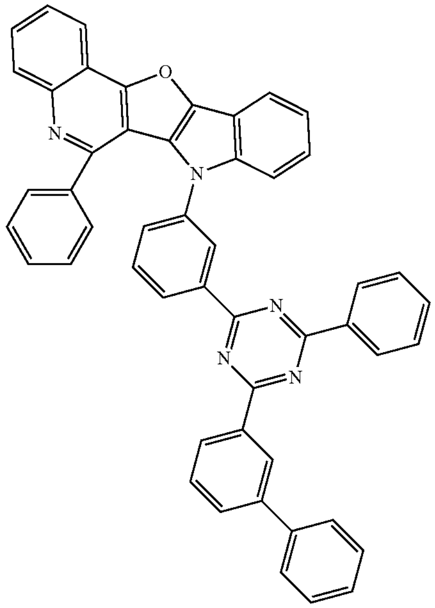
141
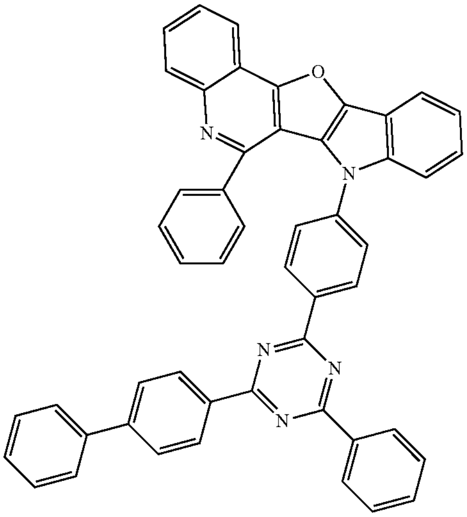

-continued
142
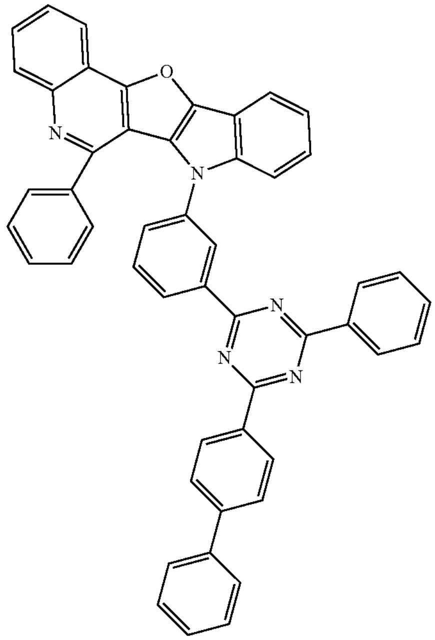
143
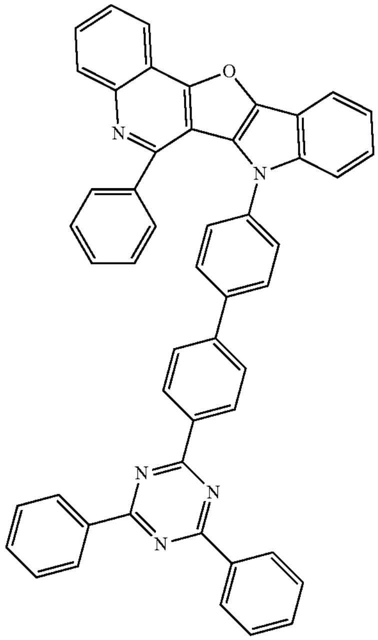
-continued
144
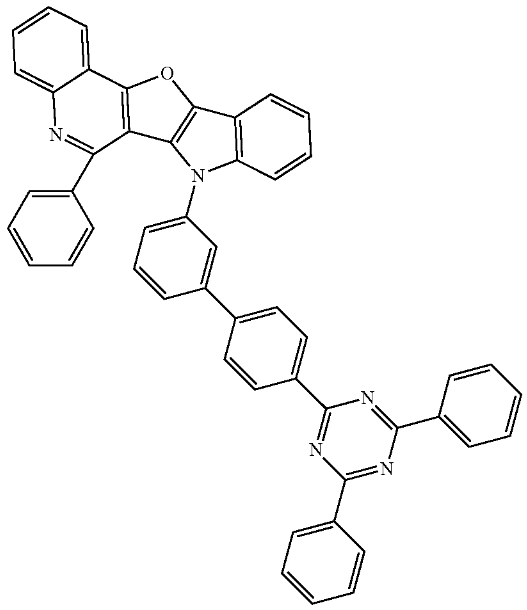
145
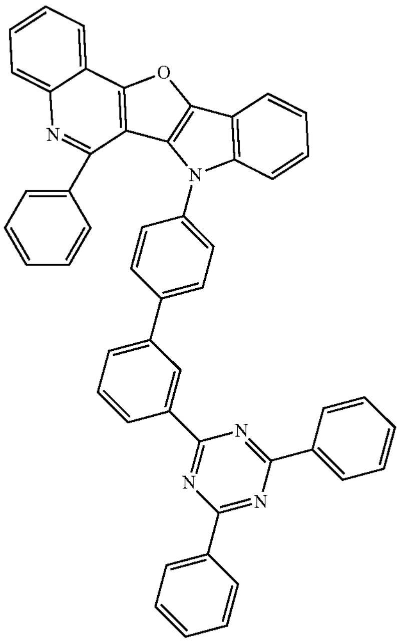

-continued
146
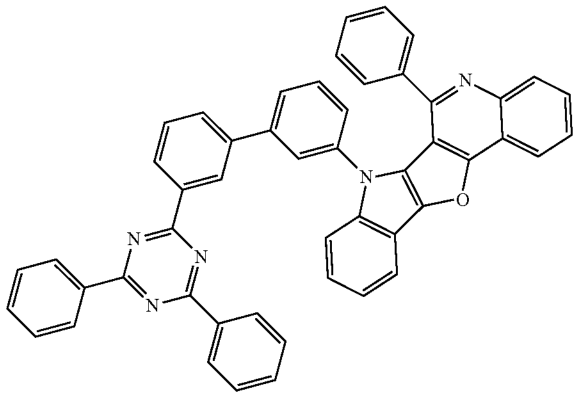
147
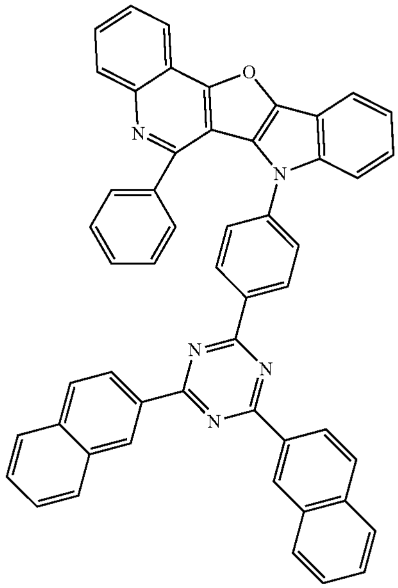
148
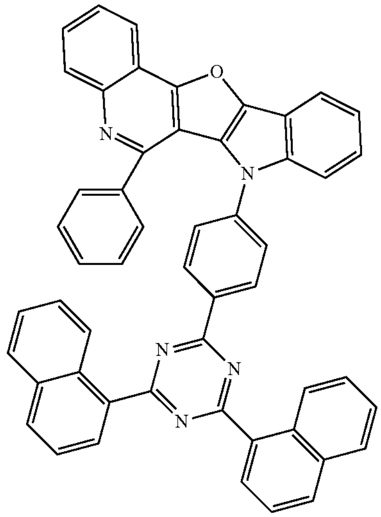
-continued
149
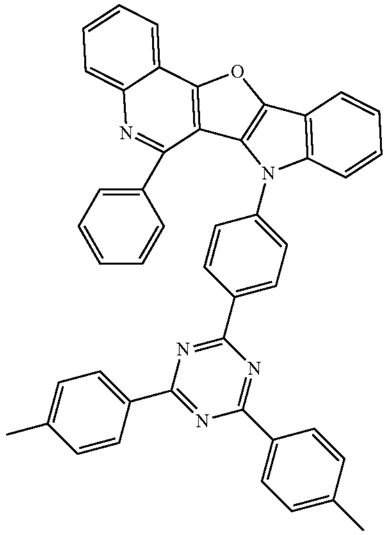
150
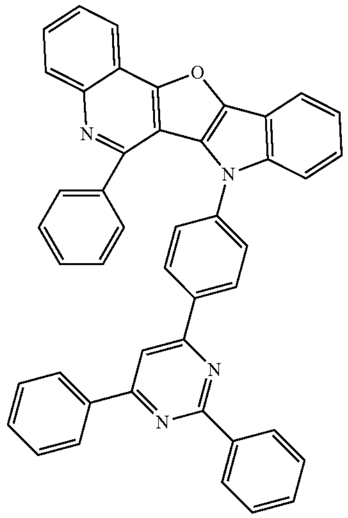
151
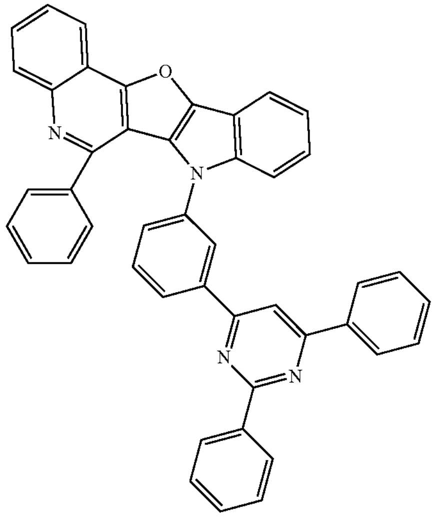

-continued
152
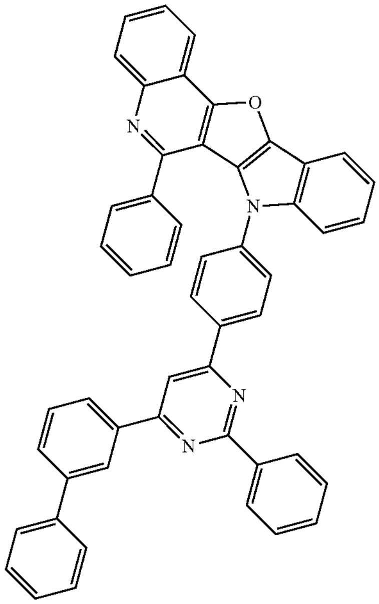
153
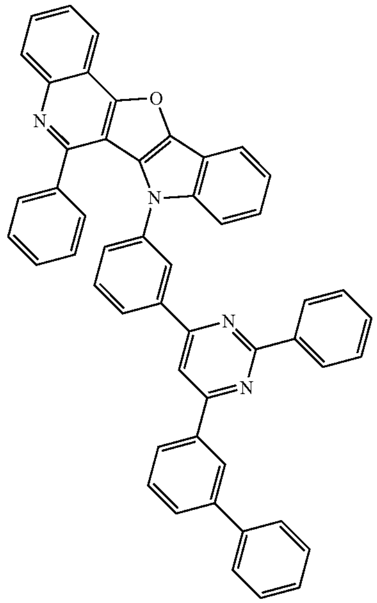
154
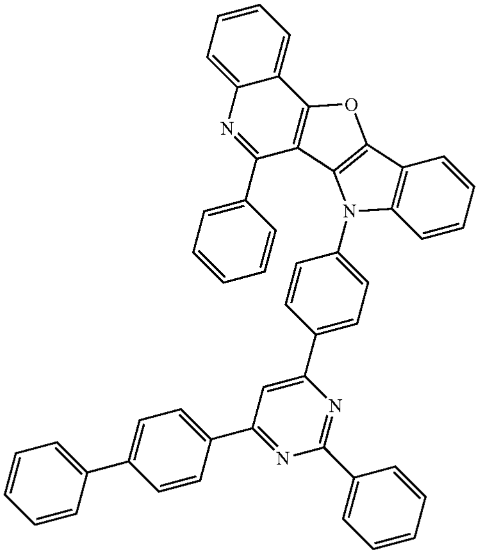
155
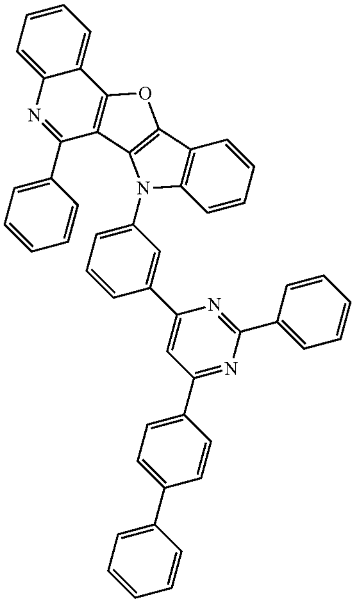

-continued
156
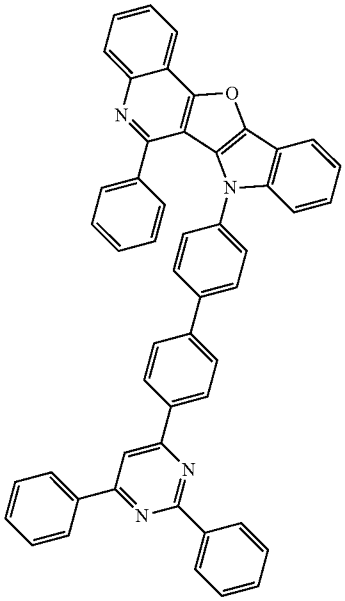
157
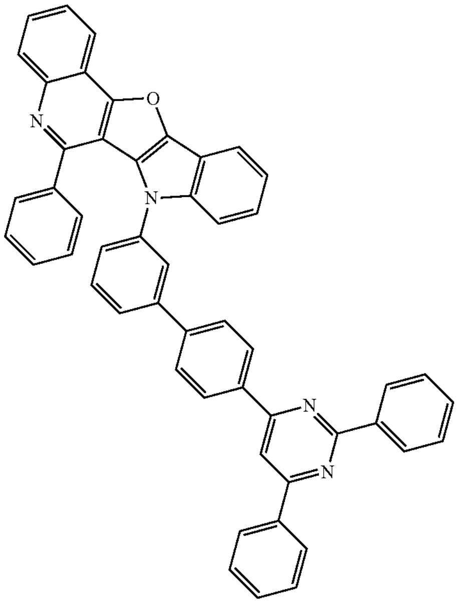
-continued
158
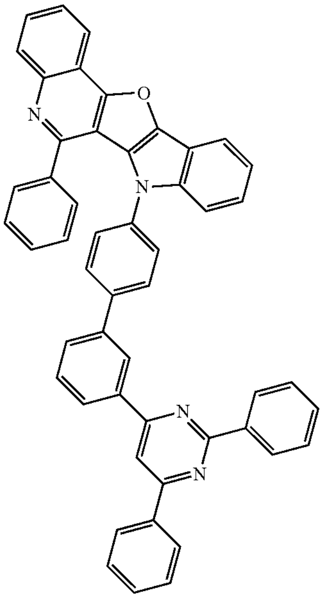
159
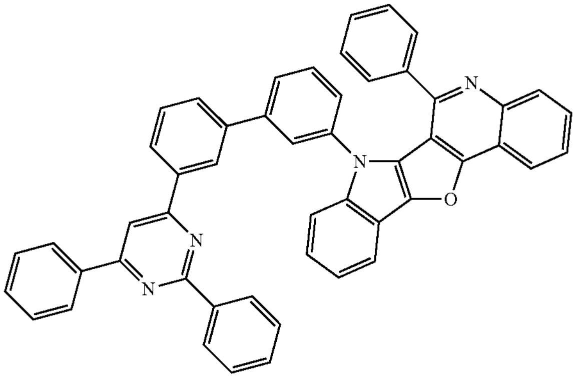
160
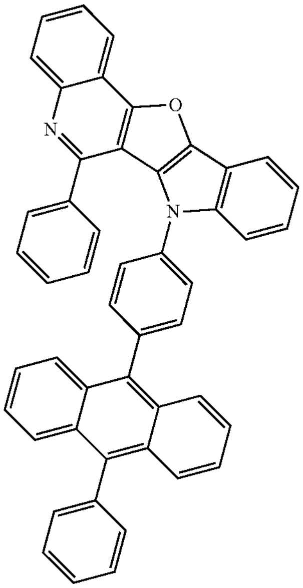

-continued
161
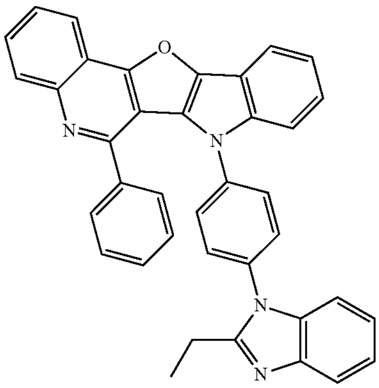
162
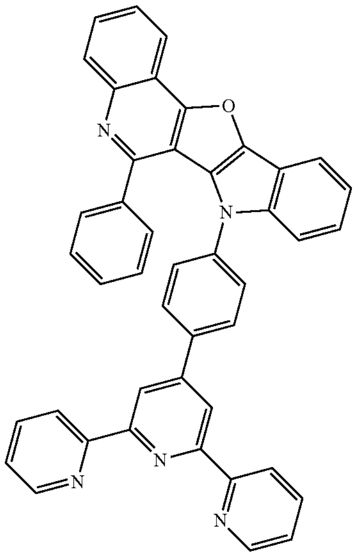
163
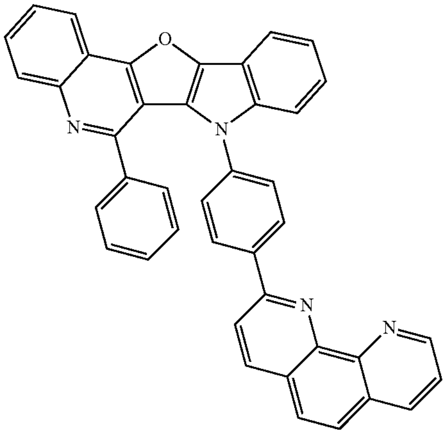
-continued
164
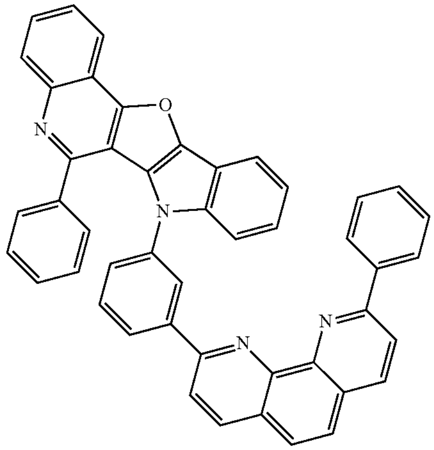
165
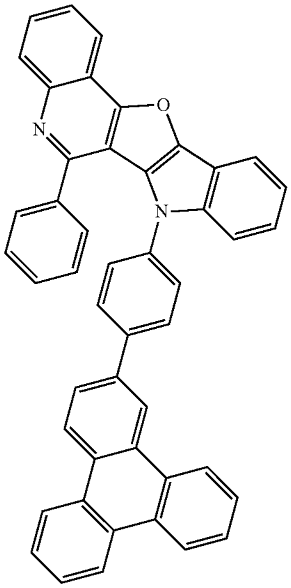
166
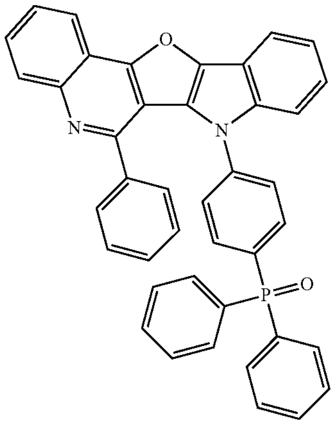

-continued
167
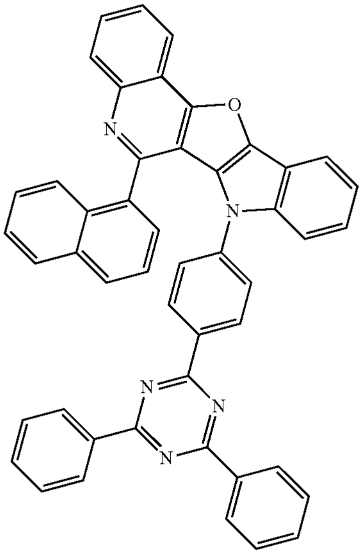
168
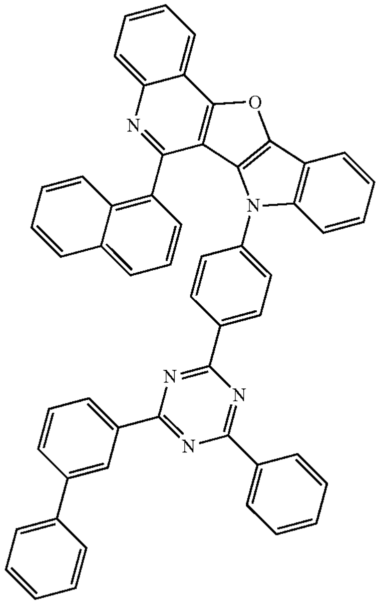
-continued
169
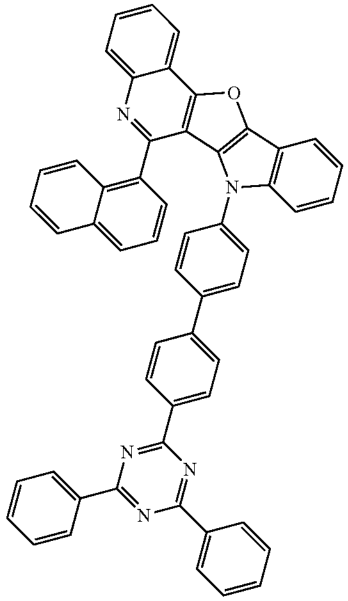
170
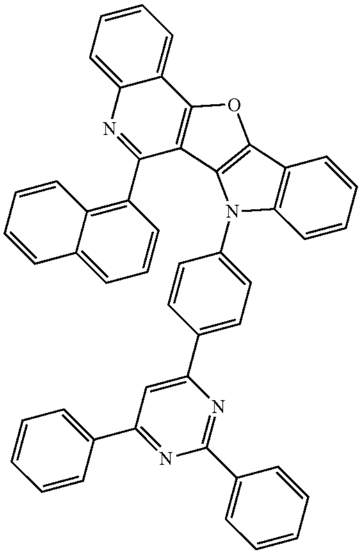

-continued
171
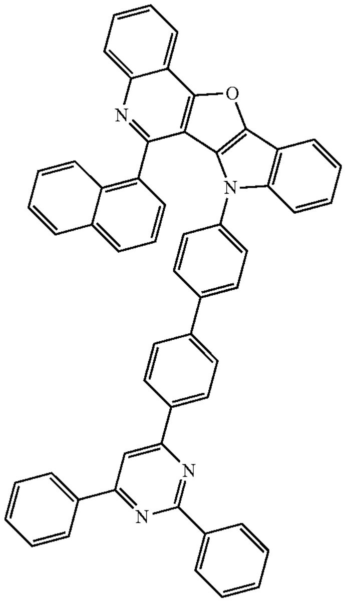
172
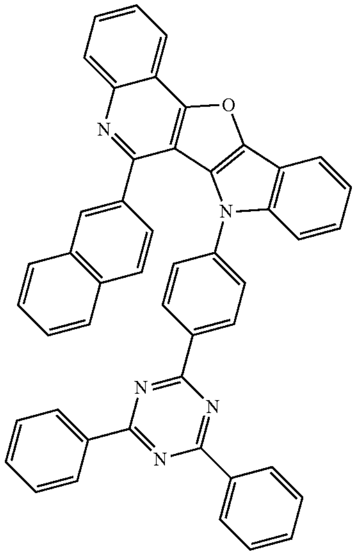
-continued
173
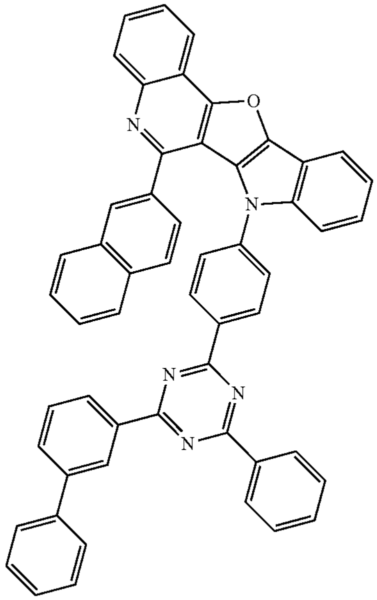
174
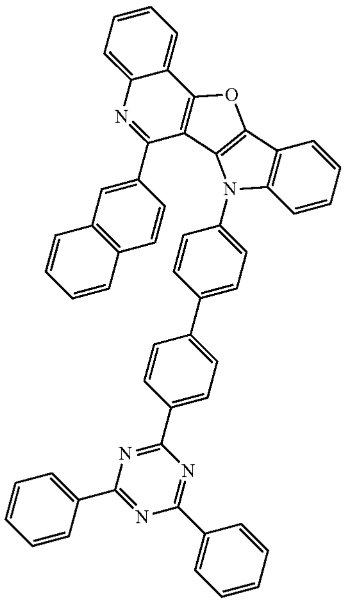

-continued
175
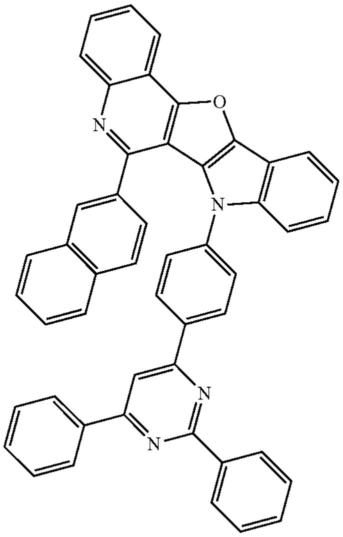
176
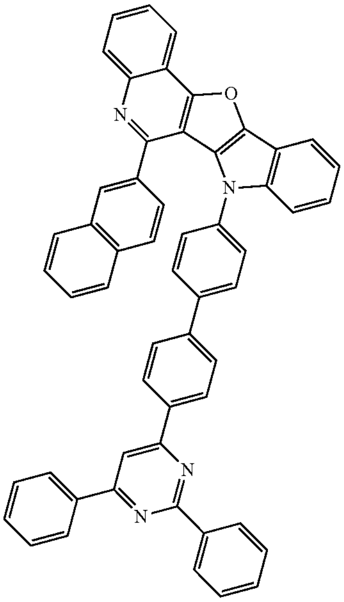
-continued
177
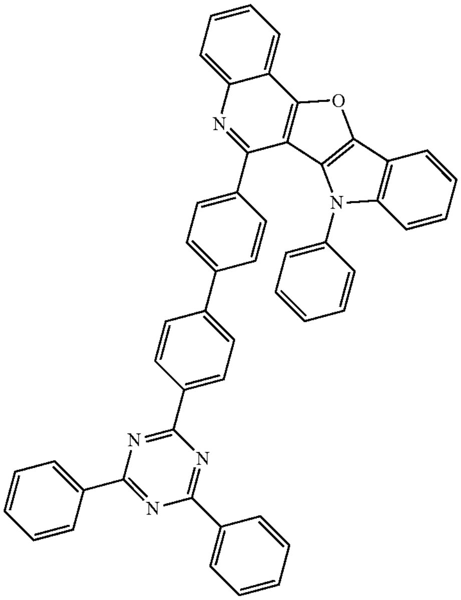
178
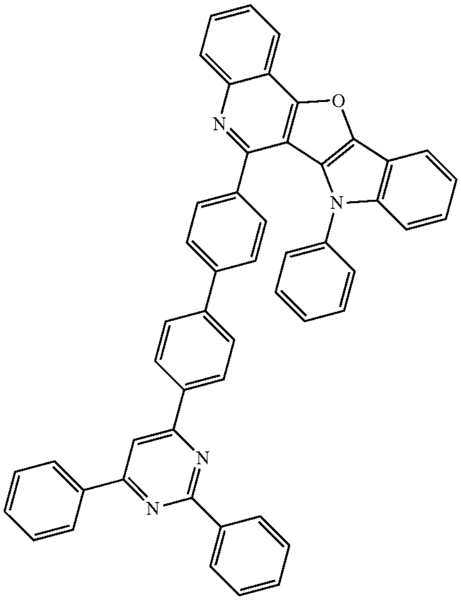

-continued
179
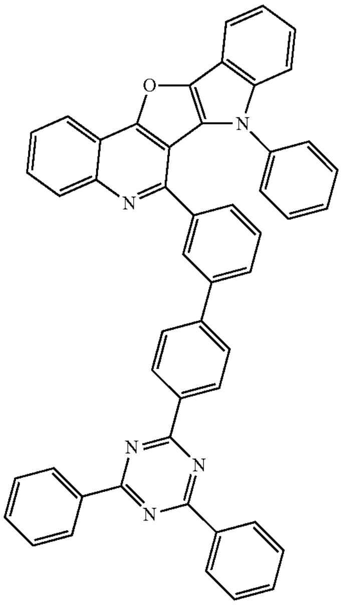
180
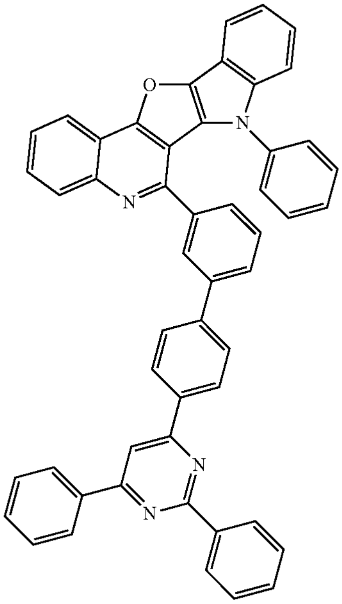
-continued
181
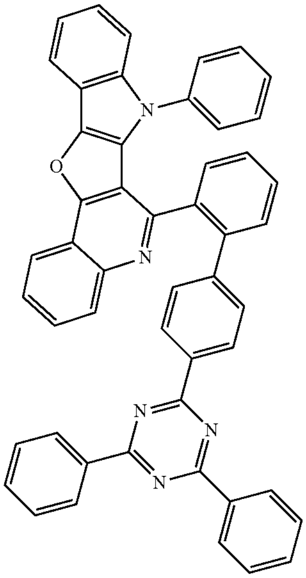
182
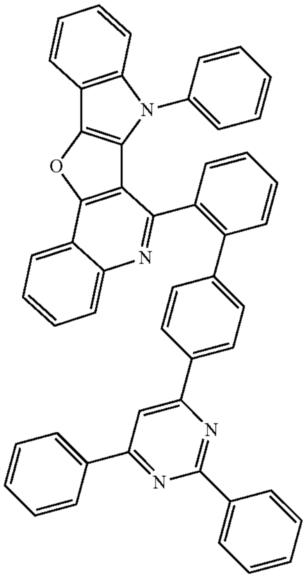

183
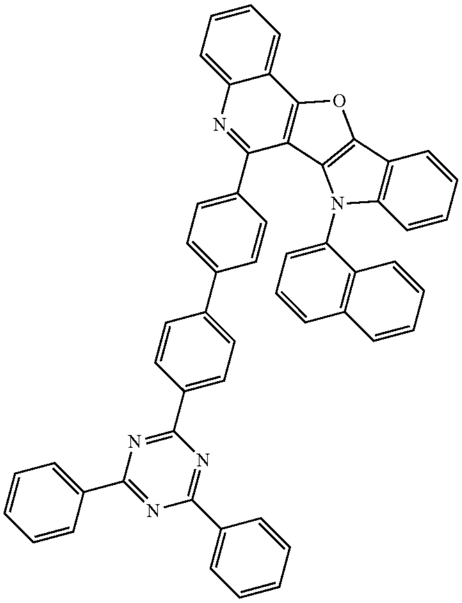
184
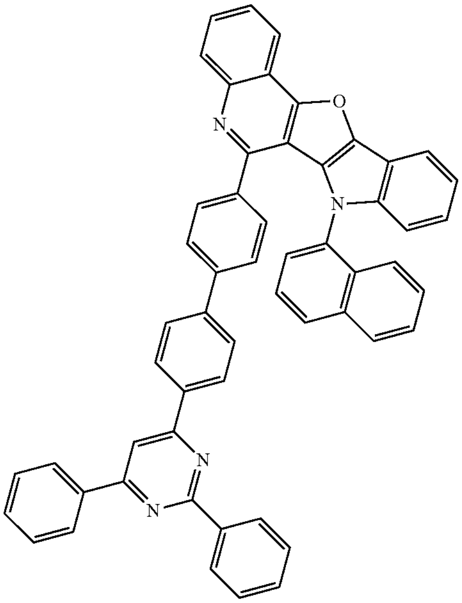
185
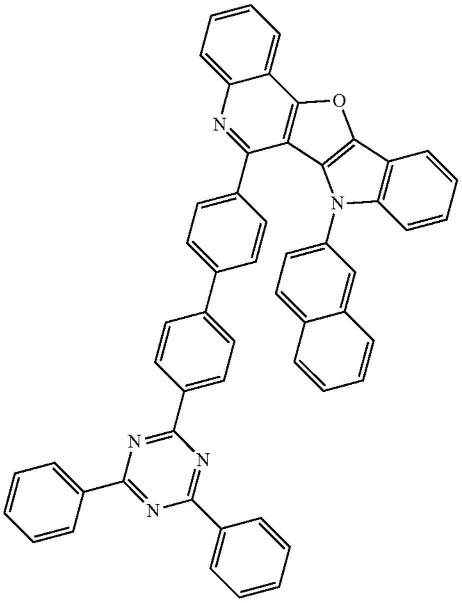
186
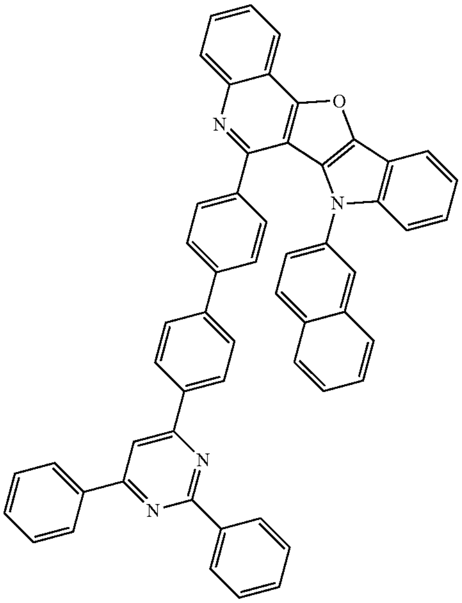

-continued
187
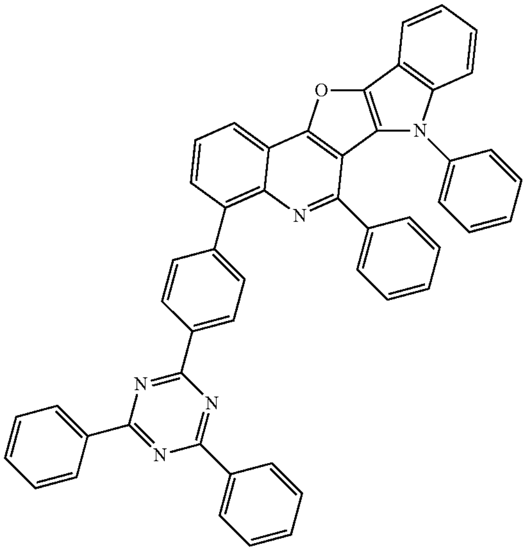
188
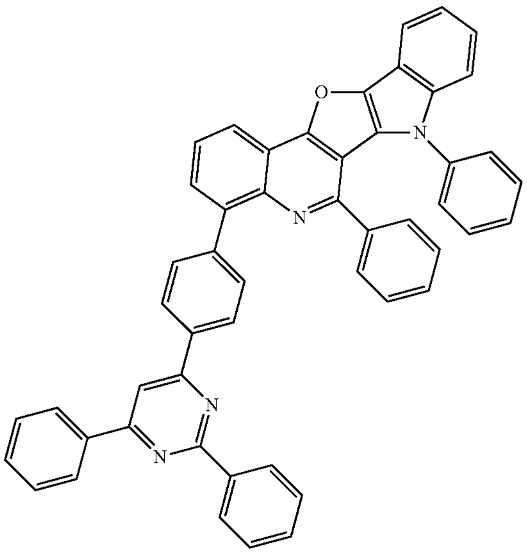
-continued
189
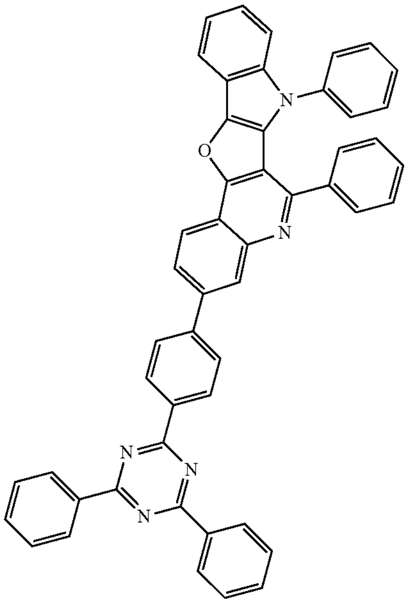
190
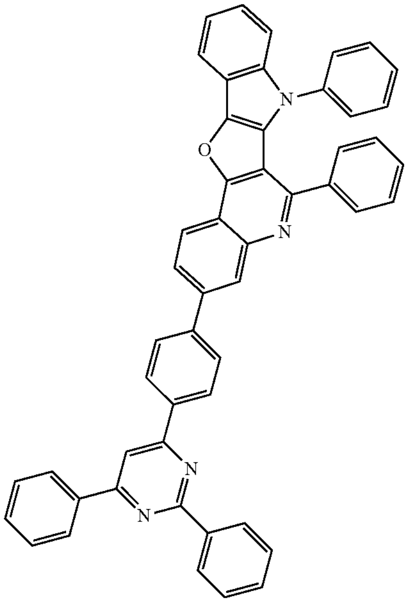
191
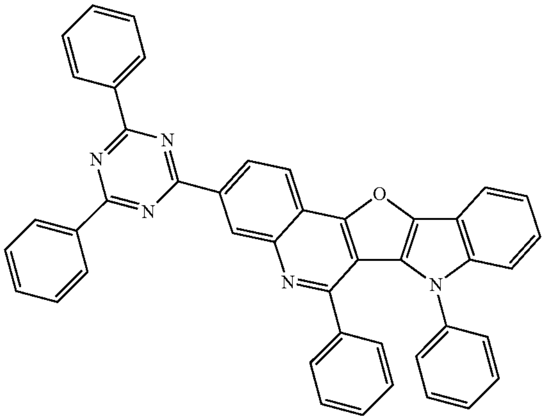

-continued
192
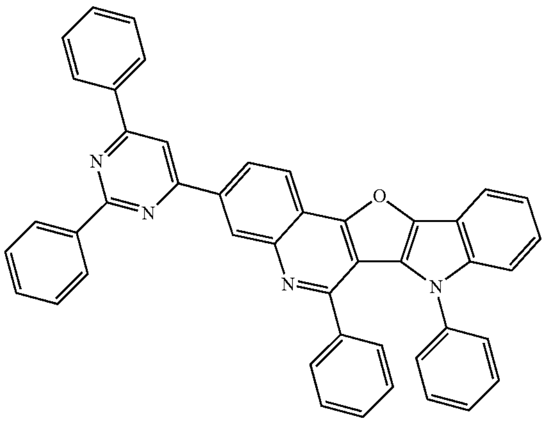
193
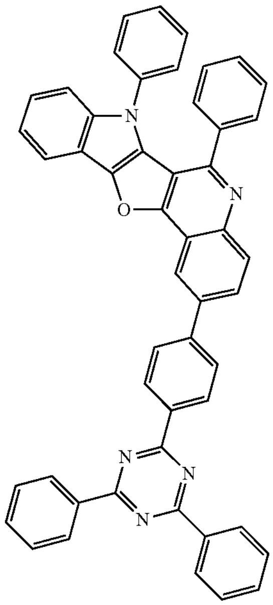
194
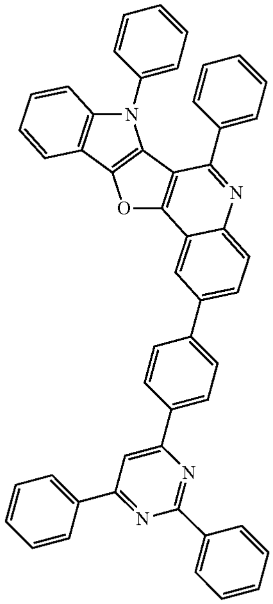
-continued
195
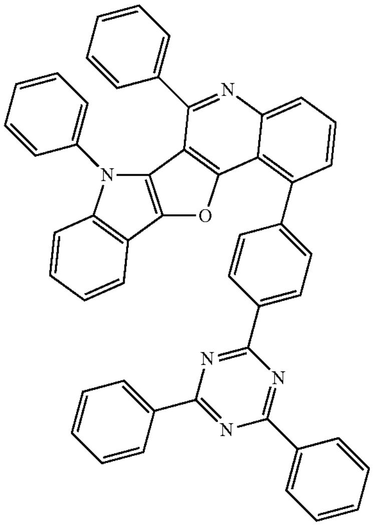
196
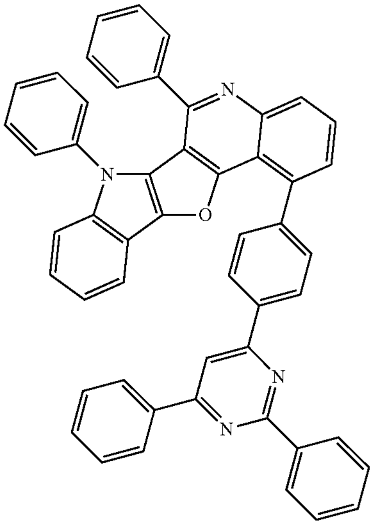
197
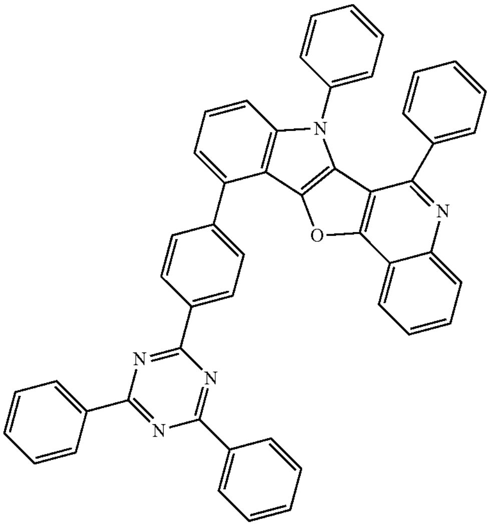

198
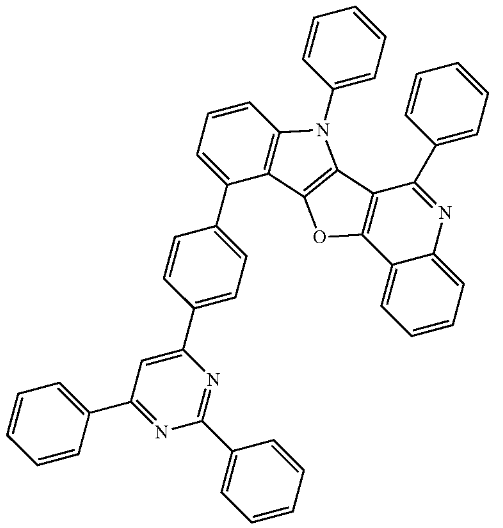
199
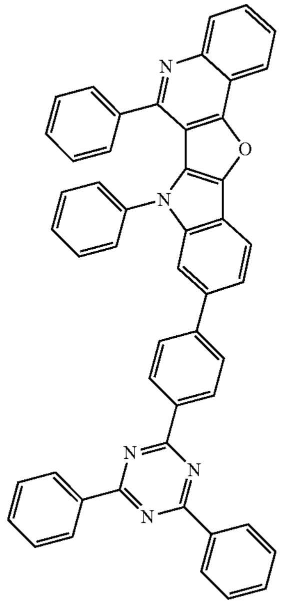
200
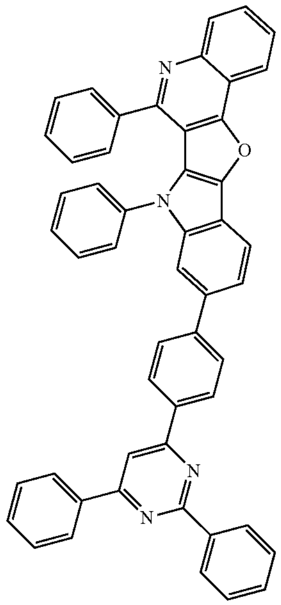
201
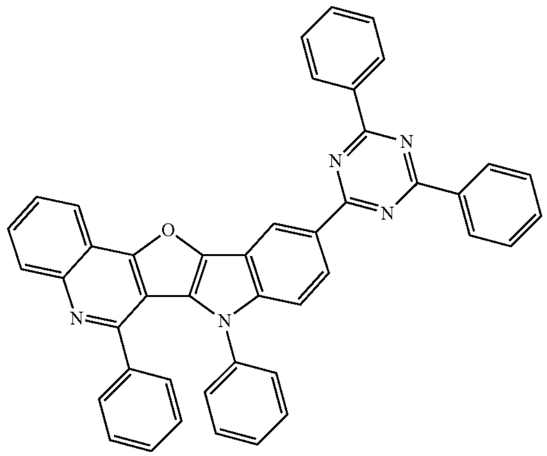
202
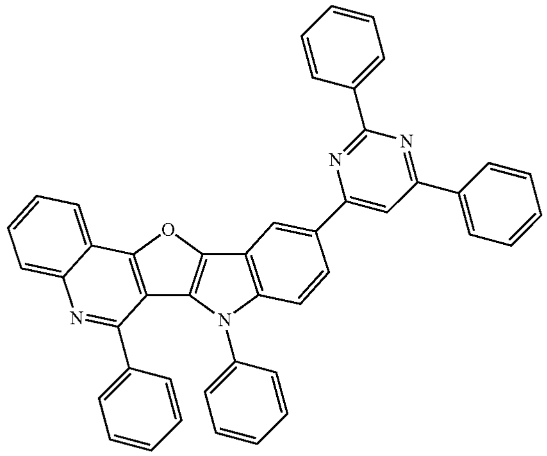

-continued
203
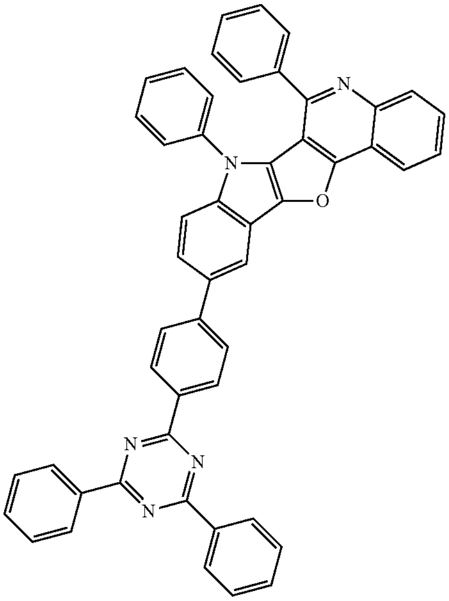
204
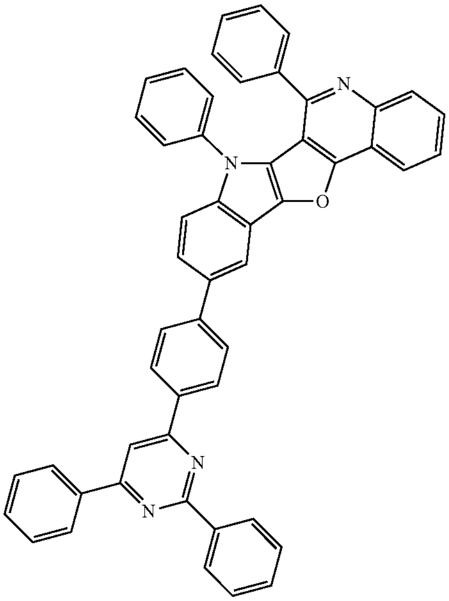
-continued
205
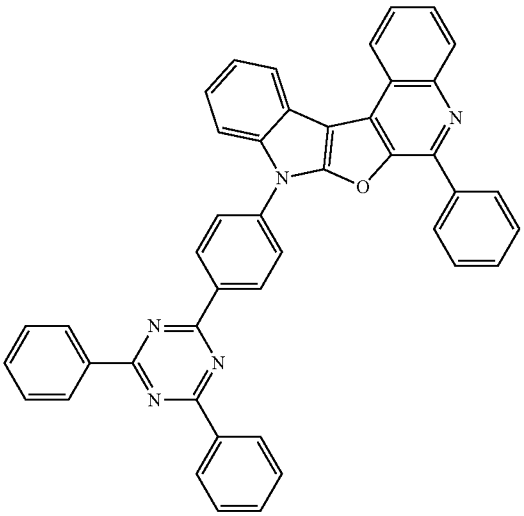
206
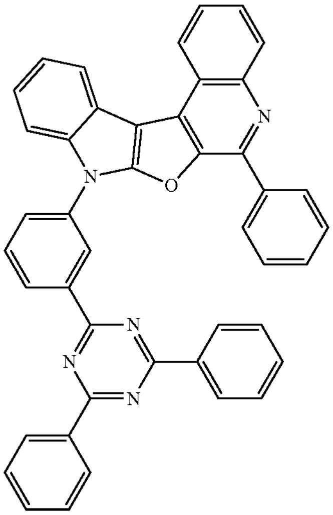
207
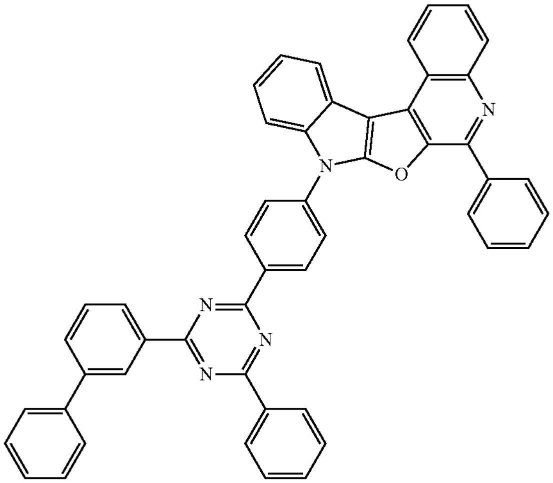

208
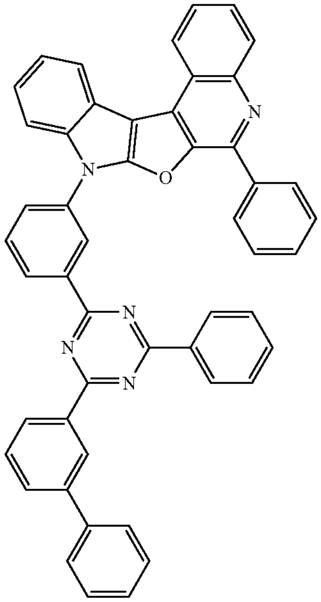
209
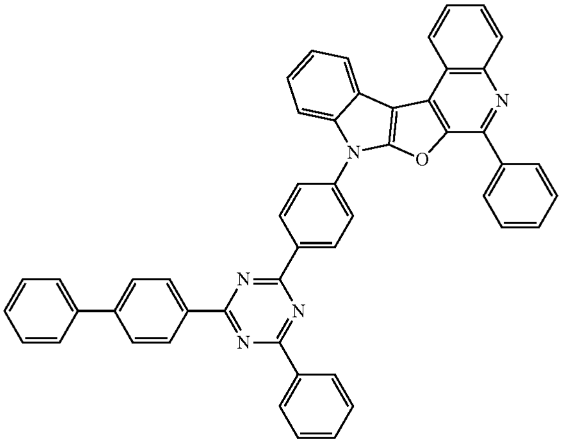
210
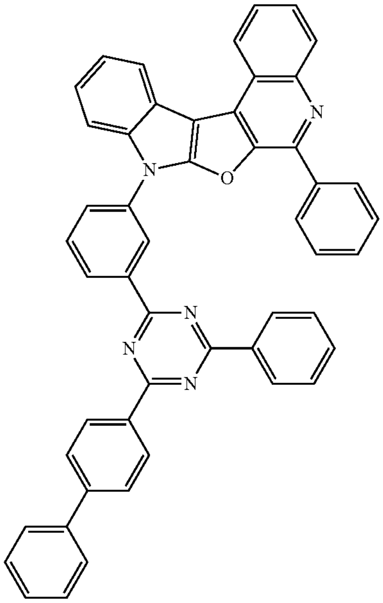
211
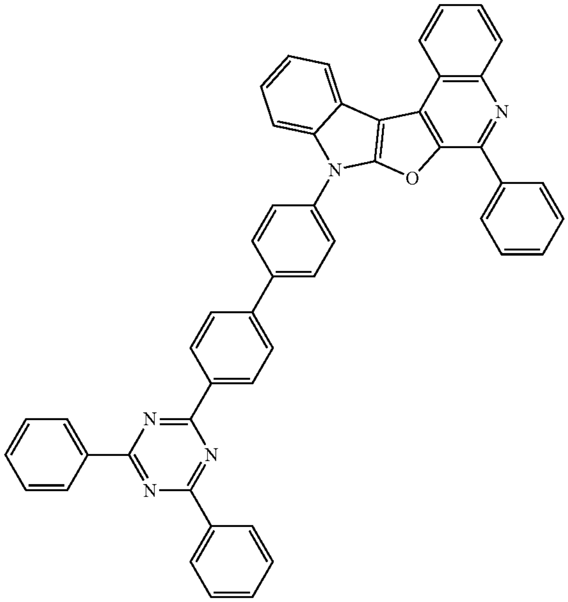
212
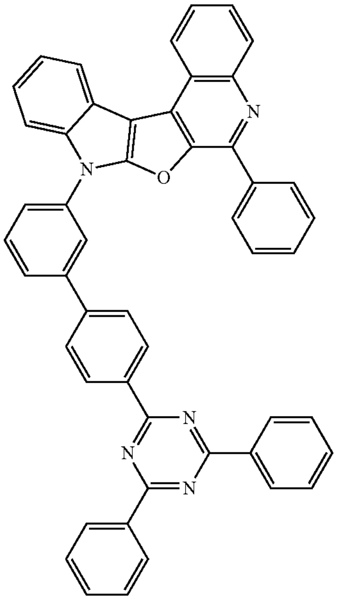

-continued
213
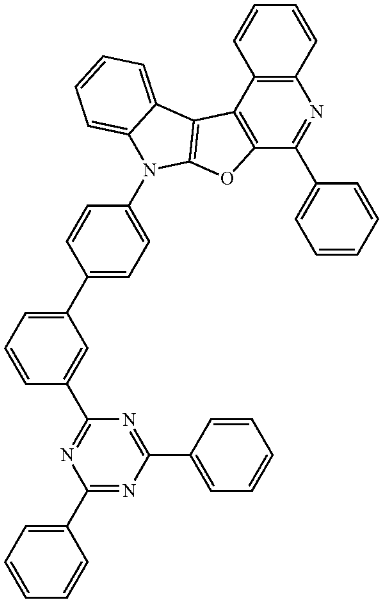
214
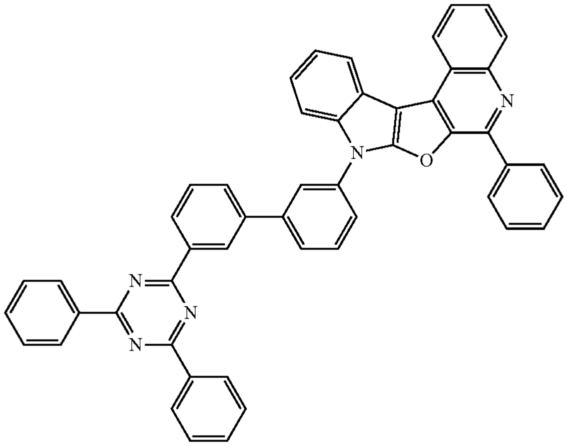
215
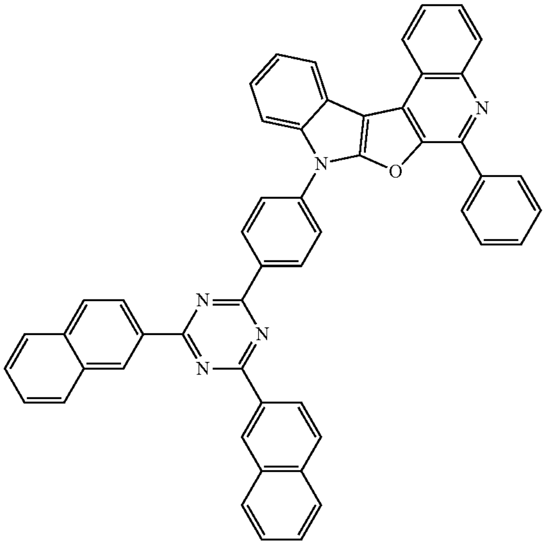
-continued
216
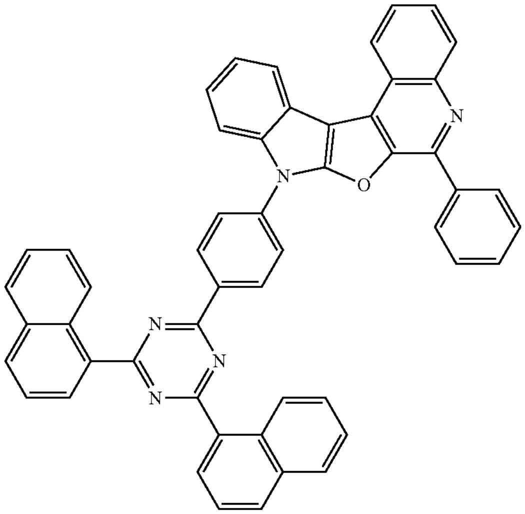
217
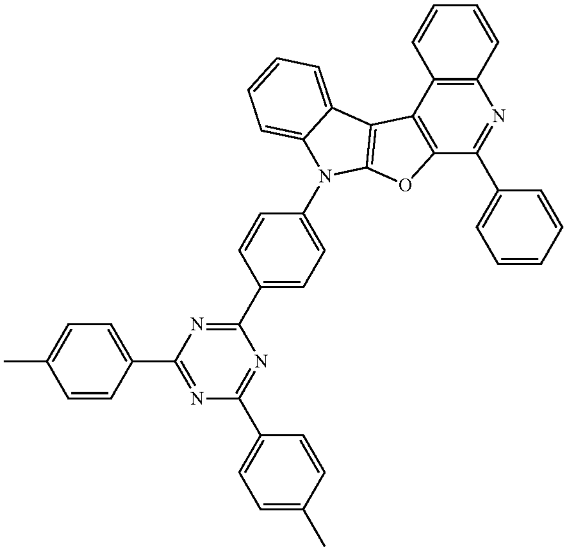
218
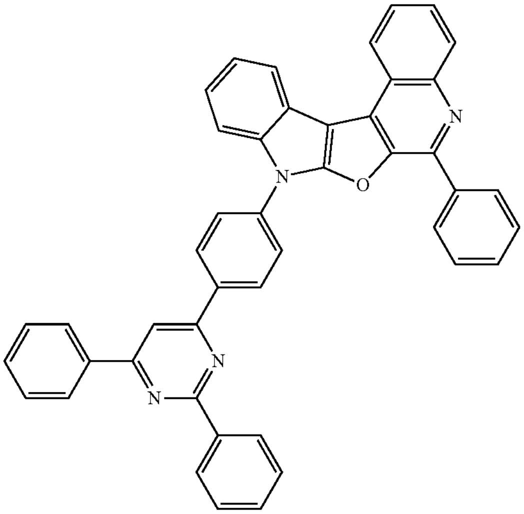

-continued
219
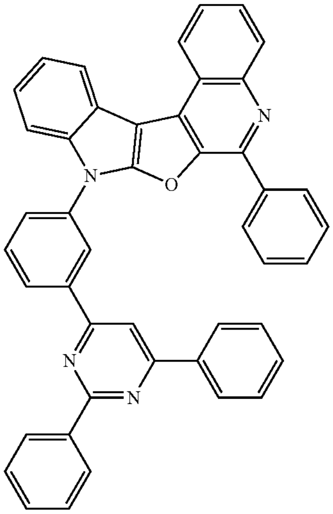
220
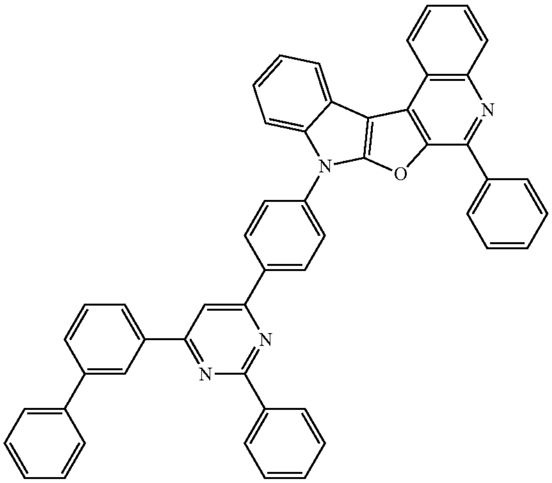
221
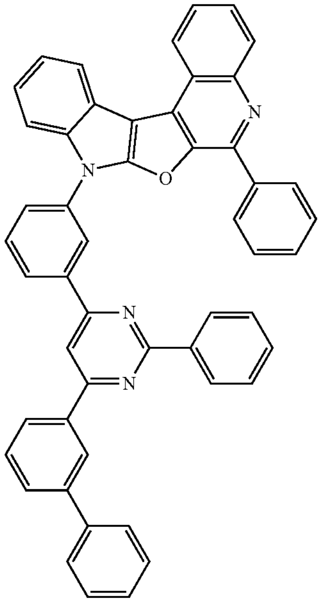
-continued
222
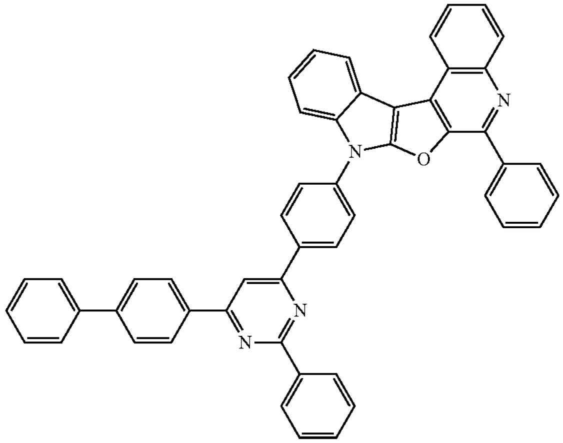
223
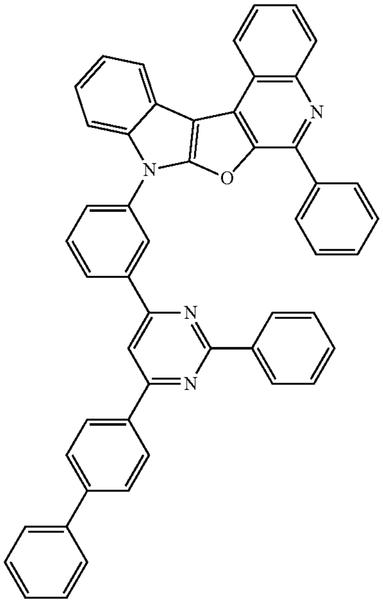

-continued
224
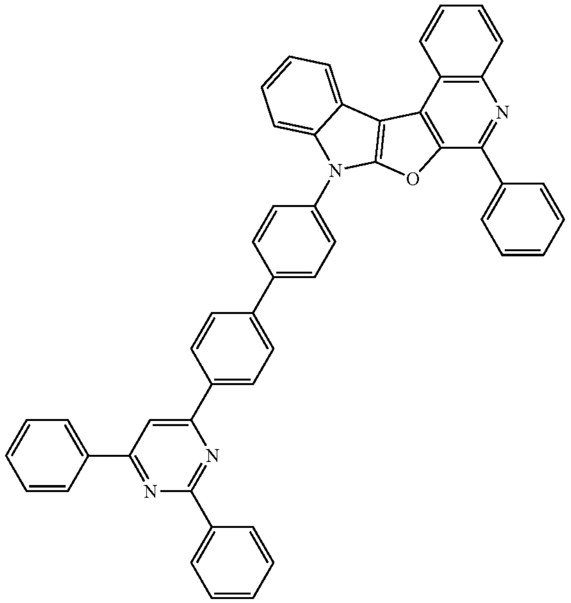
-continued
226
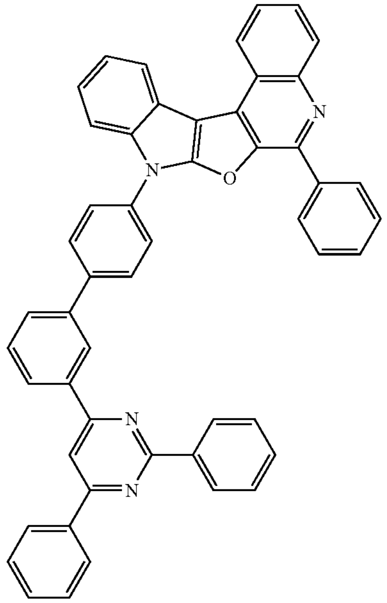
225
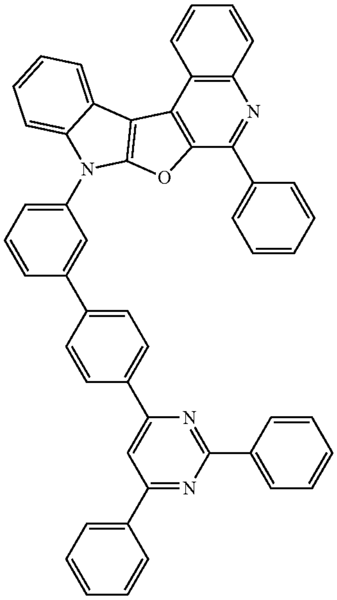
227
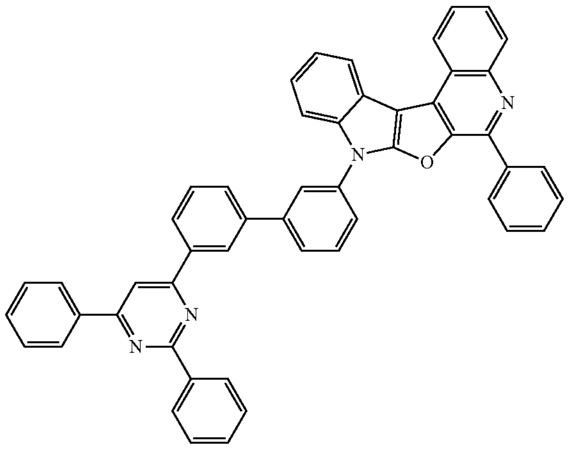

-continued
228
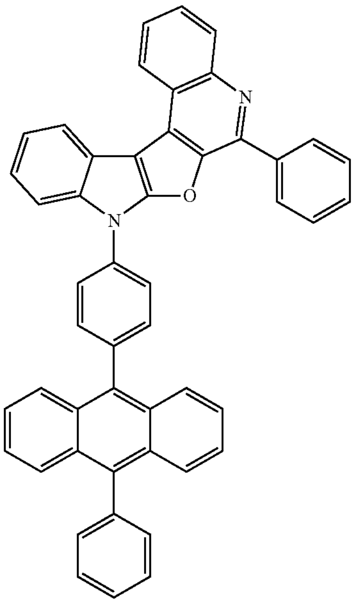
229
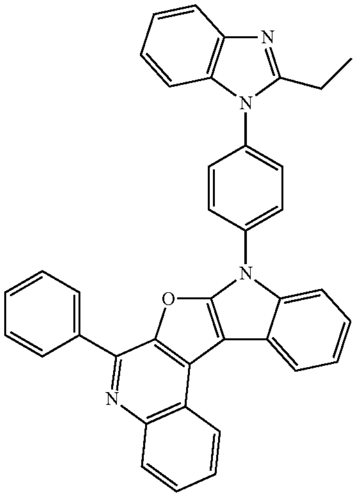
230
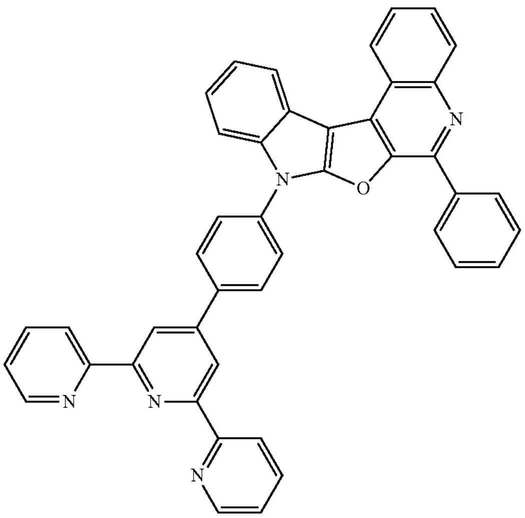
-continued
231
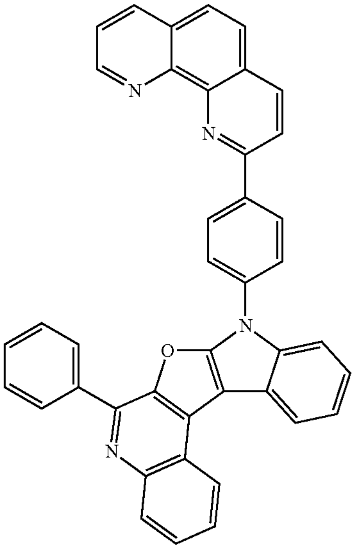
232
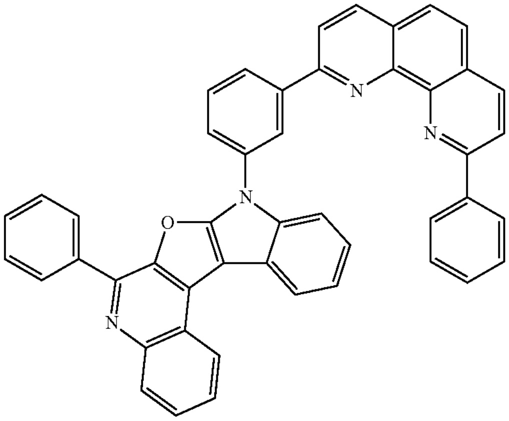
233
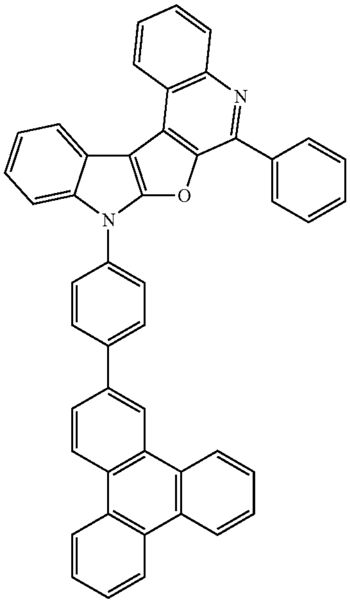

-continued
234
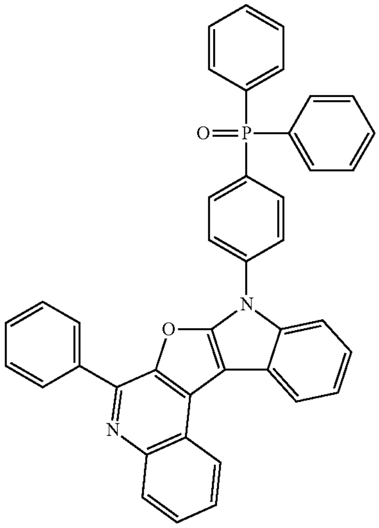
235
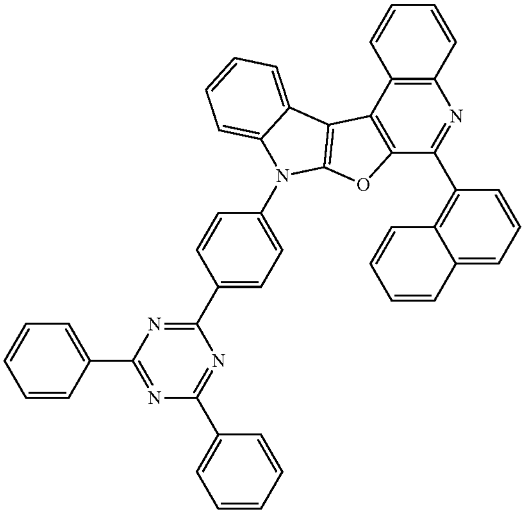
236
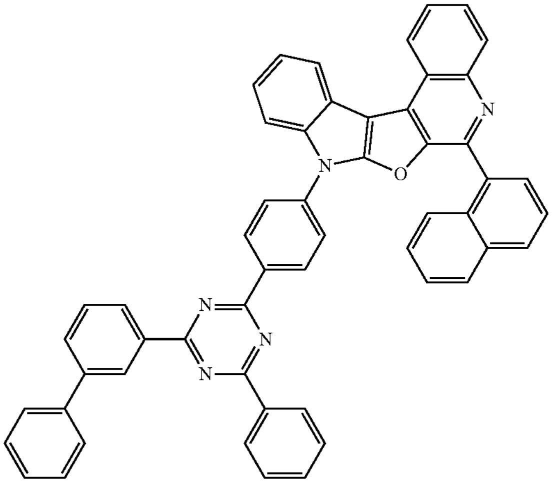
-continued
237
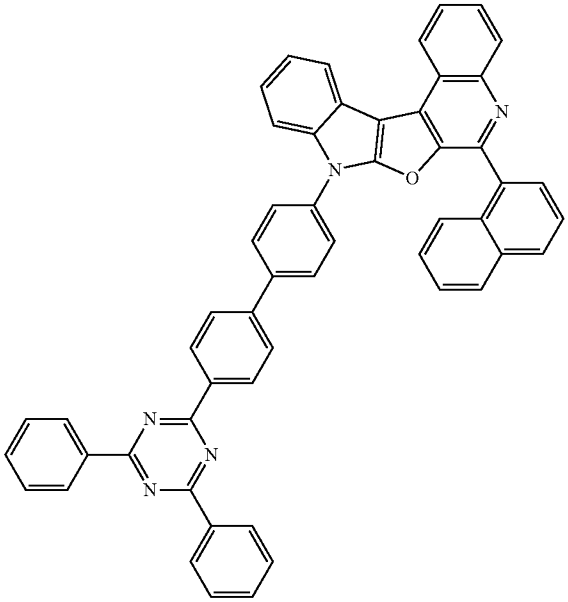
238
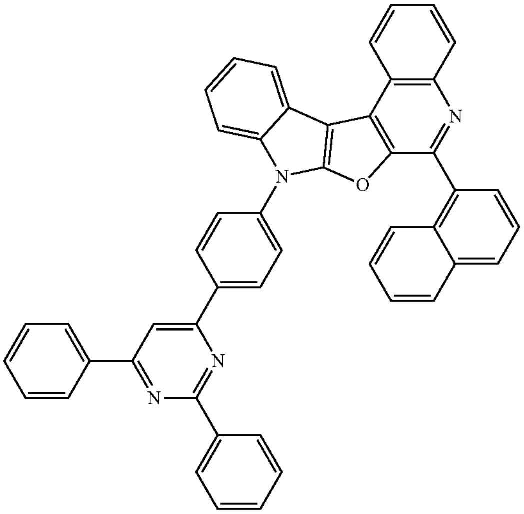

239
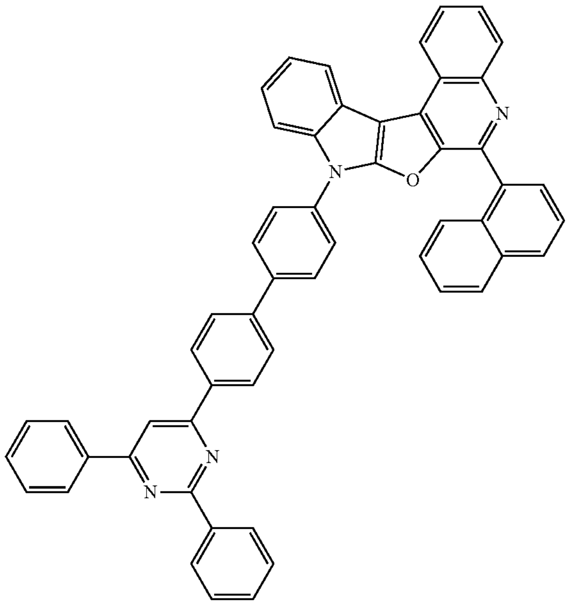
240
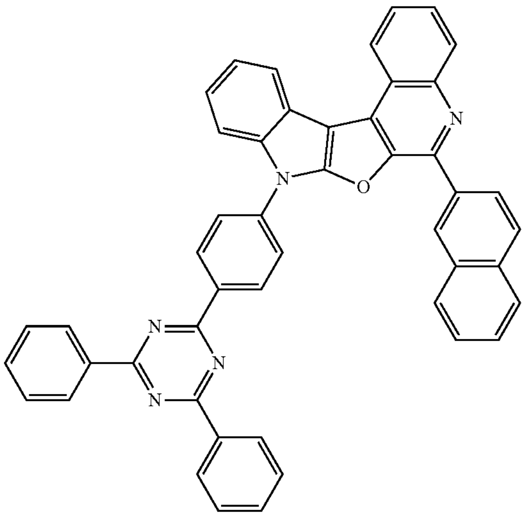
241
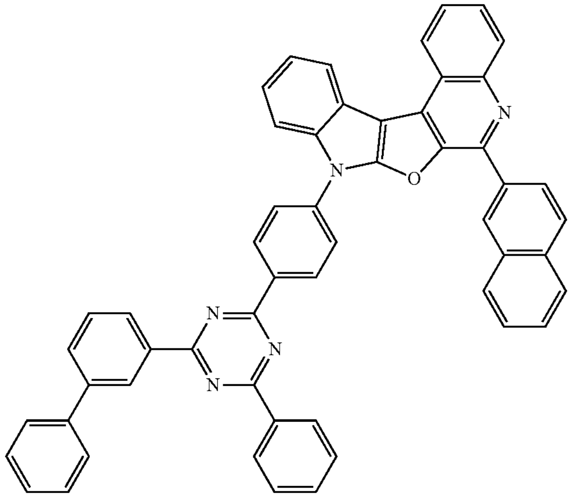
242
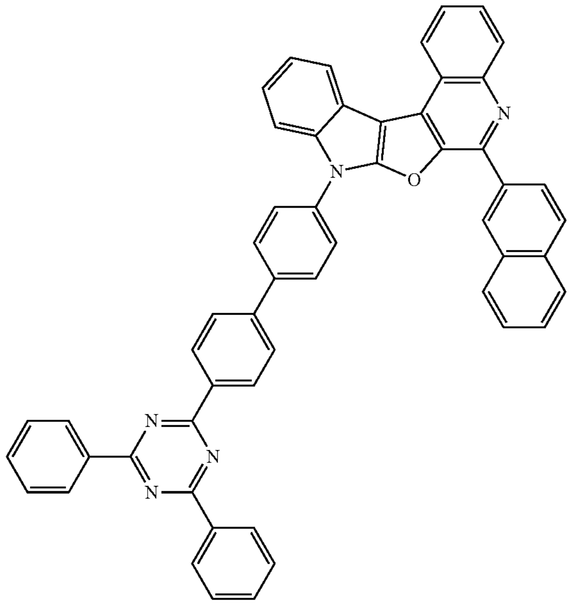

-continued
243
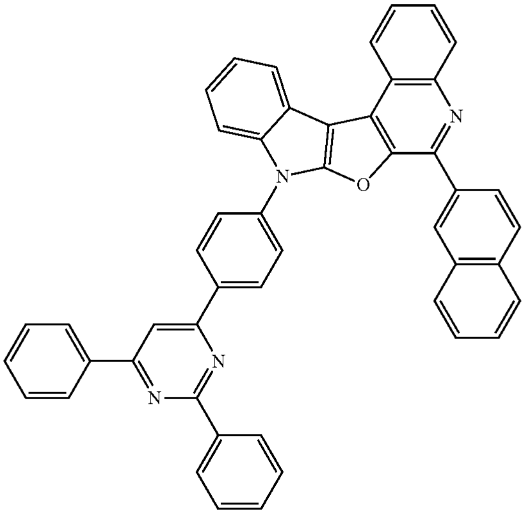
244
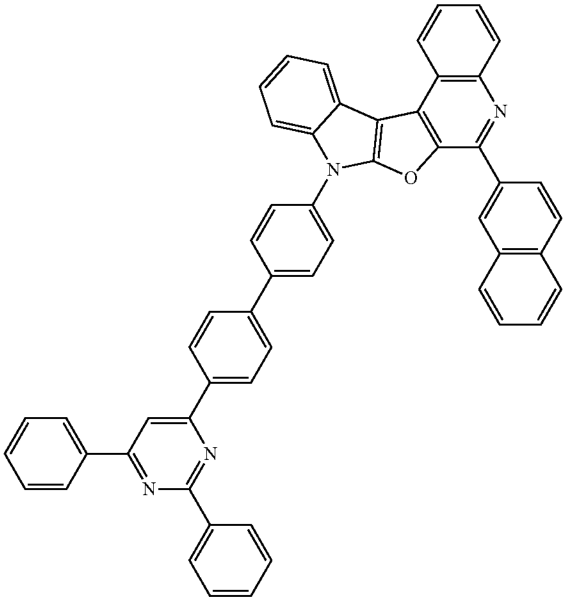
245
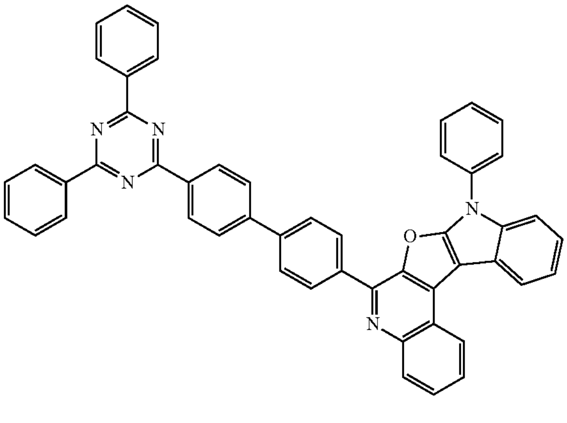
-continued
246
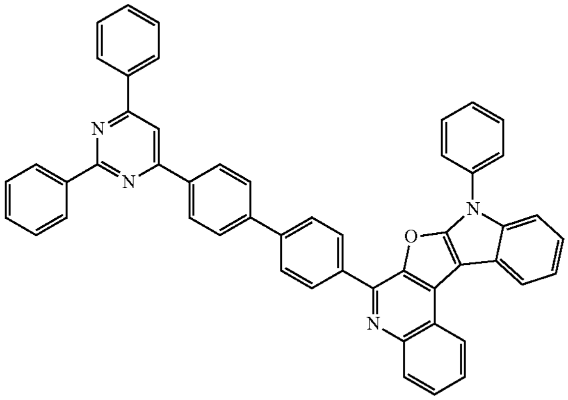
247
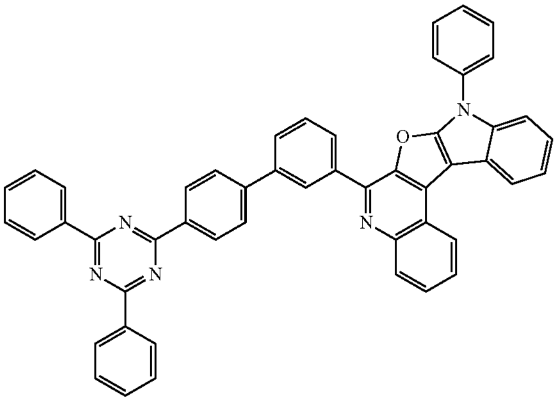
248
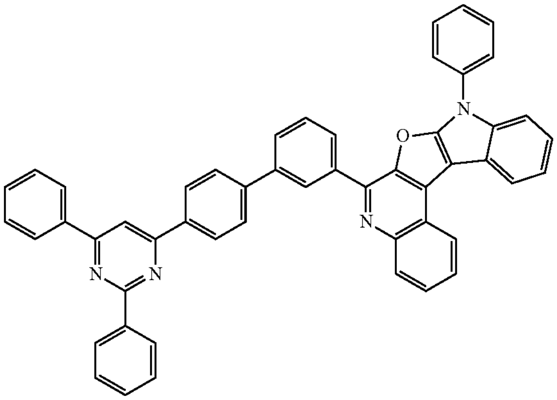

-continued
249
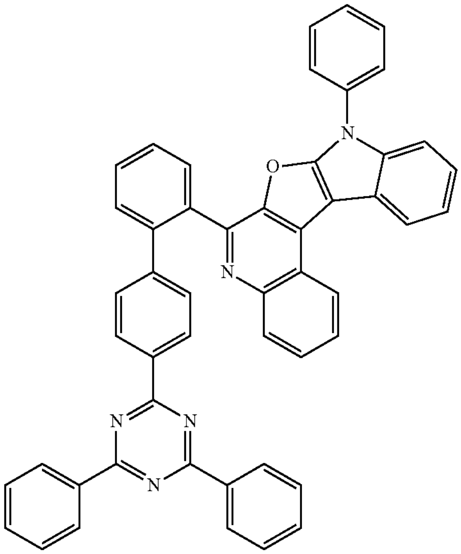
250
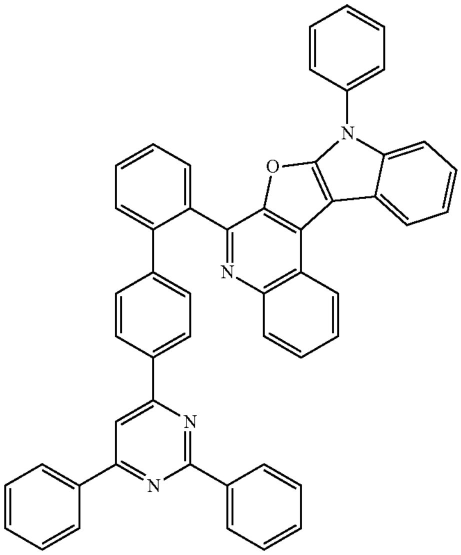
251
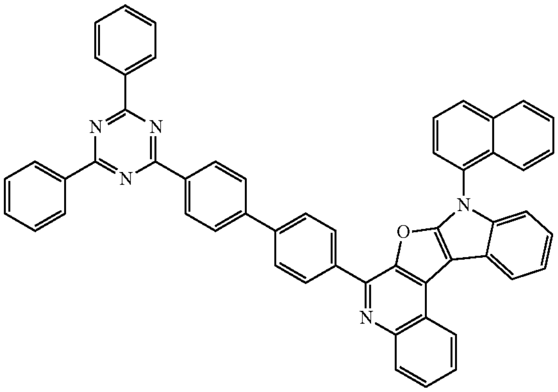
-continued
252
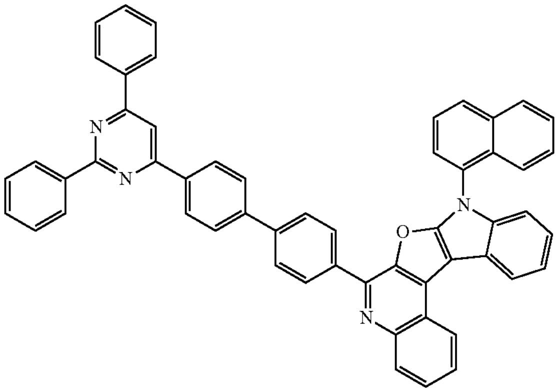
253
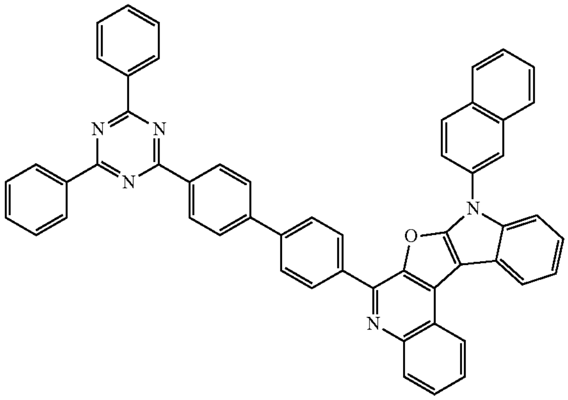
254
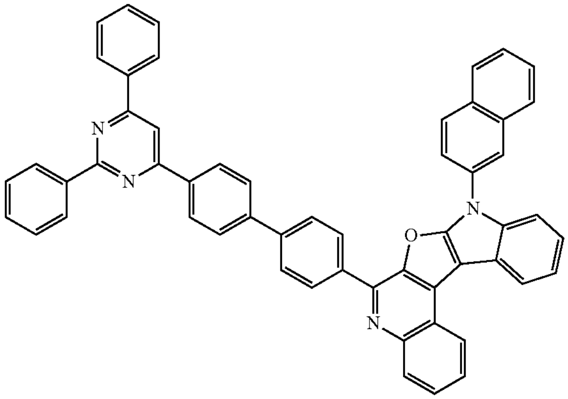

-continued
255
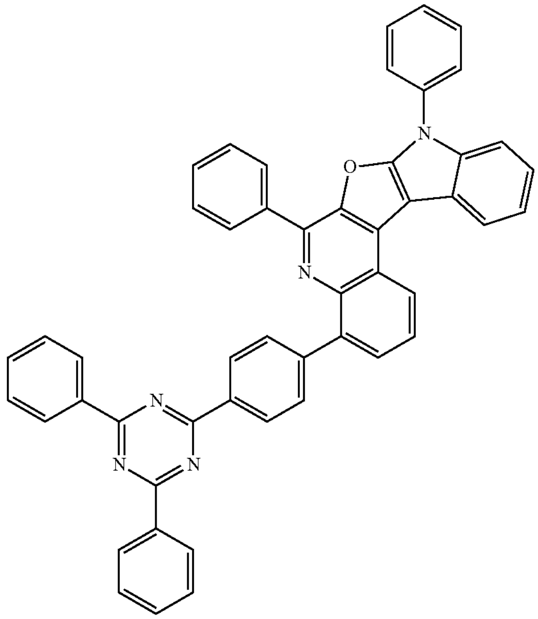
256
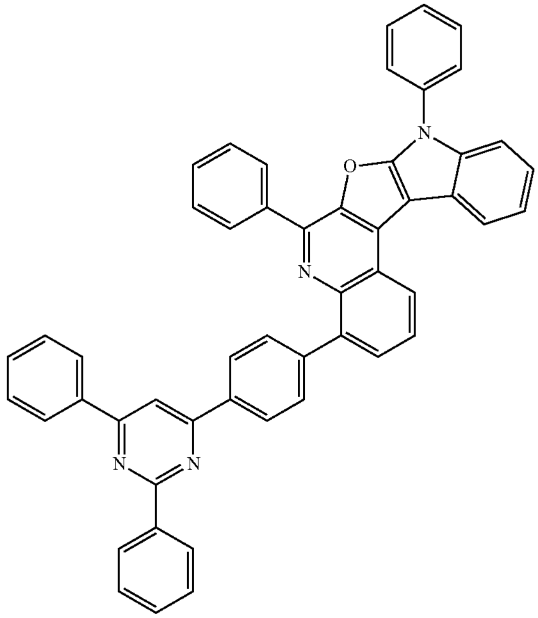
-continued
257
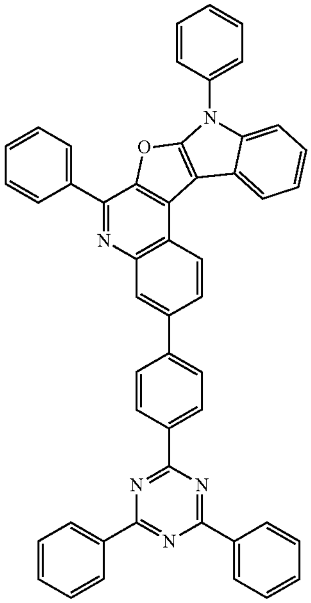
258
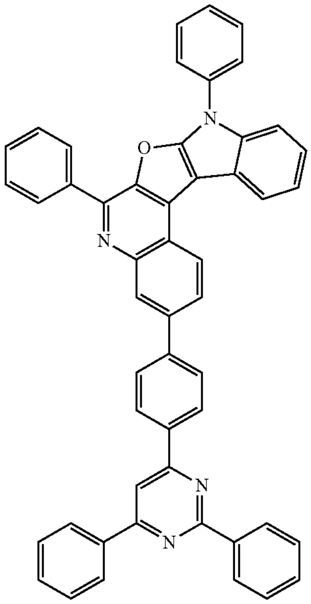

-continued
259
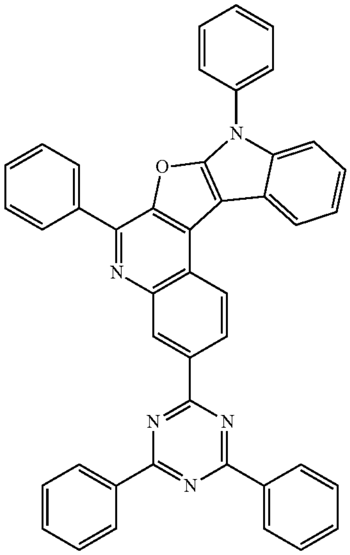
260
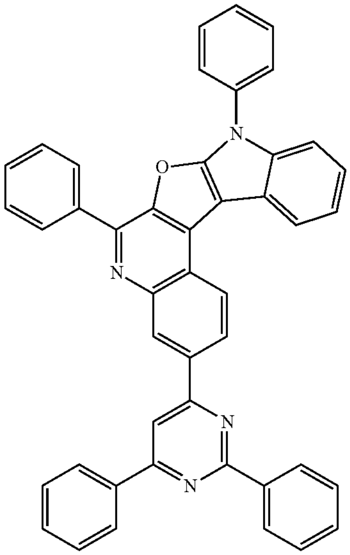
-continued
261
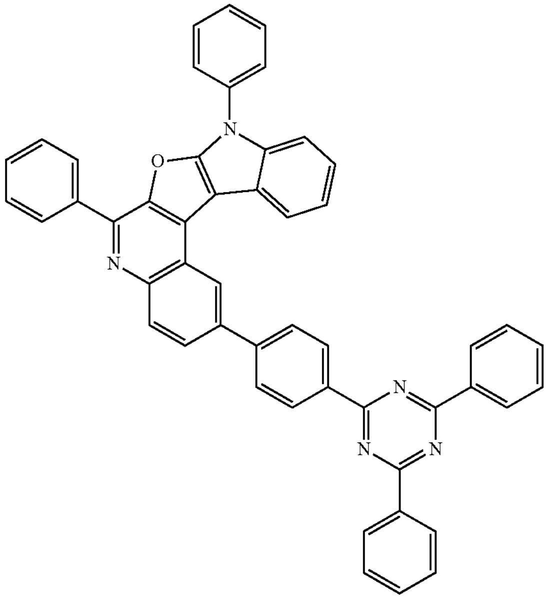
262
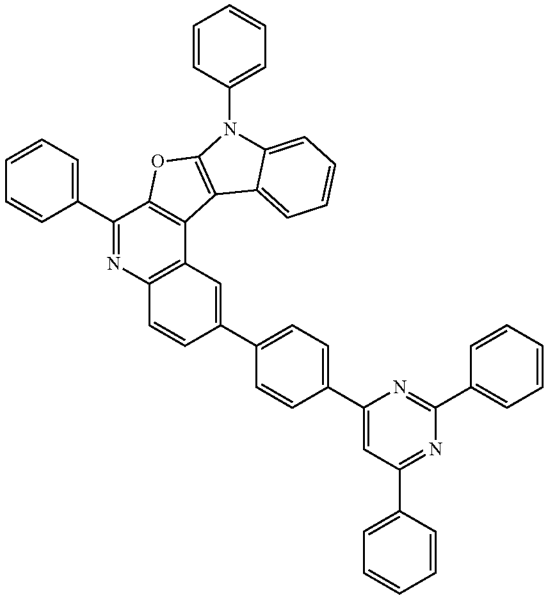

-continued
263
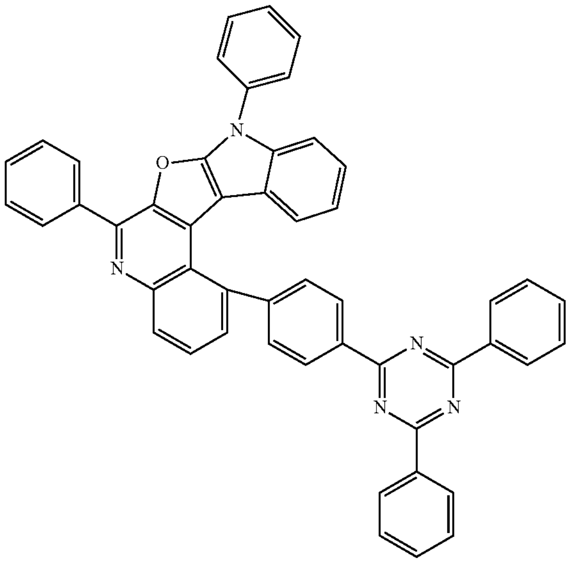
264
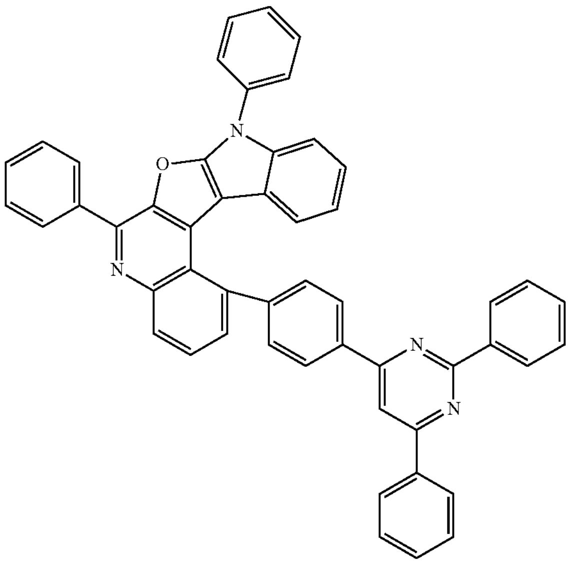
-continued
265
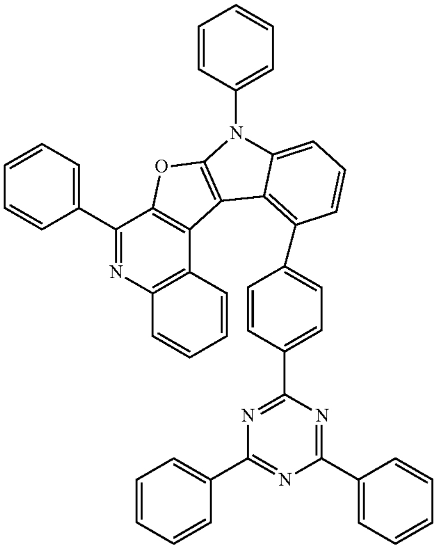
266
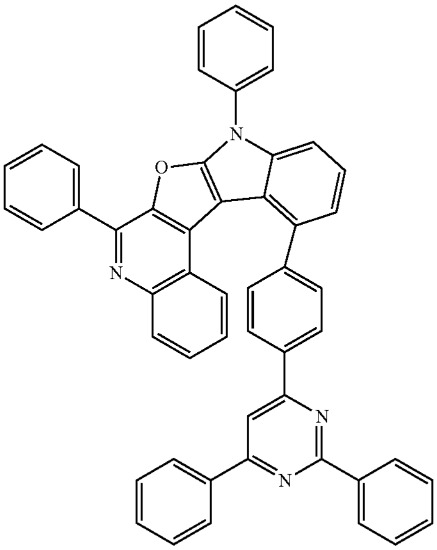
267
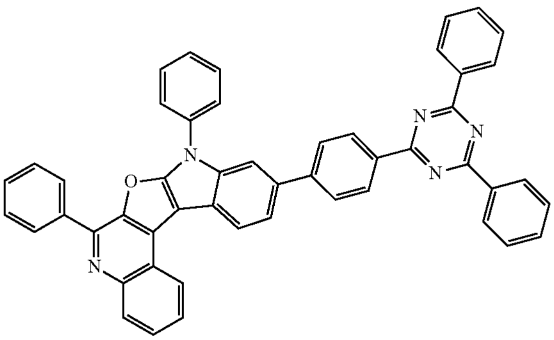

-continued

268

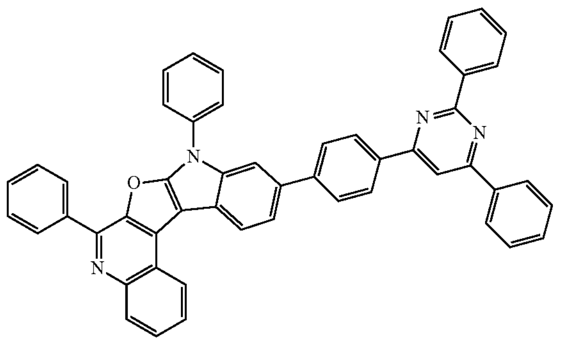

269

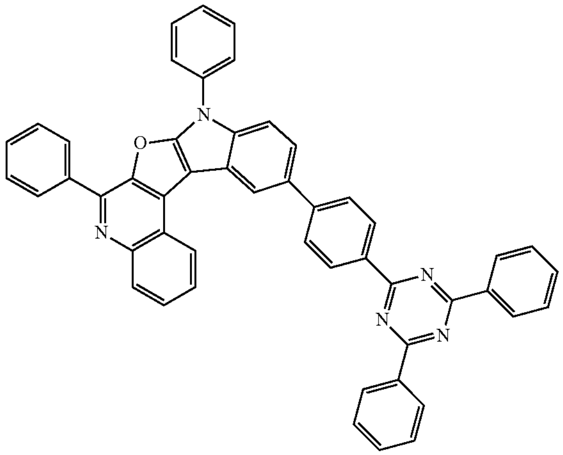

270

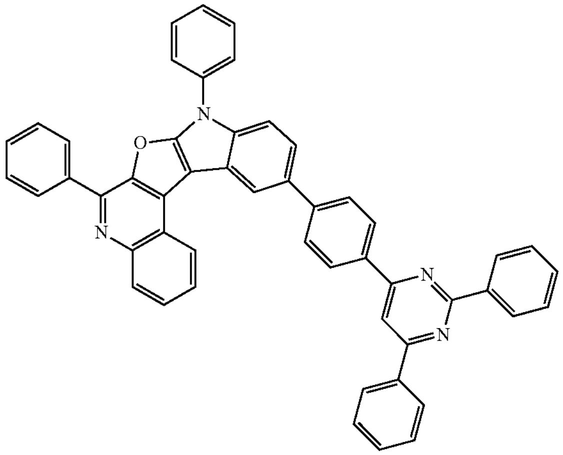

-continued

271

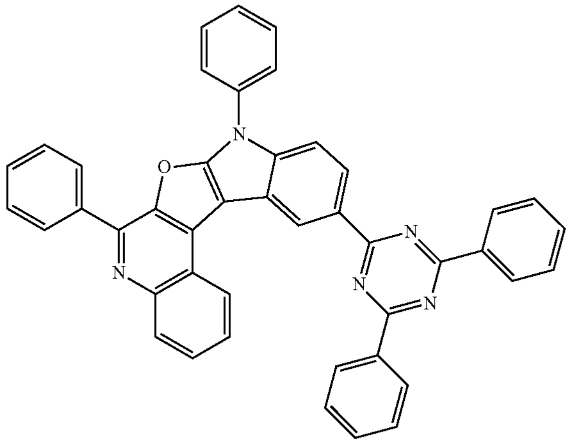

272

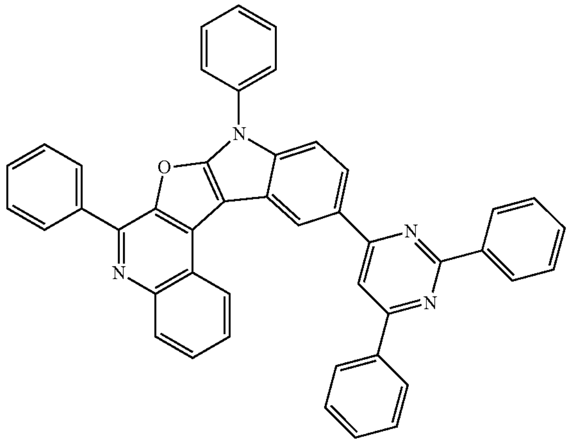

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In one embodiment of the present application, the organic material layer comprises a hole injection layer, and the hole injection layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 4 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

The organic material layer comprising Chemical Formula 1 may further comprise other materials as necessary.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application comprises an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer, the second hole blocking layer and the like described in FIG. 4 may not be included in some cases.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

[Preparation Example 1] Preparation of Intermediate A1

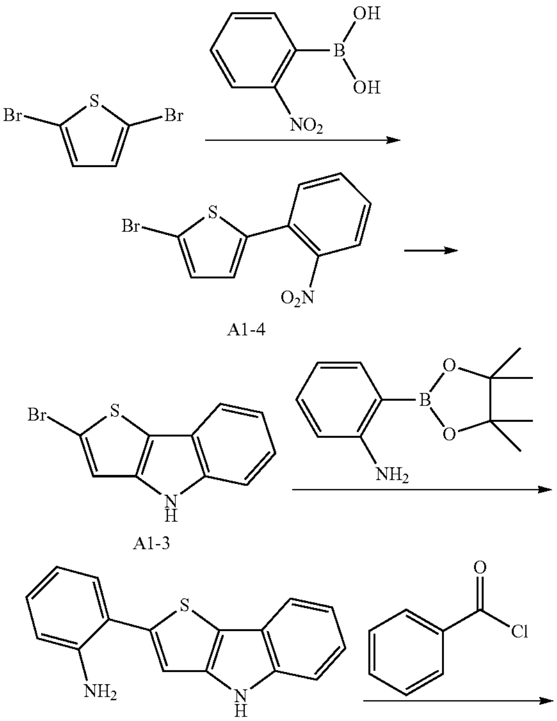

A1-4

A1-3

A1-2

-continued

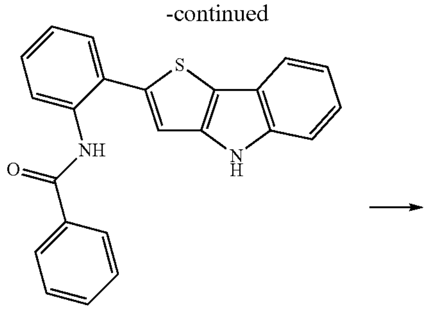

A1-1

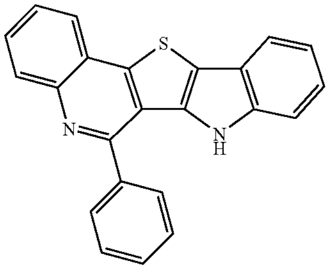

A1

Preparation of Intermediate A1-4

To a one-neck round bottom flask, 2,5-dibromothiophene (50 g, 206.67 mmol), (2-nitrophenyl)boronic acid (34.5 g, 206.67 mmol), $K_2CO_3$ (85.69 g, 620.01 mmol), $Pd(PPh_3)_4$ (7.16 g, 6.20 mmol), toluene (500 ml), EtOH (100 ml) and $H_2O$ (100 ml) were introduced, and stirred for 12 hours under reflux. After the reaction was finished, the result was extracted with methylene chloride (MC) and $H_2O$, and, after removing the solvent, purified by column chromatography using dichloromethane and hexane as a developing solvent to obtain Intermediate A1-4 (35 g, 59%).

Preparation of Intermediate A1-3

To a one-neck round bottom flask, Intermediate A1-4 (35 g, 123.18 mmol), triphenylphosphine (80.77 g, 307.96 mmol) and 1,2-dichlorobenzene (400 ml) were introduced, and stirred for 12 hours under reflux. After the reaction was finished, the result was extracted with methylene chloride (MC) and $H_2O$, and, after removing the solvent, purified by column chromatography using dichloromethane and hexane as a developing solvent to obtain Intermediate A1-3 (27 g, 86%).

Preparation of Intermediate A1-2

To a one-neck round bottom flask, Intermediate A1-3 (27 g, 107.09 mmol), 2-(4,4,5,5-tetramethyl-1,3,2-dioxaborolan-2-yl)aniline (24.63 g, 112.44 mmol), $K_2CO_3$ (44.40 g, 321.26 mmol), $Pd(PPh_3)_4$ (3.71 g, 3.21 mmol), toluene (300 ml), EtOH (60 ml) and $H_2O$ (60 ml) were introduced, and stirred for 13 hours under reflux. After the reaction was finished, the result was extracted with methylene chloride (MC) and $H_2O$, and, after removing the solvent, purified by column chromatography using dichloromethane and hexane as a developing solvent to obtain Intermediate A1-2 (25 g, 88%).

Preparation of Intermediate A1-1

After dissolving Intermediate A1-2 (27 g, 107.09 mmol) in methylene chloride (MC) (300 ml) in a one-neck round bottom flask, triethylamine (TEA) (28.71 g, 283.73 mmol) was introduced thereto. After lowering the temperature from room temperature to 0° C., benzoyl chloride (14.62 g, 104.03 mmol) dissolved in methylene chloride (MC) was slowly added dropwise thereto. After the reaction was completed, the result was extracted with methylene chloride (MC) and distilled water.

After drying the organic layer with anhydrous $MgSO_4$, the solvent was removed using a rotary evaporator, and the result was purified by column chromatography using dichloromethane and hexane as a developing solvent to obtain Intermediate A1-1 (31 g, 89%).

Preparation of Intermediate A1

To a one-neck round bottom flask, Intermediate A1-1 (31 g, 84.14 mmol), $POCl_3$ (14.19 g, 92.55 mmol) and nitrobenzene (300 ml) were introduced, and stirred for 6 hours under reflux. After the reaction was completed, the result was neutralized using an aqueous $NaHCO_3$ solution, and then extracted with methylene chloride (MC) and distilled water. After drying the organic layer with anhydrous $MgSO_4$, the solvent was removed using a rotary evaporator, and the result was purified by column chromatography using dichloromethane and hexane as a developing solvent to obtain Intermediate A1 (25 g, 84%).

Intermediates were synthesized in the same manner as in Preparation Example 1, except that S1 of the following Table 1 was used instead of 2,5-dibromothiophene, S2 of the following Table 1 was used instead of (2-nitrophenyl)boronic acid, S3 of the following Table 1 was used instead of 2-(4,4,5,5-tetramethyl-1,3,2-dioxaborolan-2-yl)aniline, and S4 of the following Table 1 was used instead of benzoyl chloride.

TABLE 1

| Intermediate | S1 | S2 | S3 |
|---|---|---|---|
| A2 | 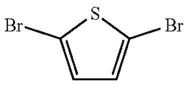 | 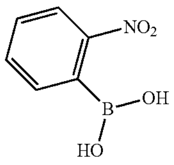 | 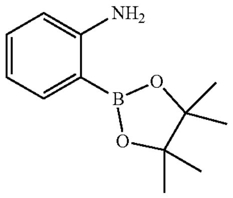 |

TABLE 1-continued
| | | | |
|---|---|---|---|
| A3 | 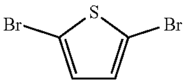 | 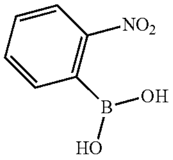 | 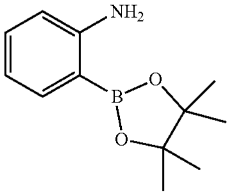 |
| A4 | 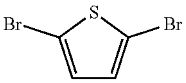 | 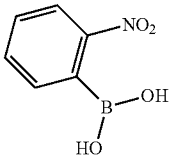 | 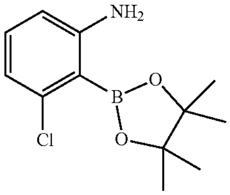 |
| A5 | 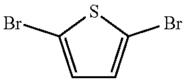 | 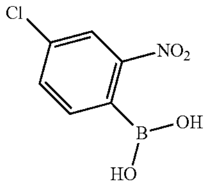 | 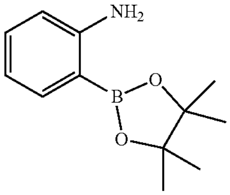 |
| A6 | 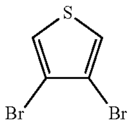 | 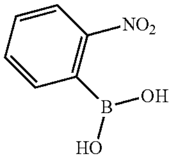 | 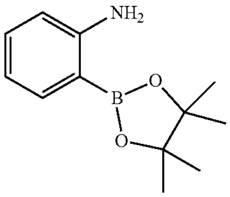 |
| A7 | 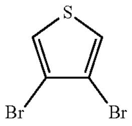 | 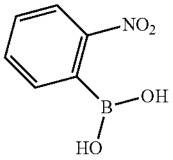 | 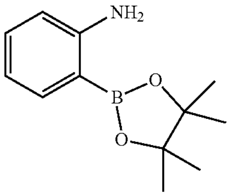 |
| A8 | 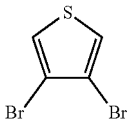 | 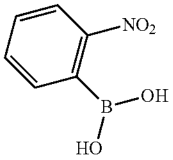 | 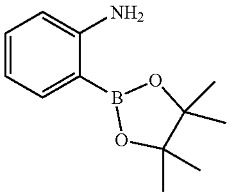 |
| A9 | 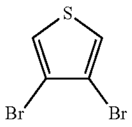 | 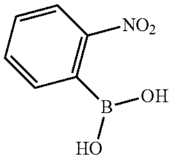 | 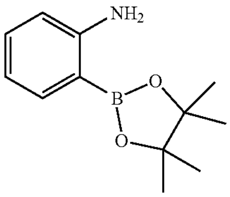 |
| A10 | 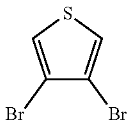 | 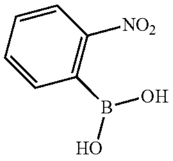 | 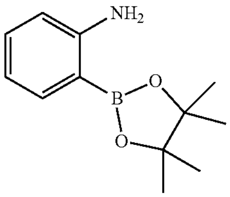 |

TABLE 1-continued
| | | | |
|---|---|---|---|
| A11 | 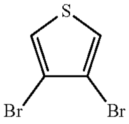 | 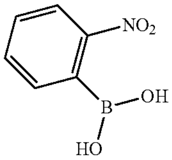 | 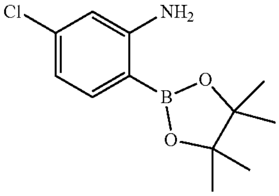 |
| A12 | 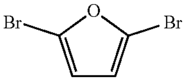 | 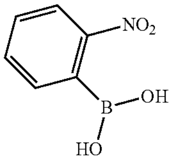 | 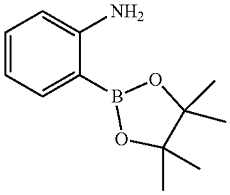 |
| A13 | 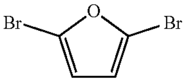 | 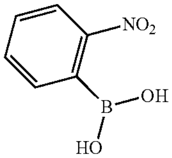 | 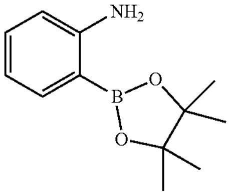 |
| A14 | 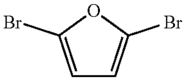 | 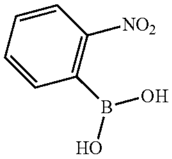 | 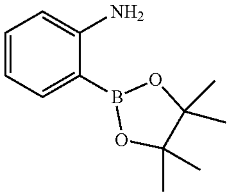 |
| A15 | 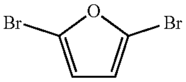 | 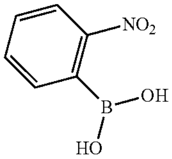 | 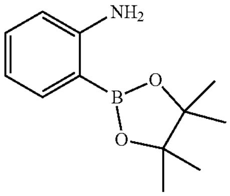 |
| A16 | 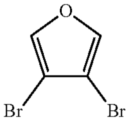 | 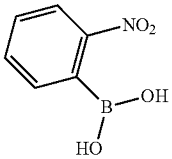 | 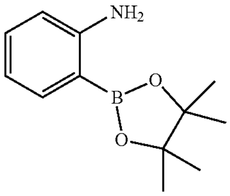 |
| A17 | 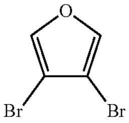 | 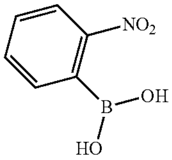 | 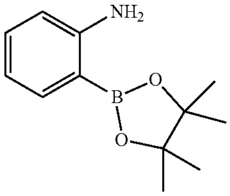 |

TABLE 1-continued
| | | | |
|---|---|---|---|
| A18 | 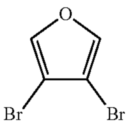 | 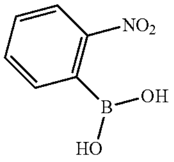 | 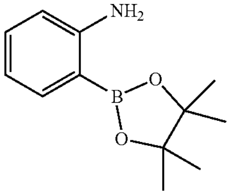 |
| Intermediate | S4 | Structure | Yield |
|---|---|---|---|
| A2 | 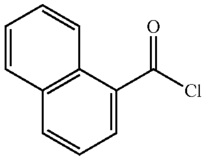 | 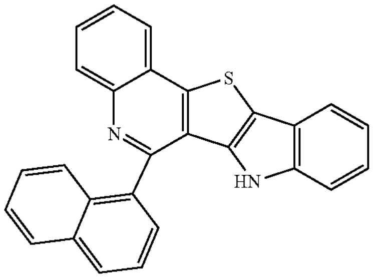 [SMILES: c1ccc2c(-c3nc4ccccc4c4sc5c6ccccc6[nH]c5c34)cccc2c1] | 81% |
| A3 | 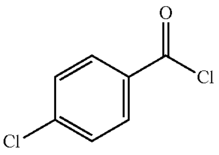 | 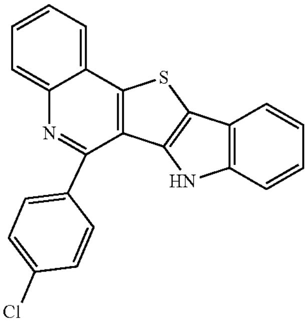 [SMILES: Clc1ccc(-c2nc3ccccc3c3sc4c5ccccc5[nH]c4c23)cc1] | 75% |
| A4 | 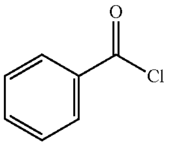 | 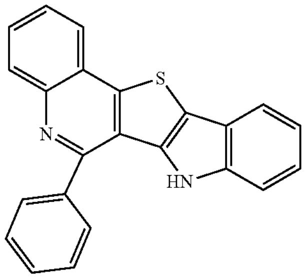 [SMILES: c1ccc(-c2nc3ccccc3c3sc4c5ccccc5[nH]c4c23)cc1] | 85% |
| A5 | 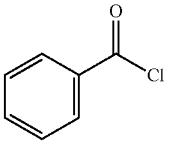 | 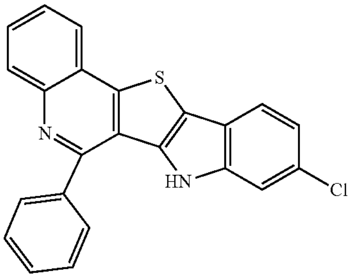 [SMILES: Clc1ccc2c(c1)[nH]c1c2sc2c3ccccc3nc(-c3ccccc3)c12] | 80% |

TABLE 1-continued
| | | | |
|---|---|---|---|
| A6 | 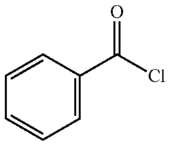 | 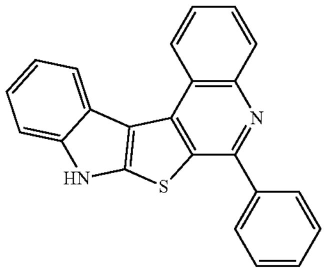 [SMILES: c1ccc(-c2nc3ccccc3c3c2sc2[nH]c4ccccc4c23)cc1] | 86% |
| A7 | 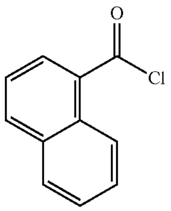 | 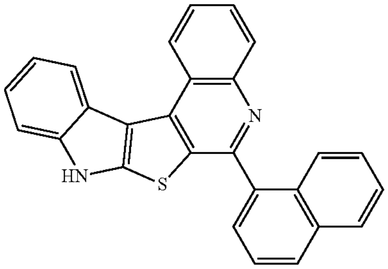 [SMILES: c1ccc2c(-c3nc4ccccc4c4c3sc3[nH]c5ccccc5c34)cccc2c1] | 79% |
| A8 | 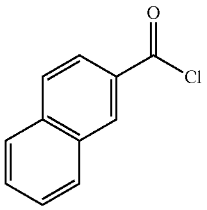 | 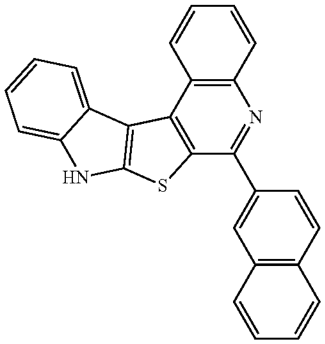 [SMILES: c1ccc2cc(-c3nc4ccccc4c4c3sc3[nH]c5ccccc5c34)ccc2c1] | 72% |
| A9 | 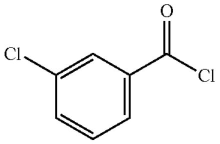 | 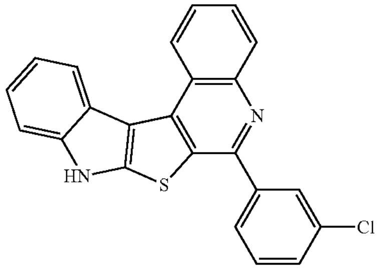 [SMILES: Clc1cccc(-c2nc3ccccc3c3c2sc2[nH]c4ccccc4c23)c1] | 70% |
| A10 | 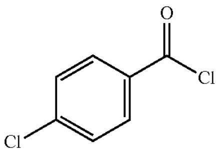 | 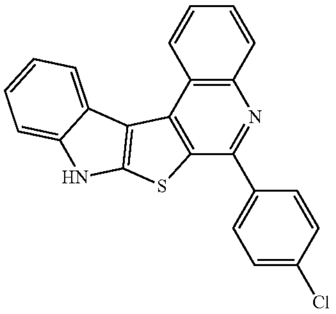 [SMILES: Clc1ccc(-c2nc3ccccc3c3c2sc2[nH]c4ccccc4c23)cc1] | 75% |

TABLE 1-continued
| | | | |
|---|---|---|---|
| A11 | 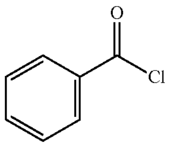 | 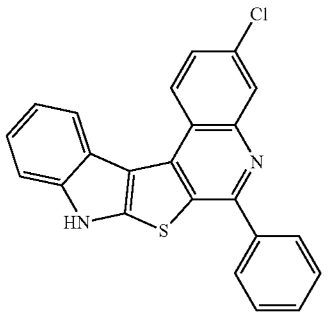 | 84% |
| A12 | 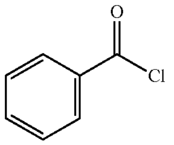 | 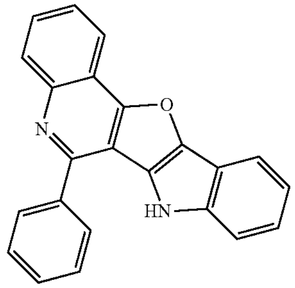 [SMILES: c1ccc(-c2nc3ccccc3c3oc4c5ccccc5[nH]c4c23)cc1] | 75% |
| A13 | 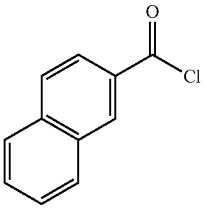 | 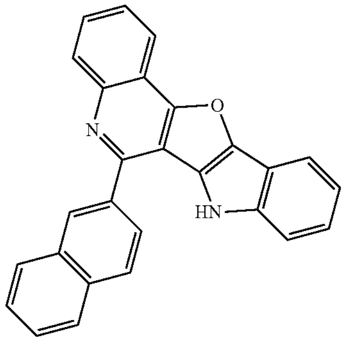 [SMILES: c1ccc2cc(-c3nc4ccccc4c4oc5c6ccccc6[nH]c5c34)ccc2c1] | 73% |
| A14 | 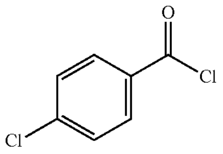 | 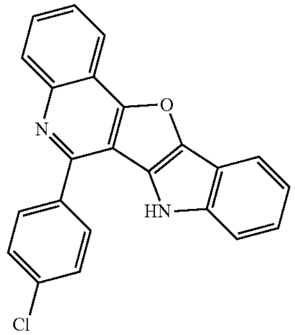 [SMILES: Clc1ccc(-c2nc3ccccc3c3oc4c5ccccc5[nH]c4c23)cc1] | 80% |
| A15 | 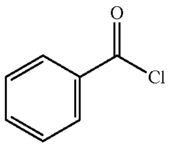 | 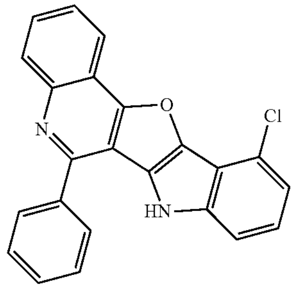 [SMILES: Clc1cccc2[nH]c3c(oc4c5ccccc5nc(-c5ccccc5)c34)c12] | 83% |

TABLE 1-continued
| | | | |
|---|---|---|---|
| A16 | 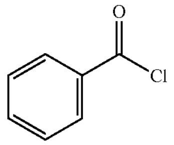 | 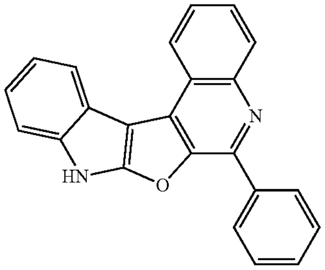 | 79% |
| A17 | 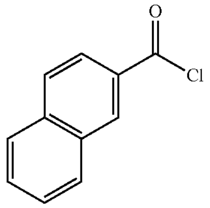 | 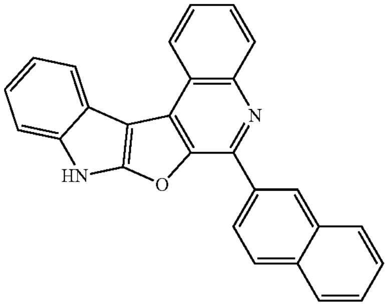 [SMILES: c1ccc2cc(-c3nc4ccccc4c4c3oc3[nH]c5ccccc5c34)ccc2c1] | 75% |
| A18 | 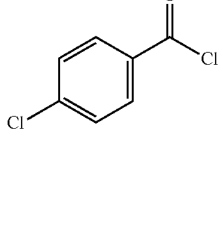 | 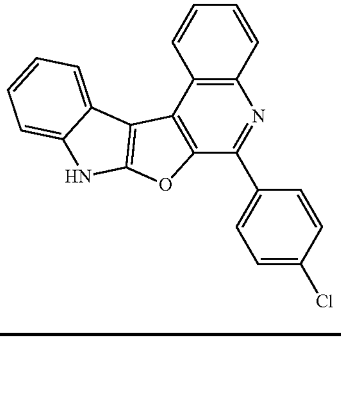 | 80% |

[Preparation Example 2] Preparation of Intermediate B1

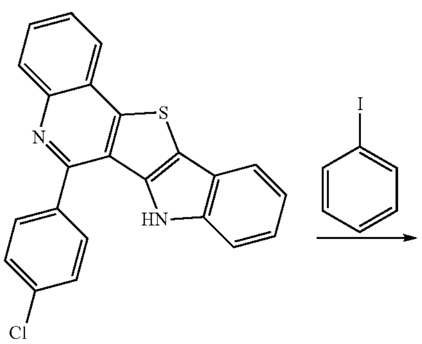

B1-2

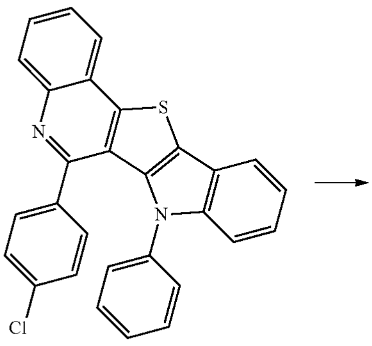

B1-1

-continued

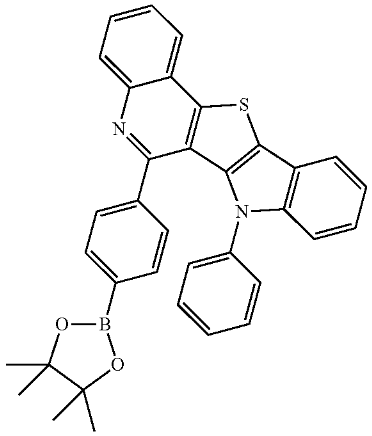

B1

Preparation of Intermediate B1-1

To a one-neck round bottom flask, Intermediate B1-2 (20 g, 51.96 mmol), iodobenzene (10.60 g, 51.96 mmol), $K_3PO_4$ (22.06 g, 103.93 mmol), CuI (9.90 g, 51.96 mmol), trans-1,2-diamino cyclohexane (6.2 ml, 51.96 mmol) and 1,4-dioxane (200 ml) were introduced, and stirred for 18 hours under reflux. After the reaction was finished, the result was extracted with methylene chloride (MC) and $H_2O$, and, after removing the solvent, purified by column chromatography using dichloromethane and hexane as a developing solvent to obtain Intermediate B1-1 (20 g, 83%).

Preparation of Intermediate B1

To a one-neck round bottom flask, Intermediate B1-1 (20 g, 43.39 mmol), bis(pinacolato)diboron (14.32 g, 56.40 mmol), KOAc (12.77 g, 130.16 mmol), $Pd(dba)_2$ (1.25 g, 2.17 mmol), Xphos (2.07 g, 4.34 mmol) and 1,4-dioxane (200 ml) were introduced, and stirred for 6 hours under reflux. After the reaction was finished, the result was extracted with methylene chloride (MC) and $H_2O$, and, after removing the solvent, purified by column chromatography using dichloromethane and hexane as a developing solvent to obtain Intermediate B1 (21 g, 87%).

Intermediates were synthesized in the same manner as in Preparation Example 2 except that Intermediate A of the following Table 2 was used instead of Intermediate B1-2, and S5 of the following Table 2 was used instead of iodobenzene.

TABLE 2
| Inter-mediate | Intermediate A | S5 | Structure | Yield |
|---|---|---|---|---|
| B2 | 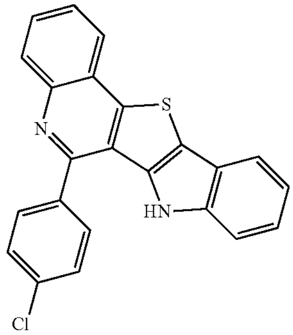 | 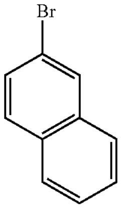 | 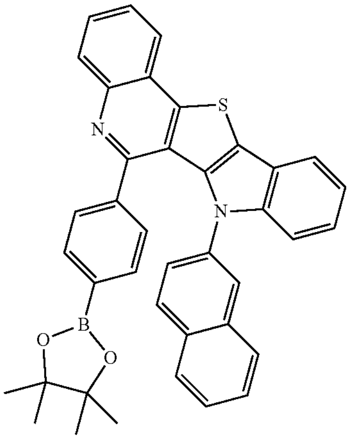 [SMILES: CC1(C)OB(c2ccc(-c3nc4ccccc4c4sc5c6ccccc6n(-c6ccc7ccccc7c6)c5c34)cc2)OC1(C)C] | 76% |
| B3 | 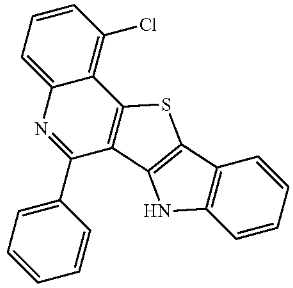 [SMILES: Clc1cccc2nc(-c3ccccc3)c3c4[nH]c5ccccc5c4sc3c12] | 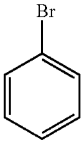 | 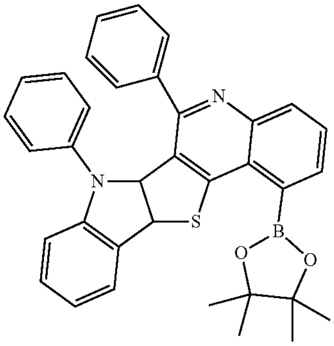 [SMILES: CC1(C)OB(c2cccc3nc(-c4ccccc4)c4c(c23)SC2c3ccccc3N(c3ccccc3)C42)OC1(C)C] | 75% |
| B4 | 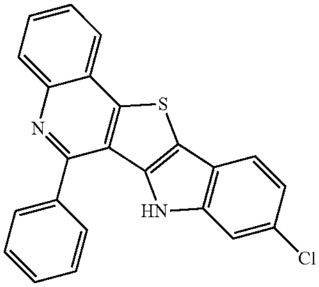 [SMILES: Clc1ccc2c(c1)[nH]c1c2sc2c3ccccc3nc(-c3ccccc3)c12] | 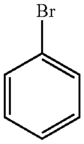 | 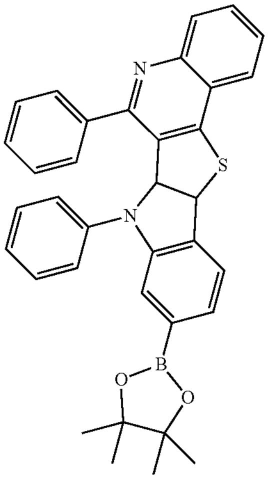 [SMILES: CC1(C)OB(c2ccc3c(c2)N(c2ccccc2)C2c4c(-c5ccccc5)nc5ccccc5c4SC32)OC1(C)C] | 82% |
| B5 | 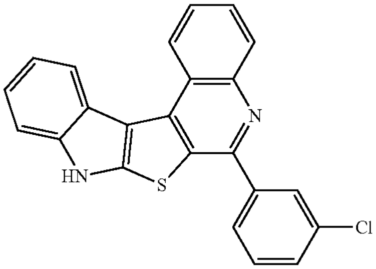 [SMILES: Clc1cccc(-c2nc3ccccc3c3c2sc2[nH]c4ccccc4c23)c1] | 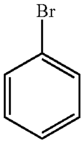 | 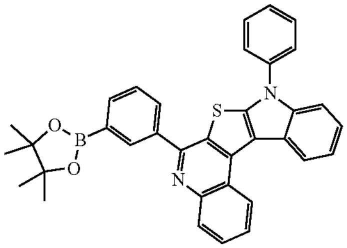 [SMILES: CC1(C)OB(c2cccc(-c3nc4ccccc4c4c3sc3c4c4ccccc4n3-c3ccccc3)c2)OC1(C)C] | 80% |

TABLE 2-continued
| Inter-mediate | Intermediate A | S5 | Structure | Yield |
|---|---|---|---|---|
| B6 | 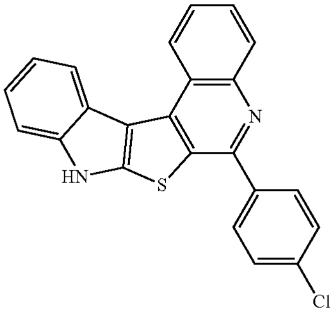 | 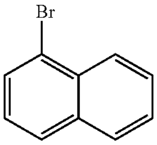 | 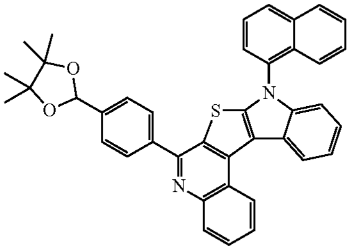 [SMILES: CC1(C)OC(c2ccc(-c3nc4ccccc4c4c3sc3c4c4ccccc4n3-c3cccc4ccccc34)cc2)OC1(C)C] | 82% |
| B7 | 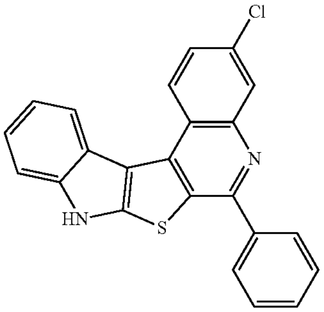 [SMILES: Clc1ccc2c(c1)nc(-c1ccccc1)c1sc3[nH]c4ccccc4c3c12] | 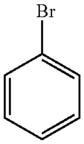 | 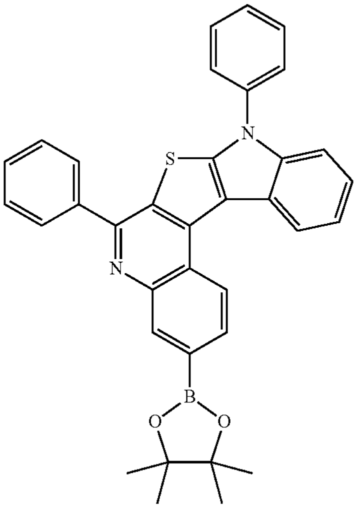 [SMILES: CC1(C)OB(c2ccc3c(c2)nc(-c2ccccc2)c2sc4c(c5ccccc5n4-c4ccccc4)c23)OC1(C)C] | 71% |
| B8 | 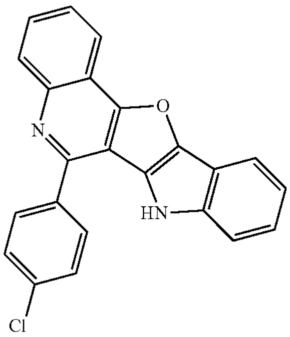 [SMILES: Clc1ccc(-c2nc3ccccc3c3oc4c5ccccc5[nH]c4c23)cc1] | 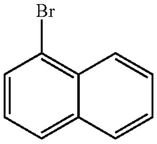 | 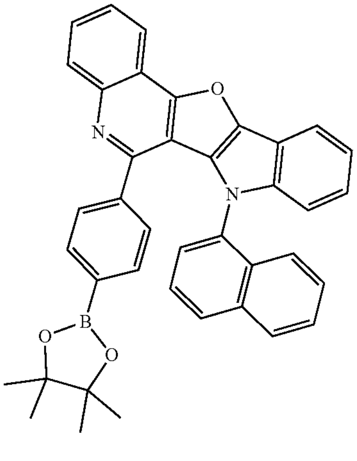 [SMILES: CC1(C)OB(c2ccc(-c3nc4ccccc4c4oc5c6ccccc6n(-c6cccc7ccccc67)c5c34)cc2)OC1(C)C] | 72% |

TABLE 2-continued
| Inter-mediate | Intermediate A | S5 | Structure | Yield |
|---|---|---|---|---|
| B9 | 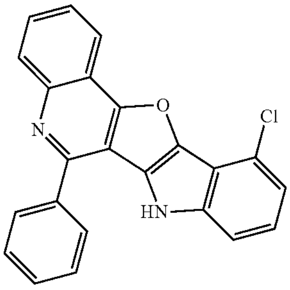 [SMILES: Clc1cccc2[nH]c3c(oc4c5ccccc5nc(-c5ccccc5)c34)c12] | 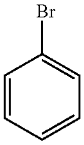 | 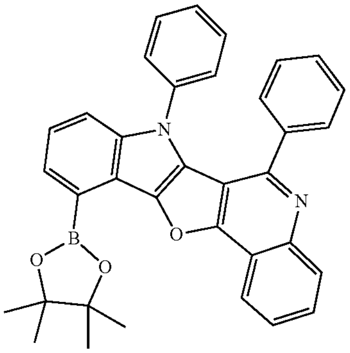 [SMILES: CC1(C)OB(c2cccc3c2c2oc4c5ccccc5nc(-c5ccccc5)c4c2n3-c2ccccc2)OC1(C)C] | 75% |
| B10 | 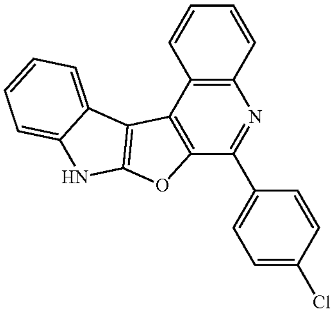 [SMILES: Clc1ccc(-c2nc3ccccc3c3c2oc2[nH]c4ccccc4c23)cc1] | 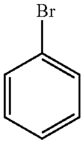 | 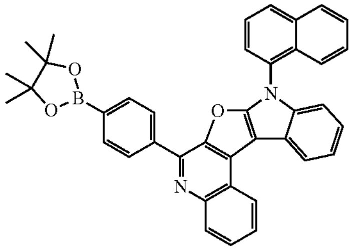 [SMILES: CC1(C)OB(c2ccc(-c3nc4ccccc4c4c3oc3c4c4ccccc4n3-c3cccc4ccccc34)cc2)OC1(C)C] | 83% |
[Preparation Example 3] Preparation of Compound 001
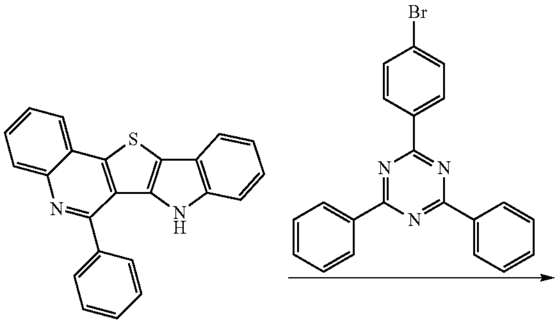
A1
-continued
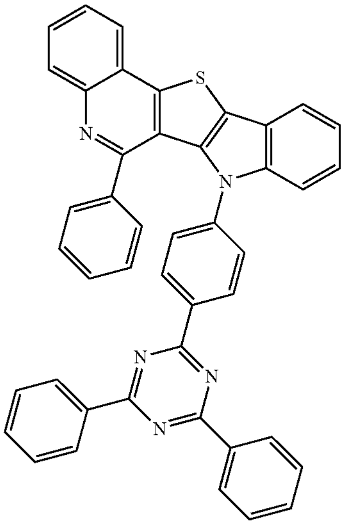
001

Preparation of Compound 001

To a one-neck round bottom flask, Intermediate A1 (7 g, 19.97 mmol), 2-(4-bromophenyl)-4,6-diphenyl-1,3,5-triazine (7.76 g, 19.97 mmol), $K_3PO_4$ (8.48 g, 39.95 mmol), CuI (3.80 g, 19.97 mmol), trans-1,2-diaminocyclohexane (2.4 ml, 19.97 mmol) and 1,4-dioxane (100 ml) were introduced, and stirred for 18 hours under reflux. After the reaction was finished, the result was extracted with methylene chloride (MC) and $H_2O$, and, after removing the solvent, purified by column chromatography using dichloromethane and hexane as a developing solvent to obtain Compound 001 (9 g, 68%).

Final compounds were synthesized in the same manner as in Preparation Example 3 except that Intermediate A of the following Table 3 was used instead of Intermediate A1, and S6 of the following Table 3 was used instead of 2-(4-bromophenyl)-4,6-diphenyl-1,3,5-triazine.

TABLE 3

| Compound | Intermediate A | S6 |
|---|---|---|
| 005 | 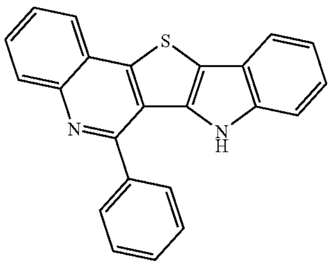 | 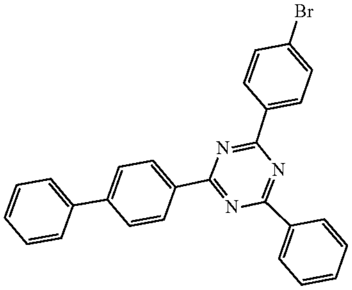 |
| 007 | 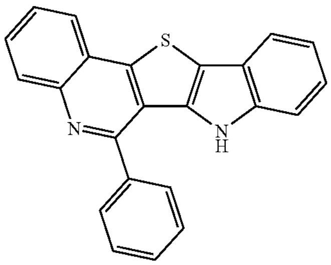 [SMILES: c1ccc(-c2nc3ccccc3c3sc4c5ccccc5[nH]c4c23)cc1] | 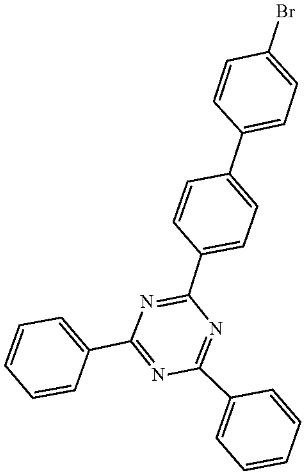 |
| 008 | 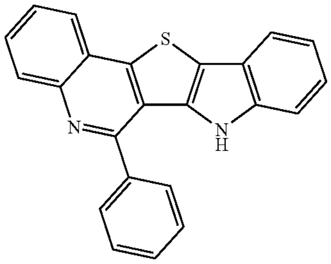 [SMILES: c1ccc(-c2nc3ccccc3c3sc4c5ccccc5[nH]c4c23)cc1] | 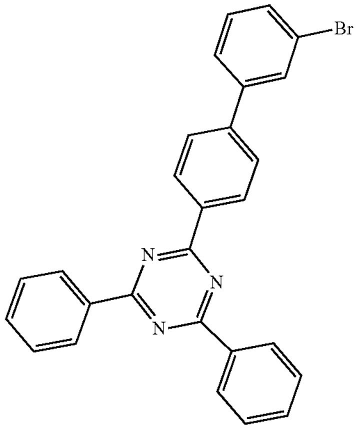 |

TABLE 3-continued
| | | |
|---|---|---|
| 011 | 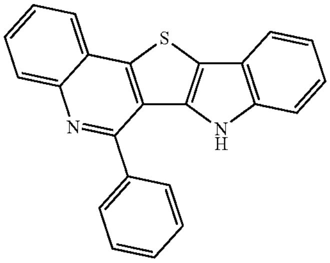 [SMILES: c1ccc(-c2nc3ccccc3c3sc4c5ccccc5[nH]c4c23)cc1] | 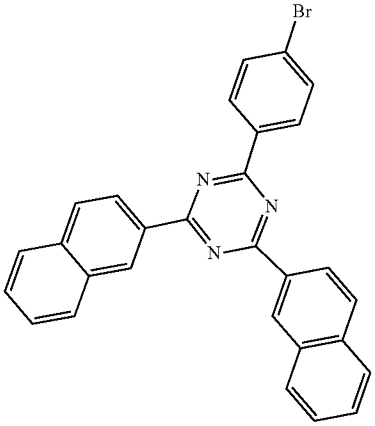 |
| 014 | 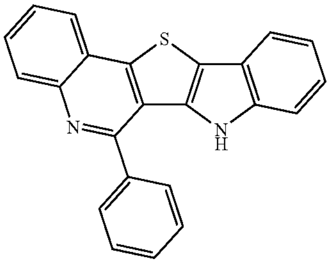 [SMILES: c1ccc(-c2nc3ccccc3c3sc4c5ccccc5[nH]c4c23)cc1] | 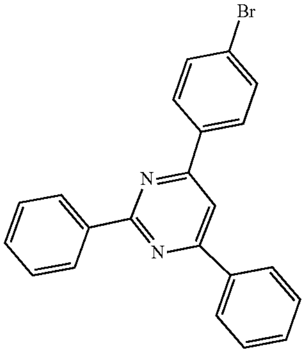 |
| 023 | 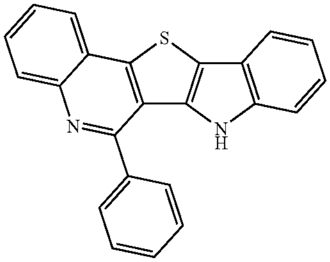 [SMILES: c1ccc(-c2nc3ccccc3c3sc4c5ccccc5[nH]c4c23)cc1] | 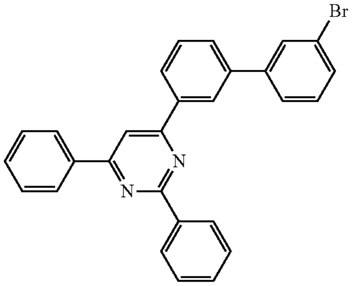 |
| 025 | 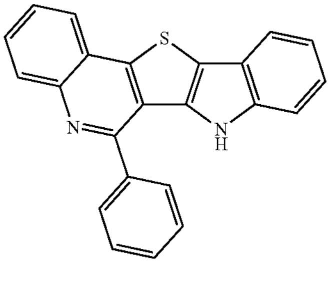 [SMILES: c1ccc(-c2nc3ccccc3c3sc4c5ccccc5[nH]c4c23)cc1] | 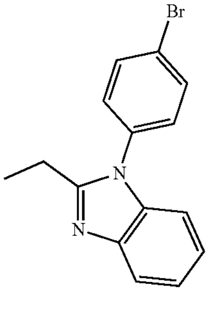 |

TABLE 3-continued
| | | |
|---|---|---|
| 026 | 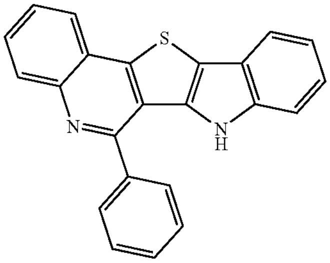 [SMILES: c1ccc(-c2nc3ccccc3c3sc4c5ccccc5[nH]c4c23)cc1] | 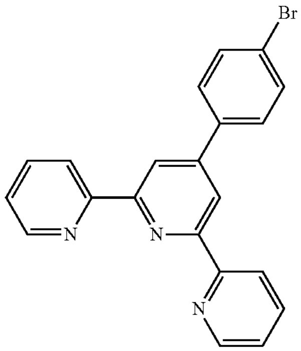 |
| 027 | 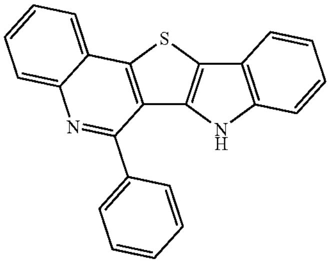 [SMILES: c1ccc(-c2nc3ccccc3c3sc4c5ccccc5[nH]c4c23)cc1] | 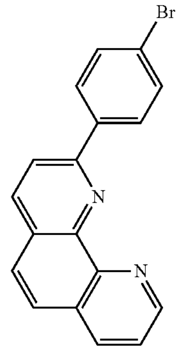 |
| 028 | 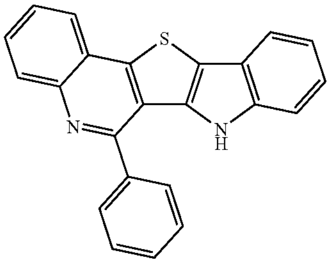 [SMILES: c1ccc(-c2nc3ccccc3c3sc4c5ccccc5[nH]c4c23)cc1] | 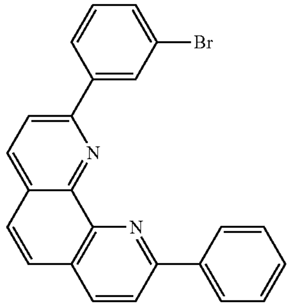 |
| 029 | 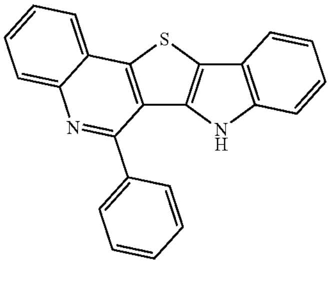 [SMILES: c1ccc(-c2nc3ccccc3c3sc4c5ccccc5[nH]c4c23)cc1] | 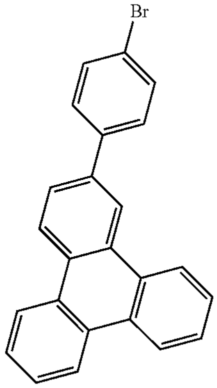 |

TABLE 3-continued
| | | |
|---|---|---|
| 031 | 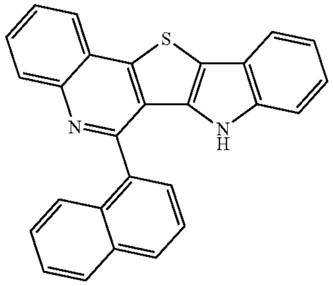 [SMILES: c1ccc2c(-c3nc4ccccc4c4sc5c6ccccc6[nH]c5c34)cccc2c1] | 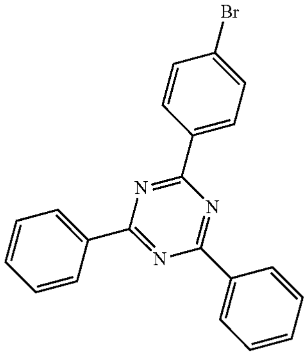 |
| 069 | 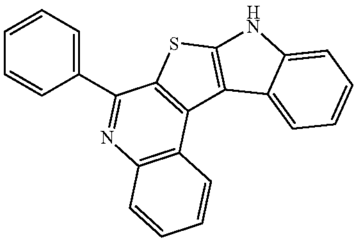 [SMILES: c1ccc(-c2nc3ccccc3c3c2sc2[nH]c4ccccc4c23)cc1] | 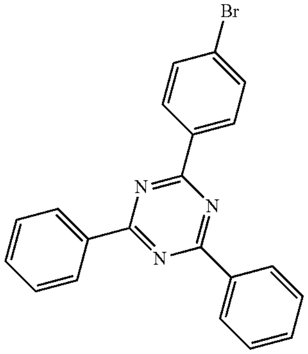 |
| 071 | 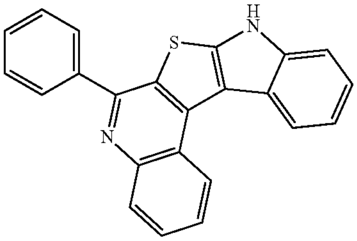 [SMILES: c1ccc(-c2nc3ccccc3c3c2sc2[nH]c4ccccc4c23)cc1] | 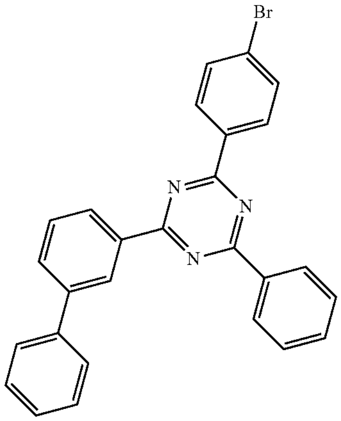 |
| 075 | 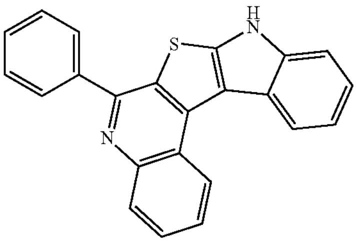 [SMILES: c1ccc(-c2nc3ccccc3c3c2sc2[nH]c4ccccc4c23)cc1] | 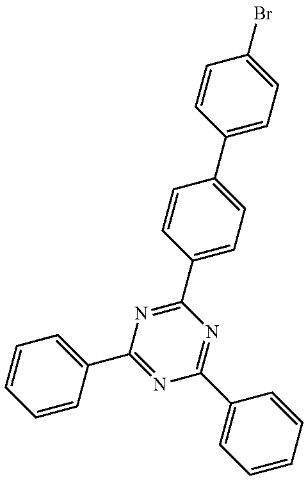 |

TABLE 3-continued
| | | |
|---|---|---|
| 082 | 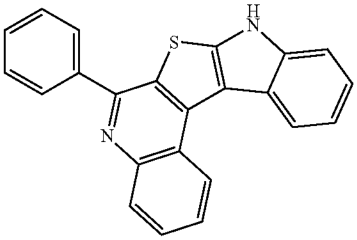 [SMILES: c1ccc(-c2nc3ccccc3c3c2sc2[nH]c4ccccc4c23)cc1] | 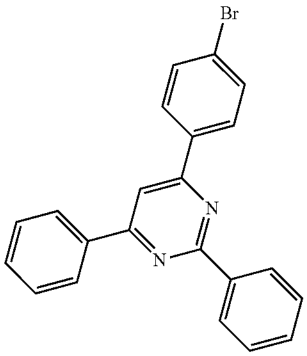 |
| 092 | 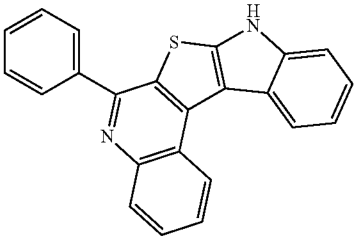 [SMILES: c1ccc(-c2nc3ccccc3c3c2sc2[nH]c4ccccc4c23)cc1] | 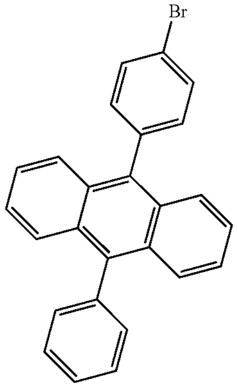 |
| 093 | 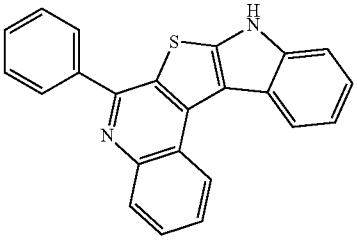 [SMILES: c1ccc(-c2nc3ccccc3c3c2sc2[nH]c4ccccc4c23)cc1] | 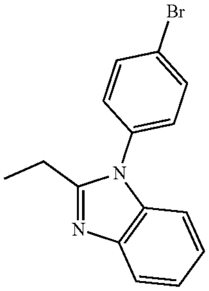 |
| 094 | 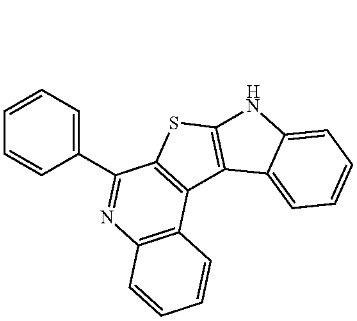 [SMILES: c1ccc(-c2nc3ccccc3c3c2sc2[nH]c4ccccc4c23)cc1] | 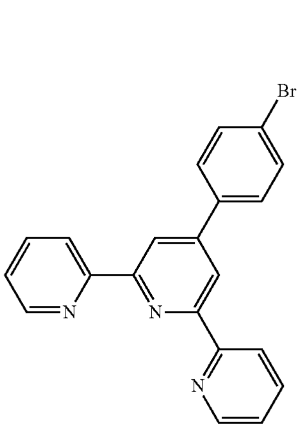 |

TABLE 3-continued
| | | |
|---|---|---|
| 095 | 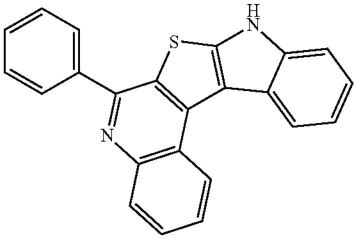 [SMILES: c1ccc(-c2nc3ccccc3c3c2sc2[nH]c4ccccc4c23)cc1] | 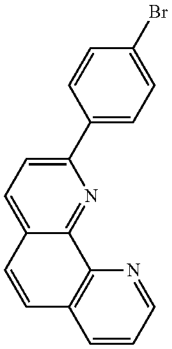 [SMILES: Brc1ccc(-c2ccc3ccc4cccnc4c3n2)cc1] |
| 096 | 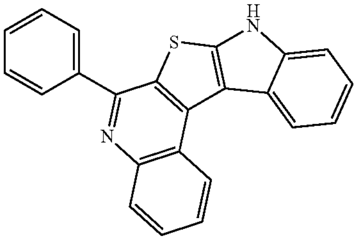 [SMILES: c1ccc(-c2nc3ccccc3c3c2sc2[nH]c4ccccc4c23)cc1] | 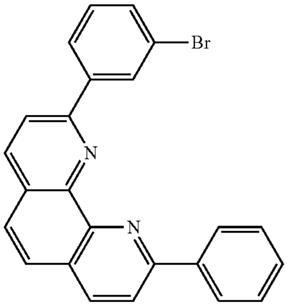 [SMILES: Brc1cccc(-c2ccc3ccc4ccc(-c5ccccc5)nc4c3n2)c1] |
| 097 | 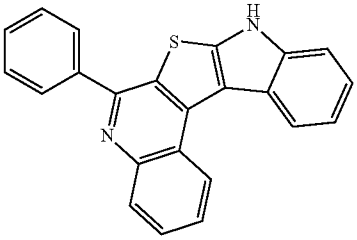 [SMILES: c1ccc(-c2nc3ccccc3c3c2sc2[nH]c4ccccc4c23)cc1] | 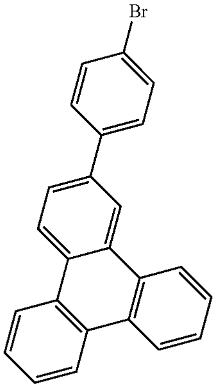 [SMILES: Brc1ccc(-c2ccc3c4ccccc4c4ccccc4c3c2)cc1] |
| 099 | 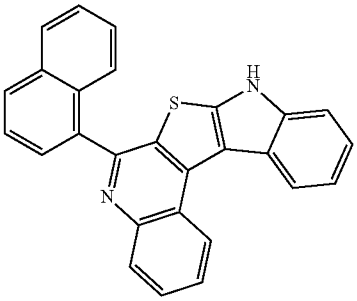 [SMILES: c1ccc2c(-c3nc4ccccc4c4c3sc3[nH]c5ccccc5c34)cccc2c1] | 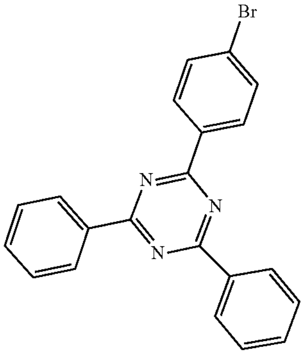 [SMILES: Brc1ccc(-c2nc(-c3ccccc3)nc(-c3ccccc3)n2)cc1] |

TABLE 3-continued
| | | |
|---|---|---|
| 106 | 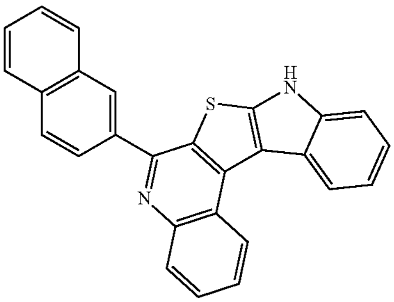 [SMILES: c1ccc2cc(-c3nc4ccccc4c4c3sc3[nH]c5ccccc5c34)ccc2c1] | 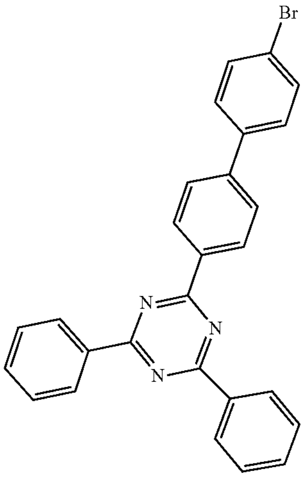 [SMILES: Brc1ccc(-c2ccc(-c3nc(-c4ccccc4)nc(-c4ccccc4)n3)cc2)cc1] |
| 137 | 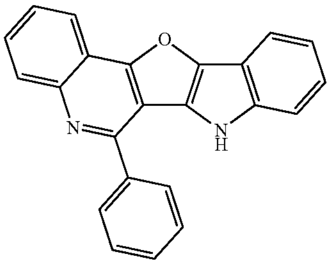 | 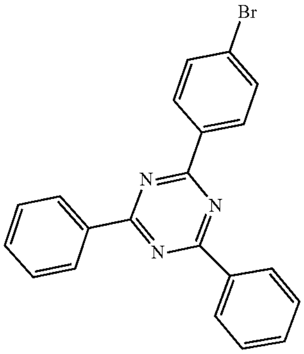 [SMILES: Brc1ccc(-c2nc(-c3ccccc3)nc(-c3ccccc3)n2)cc1] |
| 150 | 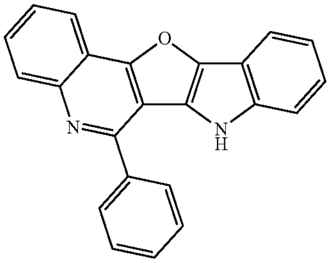 | 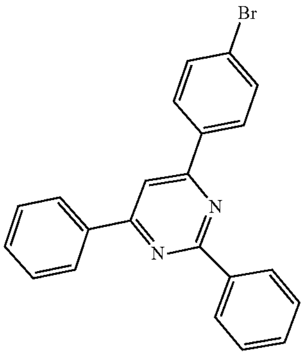 [SMILES: Brc1ccc(-c2cc(-c3ccccc3)nc(-c3ccccc3)n2)cc1] |
| 162 | 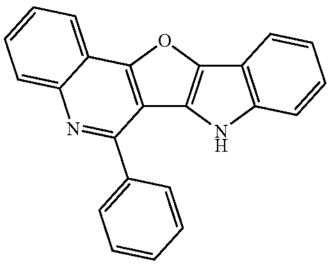 | 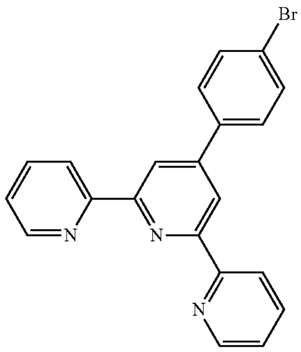 [SMILES: Brc1ccc(-c2cc(-c3ccccn3)nc(-c3ccccn3)c2)cc1] |

TABLE 3-continued
| | | |
|---|---|---|
| 163 | 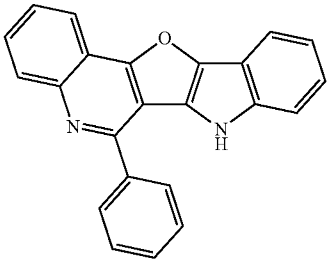 | 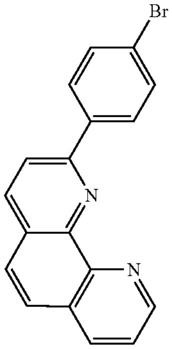 [SMILES: Brc1ccc(-c2ccc3ccc4cccnc4c3n2)cc1] |
| 164 | 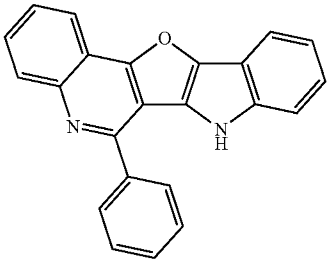 [SMILES: c1ccc(-c2nc3ccccc3c3oc4c5ccccc5[nH]c4c23)cc1] | 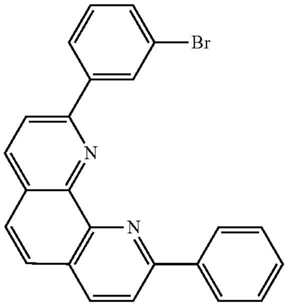 [SMILES: Brc1cccc(-c2ccc3ccc4ccc(-c5ccccc5)nc4c3n2)c1] |
| 165 | 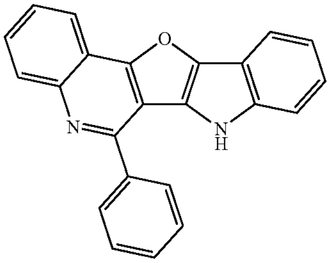 [SMILES: c1ccc(-c2nc3ccccc3c3oc4c5ccccc5[nH]c4c23)cc1] | 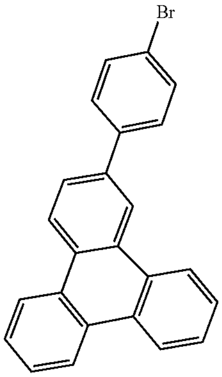 [SMILES: Brc1ccc(-c2ccc3c4ccccc4c4ccccc4c3c2)cc1] |
| 175 | 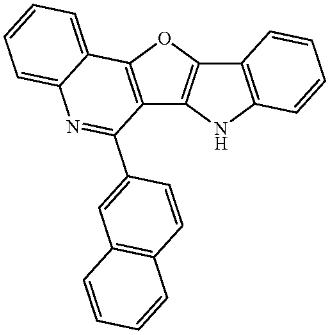 [SMILES: c1ccc2cc(-c3nc4ccccc4c4oc5c6ccccc6[nH]c5c34)ccc2c1] | 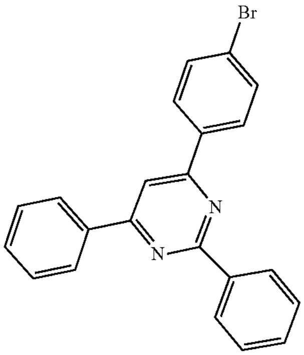 [SMILES: Brc1ccc(-c2cc(-c3ccccc3)nc(-c3ccccc3)n2)cc1] |

TABLE 3-continued
| | | |
|---|---|---|
| 205 | 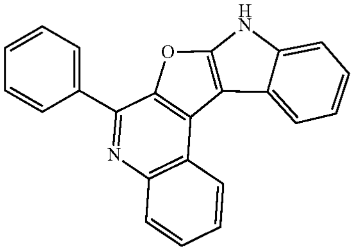 [SMILES: c1ccc(-c2nc3ccccc3c3c2oc2[nH]c4ccccc4c23)cc1] | 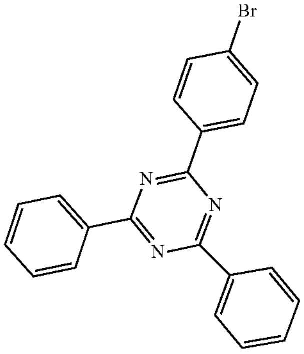 [SMILES: Brc1ccc(-c2nc(-c3ccccc3)nc(-c3ccccc3)n2)cc1] |
| 218 | 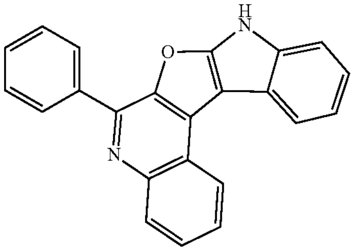 [SMILES: c1ccc(-c2nc3ccccc3c3c2oc2[nH]c4ccccc4c23)cc1] | 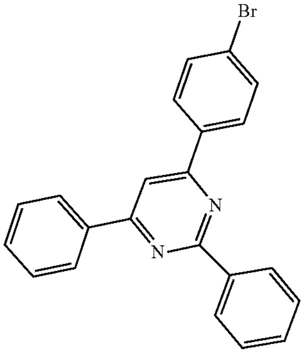 [SMILES: Brc1ccc(-c2cc(-c3ccccc3)nc(-c3ccccc3)n2)cc1] |
| 224 | 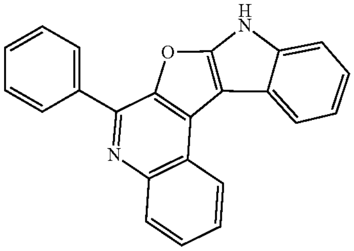 [SMILES: c1ccc(-c2nc3ccccc3c3c2oc2[nH]c4ccccc4c23)cc1] | 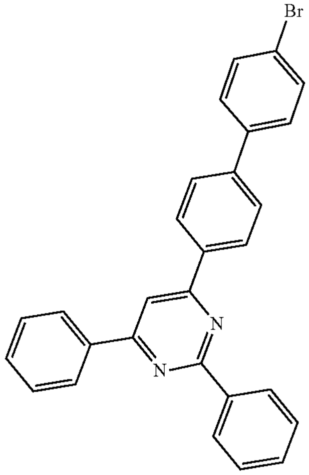 [SMILES: Brc1ccc(-c2ccc(-c3cc(-c4ccccc4)nc(-c4ccccc4)n3)cc2)cc1] |
| 230 | 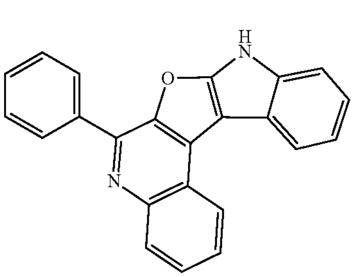 [SMILES: c1ccc(-c2nc3ccccc3c3c2oc2[nH]c4ccccc4c23)cc1] | 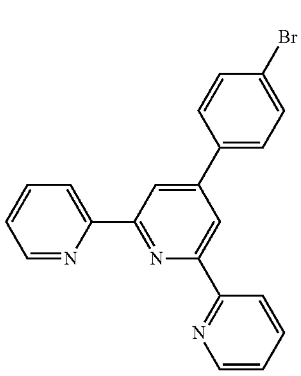 [SMILES: Brc1ccc(-c2cc(-c3ccccn3)nc(-c3ccccn3)c2)cc1] |

TABLE 3-continued
| | | |
|---|---|---|
| 231 | 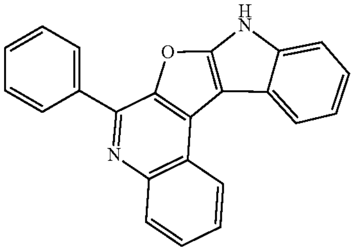 [SMILES: c1ccc(-c2nc3ccccc3c3c2oc2[nH]c4ccccc4c23)cc1] | 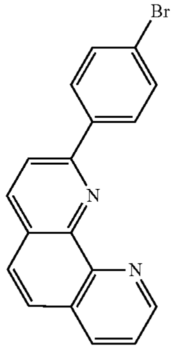 [SMILES: Brc1ccc(-c2ccc3ccc4cccnc4c3n2)cc1] |
| 232 | 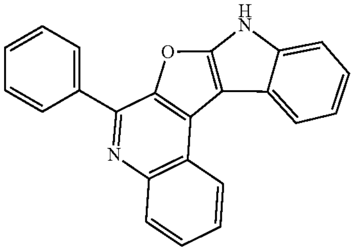 [SMILES: c1ccc(-c2nc3ccccc3c3c2oc2[nH]c4ccccc4c23)cc1] | 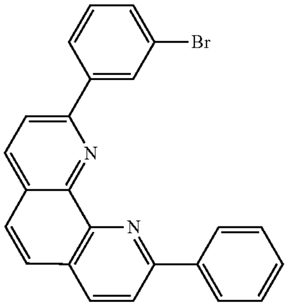 [SMILES: Brc1cccc(-c2ccc3ccc4ccc(-c5ccccc5)nc4c3n2)c1] |
| 233 | 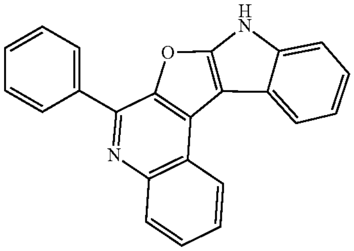 [SMILES: c1ccc(-c2nc3ccccc3c3c2oc2[nH]c4ccccc4c23)cc1] | 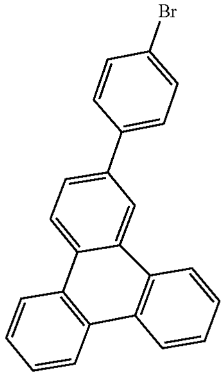 [SMILES: Brc1ccc(-c2ccc3c4ccccc4c4ccccc4c3c2)cc1] |
| 240 | 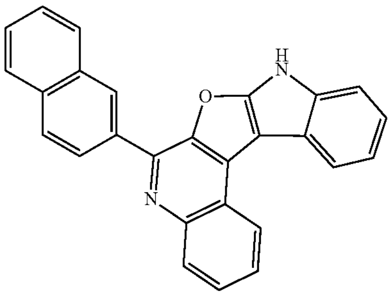 [SMILES: c1ccc2cc(-c3nc4ccccc4c4c3oc3[nH]c5ccccc5c34)ccc2c1] | 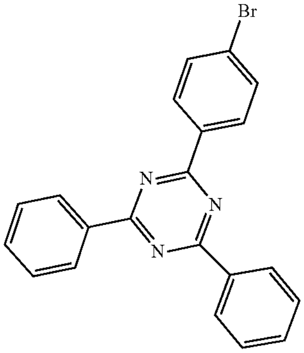 [SMILES: Brc1ccc(-c2nc(-c3ccccc3)nc(-c3ccccc3)n2)cc1] |

TABLE 3-continued
| Compound | Structure | Yield |
| --- | --- | --- |
| 005 | 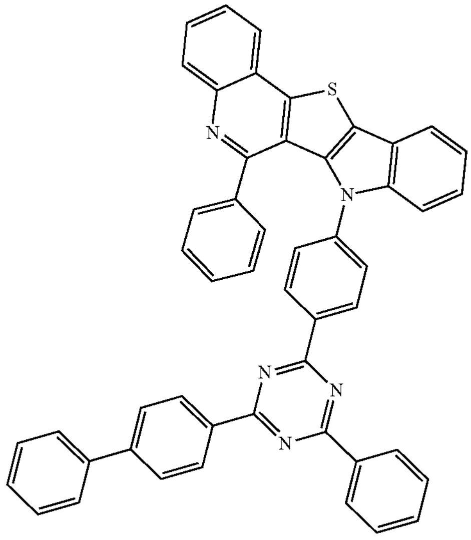 [SMILES: c1ccc(-c2ccc(-c3nc(-c4ccccc4)nc(-c4ccc(-n5c6ccccc6c6sc7c8ccccc8nc(-c8ccccc8)c7c65)cc4)n3)cc2)cc1] | 76% |
| 007 | 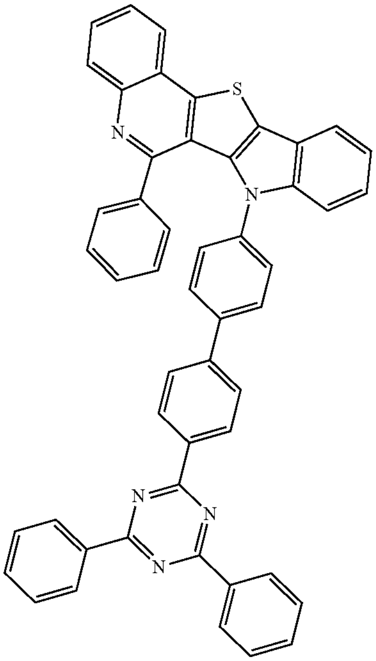 [SMILES: c1ccc(-c2nc(-c3ccccc3)nc(-c3ccc(-c4ccc(-n5c6ccccc6c6sc7c8ccccc8nc(-c8ccccc8)c7c65)cc4)cc3)n2)cc1] | 72% |

TABLE 3-continued
| | | |
|---|---|---|
| 008 | 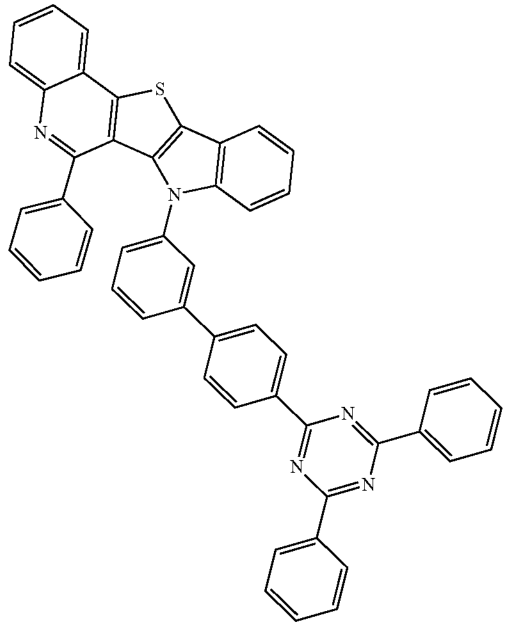 [SMILES: c1ccc(-c2nc(-c3ccccc3)nc(-c3ccc(-c4cccc(-n5c6ccccc6c6sc7c8ccccc8nc(-c8ccccc8)c7c65)c4)cc3)n2)cc1] | 72% |
| 011 | 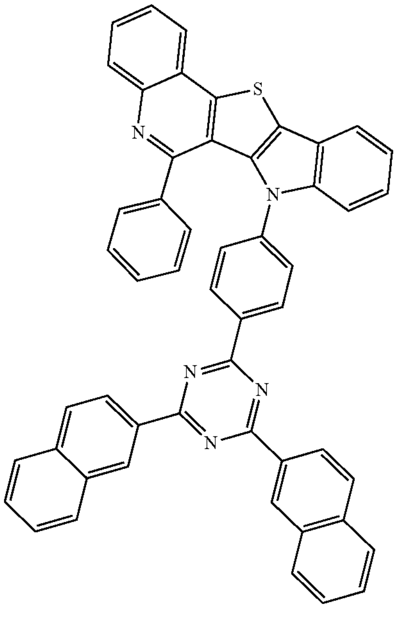 [SMILES: c1ccc(-c2nc3ccccc3c3sc4c5ccccc5n(-c5ccc(-c6nc(-c7ccc8ccccc8c7)nc(-c7ccc8ccccc8c7)n6)cc5)c4c23)cc1] | 80% |

TABLE 3-continued
| | | |
|---|---|---|
| 014 | 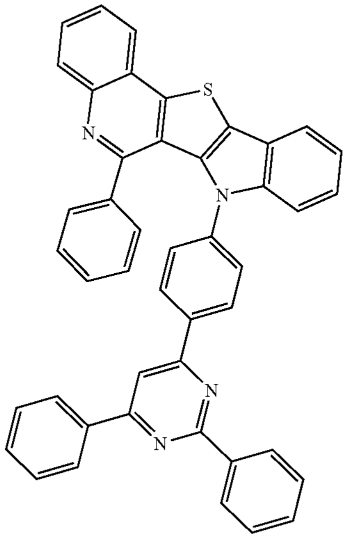 [SMILES: c1ccc(-c2cc(-c3ccc(-n4c5ccccc5c5sc6c7ccccc7nc(-c7ccccc7)c6c54)cc3)nc(-c3ccccc3)n2)cc1] | 67% |
| 023 | 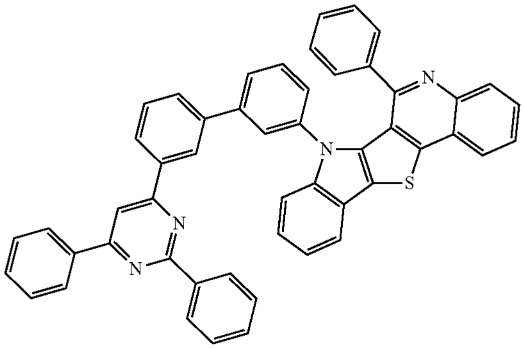 [SMILES: c1ccc(-c2cc(-c3cccc(-c4cccc(-n5c6ccccc6c6sc7c8ccccc8nc(-c8ccccc8)c7c65)c4)c3)nc(-c3ccccc3)n2)cc1] | 75% |
| 025 | 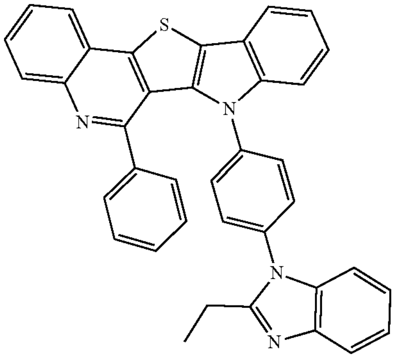 [SMILES: CCc1nc2ccccc2n1-c1ccc(-n2c3ccccc3c3sc4c5ccccc5nc(-c5ccccc5)c4c32)cc1] | 72% |

TABLE 3-continued
| | | |
|---|---|---|
| 026 | 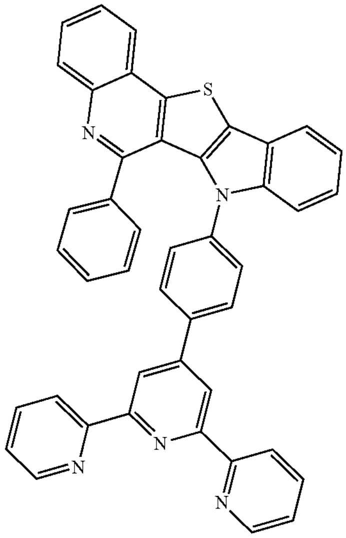 [SMILES: c1ccc(-c2nc3ccccc3c3sc4c5ccccc5n(-c5ccc(-c6cc(-c7ccccn7)nc(-c7ccccn7)c6)cc5)c4c23)cc1] | 79% |
| 027 | 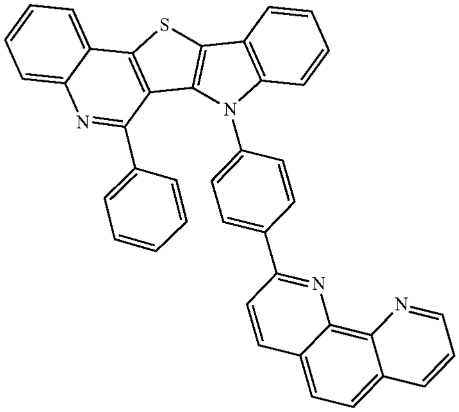 [SMILES: c1ccc(-c2nc3ccccc3c3sc4c5ccccc5n(-c5ccc(-c6ccc7ccc8cccnc8c7n6)cc5)c4c23)cc1] | 80% |
| 028 | 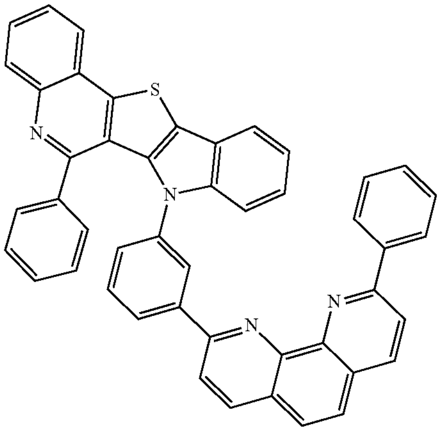 [SMILES: c1ccc(-c2ccc3ccc4ccc(-c5cccc(-n6c7ccccc7c7sc8c9ccccc9nc(-c9ccccc9)c8c76)c5)nc4c3n2)cc1] | 71% |

TABLE 3-continued
| | | |
|---|---|---|
| 029 | 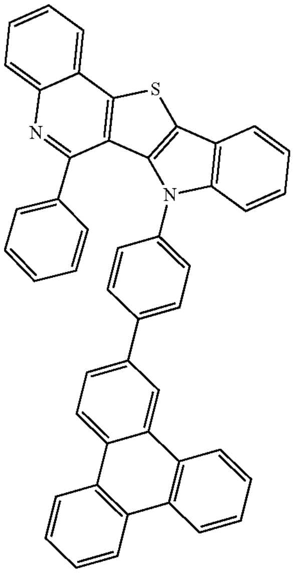 [SMILES: c1ccc(-c2nc3ccccc3c3sc4c5ccccc5n(-c5ccc(-c6ccc7c8ccccc8c8ccccc8c7c6)cc5)c4c23)cc1] | 74% |
| 031 | 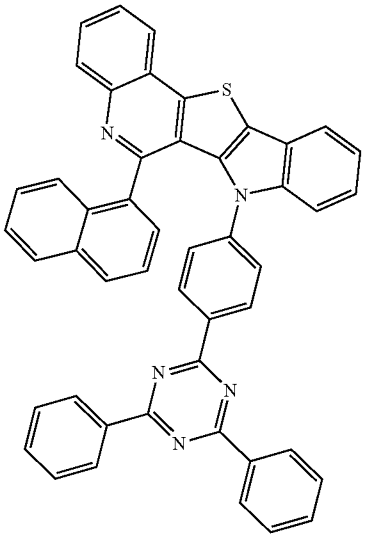 [SMILES: c1ccc(-c2nc(-c3ccccc3)nc(-c3ccc(-n4c5ccccc5c5sc6c7ccccc7nc(-c7cccc8ccccc78)c6c54)cc3)n2)cc1] | 75% |
| 069 | 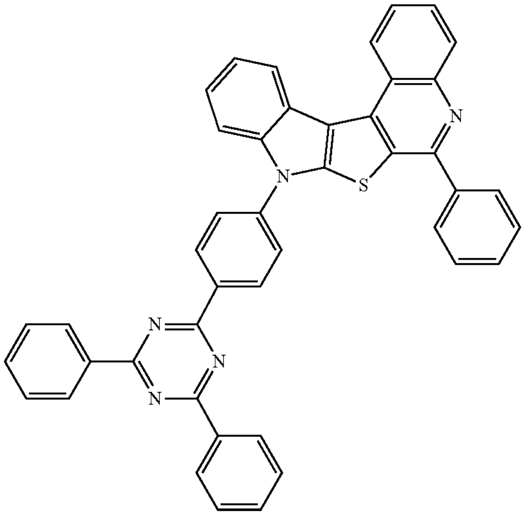 [SMILES: c1ccc(-c2nc(-c3ccccc3)nc(-c3ccc(-n4c5ccccc5c5c6c(sc54)c(-c4ccccc4)nc4ccccc46)cc3)n2)cc1] | 78% |

TABLE 3-continued
| | | |
|---|---|---|
| 071 | 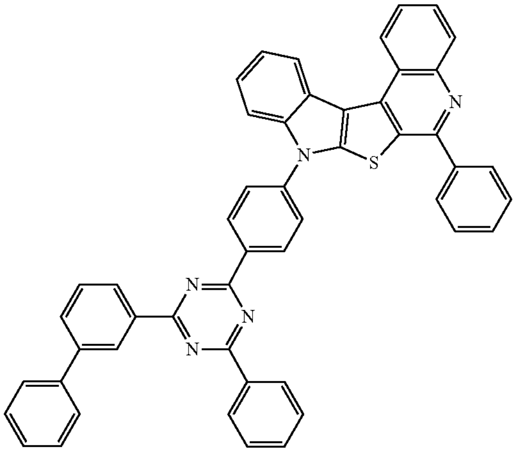 [SMILES: c1ccc(-c2cccc(-c3nc(-c4ccccc4)nc(-c4ccc(-n5c6ccccc6c6c7c(sc65)c(-c5ccccc5)nc5ccccc57)cc4)n3)c2)cc1] | 75% |
| 075 | 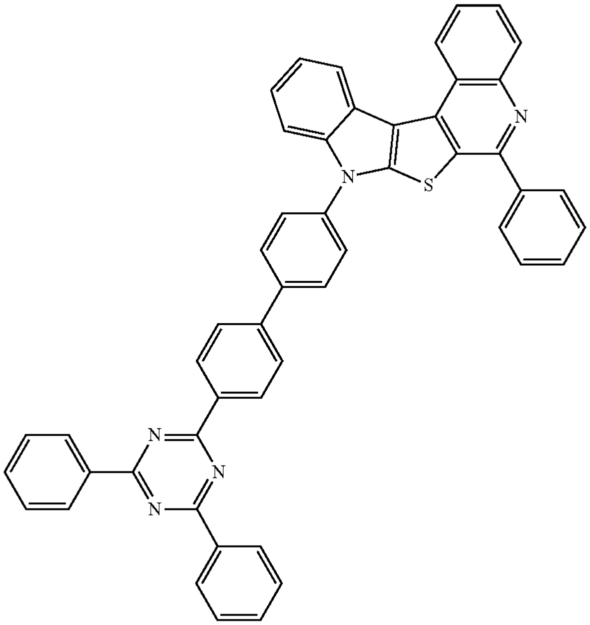 [SMILES: c1ccc(-c2nc(-c3ccccc3)nc(-c3ccc(-c4ccc(-n5c6ccccc6c6c7c(sc65)c(-c5ccccc5)nc5ccccc57)cc4)cc3)n2)cc1] | 72% |
| 082 | 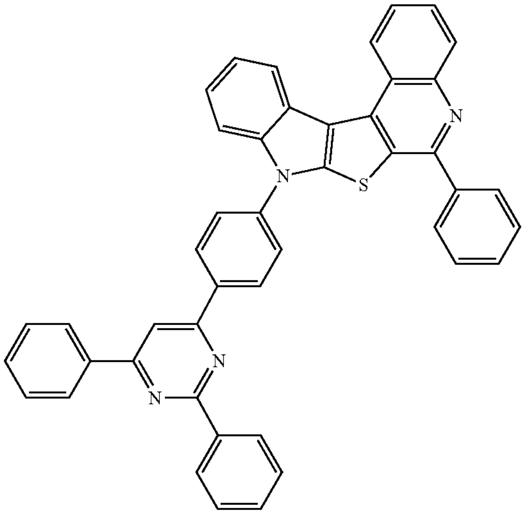 | 75% |

TABLE 3-continued
| | | |
|---|---|---|
| 092 | 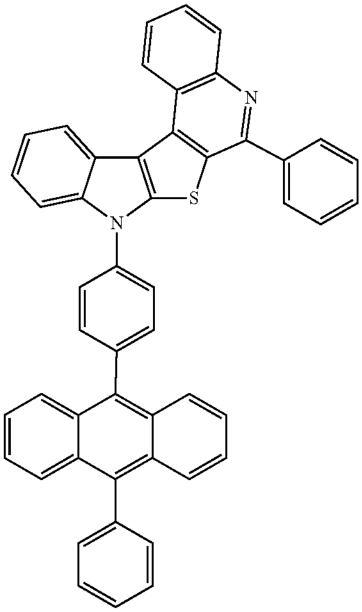 [SMILES: c1ccc(-c2c3ccccc3c(-c3ccc(-n4c5ccccc5c5c6c(sc54)c(-c4ccccc4)nc4ccccc46)cc3)c3ccccc23)cc1] | 73% |
| 093 | 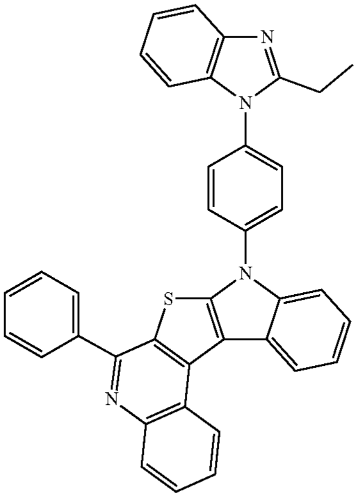 [SMILES: CCc1nc2ccccc2n1-c1ccc(-n2c3ccccc3c3c4c(sc32)c(-c2ccccc2)nc2ccccc24)cc1] | 76% |
| 094 | 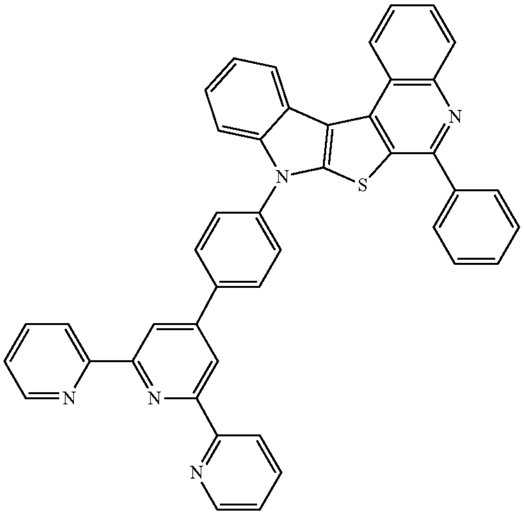 [SMILES: c1ccc(-c2nc3ccccc3c3c2sc2c3c3ccccc3n2-c2ccc(-c3cc(-c4ccccn4)nc(-c4ccccn4)c3)cc2)cc1] | 70% |

TABLE 3-continued
| | | |
|---|---|---|
| 095 | 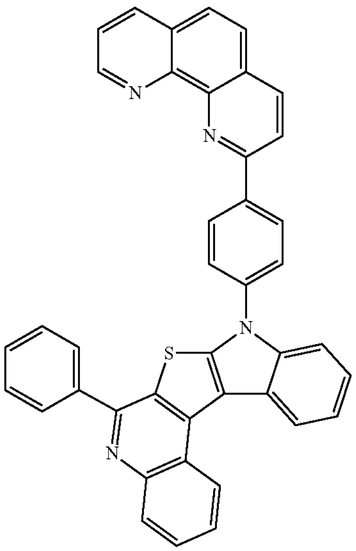 [SMILES: c1ccc(-c2nc3ccccc3c3c2sc2c3c3ccccc3n2-c2ccc(-c3ccc4ccc5cccnc5c4n3)cc2)cc1] | 75% |
| 096 | 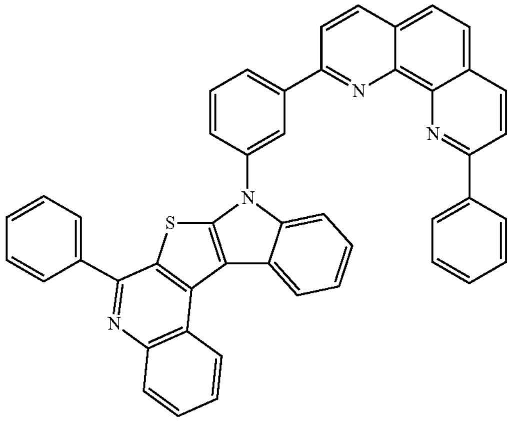 [SMILES: c1ccc(-c2ccc3ccc4ccc(-c5cccc(-n6c7ccccc7c7c8c(sc76)c(-c6ccccc6)nc6ccccc68)c5)nc4c3n2)cc1] | 81% |
| 097 | 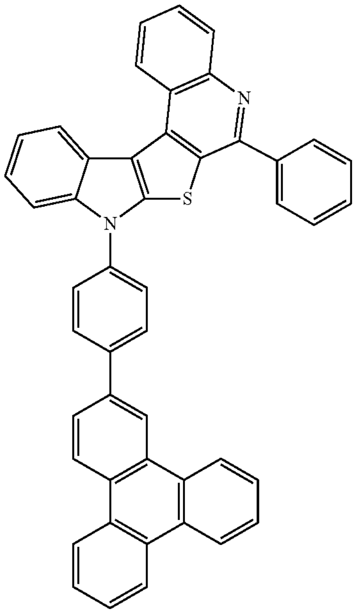 [SMILES: c1ccc(-c2nc3ccccc3c3c2sc2c3c3ccccc3n2-c2ccc(-c3ccc4c5ccccc5c5ccccc5c4c3)cc2)cc1] | 75% |

TABLE 3-continued
| | | |
|---|---|---|
| 099 | 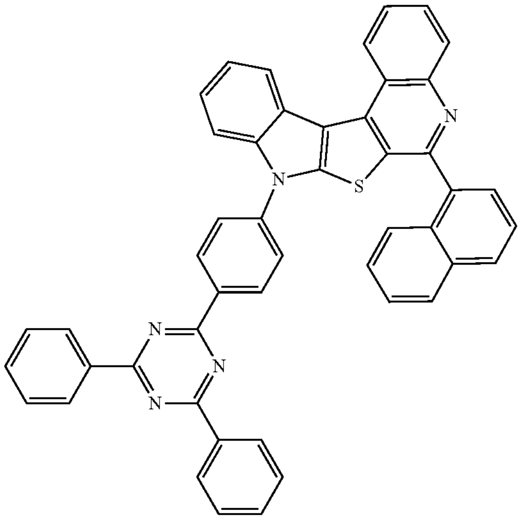 [SMILES: c1ccc(-c2nc(-c3ccccc3)nc(-c3ccc(-n4c5ccccc5c5c6c(sc54)c(-c4cccc5ccccc45)nc4ccccc46)cc3)n2)cc1] | 72% |
| 106 | 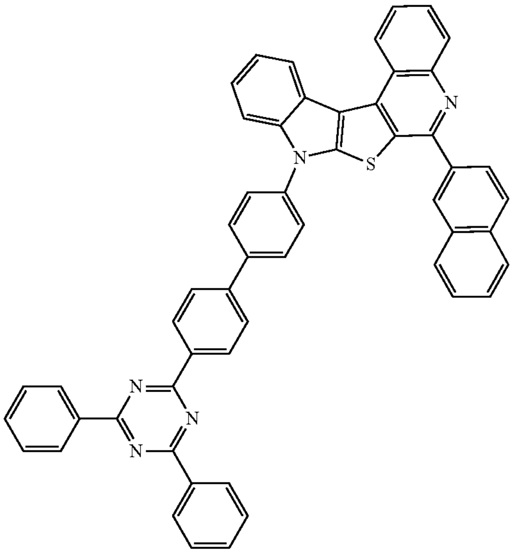 [SMILES: c1ccc(-c2nc(-c3ccccc3)nc(-c3ccc(-c4ccc(-n5c6ccccc6c6c7c(sc65)c(-c5ccc6ccccc6c5)nc5ccccc57)cc4)cc3)n2)cc1] | 75% |
| 137 | 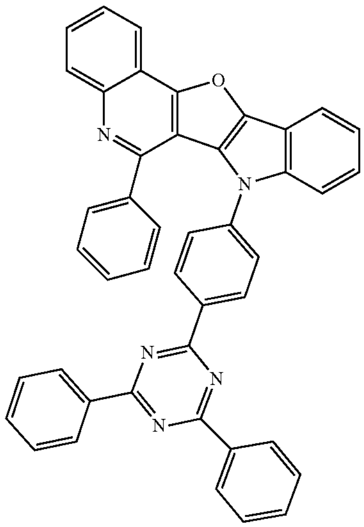 [SMILES: c1ccc(-c2nc(-c3ccccc3)nc(-c3ccc(-n4c5ccccc5c5oc6c7ccccc7nc(-c7ccccc7)c6c54)cc3)n2)cc1] | 77% |

TABLE 3-continued
| | | |
|---|---|---|
| 150 | 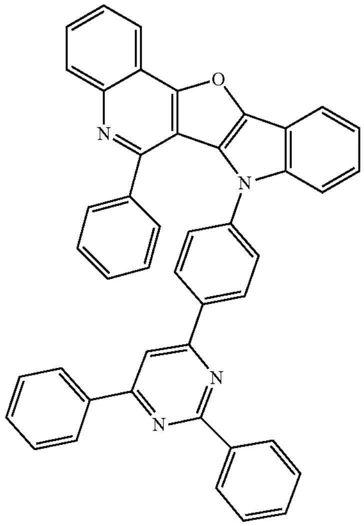 [SMILES: c1ccc(-c2cc(-c3ccc(-n4c5ccccc5c5oc6c7ccccc7nc(-c7ccccc7)c6c54)cc3)nc(-c3ccccc3)n2)cc1] | 73% |
| 162 | 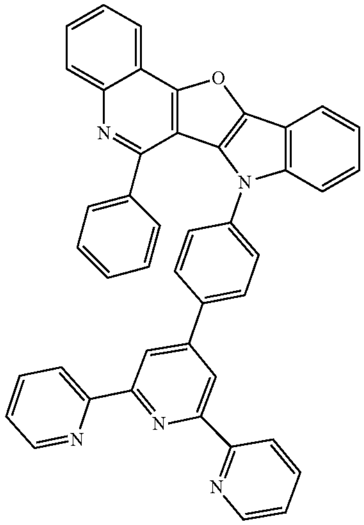 [SMILES: c1ccc(-c2nc3ccccc3c3oc4c5ccccc5n(-c5ccc(-c6cc(-c7ccccn7)nc(-c7ccccn7)c6)cc5)c4c23)cc1] | 72% |
| 163 | 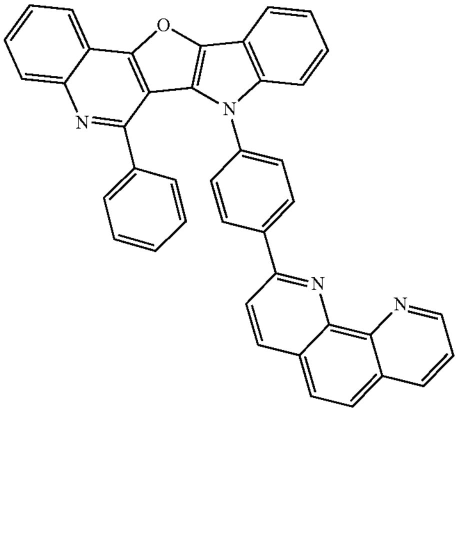 [SMILES: c1ccc(-c2nc3ccccc3c3oc4c5ccccc5n(-c5ccc(-c6ccc7ccc8cccnc8c7n6)cc5)c4c23)cc1] | 75% |

TABLE 3-continued
| | | |
|---|---|---|
| 164 | 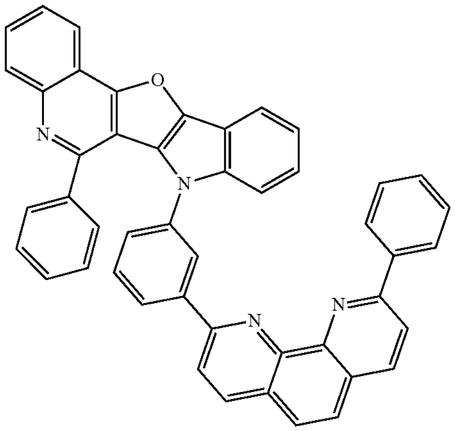 | 70% |
| 165 | 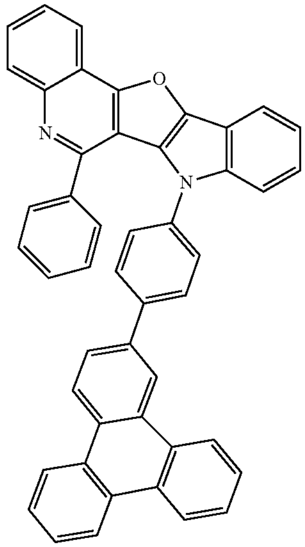 [SMILES: c1ccc(-c2nc3ccccc3c3oc4c5ccccc5n(-c5ccc(-c6ccc7c8ccccc8c8ccccc8c7c6)cc5)c4c23)cc1] | 69% |
| 175 | 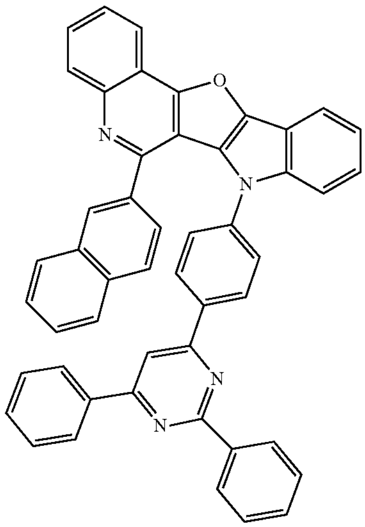 [SMILES: c1ccc(-c2cc(-c3ccc(-n4c5ccccc5c5oc6c7ccccc7nc(-c7ccc8ccccc8c7)c6c54)cc3)nc(-c3ccccc3)n2)cc1] | 72% |

TABLE 3-continued
| | | |
|---|---|---|
| 205 | 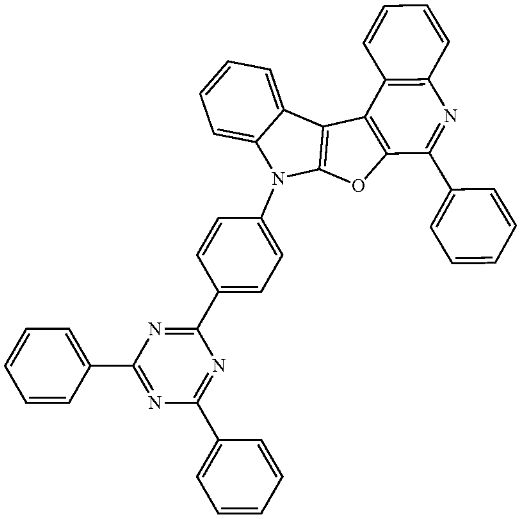 | 70% |
| 218 | 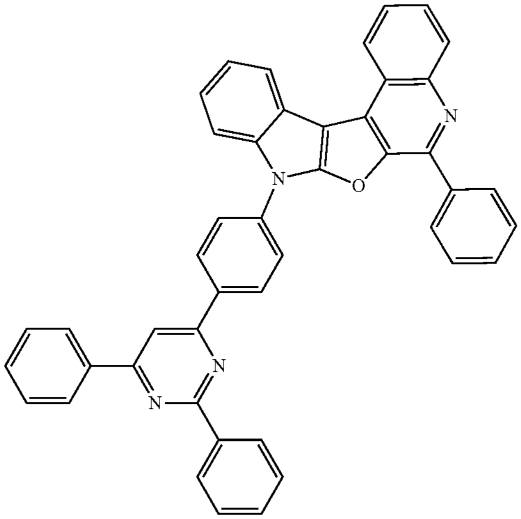 [SMILES: c1ccc(-c2cc(-c3ccc(-n4c5ccccc5c5c6c(oc54)c(-c4ccccc4)nc4ccccc46)cc3)nc(-c3ccccc3)n2)cc1] | 73% |
| 224 | 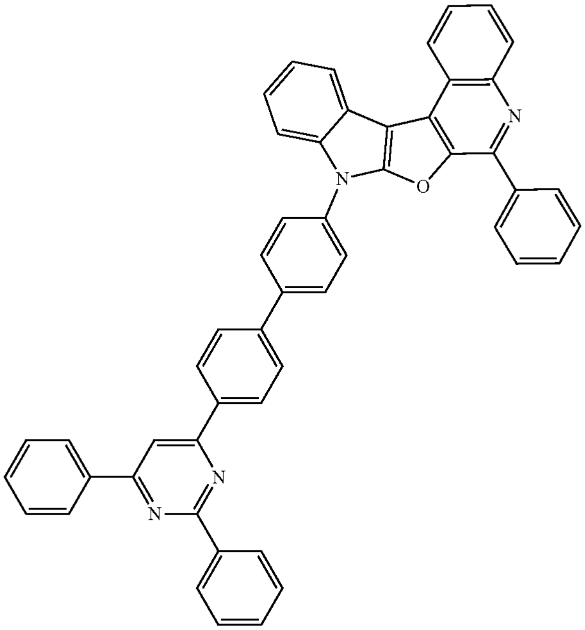 [SMILES: c1ccc(-c2cc(-c3ccc(-c4ccc(-n5c6ccccc6c6c7c(oc65)c(-c5ccccc5)nc5ccccc57)cc4)cc3)nc(-c3ccccc3)n2)cc1] | 67% |

TABLE 3-continued
230 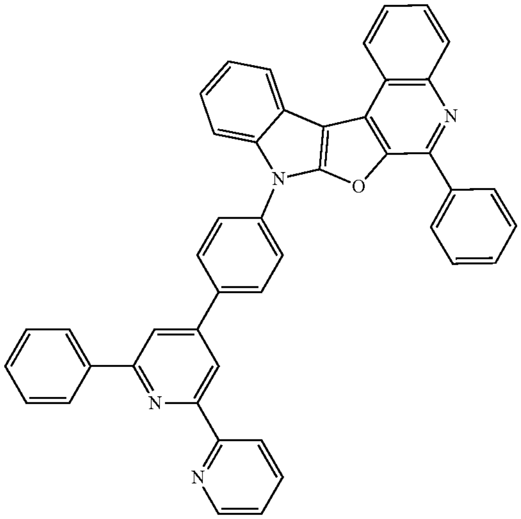 72%
231 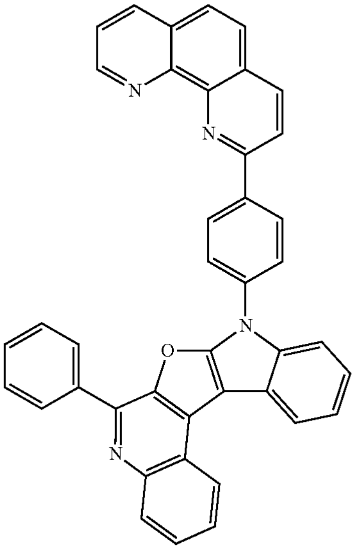 [SMILES: c1ccc(-c2nc3ccccc3c3c2oc2c3c3ccccc3n2-c2ccc(-c3ccc4ccc5cccnc5c4n3)cc2)cc1] 72%
232 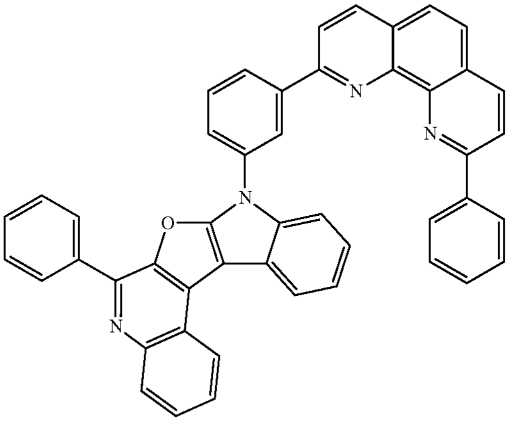 [SMILES: c1ccc(-c2ccc3ccc4ccc(-c5cccc(-n6c7ccccc7c7c8c(oc76)c(-c6ccccc6)nc6ccccc68)c5)nc4c3n2)cc1] 71%

TABLE 3-continued
| | | |
|---|---|---|
| 233 | 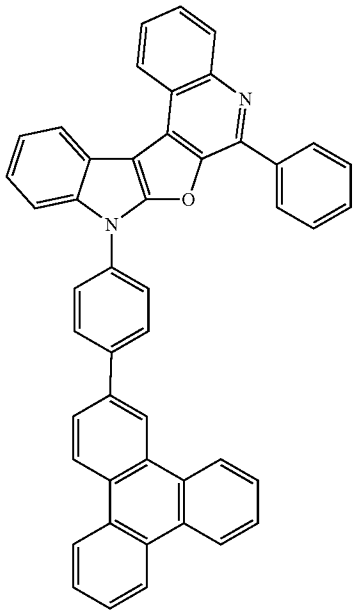 [SMILES: c1ccc(-c2nc3ccccc3c3c2oc2c3c3ccccc3n2-c2ccc(-c3ccc4c5ccccc5c5ccccc5c4c3)cc2)cc1] | 83% |
| 240 | 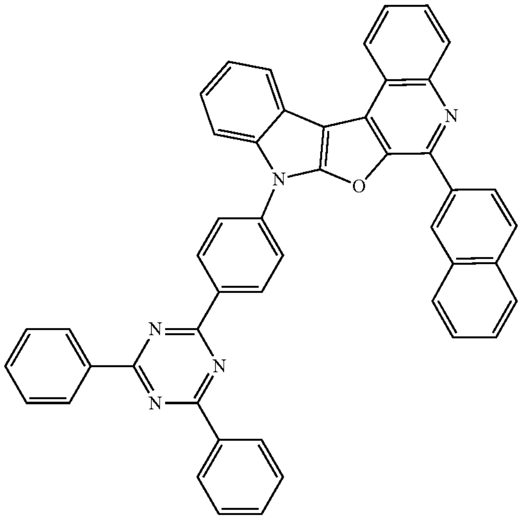 [SMILES: c1ccc(-c2nc(-c3ccccc3)nc(-c3ccc(-n4c5ccccc5c5c6c(oc54)c(-c4ccc5ccccc5c4)nc4ccccc46)cc3)n2)cc1] | 71% |

[Preparation Example 4] Preparation of Compound 041

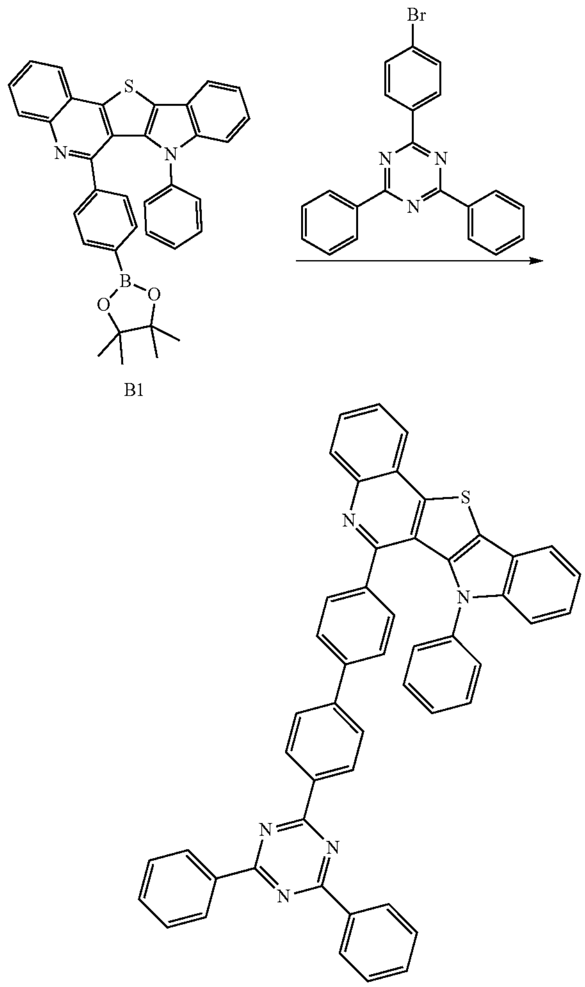

B1

041

Preparation of Compound 041

To a one-neck round bottom flask, Intermediate B1 (8 g, 14.48 mmol), 2-(4-bromophenyl)-4,6-diphenyl-1,3,5-triazine (5.9 g, 15.20 mmol), $K_2CO_3$ (6.00 g, 43.44 mmol), $Pd(PPh_3)_4$ (0.5 g, 0.43 mmol), toluene (100 ml), EtOH (20 ml) and $H_2O$ (20 ml) were introduced, and stirred for 10 hours under reflux. After the reaction was finished, the result was extracted with methylene chloride (MC) and $H_2O$, and, after removing the solvent, purified by column chromatography using dichloromethane and hexane as a developing solvent to obtain Compound 041 (8 g, 75%).

Final compounds were synthesized in the same manner as in Preparation Example 4 except that Intermediate B of the following Table 4 was used instead of Intermediate B1, and S7 of the following Table 4 was used instead of 2-(4-bromophenyl)-4,6-diphenyl-1,3,5-triazine.

TABLE 4

| Compound | Intermediate B | S7 |
|---|---|---|
| 049 | 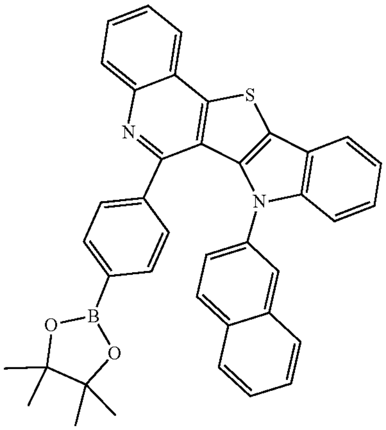 [SMILES: CC1(C)OB(c2ccc(-c3nc4ccccc4c4sc5c6ccccc6n(-c6ccc7ccccc7c6)c5c34)cc2)OC1(C)C] | 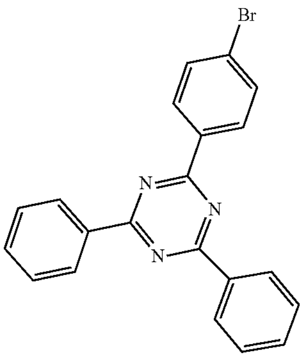 |

TABLE 4-continued
| | | |
|---|---|---|
| 059 | 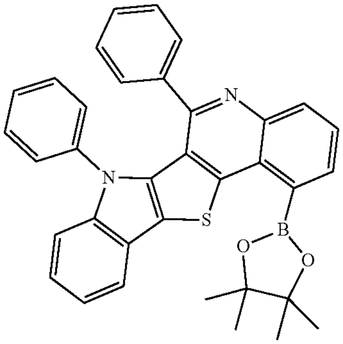 [SMILES: CC1(C)OB(c2cccc3nc(-c4ccccc4)c4c(sc5c6ccccc6n(-c6ccccc6)c54)c23)OC1(C)C] | 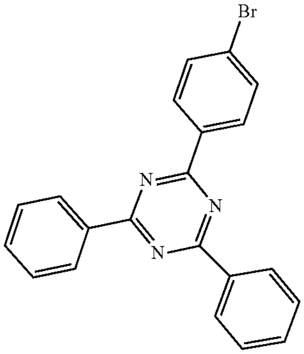 |
| 063 | 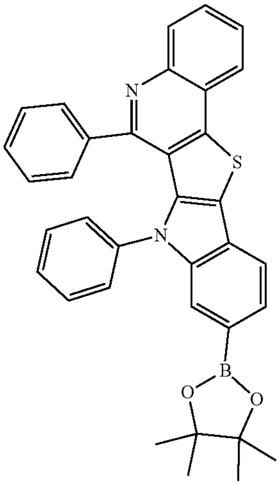 [SMILES: CC1(C)OB(c2ccc3c4sc5c6ccccc6nc(-c6ccccc6)c5c4n(-c4ccccc4)c3c2)OC1(C)C] | 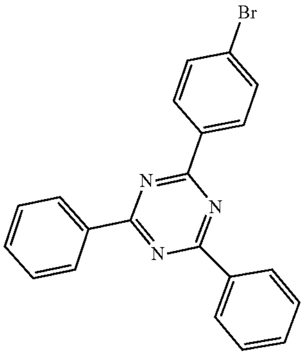 |
| 111 | 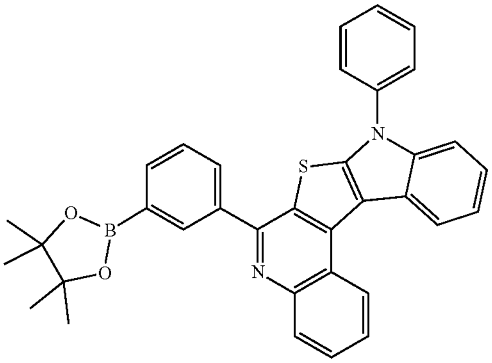 [SMILES: CC1(C)OB(c2cccc(-c3nc4ccccc4c4c3sc3c4c4ccccc4n3-c3ccccc3)c2)OC1(C)C] | 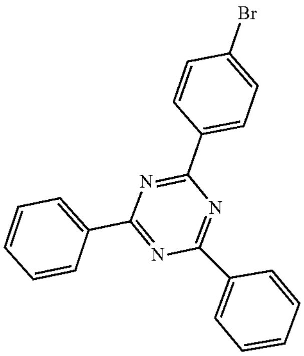 |
| 116 | 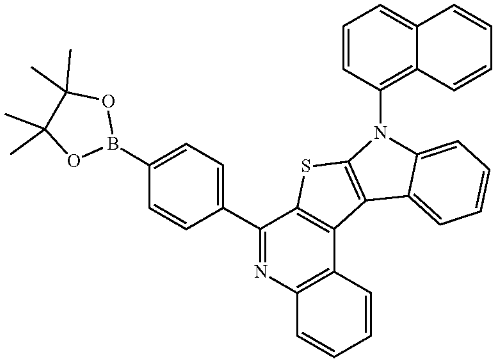 [SMILES: CC1(C)OB(c2ccc(-c3nc4ccccc4c4c3sc3c4c4ccccc4n3-c3cccc4ccccc34)cc2)OC1(C)C] | 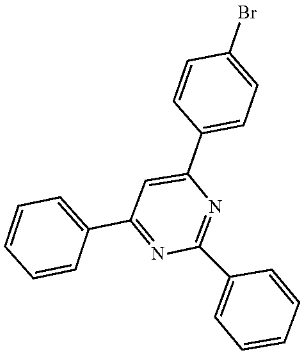 |

TABLE 4-continued
| | | |
|---|---|---|
| 123 | 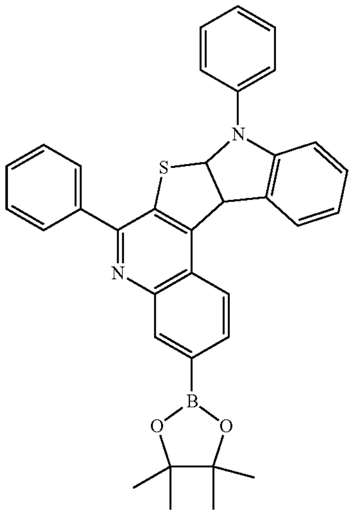 [SMILES: CC1(C)OB(c2ccc3c4c(c(-c5ccccc5)nc3c2)SC2C4c3ccccc3N2c2ccccc2)OC1(C)C] | 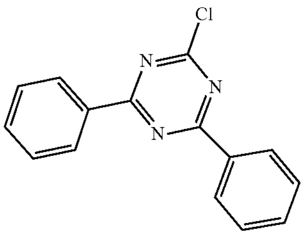 |
| 184 | 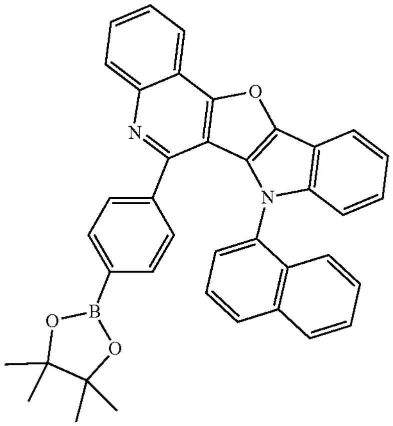 [SMILES: CC1(C)OB(c2ccc(-c3nc4ccccc4c4oc5c6ccccc6n(-c6cccc7ccccc67)c5c34)cc2)OC1(C)C] | 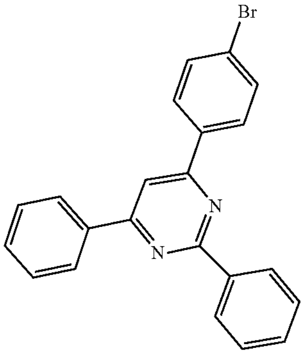 |
| 197 | 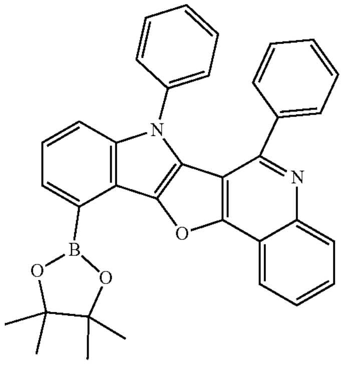 [SMILES: CC1(C)OB(c2cccc3c2c2oc4c5ccccc5nc(-c5ccccc5)c4c2n3-c2ccccc2)OC1(C)C] | 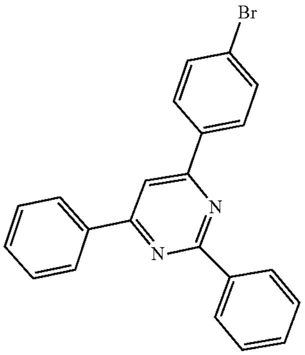 |

TABLE 4-continued
| | | |
|---|---|---|
| 246 | 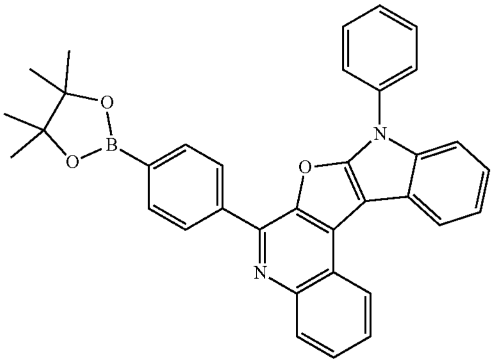 [SMILES: CC1(C)OB(c2ccc(-c3nc4ccccc4c4c3oc3c4c4ccccc4n3-c3ccccc3)cc2)OC1(C)C] | 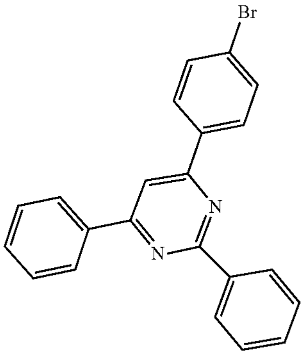 |
| Compound | Structure | Yield |
|---|---|---|
| 049 | 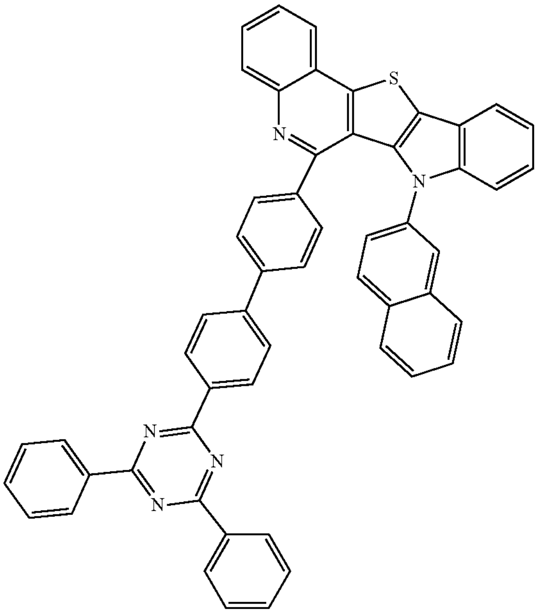 [SMILES: c1ccc(-c2nc(-c3ccccc3)nc(-c3ccc(-c4ccc(-c5nc6ccccc6c6sc7c8ccccc8n(-c8ccc9ccccc9c8)c7c56)cc4)cc3)n2)cc1] | 74% |
| 059 | 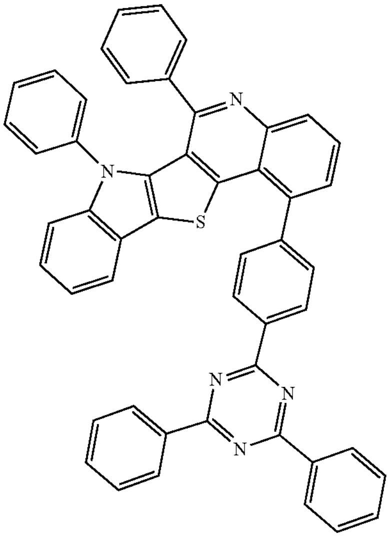 [SMILES: c1ccc(-c2nc(-c3ccccc3)nc(-c3ccc(-c4cccc5nc(-c6ccccc6)c6c(sc7c8ccccc8n(-c8ccccc8)c76)c45)cc3)n2)cc1] | 82% |

TABLE 4-continued
| | | |
|---|---|---|
| 063 | 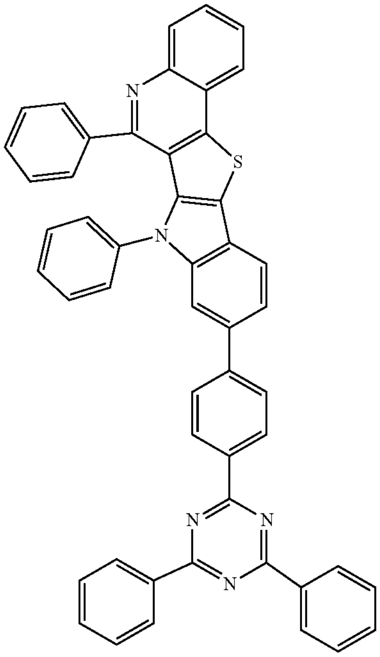 [SMILES: c1ccc(-c2nc(-c3ccccc3)nc(-c3ccc(-c4ccc5c6sc7c8ccccc8nc(-c8ccccc8)c7c6n(-c6ccccc6)c5c4)cc3)n2)cc1] | 81% |
| 111 | 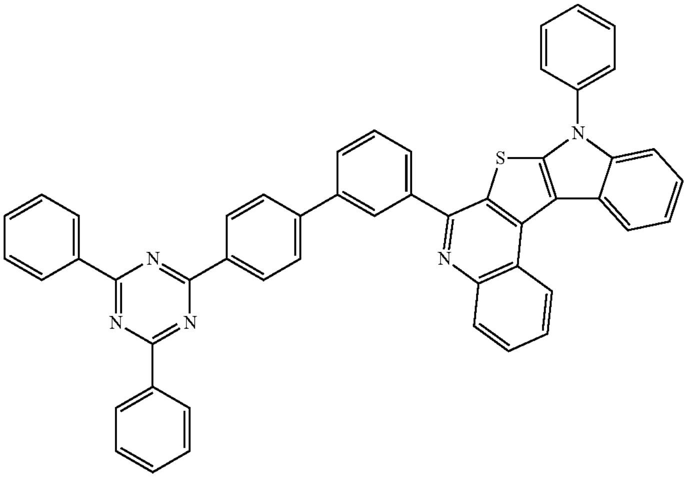 [SMILES: c1ccc(-c2nc(-c3ccccc3)nc(-c3ccc(-c4cccc(-c5nc6ccccc6c6c5sc5c6c6ccccc6n5-c5ccccc5)c4)cc3)n2)cc1] | 79% |
| 116 | 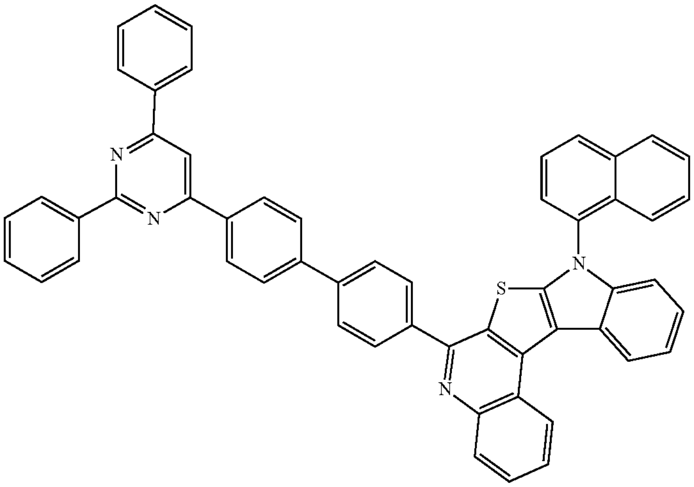 [SMILES: c1ccc(-c2cc(-c3ccc(-c4ccc(-c5nc6ccccc6c6c5sc5c6c6ccccc6n5-c5cccc6ccccc56)cc4)cc3)nc(-c3ccccc3)n2)cc1] | 72% |

TABLE 4-continued
123
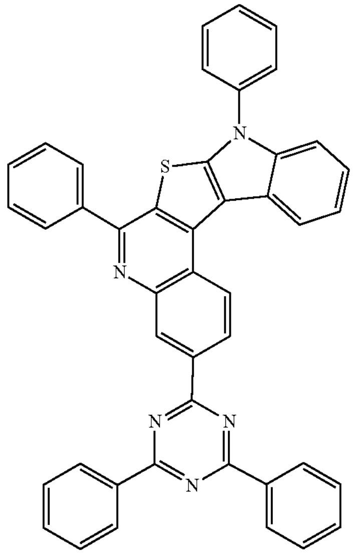 [SMILES: c1ccc(-c2nc(-c3ccccc3)nc(-c3ccc4c(c3)nc(-c3ccccc3)c3sc5c(c6ccccc6n5-c5ccccc5)c34)n2)cc1]
72%
184
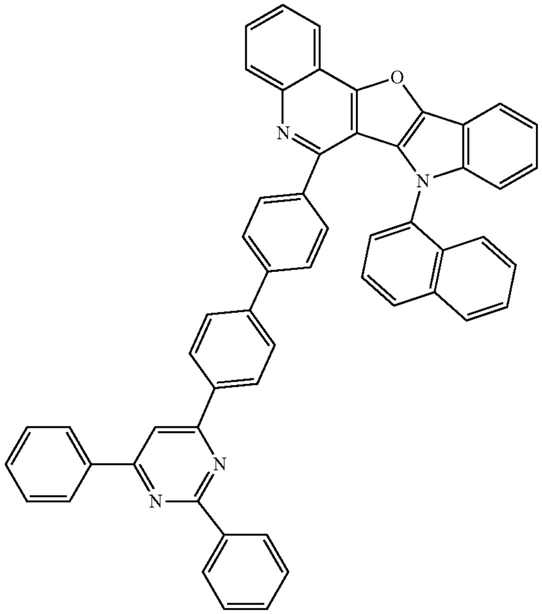 [SMILES: c1ccc(-c2cc(-c3ccc(-c4ccc(-c5nc6ccccc6c6oc7c8ccccc8n(-c8cccc9ccccc89)c7c56)cc4)cc3)nc(-c3ccccc3)n2)cc1]
71%

TABLE 4-continued

| | | |
|---|---|---|
| 197 | 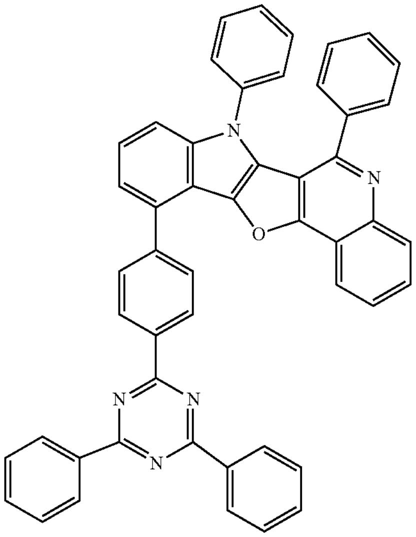 [SMILES: c1ccc(-c2nc(-c3ccccc3)nc(-c3ccc(-c4cccc5c4c4oc6c7ccccc7nc(-c7ccccc7)c6c4n5-c4ccccc4)cc3)n2)cc1] | 81% |
| 246 | 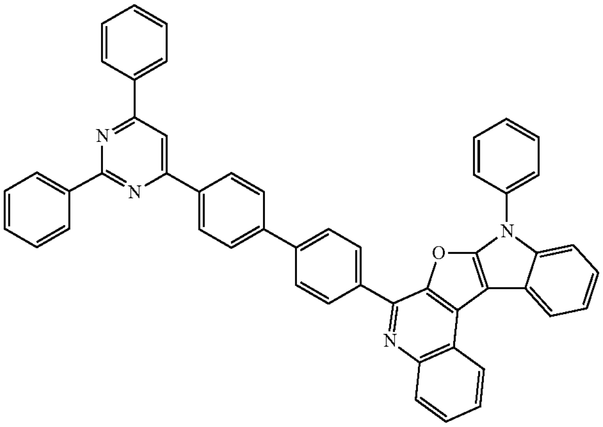 [SMILES: c1ccc(-c2cc(-c3ccc(-c4ccc(-c5nc6ccccc6c6c5oc5c6c6ccccc6n5-c5ccccc5)cc4)cc3)nc(-c3ccccc3)n2)cc1] | 71% |

Compounds other than the compounds described in Preparation Examples 1 to 4 and Tables 1 to 4 were also prepared in the same manner as the compounds described in Preparation Examples 1 to 4 and Tables 1 to 4, and the synthesis identification results are shown in the following Table 5 and Table 6.

Table 5 shows measurement values of 1H NMR ($CDCl_3$, 300 Mz), and Table 6 shows measurement values of FD-mass spectrometry (FD-MS: field desorption mass spectrometry).

TABLE 5

| NO | $^1$H NMR ($CDCl_3$, 300 Mz) |
|---|---|
| 001 | 8.43 (1H, d), 8.30-8.28 (6H, m), 8.06 (1H, d), 7.98-7.94 (2H, m), 7.79-7.78 (3H, m), 7.68-7.25 (14H, m), |
| 005 | 8.43 (1H, d), 8.30-8.28 (4H, m), 8.06 (1H, d), 7.98-7.94 (2H, m), 7.85-7.78 (5H, m), 7.68-7.25 (18H, m) |
| 007 | 8.43 (1H, d), 8.30-8.28 (6H, m), 8.06 (1H, d), 7.98-7.94 (2H, m), 7.85-7.78 (5H, m), 7.68-7.25 (16H, m) |
| 008 | 8.43 (1H, d), 8.30-8.28 (6H, m), 8.09-8.06 (2H, m), 7.98-7.94 (2H, m), 7.85-7.78 (3H, m), 7.60-7.25 (17H, m) |
| 011 | 9.09 (2H, d), 8.49-8.43 (3H, m), 8.30 (2H, d), 8.06-7.92 (9H, m), 7.79-7.78 (3H, m), 7.68-7.47 (10H, m), 7.33-7.25 (2H, m) |
| 014 | 8.43 (1H, d), 8.30-8.23 (5H, m), 8.06 (1H, d), 7.98-7.94 (2H, m), 7.79-7.78 (5H, m), 7.68-7.25 (14H, m) |

TABLE 5-continued

| NO | $^1$H NMR ($CDCl_3$, 300 Mz) |
|---|---|
| 023 | 8.43 (1H, d), 8.30-8.23 (5H, m), 8.09-8.06 (2H, m), 7.98-7.94 (2H, m), 7.79-7.70 (5H, m), 7.60-7.25 (17H, m) |
| 024 | 8.43 (1H, d), 8.30 (2H, d), 8.06 (1H, d), 7.98-7.91 (6H, m), 7.79-7.78 (3H, m), 7.68-7.25 (17H, m) |
| 025 | 8.56 (1H, d), 8.30 (2H, d), 8.06 (1H, d), 7.98-7.94 (2H, m), 7.78 (1H, t), 7.62-7.47 (9H, m), 7.33-7.22 (4H, m), 2.85 (2H, q), 1.25 (3H, t) |
| 026 | 9.30 (2H, d), 9.15 (2H, s), 8.53 (2H, d), 8.43 (1H, d), 8.30 (2H, d), 8.06-7.94 (3H, m), 7.79-7.47 (11H, m), 7.33-7.25 (2H, m), 7.14 (2H, t) |
| 027 | 8.83 (1H, d), 8.43-8.30 (6H, m), 8.10-7.94 (5H, m), 7.81-7.71 (4H, m), 7.60-7.47 (5H, m), 7.35-7.25 (3H, m) |
| 028 | 8.60 (1H, s), 8.43 (1H, d), 8.30 (5H, d), 8.10-8.06 (4H, m), 7.98-7.94 (2H, m), 7.81-7.78 (2H, m), 7.60-7.47 (9H, m), 7.35-7.25 (4H, m) |
| 029 | 9.15 (1H, s), 8.93 (2H, d), 8.43 (1H, d), 8.30 (2H, d), 8.12-7.47 (20H, m), 7.33-7.22 (2H, m) |
| 031 | 8.55 (1H, d), 8.46-8.43 (2H, m), 8.28 (4H, d), 8.10-8.06 (3H, m), 7.98-7.94 (2H, m), 7.79-7.78 (3H, m), 7.68-7.25 (14H, m) |
| 041 | 8.81 (2H, d), 8.43 (1H, d), 8.28 (4H, d), 8.06 (1H, d), 7.98-7.78 (7H, m), 7.60-7.25 (16H, m) |
| 049 | 8.81 (2H, d), 8.43 (1H, d), 8.28 (4H, d), 8.06-7.78 (12H, m), 7.60-7.25 (14H, m) |
| 059 | 8.43 (1H, d), 8.30-8.28 (6H, m), 8.03-7.94 (4H, m), 7.85 (2H, d), 7.58-7.25 (18H, m) |
| 063 | 8.49 (1H, d), 8.30-8.28 (6H, m), 8.10-8.06 (2H, m), 7.98 (1H, d), 7.85-7.78 (3H, m), 7.62-7.41 (16H, m), 7.25 (2H, d) |

TABLE 5-continued

| NO | $^1H$ NMR ($CDCl_3$, 300 Mz) |
|---|---|
| 069 | 8.55 (1H, d), 8.30-8.28 (6H, m), 8.06 (1H, d), 7.98-7.94 (2H, m), 7.79-7.78 (3H, m), 7.68-7.25 (14H, m) |
| 071 | 8.55 (1H, d), 8.30-8.24 (5H, m), 8.06 (1H, d), 7.98-7.94 (2H, m), 7.79-7.78 (3H, m), 7.68-7.25 (19H, m) |
| 075 | 8.55 (1H, d), 8.30-8.29 (6H, m), 8.06 (1H, d), 7.98-7.94 (2H, m), 7.85-7.78 (5H, m), 7.68-7.25 (16H, m) |
| 082 | 8.55 (1H, d), 8.30-8.23 (5H, m), 8.06 (1H, d), 7.98-7.94 (2H, m), 7.79-7.78 (5H, m), 7.68-7.25 (14H, m) |
| 092 | 8.55 (1H, d), 8.30 (2H, d), 8.06 (1H, d), 7.98-7.91 (6H, m), 7.79-7.78 (3H, m), 7.68-7.25 (17H, m) |
| 093 | 8.56-8.55 (2H, m), 8.30 (2H, d), 8.06 (1H, d), 7.98-7.94 (2H, m), 7.78 (1H, t), 7.62-7.47 (9H, m), 7.33-7.22 (4H, m), 2.85 (2H, q), 1.25 (3H, t) |
| 094 | 9.30 (2H, d), 9.15 (2H, s), 8.56-8.53 (3H, m), 8.30 (2H, d), 8.06-7.94 (3H, m), 7.79-7.47 (11H, m), 7.33-7.25 (2H, m), 7.14 (2H, t) |
| 095 | 8.83 (1H, d), 8.38-8.30 (5H, m), 8.10-7.94 (5H, m), 7.81-7.71 (4H, m), 7.60-7.47 (5H, m), 7.35-7.25 (3H, m) |
| 096 | 8.60-8.55 (2H, m), 8.30 (5H, d), 8.10-8.06 (4H, m), 7.98-7.94 (2H, m), 7.81-7.78 (2H, m), 7.60-7.47 (9H, m), 7.35-7.25 (4H, m) |
| 097 | 9.15 (1H, s), 8.93 (2H, d), 8.55 (1H, d), 8.30 (2H, d), 8.18-7.47 (20H, m), 7.33-7.25 (2H, m) |
| 099 | 8.55 (2H, d), 8.46 (1H, d), 8.28 (4H, d), 8.10-8.06 (3H, m), 7.98-7.94 (2H, m), 7.79-7.78 (3H, m), 7.68-7.25 (14H, m) |
| 106 | 8.85 (1H, d), 8.55 (1H, d), 8.38 (1H, d), 8.28 (4H, d), 8.06-7.94 (6H, m), 7.85-7.78 (5H, m), 7.68-7.25 (15H, m) |
| 111 | 8.55 (1H, d), 8.28-8.21 (6H, m), 8.06 (1H, d), 7.98-7.94 (2H, m), 7.85-7.78 (3H, m), 7.60-7.25 (18H, m) |
| 116 | 8.81 (2H, d), 8.55 (1H, d), 8.30-8.23 (5H, m), 8.08-7.78 (13H, m), 7.60-7.25 (13H, m) |
| 123 | 8.55 (1H, d), 8.30-8.27 (7H, m), 8.12 (1H, d), 8.03 (1H, d), 7.94 (1H, d), 7.58-7.25 (16H, m) |
| 137 | 8.43 (1H, d), 8.30-8.28 (6H, m), 8.06 (1H, d), 7.98-7.94 (2H, m), 7.79-7.78 (3H, m), 7.68-7.25 (14H, m) |
| 150 | 8.43 (1H, d), 8.30-8.23 (5H, m), 8.06 (1H, d), 7.98-7.94 (2H, m), 7.79-7.78 (6H, m), 7.68-7.25 (14H, m) |

TABLE 5-continued

| NO | $^1H$ NMR ($CDCl_3$, 300 Mz) |
|---|---|
| 162 | 9.30 (2H, d), 9.15 (2H, s), 8.53 (2H, d), 8.43 (1H, d), 8.30 (2H, d), 8.06-7.94 (3H, m), 7.79-7.47 (11H, m), 7.33-7.25 (2H, m), 7.14 (2H, t) |
| 163 | 8.83 (1H, d), 8.43-8.30 (6H, m), 8.10-7.94 (5H, m), 7.81-7.71 (4H, m), 760-7.47 (5H, m), 7.35-7.25 (3H, m) |
| 164 | 8.60 (1H, s), 8.43 (1H, d), 8.30 (5H, d), 8.10-8.06 (4H, m), 7.98-7.94 (2H, m), 7.81-7.78 (2H, m), 7.60-7.47 (9H, m), 7.35-7.25 (4H, m) |
| 165 | 9.15 (1H, s), 8.93 (2H, d), 8.43 (1H, d), 8.30 (2H, d), 8.18-7.47 (20H, m), 7.33-7.25 (2H, m) |
| 175 | 8.85 (1H, s), 8.43-8.38 (2H, m), 8.28-8.23 (3H, m), 8.06-7.94 (6H, m), 7.79-7.78 (5H, m), 7.68-7.25 (13H, m) |
| 184 | 8.81 (2H, d), 8.43 (1H, d), 8.30-8.23 (5H, m), 8.08-7.78 (13H, m), 7.60-7.25 (13H, m) |
| 197 | 8.30-8.28 (6H, m), 8.10-8.06 (2H, m), 7.98 (1H, d), 7.90-7.78 (4H, m), 7.60-7.39 (16H, m), 7.25 (2H, d) |
| 205 | 8.55 (1H, d), 8.30-8.28 (6H, m), 8.06 (1H, d), 7.98-7.94 (2H, m), 7.79-7.78 (3H, m), 7.68-7.25 (14H, m) |
| 218 | 8.55 (1H, d), 8.30-8.23 (5H, m), 8.06 (1H, d), 7.98-7.94 (2H, m), 7.79-7.78 (5H, m), 7.68-7.25 (14H, m) |
| 224 | 8.55 (1H, d), 8.30-8.23 (7H, m), 8.06 (1H, d), 7.98-7.94 (2H, m), 7.85-7.78 (7H, m), 7.68-7.25 (14H, m) |
| 230 | 9.30 (2H, d), 9.15 (2H, s), 8.55-8.53 (3H, m), 8.30 (2H, d), 8.06-7.94 (3H, m), 7.79-7.47 (11H, m), 7.33-7.25 (2H, m), 7.14 (2H, t) |
| 231 | 8.83 (1H, d), 8.55 (1H, d), 8.38-8.30 (5H, m), 8.10-7.94 (5H, m), 7.81-7.71 (4H, m), 7.60-7.47 (5H, m), 7.35-7.25 (3H, m) |
| 232 | 8.60-8.55 (2H, m), 8.30 (5H, d), 8.10-8.06 (4H, m), 7.98-7.94 (2H, m), 7.81-7.78 (2H, m), 7.60-7.47 (9H, m), 7.35-7.25 (4H, m) |
| 233 | 9.15 (1H, s), 8.93 (2H, d), 8.55 (1H, d), 8.30 (2H, d), 8.18-7.47 (20H, m), 7.33-7.25 (2H, m) |
| 240 | 8.85 (1H, d), 8.55 (1H, d), 8.38 (1H, d), 8.28 (4H, d), 8.06-7.94 (6H, m), 7.79-7.78 (3H, m), 7.68-7.25 (13H, m) |
| 246 | 8.81 (2H, d), 8.55 (1H, d), 8.30-8.23 (5H, m), 8.06 (1H, d), 7.98-7.78 (9H, m), 7.60-7.25 (14H, m) |

TABLE 6

| Compound | FD-MS | Compound | FD-MS |
|---|---|---|---|
| 001 | m/z=657.78 ($C_{44}H_{27}N_5S$=657.20) | 005 | m/z=733.88 ($C_{50}H_{31}N_5S$=733.23) |
| 007 | m/z=733.88 ($C_{50}H_{31}N_5S$=733.23) | 008 | m/z=733.88 ($C_{50}H_{31}N_5S$=733.23) |
| 011 | m/z=757.90 ($C_{52}H_{31}N_5S$=757.23) | 014 | m/z=656.80 ($C_{45}H_{28}N_4S$=656.20) |
| 023 | m/z=732.89 ($C_{51}H_{32}N_4S$=732.23) | 024 | m/z=678.84 ($C_{49}H_{30}N_2S$=678.21) |
| 025 | m/z=570.70 ($C_{38}H_{26}N_4S$=570.19) | 026 | m/z=657.78 ($C_{44}H_{27}N_5S$=657.20) |
| 027 | m/z=604.72 ($C_{41}H_{24}N_4S$=604.17) | 028 | m/z=680.82 ($C_{47}H_{28}N_4S$=680.20) |
| 029 | m/z=652.80 ($C_{47}H_{28}N_2S$=652.20) | 031 | m/z=707.84 ($C_{48}H_{29}N_5S$=707.21) |
| 041 | m/z=733.88 ($C_{50}H_{31}N_5S$=733.23) | 049 | m/z=783.94 ($C_{54}H_{33}N_5S$=783.25) |
| 059 | m/z=733.88 ($C_{50}H_{31}N_5S$=733.23) | 063 | m/z=733.88 ($C_{50}H_{31}N_5S$=733.23) |
| 069 | m/z=657.78 ($C_{44}H_{27}N_5S$=657.20) | 071 | m/z=733.88 ($C_{50}H_{31}N_5S$=733.23) |
| 075 | m/z=733.88 ($C_{50}H_{31}N_5S$=733.23) | 082 | m/z=656.80 ($C_{45}H_{28}N_4S$=656.20) |
| 092 | m/z=678.84 ($C_{49}H_{30}N_2S$=678.21) | 093 | m/z=570.70 ($C_{38}H_{26}N_4S$=570.19) |
| 094 | m/z=657.78 ($C_{44}H_{27}N_5S$=657.20) | 095 | m/z=604.72 ($C_{41}H_{24}N_4S$=604.17) |
| 096 | m/z=680.82 ($C_{47}H_{28}N_4S$=680.20) | 097 | m/z=652.80 ($C_{47}H_{28}N_2S$=652.20 |
| 099 | m/z=707.84 ($C_{48}H_{29}N_5S$=707.21) | 106 | m/z=783.94 ($C_{54}H_{33}N_5S$=783.25) |
| 111 | m/z=733.88 ($C_{50}H_{31}N_5S$=733.23) | 116 | m/z=782.95 ($C_{55}H_{34}N_4S$=782.25) |
| 123 | m/z=657.78 ($C_{44}H_{27}N_5S$=657.20) | 137 | m/z=641.72 ($C_{44}H_{27}N_5O$=641.22) |
| 150 | m/z=640.73 ($C_{45}H_{28}N_4O$=640.23) | 162 | m/z=641.72 ($C_{44}H_{27}N_5O$=641.22) |
| 163 | m/z=588.66 ($C_{41}H_{24}N_4O$=588.20) | 164 | m/z=664.75 ($C_{47}H_{28}N_4O$=664.23) |
| 165 | m/z=636.74 ($C_{47}H_{28}N_2O$=636.22) | 175 | m/z=690.79 ($C_{49}H_{30}N_4O$=690.24) |
| 184 | m/z=766.88 ($C_{55}H_{34}N_4O$=766.27) | 197 | m/z=717.81 ($C_{50}H_{31}N_5O$=717.25) |
| 205 | m/z=641.72 ($C_{44}H_{27}N_5O$=641.22) | 218 | m/z=640.73 ($C_{45}H_{28}N_4O$=640.23) |
| 224 | m/z=716.83 ($C_{51}H_{32}N_4O$=716.26) | 230 | m/z=641.72 ($C_{44}H_{27}N_5O$=641.22) |
| 231 | m/z=588.66 ($C_{41}H_{24}N_4O$=588.20) | 232 | m/z=664.75 ($C_{47}H_{28}N_4O$=664.23) |
| 233 | m/z=636.74 ($C_{47}H_{28}N_2O$=636.22) | 246 | m/z=716.83 ($C_{51}H_{32}N_4O$=716.26) |

EXPERIMENTAL EXAMPLE

Experimental Example 1

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

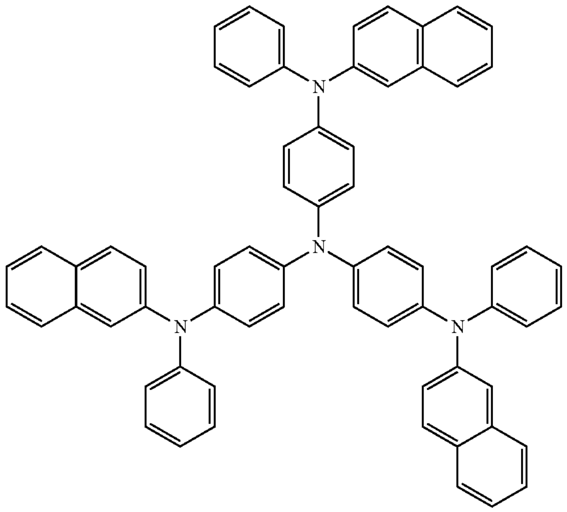

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

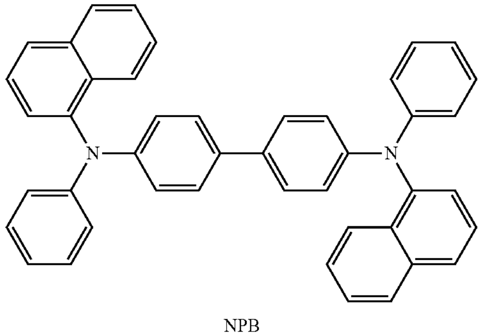 [SMILES: c1ccc(N(c2ccc(-c3ccc(N(c4ccccc4)c4cccc5ccccc45)cc3)cc2)c2cccc3ccccc23)cc1 ; "NPB"]

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

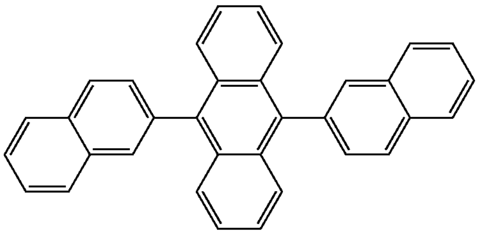

D1

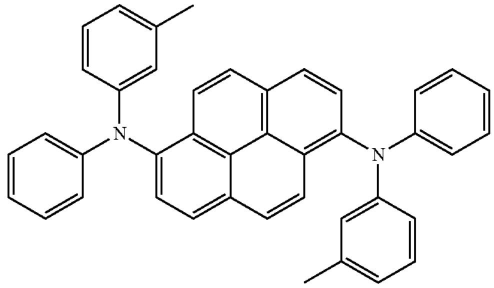

Subsequently, a compound shown in the following Table 7 was deposited to a thickness of 300 Å as an electron transfer layer.

As an electron injection layer, lithium fluoride (LiF) was deposited to a thickness of 10 Å, and an A1 cathode was employed to a thickness of 1,000 Å, and as a result, an OLED was manufactured.

Meanwhile, all the organic compounds required to manufacture the OLED were vacuum sublimation purified under $10^{-8}$ torr to $10^{-6}$ torr by each material to be used in the OLED manufacture.

Results of measuring driving voltage, light emission efficiency, color coordinate (CIE) and lifetime of the blue organic light emitting devices manufactured according to the present disclosure are as shown in the following Table 7.

TABLE 7

| | Compound | Driving Voltage (V) | Light Emission Efficiency (cd/A) | CIE (x, y) | Lifetime (T95) |
|---|---|---|---|---|---|
| Comparative Example 1-1 | E1 | 5.21 | 5.91 | (0.134, 0.100) | 60 |
| Comparative Example 1-2 | E2 | 5.13 | 6.10 | (0.134, 0.101) | 65 |
| Comparative Example 1-3 | E3 | 5.19 | 6.15 | (0.134, 0.102) | 64 |
| Example 1 | 001 | 4.46 | 6.75 | (0.134, 0.101) | 85 |
| Example 2 | 005 | 5.06 | 6.54 | (0.134, 0.102) | 67 |
| Example 3 | 007 | 5.14 | 6.30 | (0.134, 0.101) | 68 |
| Example 4 | 008 | 4.92 | 6.40 | (0.134, 0.103) | 71 |
| Example 5 | 011 | 4.53 | 7.11 | (0.134, 0.102) | 84 |
| Example 6 | 014 | 4.83 | 6.59 | (0.134, 0.101) | 73 |
| Example 7 | 023 | 5.03 | 6.52 | (0.134, 0.102) | 69 |
| Example 8 | 024 | 5.02 | 6.48 | (0.134, 0.101) | 75 |

TABLE 7-continued

| | Compound | Driving Voltage (V) | Light Emission Efficiency (cd/A) | CIE (x, y) | Lifetime (T95) |
|---|---|---|---|---|---|
| Example 9 | 025 | 4.91 | 6.39 | (0.134, 0.101) | 67 |
| Example 10 | 026 | 4.92 | 6.63 | (0.134, 0.100) | 66 |
| Example 11 | 029 | 4.99 | 6.35 | (0.134, 0.101) | 69 |
| Example 12 | 031 | 4.77 | 6.31 | (0.134, 0.100) | 105 |
| Example 13 | 041 | 4.48 | 6.62 | (0.134, 0.100) | 82 |
| Example 14 | 049 | 5.08 | 6.52 | (0.134, 0.100) | 75 |
| Example 15 | 059 | 5.10 | 6.37 | (0.134, 0.100) | 72 |
| Example 16 | 063 | 5.15 | 6.48 | (0.134, 0.100) | 69 |
| Example 17 | 069 | 4.44 | 6.68 | (0.134, 0.102) | 82 |
| Example 18 | 071 | 5.12 | 6.28 | (0.134, 0.101) | 74 |
| Example 19 | 075 | 5.09 | 6.59 | (0.134, 0.102) | 67 |
| Example 20 | 082 | 4.42 | 6.68 | (0.134, 0.100) | 80 |
| Example 21 | 092 | 4.91 | 6.44 | (0.134, 0.103) | 63 |
| Example 22 | 093 | 5.03 | 6.47 | (0.134, 0.100) | 66 |
| Example 23 | 097 | 4.86 | 6.71 | (0.134, 0.102) | 78 |
| Example 24 | 099 | 5.00 | 6.47 | (0.134, 0.100) | 71 |
| Example 25 | 106 | 5.07 | 6.46 | (0.134, 0.101) | 74 |
| Example 26 | 111 | 5.20 | 6.51 | (0.134, 0.100) | 74 |
| Example 27 | 116 | 5.03 | 6.68 | (0.134, 0.100) | 68 |
| Example 28 | 123 | 5.08 | 64 | (0.134, 0.101) | 73 |
| Example 29 | 137 | 4.38 | 6.91 | (0.134, 0.100) | 84 |
| Example 30 | 150 | 4.87 | 6.36 | (0.134, 0.100) | 69 |
| Example 31 | 165 | 4.79 | 6.61 | (0.134, 0.100) | 70 |
| Example 32 | 175 | 4.45 | 6.79 | (0.134, 0.100) | 82 |
| Example 33 | 184 | 4.85 | 6.68 | (0.134, 0.100) | 75 |
| Example 34 | 197 | 4.82 | 6.49 | (0.134, 0.102) | 78 |
| Example 35 | 205 | 5.12 | 6.44 | (0.134, 0.101) | 78 |
| Example 36 | 218 | 5.09 | 6.74 | (0.134, 0.102) | 72 |
| Example 37 | 224 | 4.72 | 6.72 | (0.134, 0.100) | 71 |
| Example 38 | 233 | 4.81 | 6.45 | (0.134, 0.103) | 70 |
| Example 39 | 240 | 5.08 | 6.60 | (0.134, 0.100) | 69 |
| Example 40 | 246 | 4.90 | 6.56 | (0.134, 0.102) | 68 |

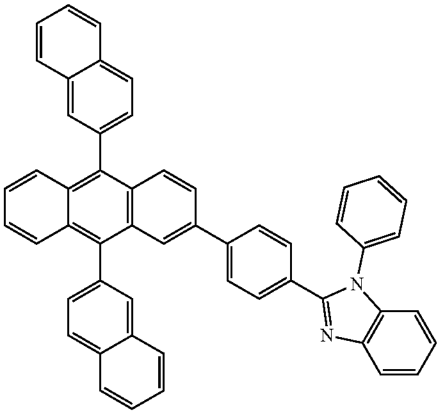

E1

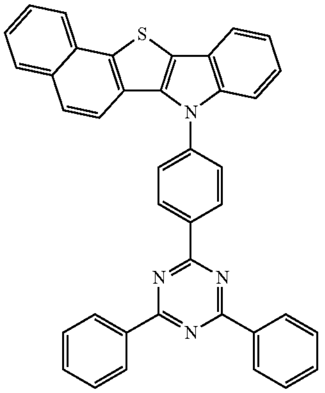

E2

TABLE 7-continued

| | Compound | Driving Voltage (V) | Light Emission Efficiency (cd/A) | CIE (x, y) | Lifetime (T95) |
|---|---|---|---|---|---|

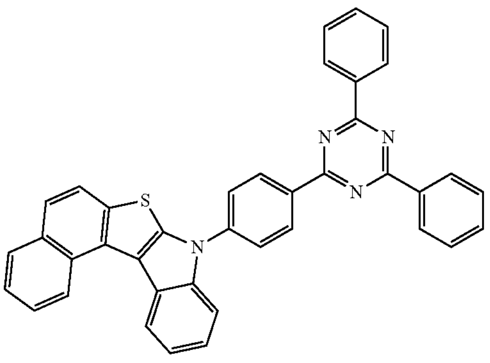

E3

As seen from the results of Table 7, the organic light emitting device using the electron transfer layer material of the blue organic light emitting device of the present disclosure had lower driving voltage, and improved light emission efficiency and lifetime compared to Comparative Examples 1-1 to 1-3. Particularly, it was identified that Compounds 001, 011, 031, 041, 069, 082, 137 and 175 were superior in all aspects of driving, efficiency and lifetime.

Such a result is considered to be due to the fact that, when using the disclosed compound having proper length and strength, and flatness as the electron transfer layer, a compound in an excited state is made by receiving electrons under a specific condition, and particularly when an excited state is formed in the hetero-skeleton site of the compound, excited energy will move to a stable state before the excited hetero-skeleton site goes through other reactions, and as a result, the relatively stabilized compound is capable of efficiently transferring electrons without the compound being decomposed or destroyed. For reference, those that are stable when excited are aryl or acene-based compounds or polycyclic hetero-compounds. When compared with Comparative Examples 1-2 and 1-3, Compounds E2 and E3 have a naphthalene ring formed in the basic skeleton, whereas the compound of the present disclosure has a quinoline-type ring formed therein instead of a naphthalene ring, which was identified to enhance electron mobility and thereby enhance a charge balance in the light emitting layer, and resultantly improve all of driving, lifetime and efficiency. In conclusion, it is considered that the compound of the present disclosure brings superiority in all aspects of driving, efficiency and lifetime by enhancing enhanced electron-transfer properties or improved stability.

Experimental Example 2

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, the ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

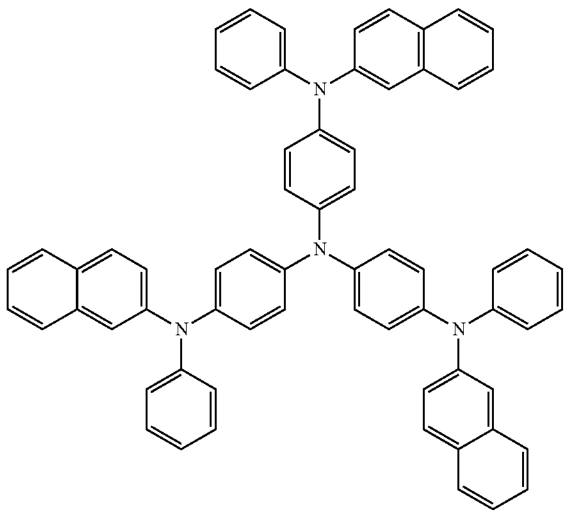

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

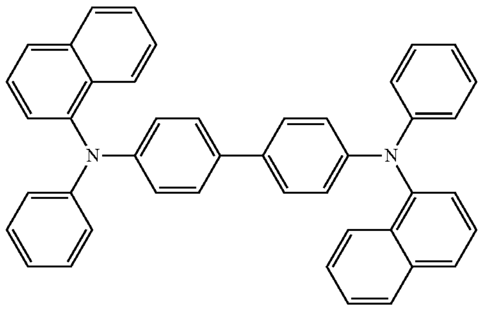

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

H1

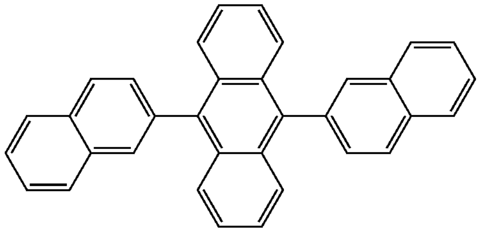

D1

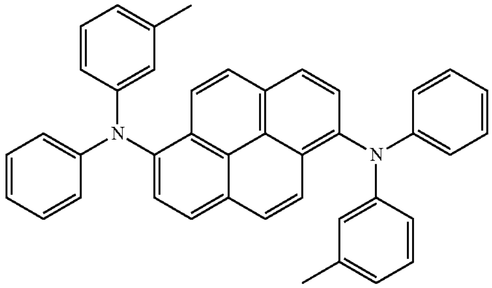

Subsequently, a hole blocking layer was formed to a thickness of 50 Å using a compound shown in the following Table 8, and then an electron transfer layer was formed on the hole blocking layer to a thickness of 250 Å using E1.

E1

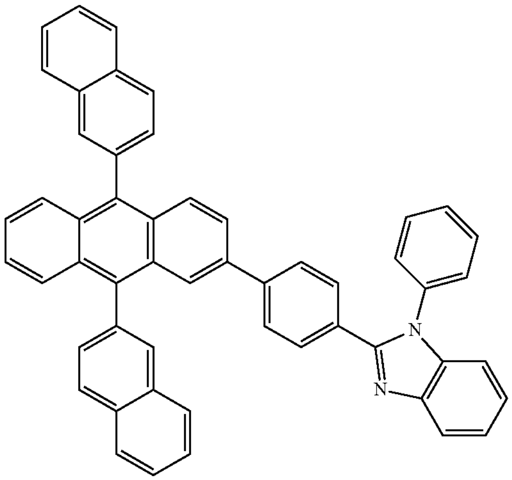

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-8}$ torr to $10^{-6}$ torr by each material to be used in the OLED manufacture.

Results of measuring driving voltage, light emission efficiency, color coordinate (CIE) and lifetime of the blue organic light emitting devices manufactured according to the present disclosure are as shown in the following Table 8.

TABLE 8

| | Compound | Driving Voltage (V) | Light Emission Efficiency (cd/A) | CIE (x, y) | Lifetime (T95) |
|---|---|---|---|---|---|
| Comparative Example 2 | E1 | 5.45 | 5.57 | (0.134, 0.100) | 55 |
| Example 41 | 005 | 5.20 | 6.17 | (0.134, 0.101) | 67 |
| Example 42 | 024 | 5.21 | 6.49 | (0.134, 0.102) | 66 |
| Example 43 | 025 | 5.11 | 6.26 | (0.134, 0.101) | 62 |
| Example 44 | 029 | 5.17 | 6.54 | (0.134, 0.103) | 61 |
| Example 45 | 041 | 5.23 | 6.19 | (0.134, 0.101) | 65 |
| Example 46 | 049 | 5.23 | 6.41 | (0.134, 0.102) | 57 |
| Example 47 | 063 | 5.15 | 6.45 | (0.134, 0.101) | 56 |
| Example 48 | 069 | 5.07 | 6.38 | (0.134, 0.103) | 59 |
| Example 49 | 092 | 5.17 | 6.24 | (0.134, 0.103) | 61 |
| Example 50 | 093 | 5.04 | 6.08 | (0.134, 0.101) | 60 |
| Example 51 | 137 | 5.09 | 6.33 | (0.134, 0.102) | 57 |
| Example 52 | 165 | 5.16 | 6.41 | (0.134, 0.101) | 58 |
| Example 53 | 205 | 5.27 | 6.52 | (0.134, 0.103) | 61 |
| Example 54 | 233 | 5.11 | 6.40 | (0.134, 0.103) | 60 |

As seen from the results of Table 8, the organic electroluminescent device using the hole blocking layer material of the blue organic electroluminescent device of the present disclosure had lower driving voltage, and significantly improved light emission efficiency and lifetime compared to Comparative Example 2.

Experimental Example 3

1) Manufacture of Organic Light Emitting Device

A transparent indium tin oxide (ITO) electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. The light emitting layer was deposited to 300 Å by doping TCz1, a host, with FIrpic, a blue phosphorescent dopant, by 8%. After forming an electron transfer layer to 400 Å using TmPyPB, a compound described in the following Table 9 was doped with $Cs_2CO_3$ by 20% to form a charge generation layer to 100 Å.

As for the second stack, $MoO_3$ was thermal vacuum deposited first to a thickness of 50 Å to form a hole injection layer. A hole transfer layer that is a common layer was formed to 100 Å by doping $MoO_3$ to TAPC by 20%, and then depositing TAPC to 300 Å. A light emitting layer was deposited to 300 Å thereon by doping TCz1, a host, with $Ir(ppy)_3$, a green phosphorescent dopant, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Meanwhile, all the organic compounds required to manufacture the OLED were vacuum sublimation purified under $10^{-8}$ torr to $10^{-6}$ torr for each material to be used in the OLED manufacture.

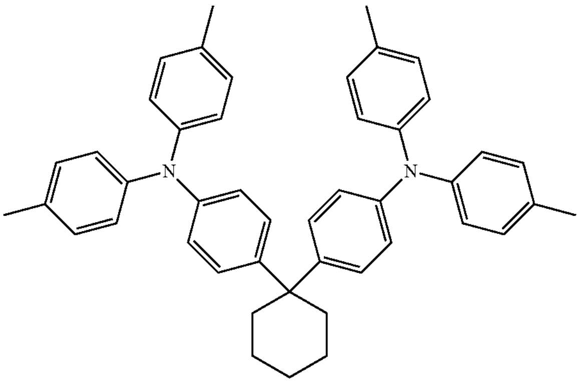

TAPC

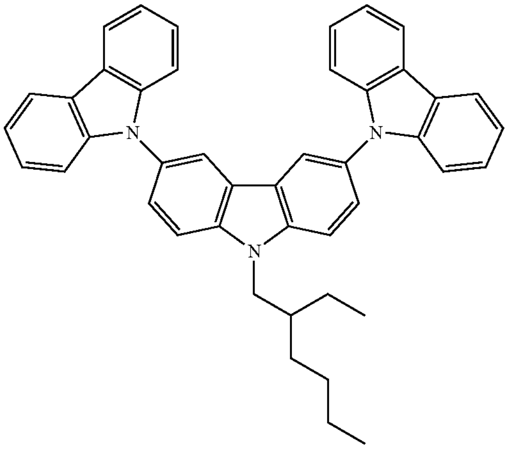

TCz1

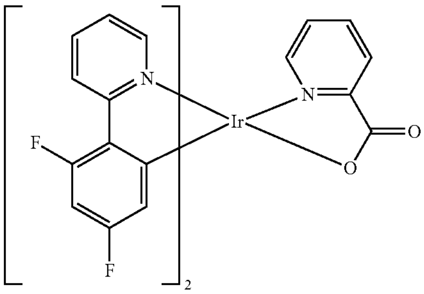

FIrpic

-continued

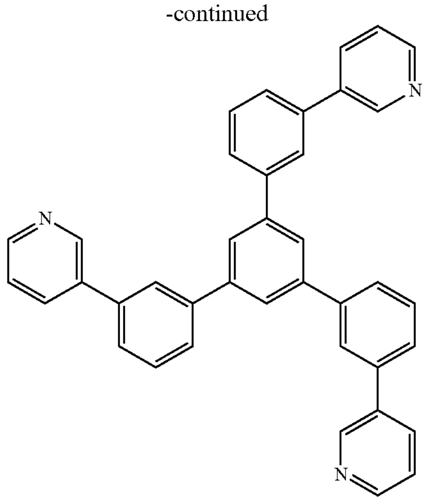

TmPyPB

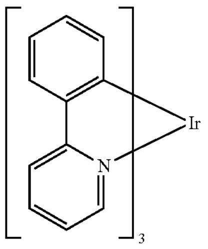

Ir(ppy)3

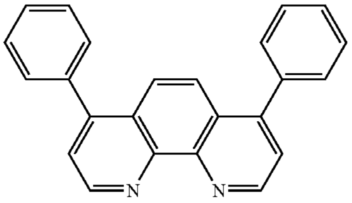

BPhen

Results of measuring driving voltage, light emission efficiency, color coordinate (CIE) and lifetime of the white organic light emitting devices manufactured according to the present disclosure are as shown in the following Table 9.

TABLE 9

| | Compound | Driving Voltage (V) | Light Emission Efficiency (cd/A) | CIE (x, y) | Lifetime (T95) |
|---|---|---|---|---|---|
| Comparative Example 3 | BPhen | 7.34 | 55.12 | (0.213, 0.430) | 35 |
| Example 55 | 026 | 6.84 | 60.47 | (0.212, 0.421) | 42 |
| Example 56 | 027 | 6.44 | 65.34 | (0.211, 0.433) | 40 |
| Example 57 | 028 | 6.56 | 63.68 | (0.214, 0.439) | 45 |
| Example 58 | 094 | 6.37 | 65.91 | (0.212, 0.424) | 41 |
| Example 59 | 095 | 6.82 | 64.18 | (0.214, 0.437) | 42 |
| Example 60 | 096 | 6.73 | 65.41 | (0.212, 0.426) | 45 |
| Example 61 | 162 | 6.72 | 63.11 | (0.214, 0.437) | 43 |
| Example 62 | 163 | 6.34 | 68.49 | (0.213, 0.424) | 48 |
| Example 63 | 164 | 6.37 | 65.09 | (0.213, 0.423) | 46 |
| Example 64 | 230 | 6.38 | 66.32 | (0.211, 0.433) | 49 |
| Example 65 | 231 | 6.49 | 67.16 | (0.214, 0.439) | 49 |
| Example 66 | 232 | 6.46 | 64.88 | (0.212, 0.424) | 51 |

As seen from the results of Table 9, it was identified that the organic electroluminescent device using the charge generation layer material of the 2-stack white organic electroluminescent device of the present disclosure had lower driving voltage and improved light emission efficiency compared to Comparative Example 3. Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal thereto, and electrons produced from a P-type charge generation layer are readily injected into the electron transfer layer through the gap state produced in the N-type charge generation layer. Accordingly, it is considered that the P-type charge generation layer may favorably inject and transfer electrons to the N-type charge generation layer, and as a result, driving voltage was lowered, and efficiency and lifetime were improved in the organic light emitting device.

The invention claimed is:

1. A heterocyclic compound represented by the following Chemical Formula 2:

[Chemical Formula 2]

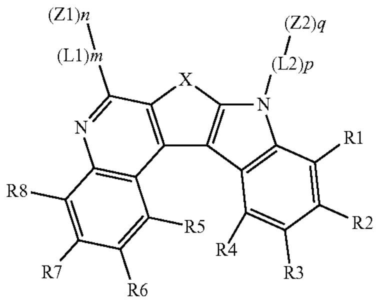

wherein, in Chemical Formula 2,

X is O; or S;

R1 to R8 are the same as or different from each other, and each independently selected from the group consisting of hydrogen; deuterium; a substituted or unsubstituted C6 to C40 aryl group; and a substituted or unsubstituted C2 to C40 heteroaryl group, L1 and L2 are a C6 to C40 monocyclic arylene group; or a C10 to C40 polycyclic arylene group, Z1 and Z2 are hydrogen; a substituted or unsubstituted C1 to C40 alkyl group; a substituted or unsubstituted C6 to C40 aryl group; a substituted or unsubstituted C2 to C40 heteroaryl group; or —P(═O)RR', R, and R' are the same as or different from each other, and each independently a substituted or unsubstituted C6 to C40 aryl group;

m and p are an integer of 1 to 4, and when m is 2 or greater, the two or more L1s are the same as or different from each other, and when p is 2 or greater, the two or more L2s are the same as or different from each other; and n and q are an integer of 1 to 6, and when n is 2 or greater, the two or more Z1s are the same as or different from each other, and when q is 2 or greater, the two or more Z2s are the same as or different from each other, "substituted or unsubstituted" means being substituted with one or more substituents selected from the group consisting of C1 to C60 linear or branched alkyl; C6 to C60 monocyclic or polycyclic aryl; C2 to C60 monocyclic or polycyclic heteroaryl; and —P(═O)RR'; or being unsubstituted, or being substituted with a substituent linking two or more substituents selected from among the substituents above, or being unsubstituted.
2. The heterocyclic compound of claim 1, wherein Chemical Formula 2 is represented by any one of the following compounds:
069
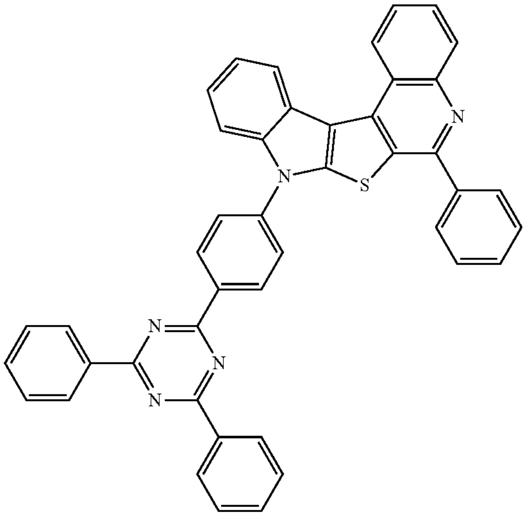
070
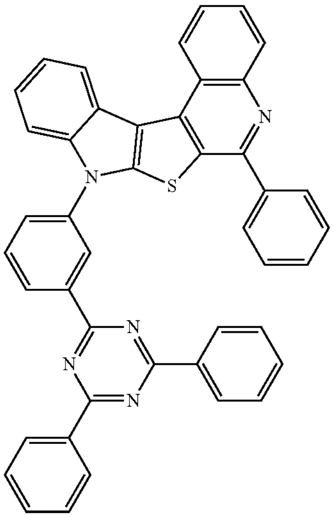
-continued
071
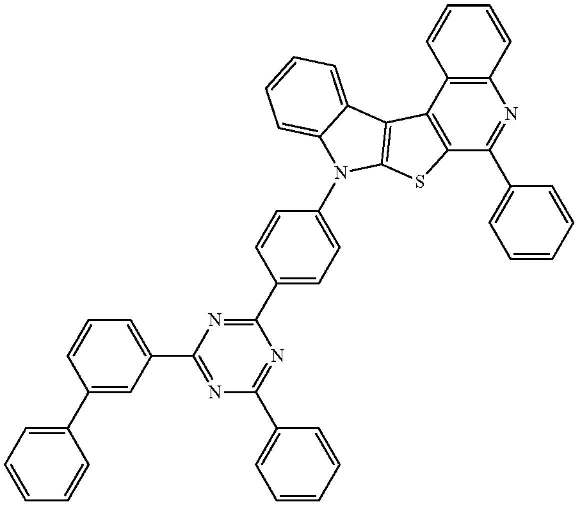
072
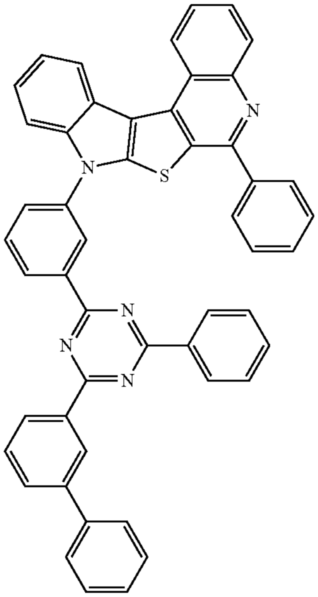
073
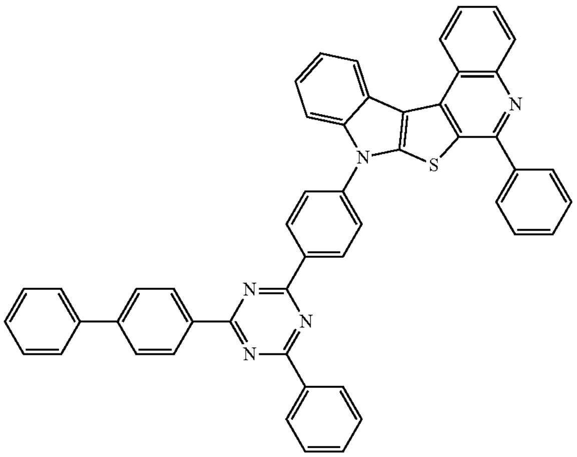

-continued
074
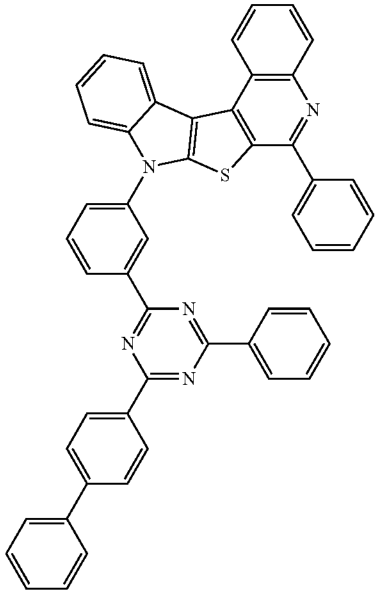
075
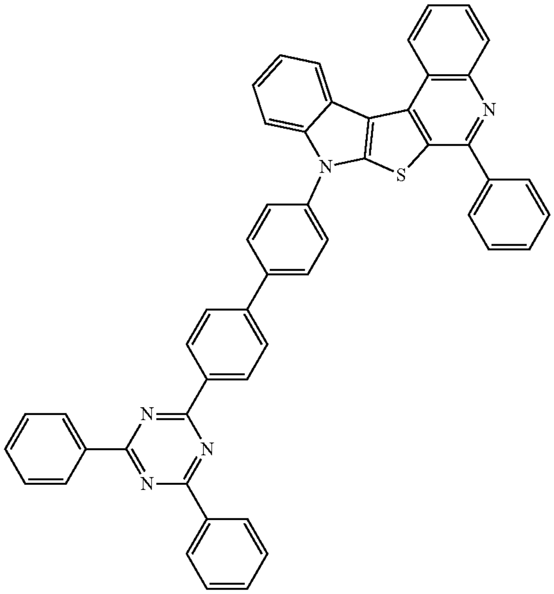
-continued
076
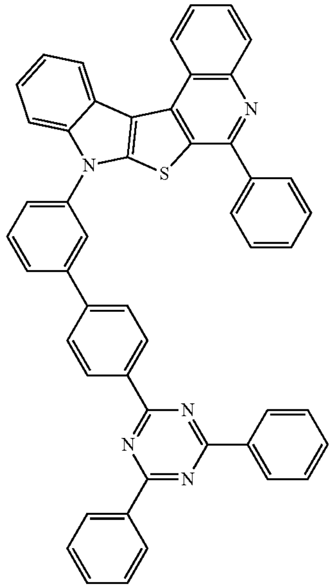
077
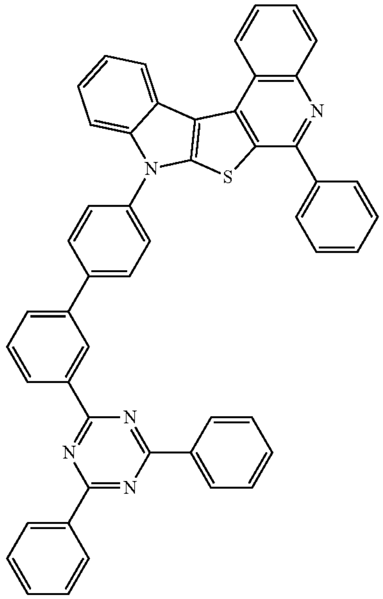
078
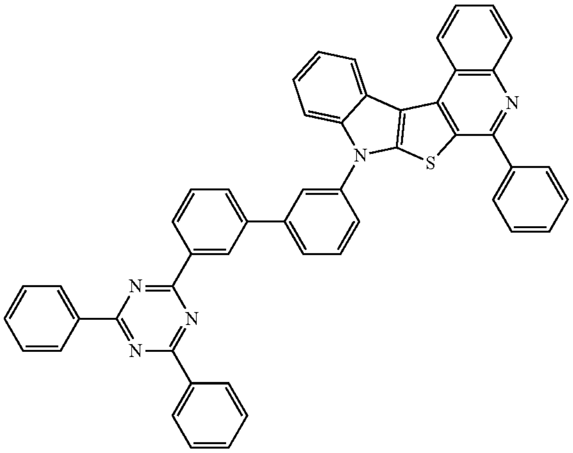

-continued
079
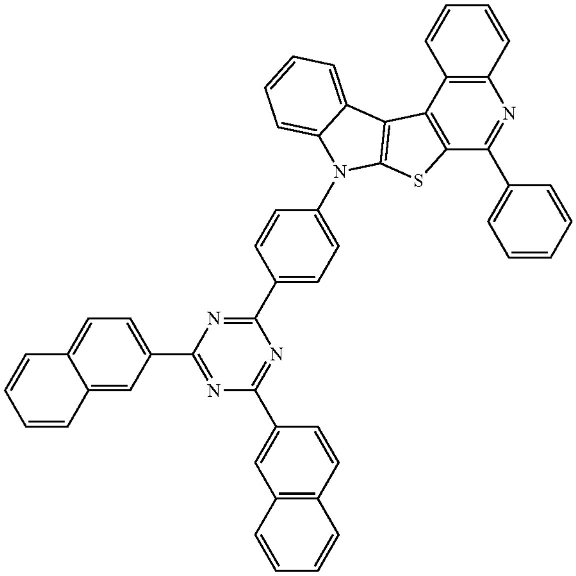
080
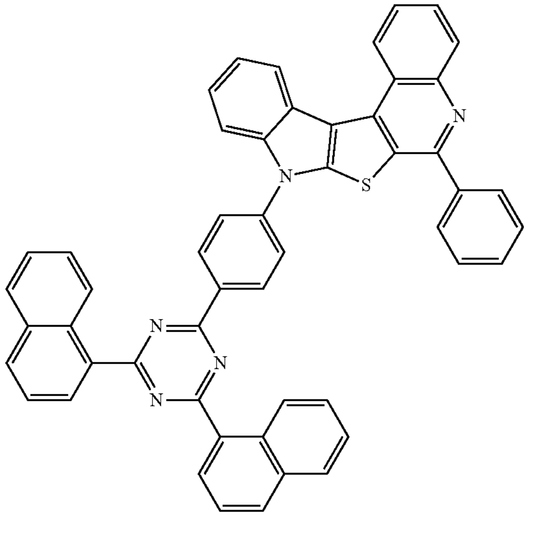
-continued
081
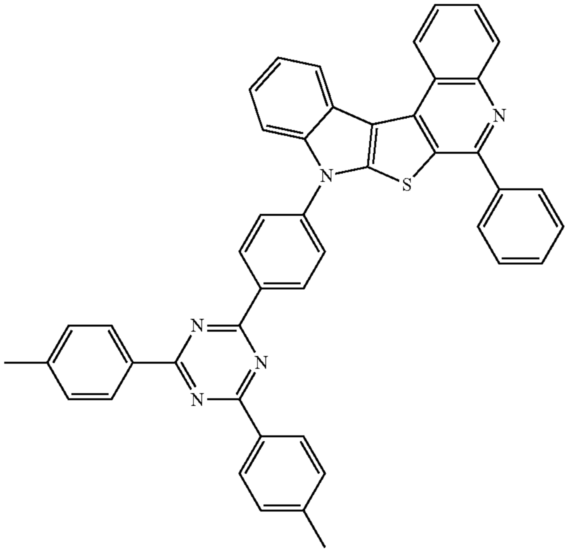
082
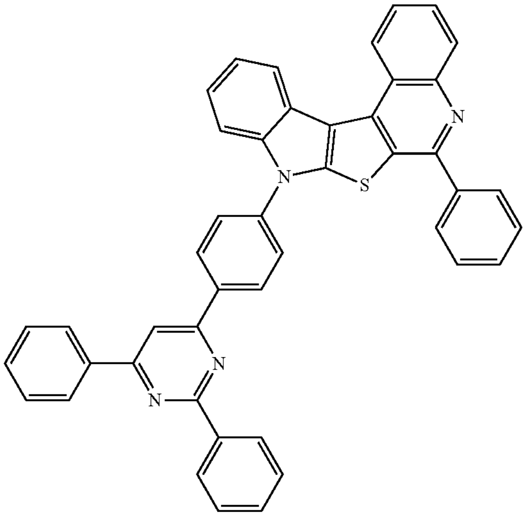
083
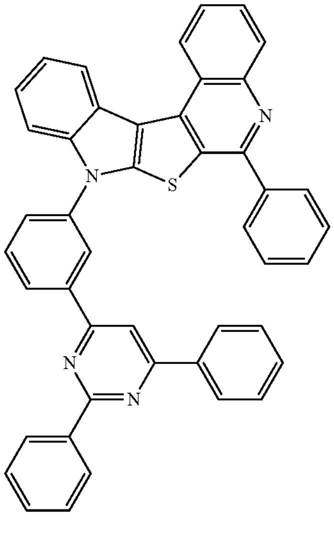

-continued
084
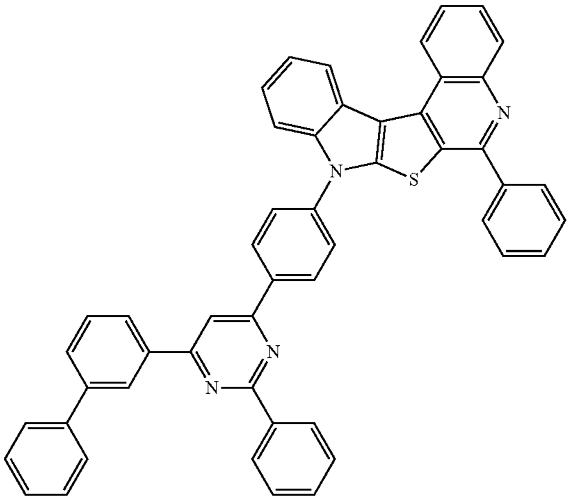
085
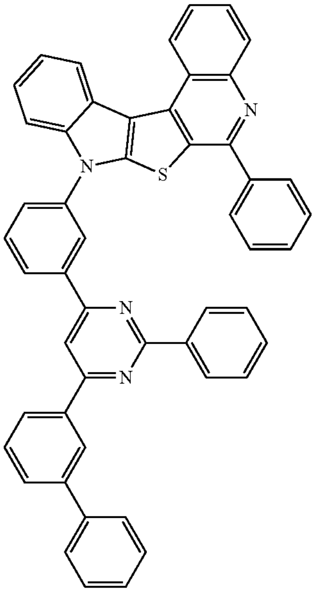
086
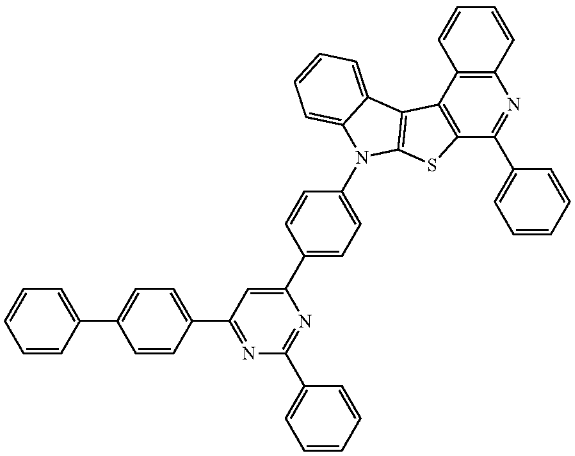
-continued
087
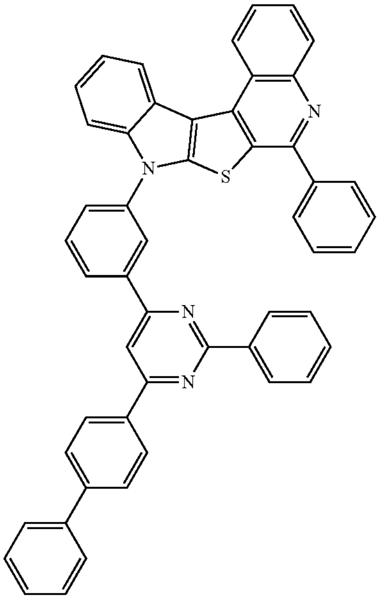
088
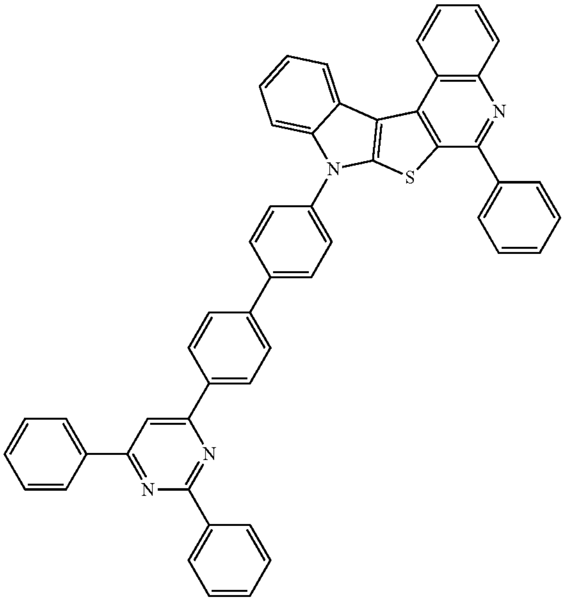

-continued
089
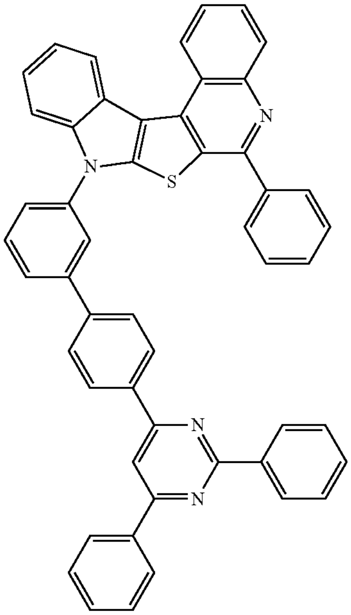
091
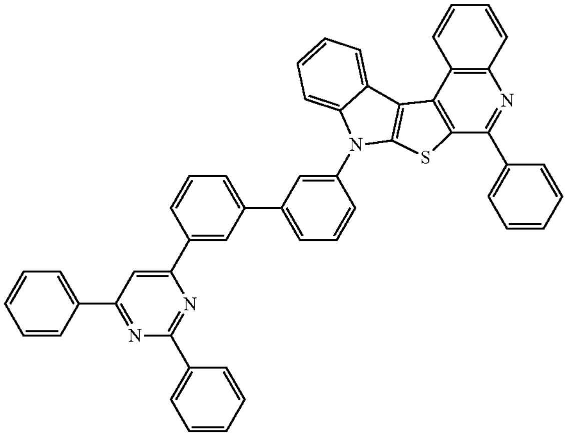
092
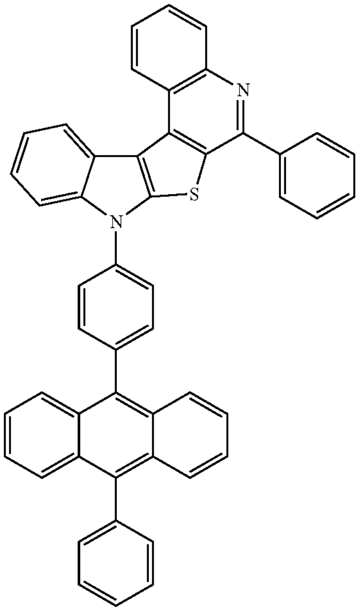
090
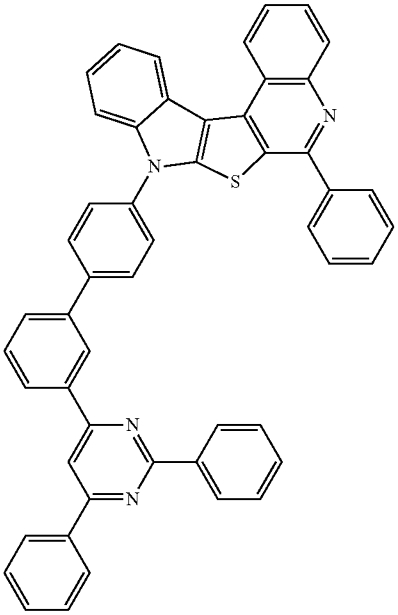
093
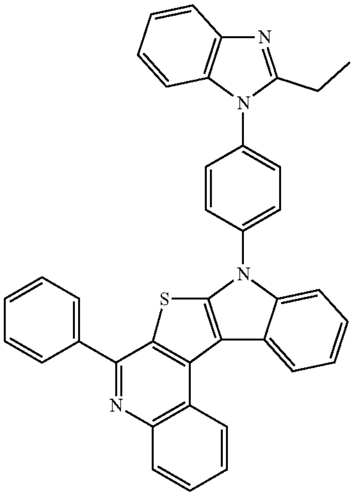

-continued
094
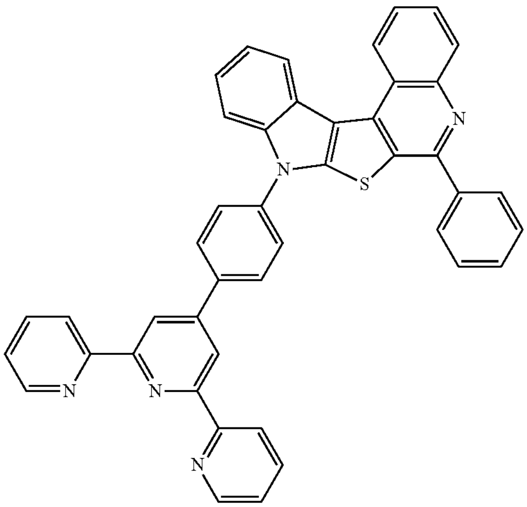
095
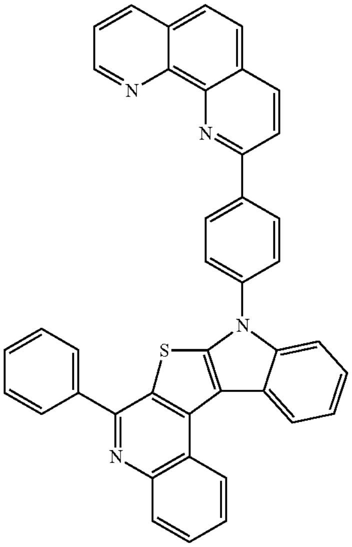
096
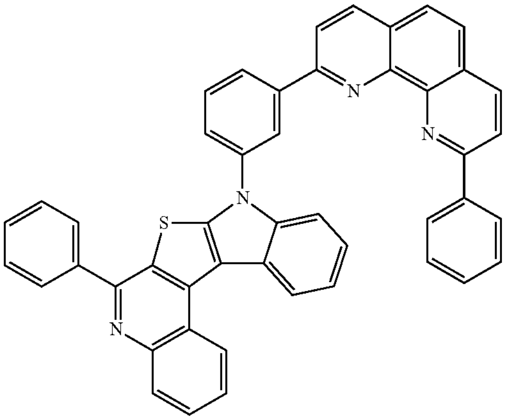
-continued
097
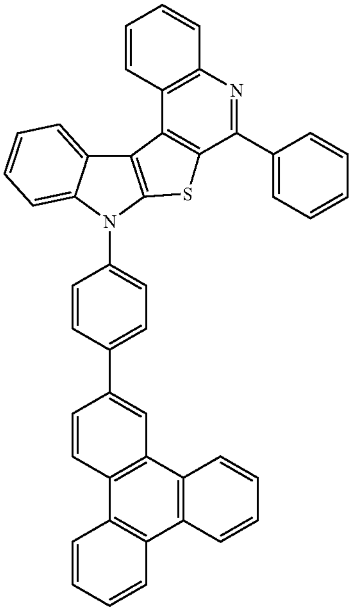
098
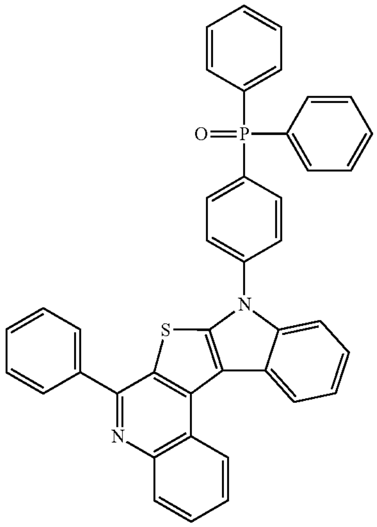
099
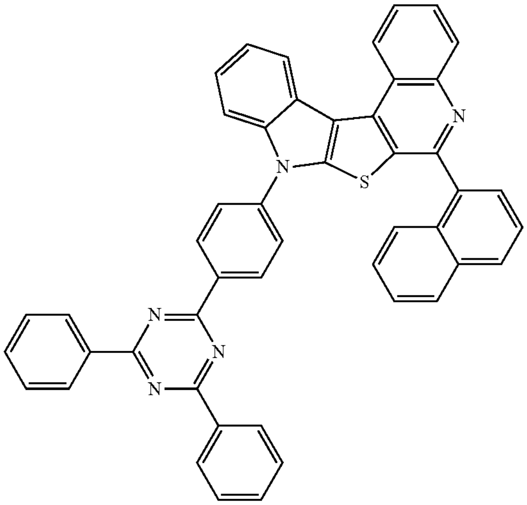

-continued
100
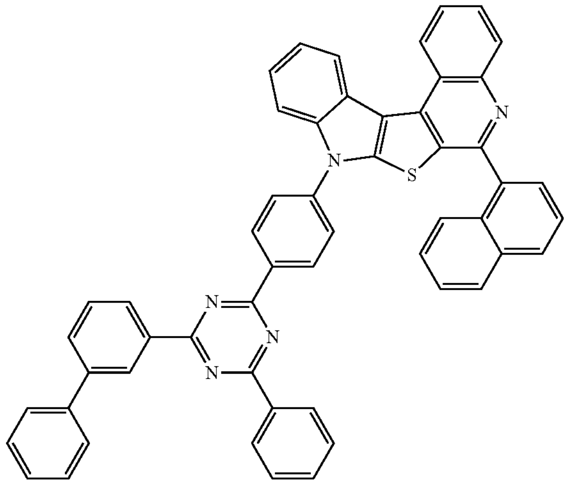
101
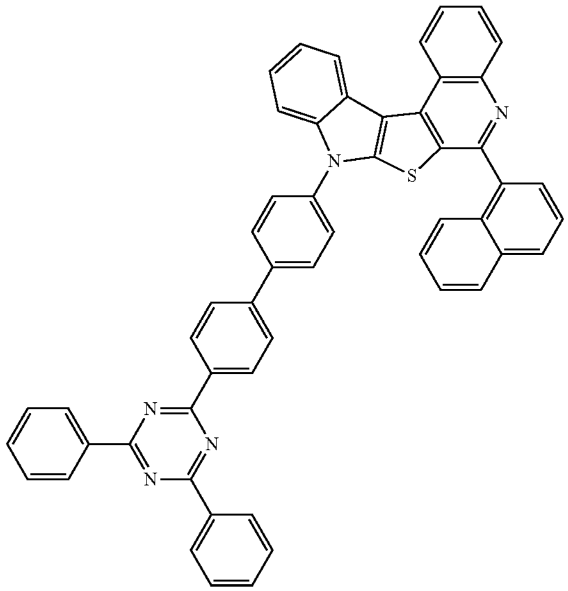
102
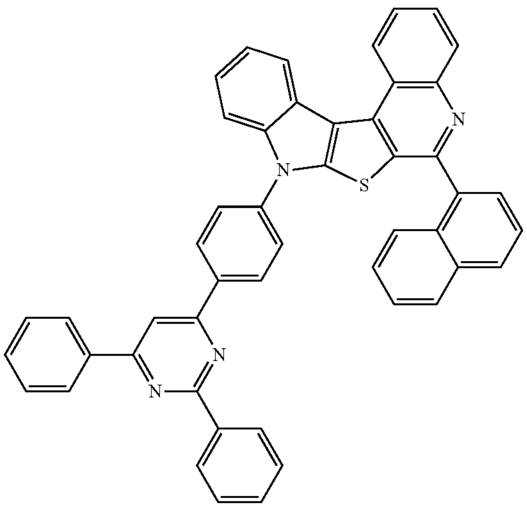
-continued
103
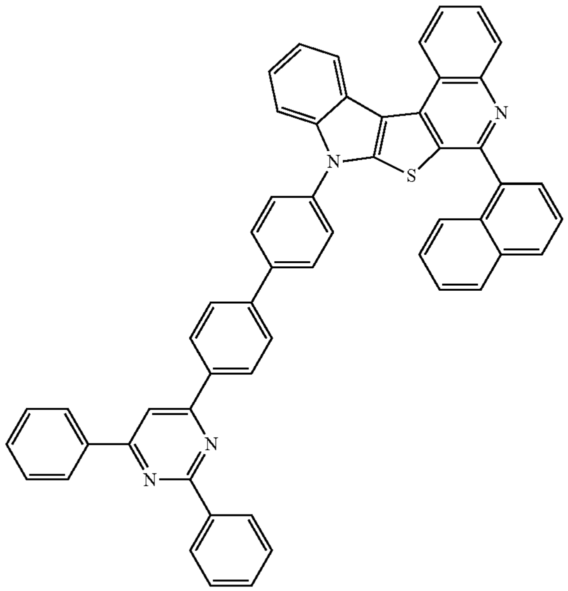
104
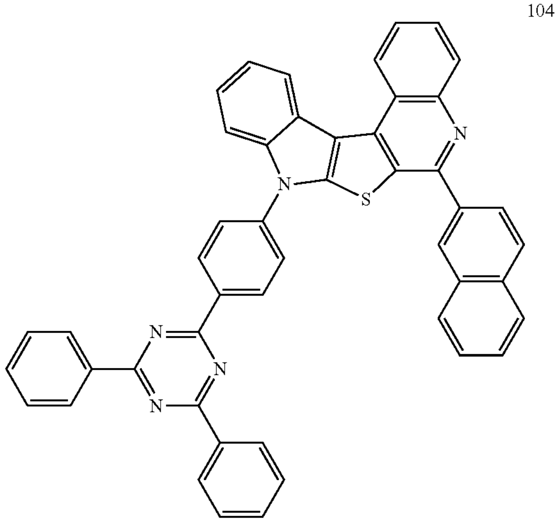
105
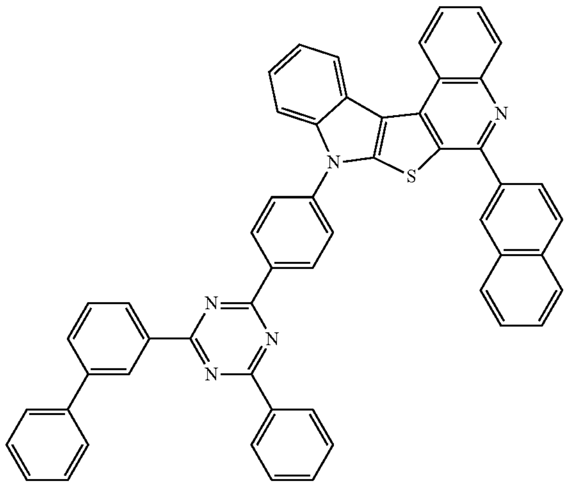

-continued
106
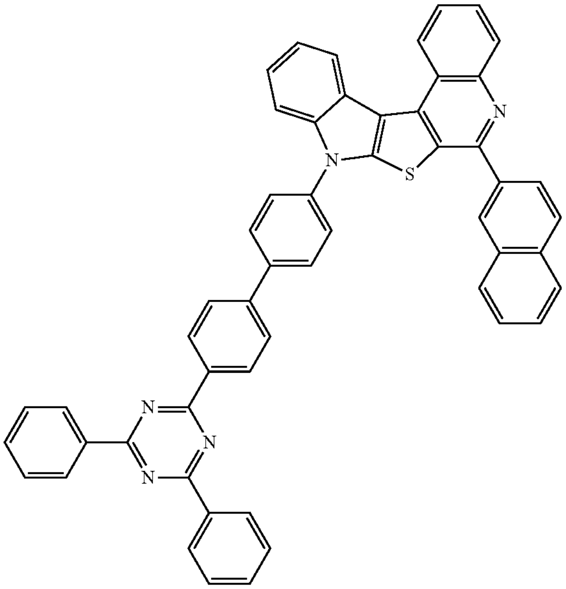
107
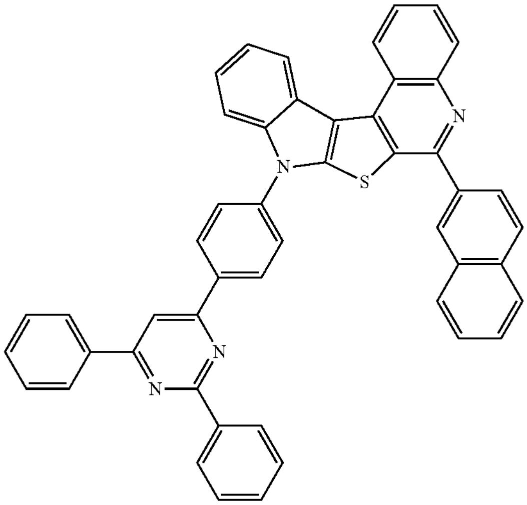
-continued
108
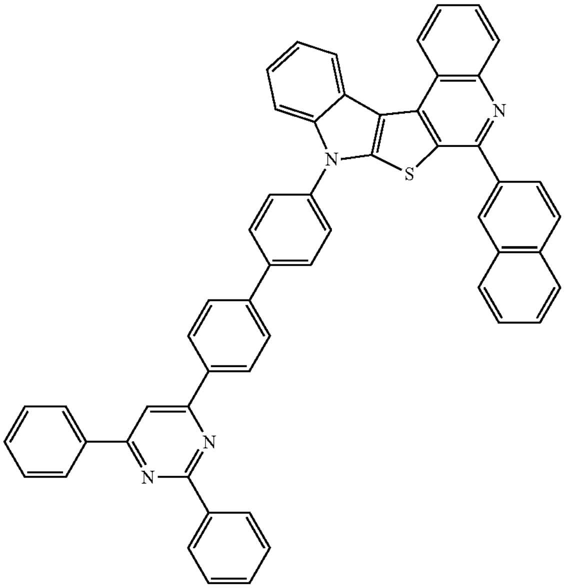
109
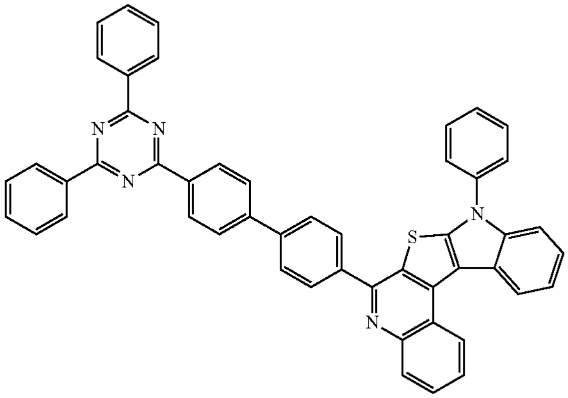
110
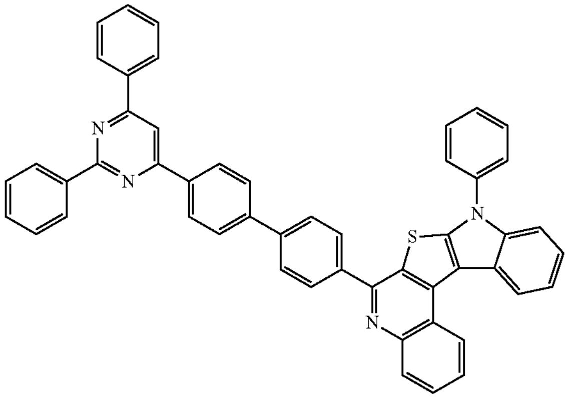

-continued
111
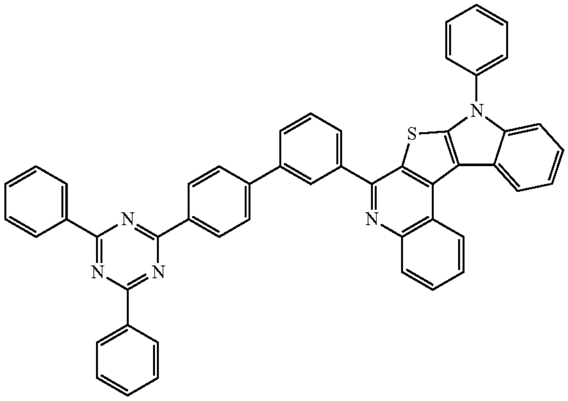
112
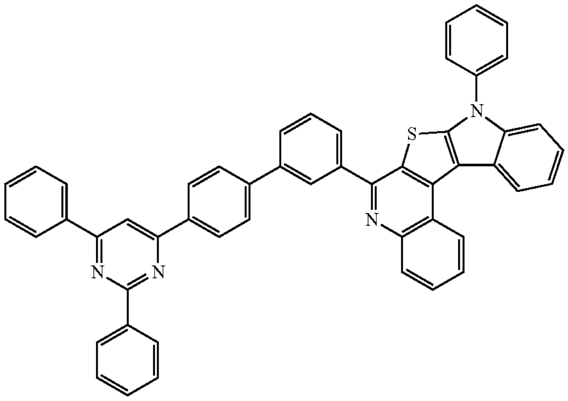
113
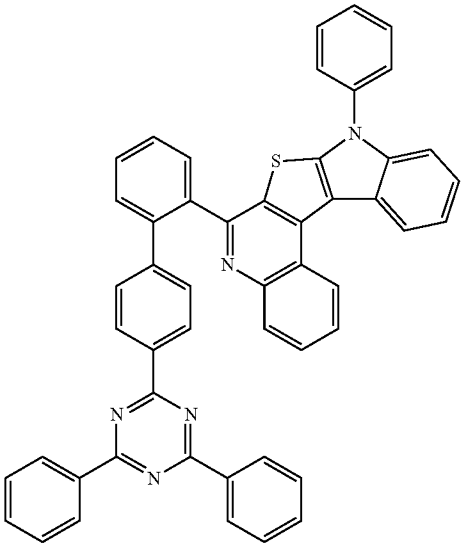
-continued
114
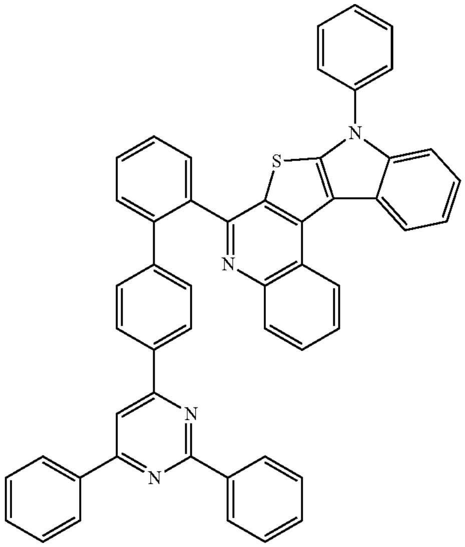
115
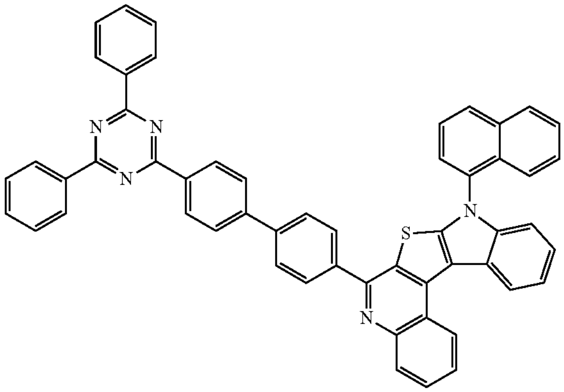
116
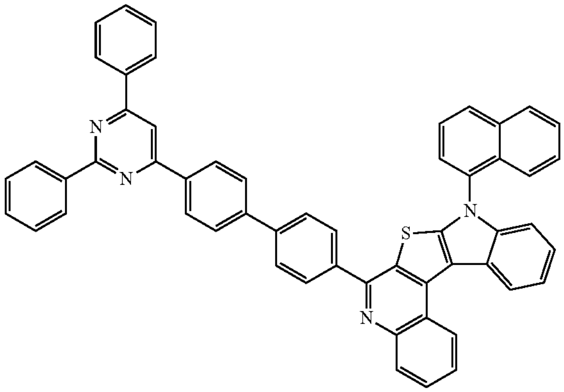

-continued
117
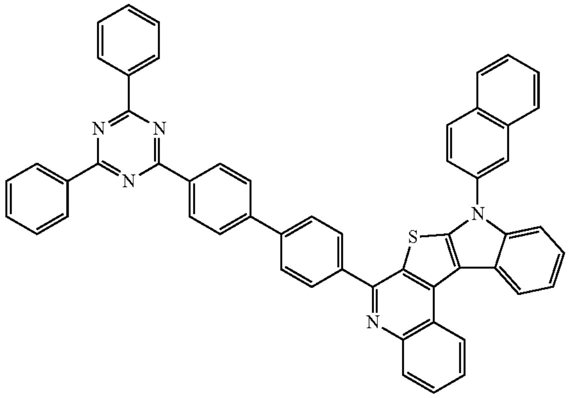
118
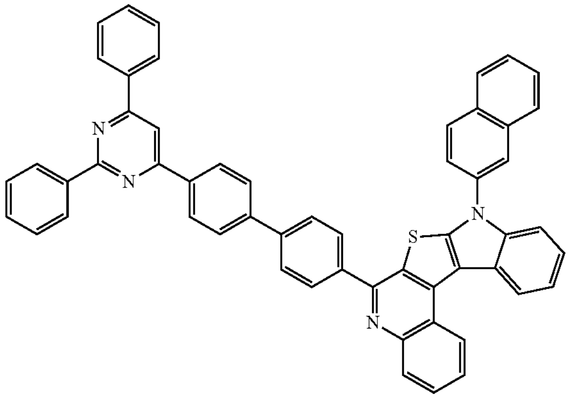
119
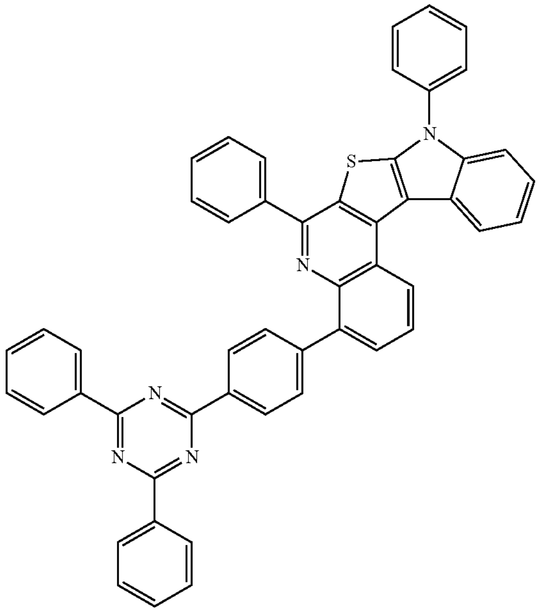
-continued
120
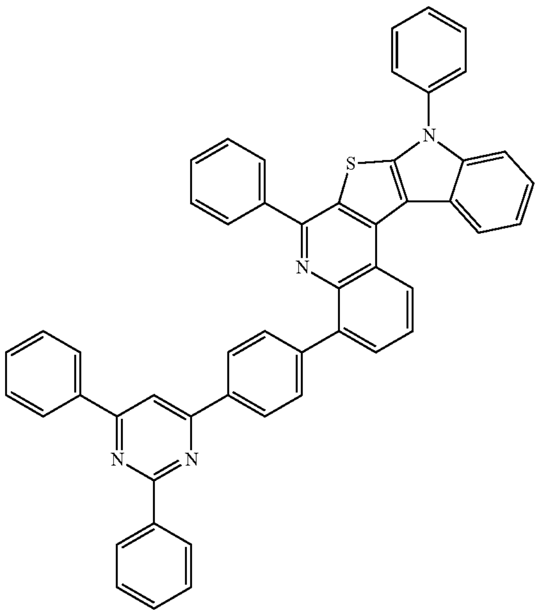
121
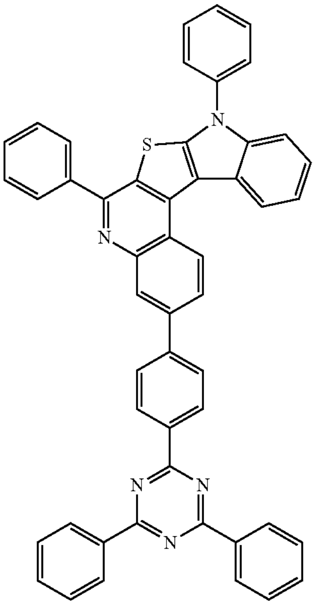

-continued
122
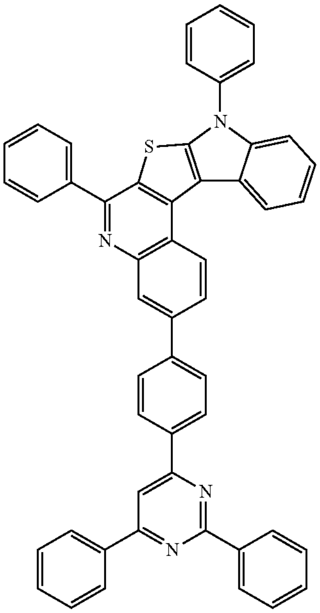
123
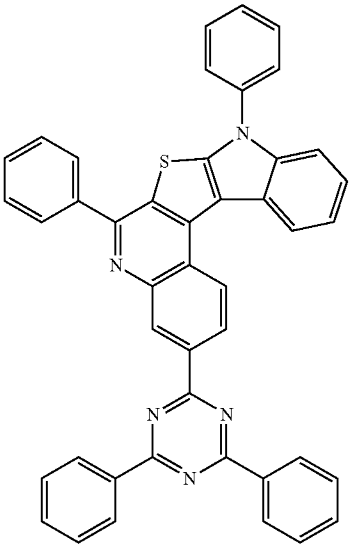
-continued
124
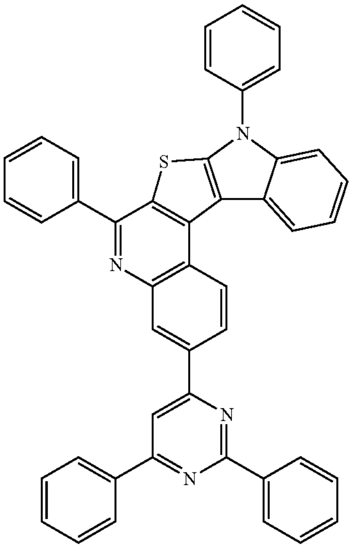
125
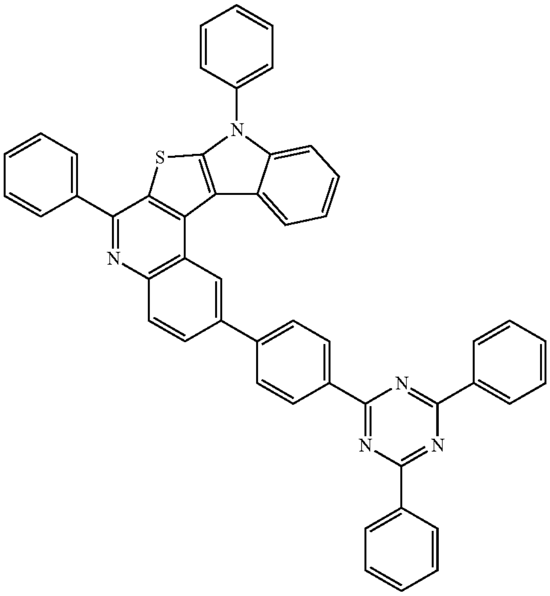

-continued
126
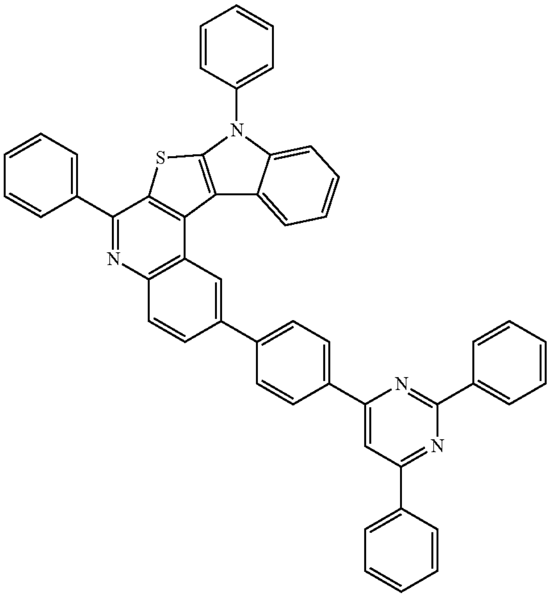
127
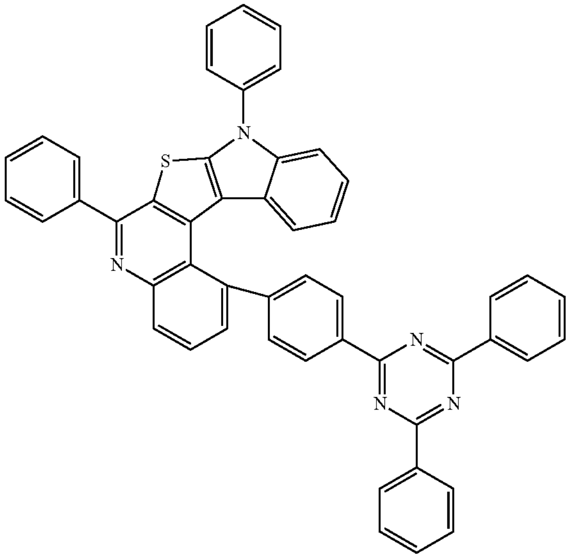
-continued
128
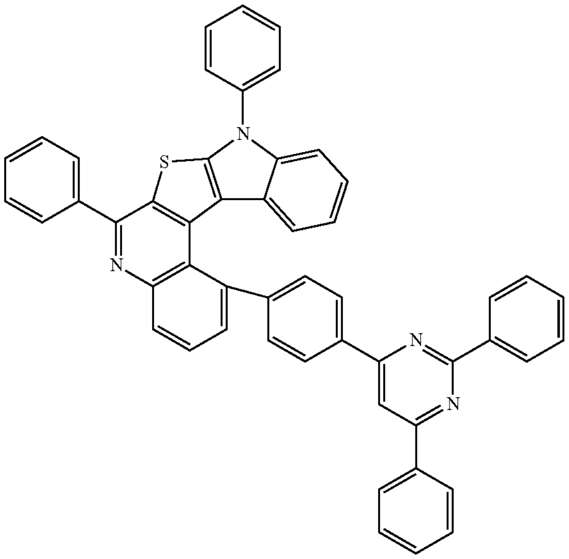
129
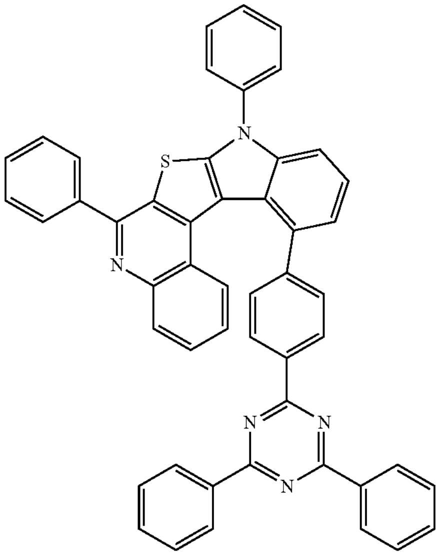

-continued
130
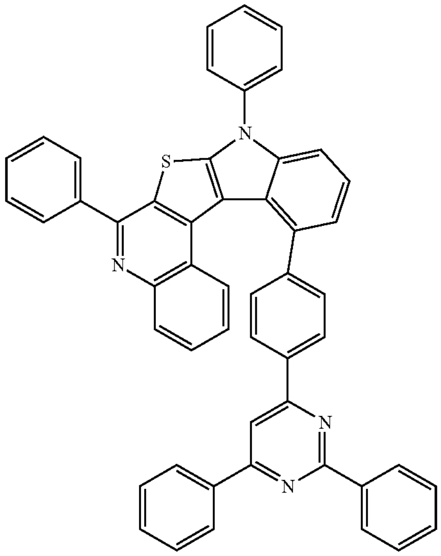
131
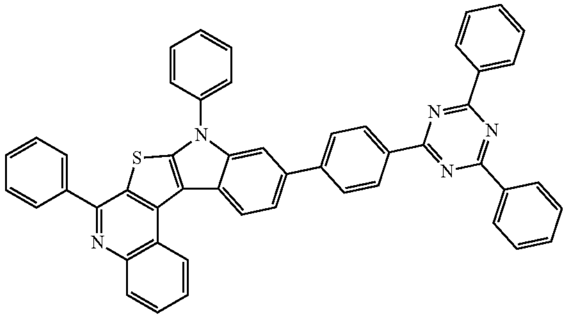
132
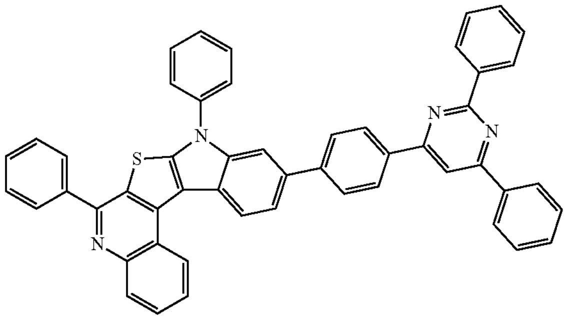
-continued
133
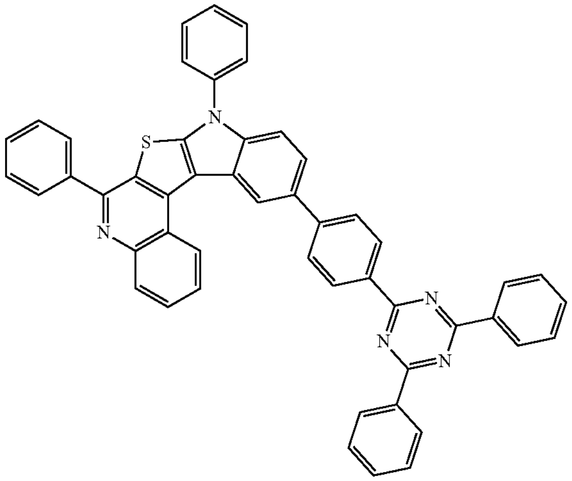
134
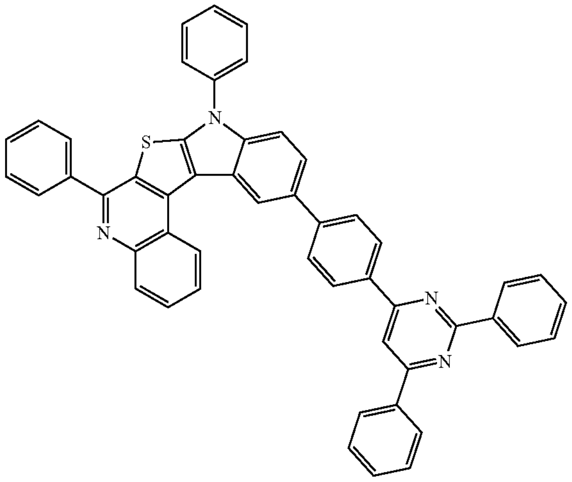
135
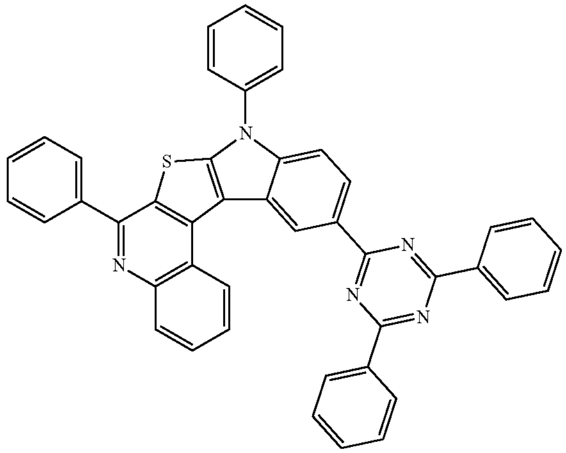

-continued
136
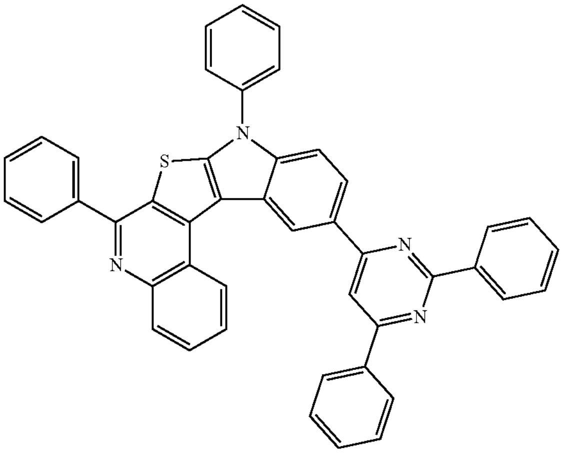
205
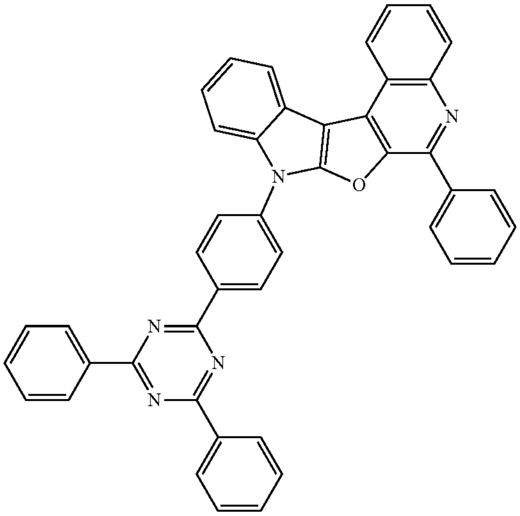
206
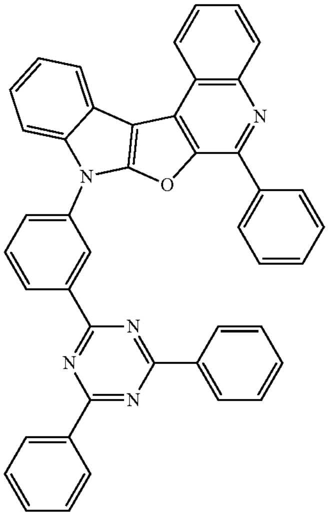
-continued
207
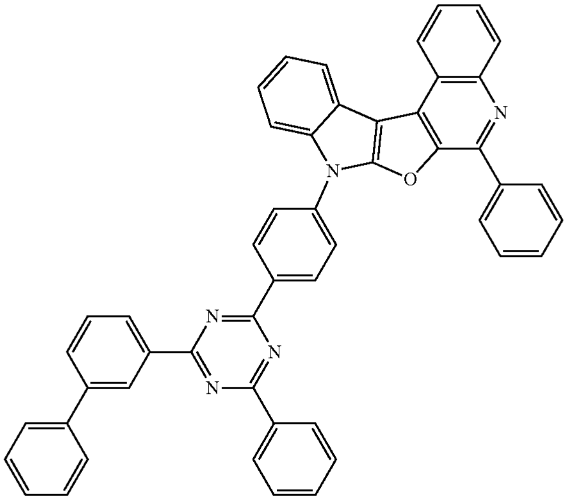
208
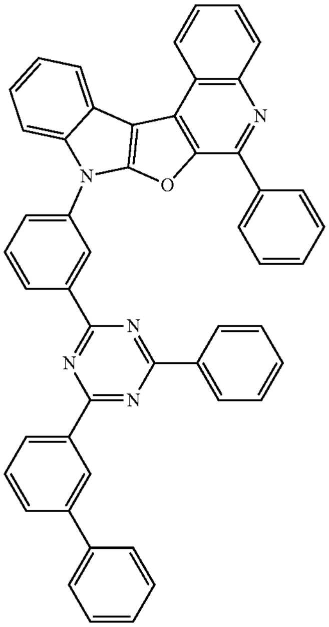
209
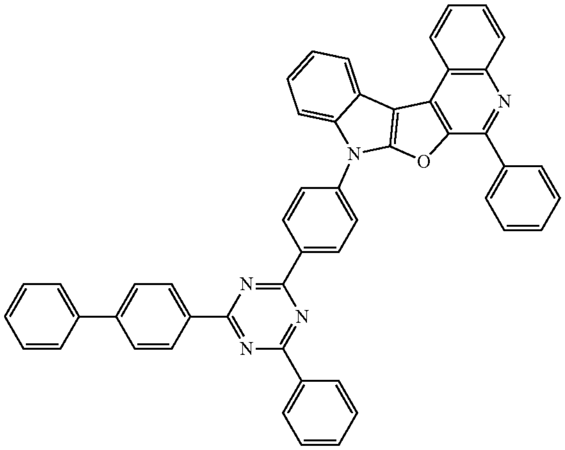

210
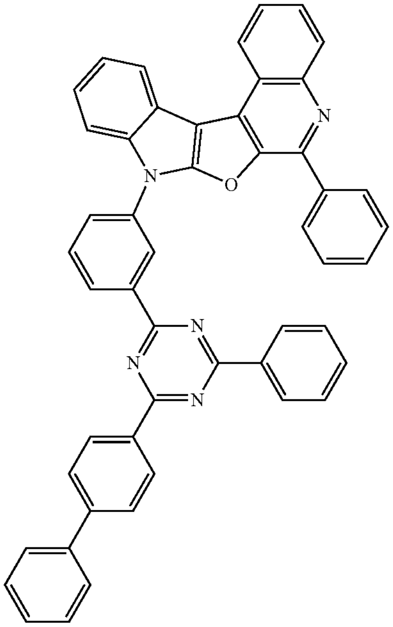
211
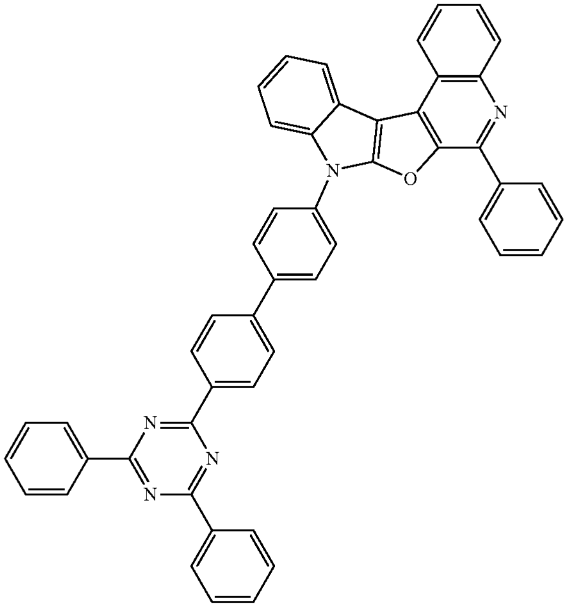
212
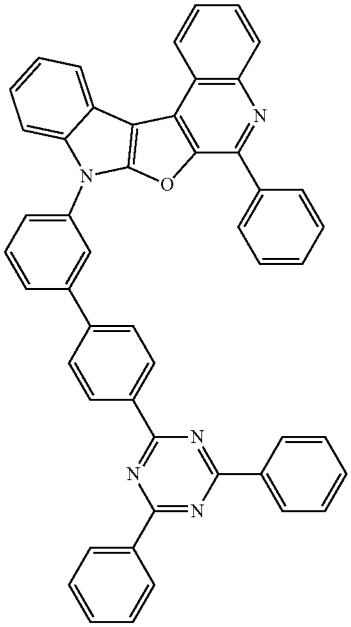
213
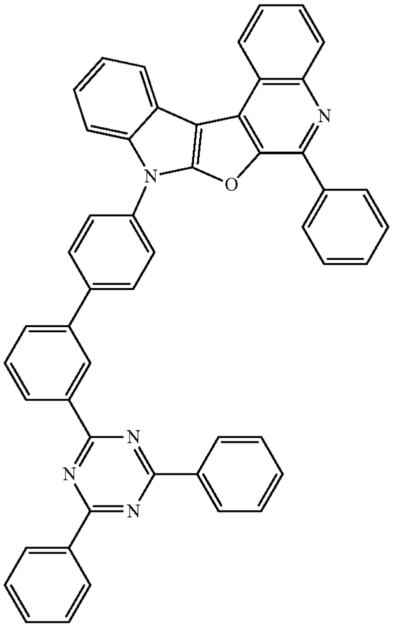

-continued
214
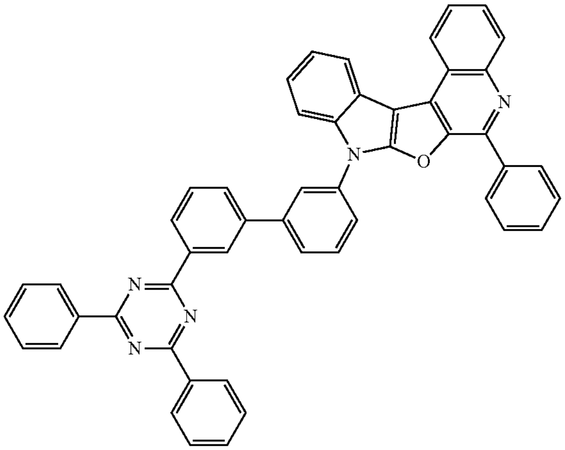
215
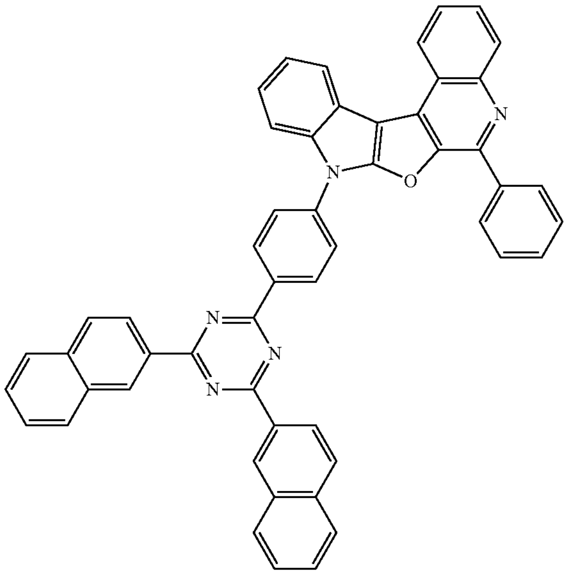
216
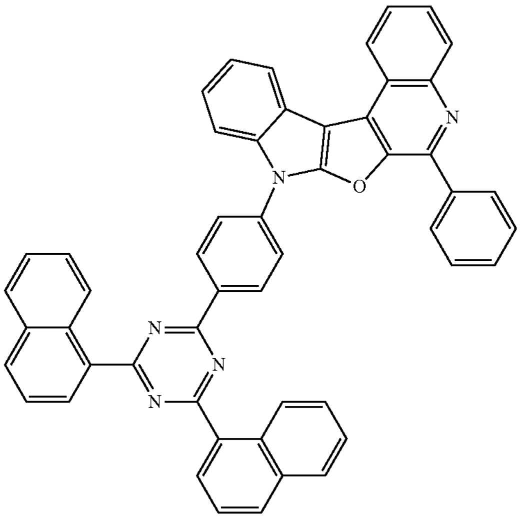
-continued
217
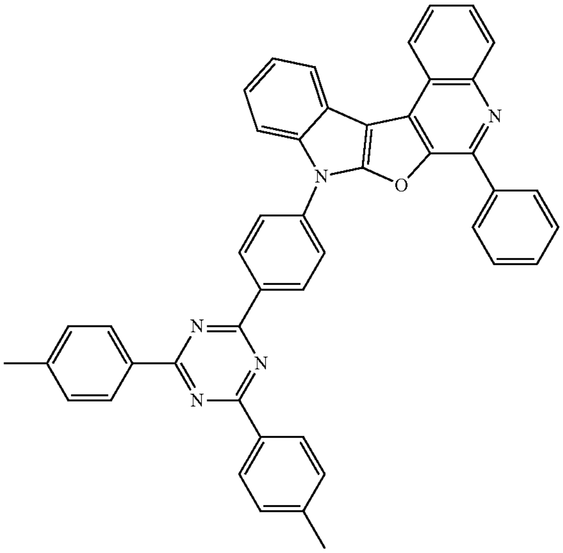
218
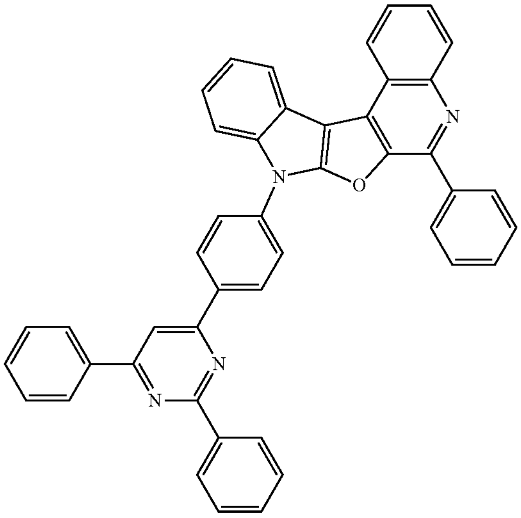
219
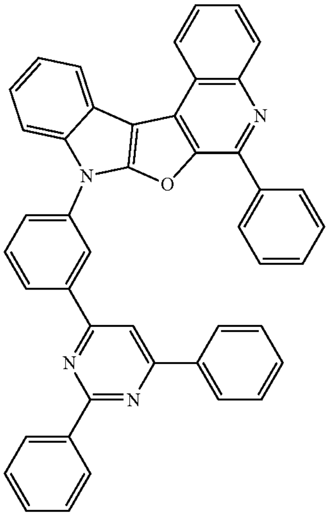

-continued
220
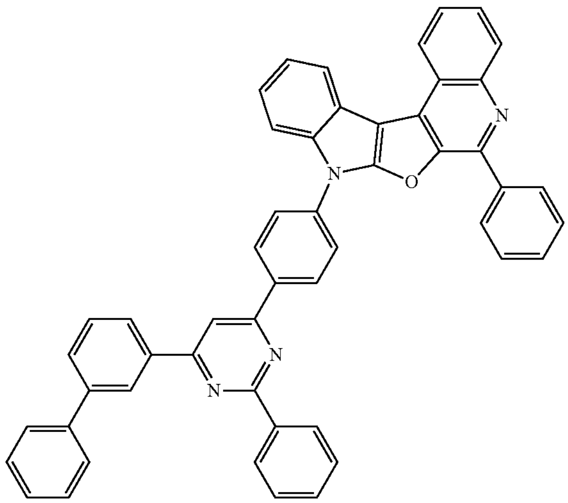
221
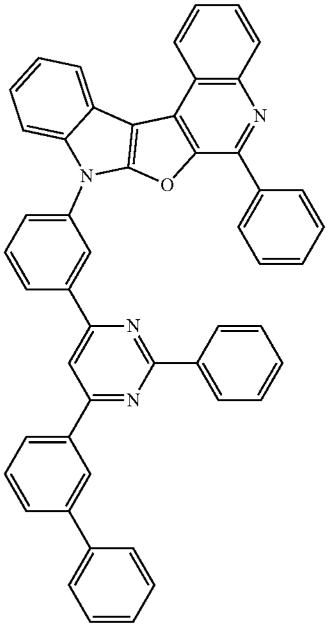
222
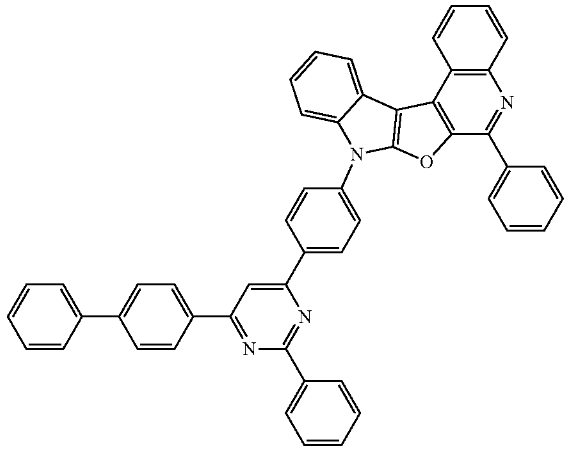
-continued
223
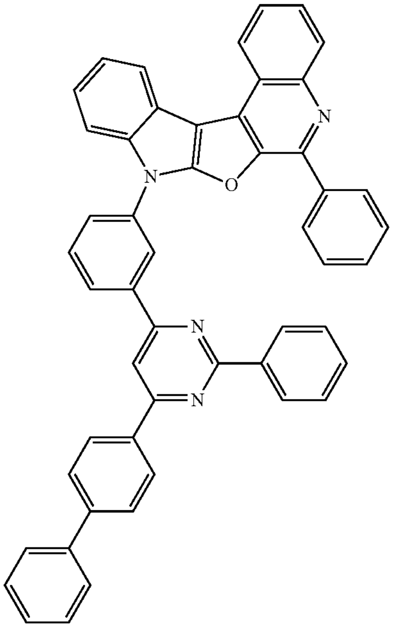
224
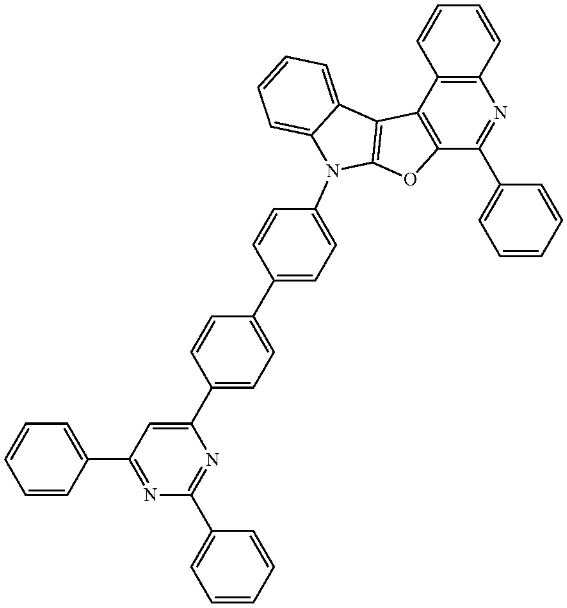

-continued
225
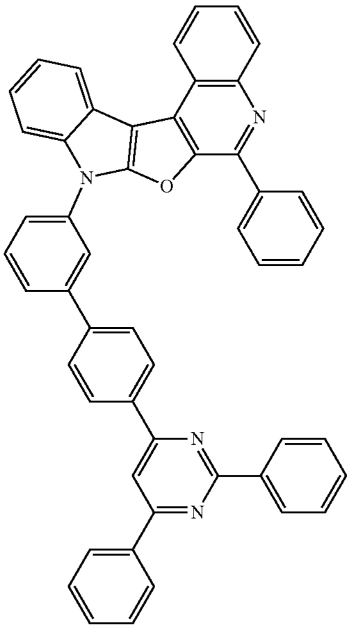
226
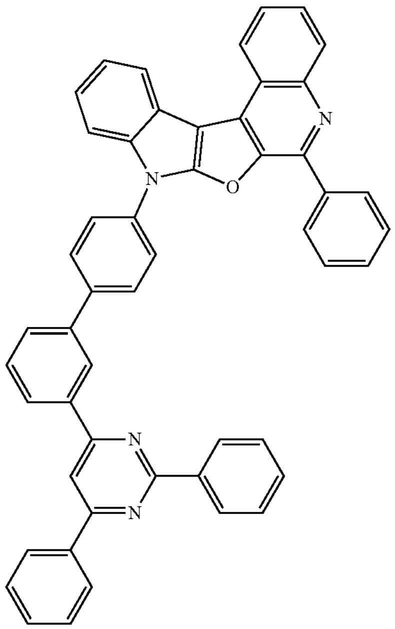
-continued
227
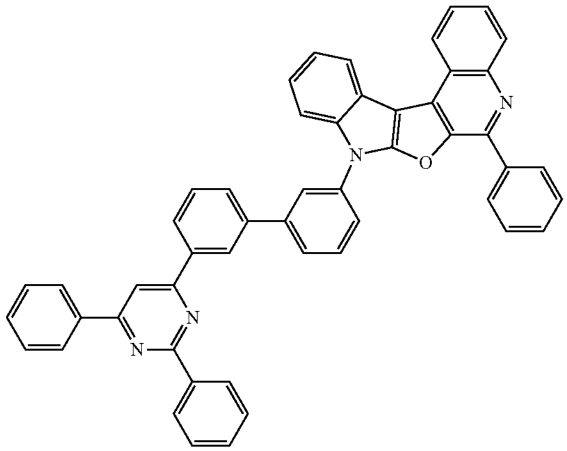
228
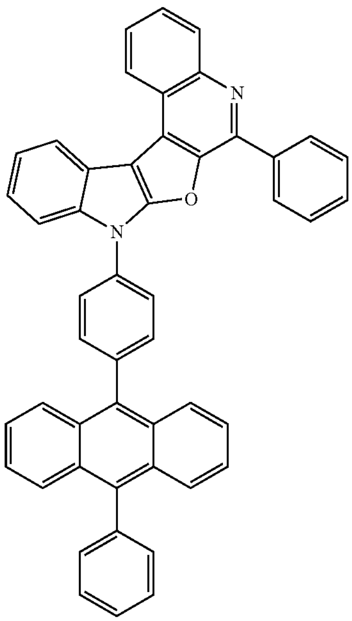
229
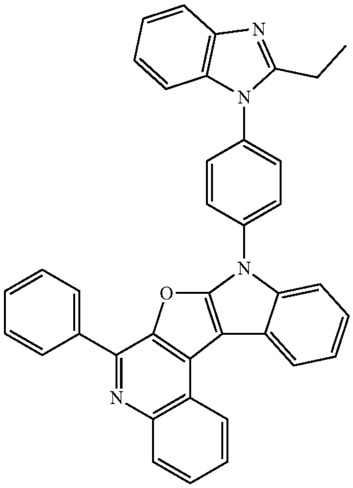

-continued
230
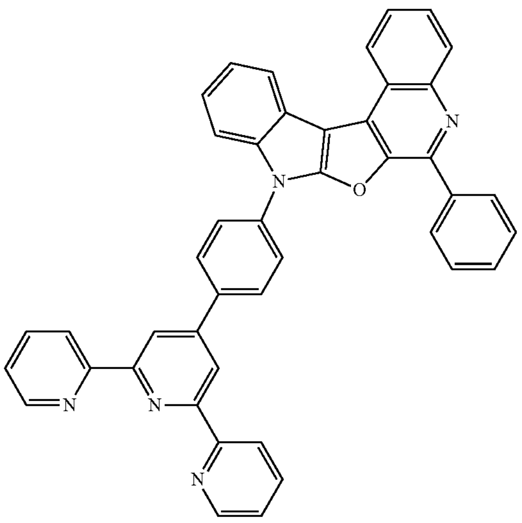
231
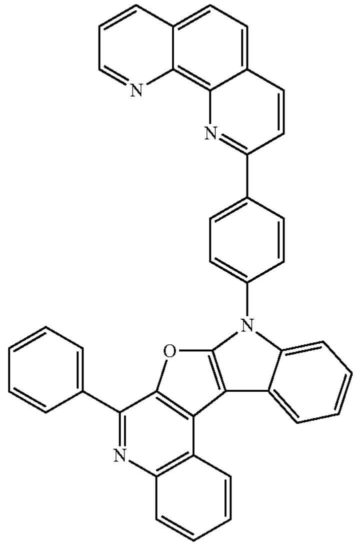
232
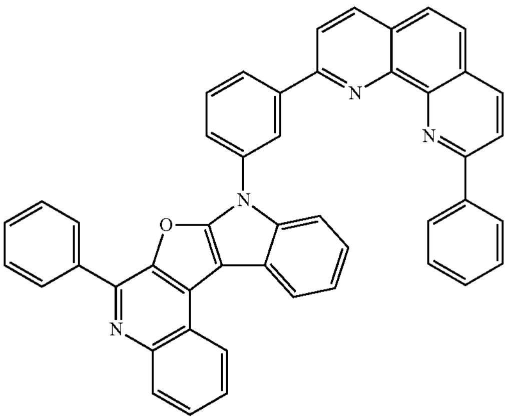
-continued
233
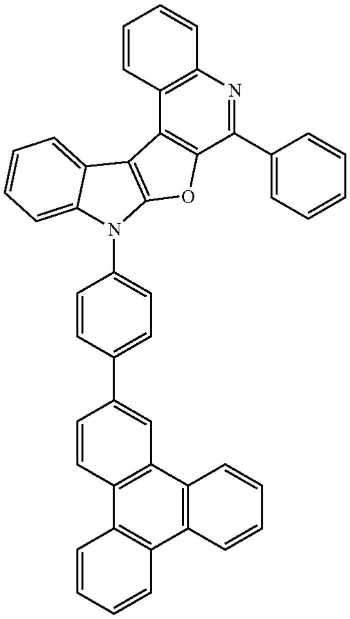
234
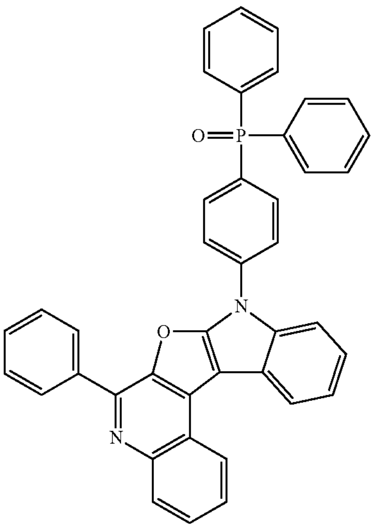

-continued
235
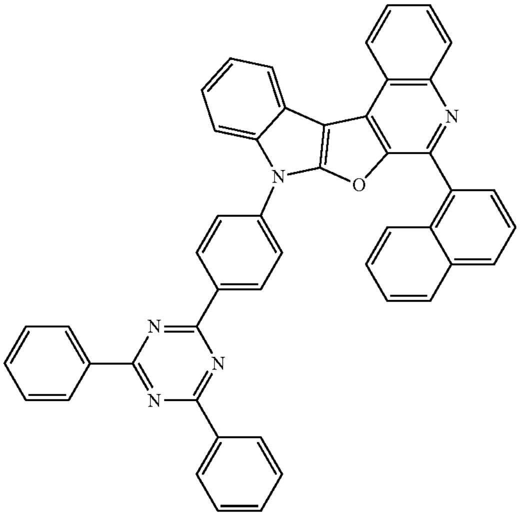
236
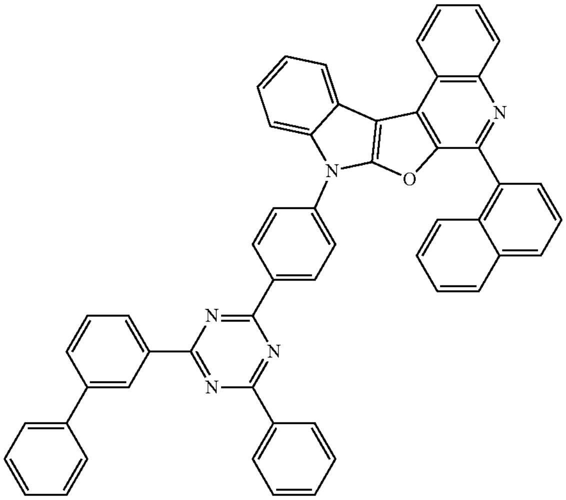
237
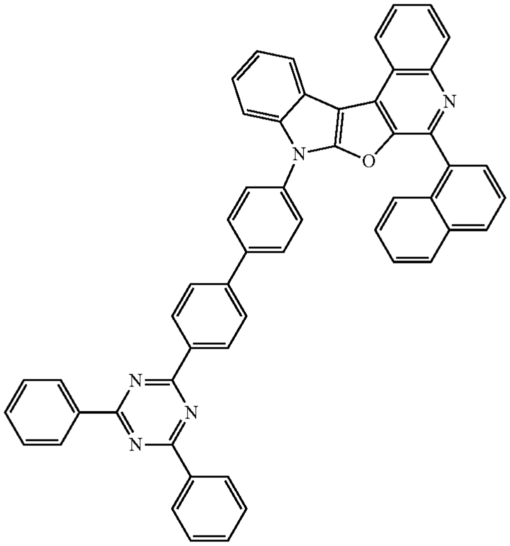
-continued
238
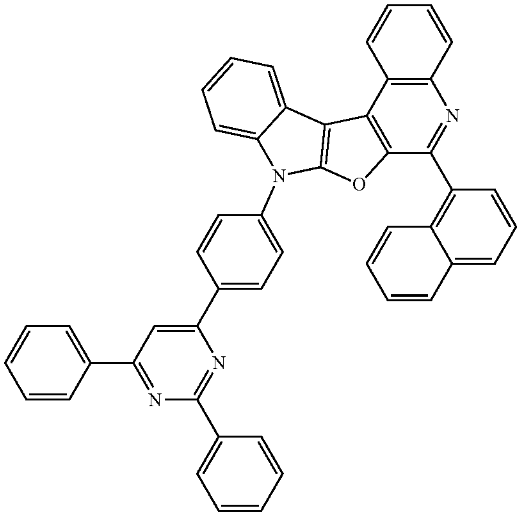
239
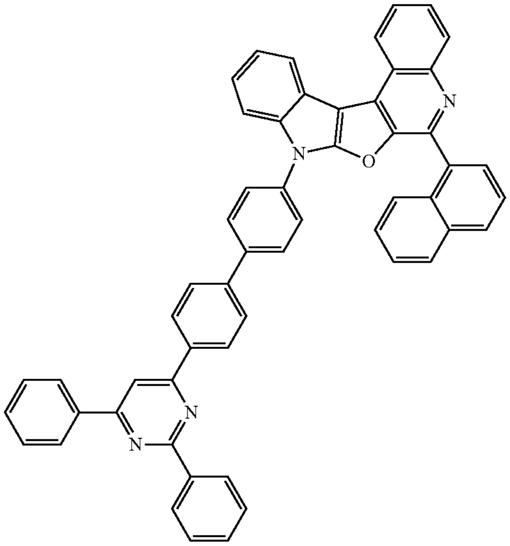

-continued
240
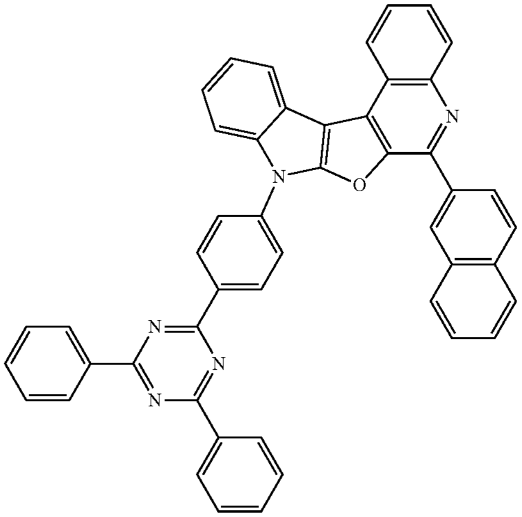
242
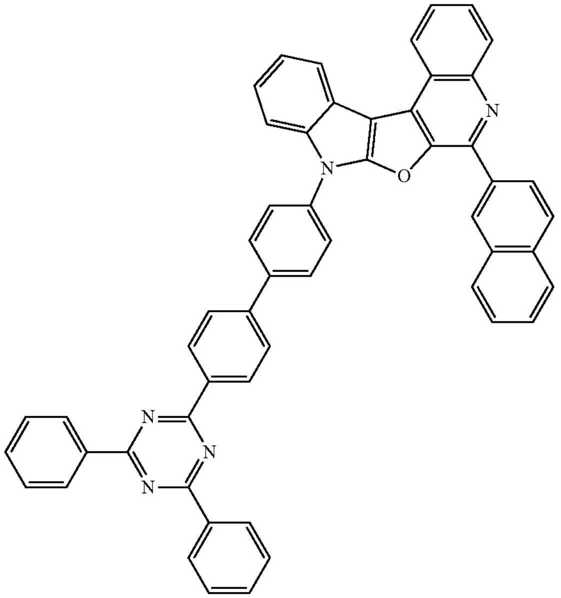
241
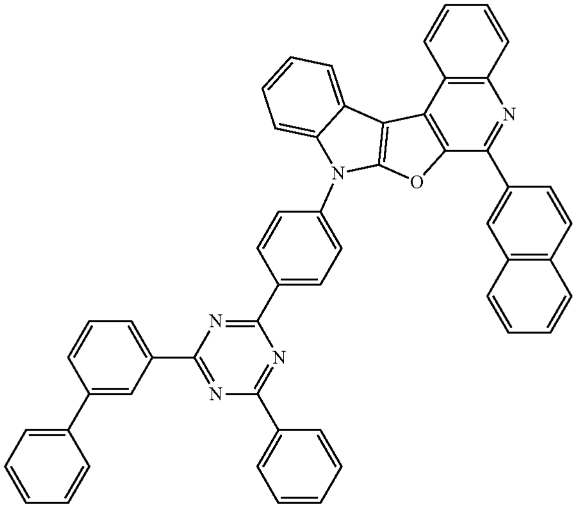
243
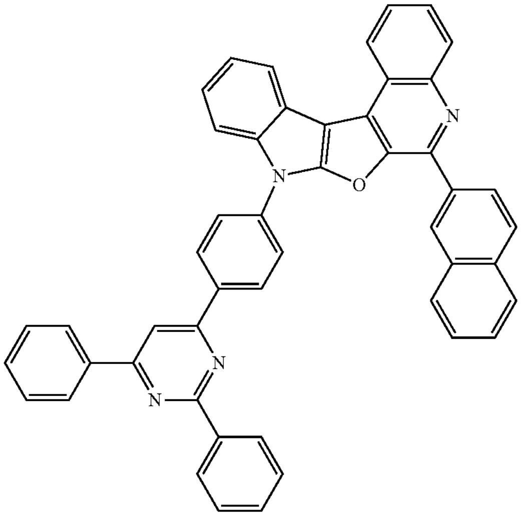

-continued
244
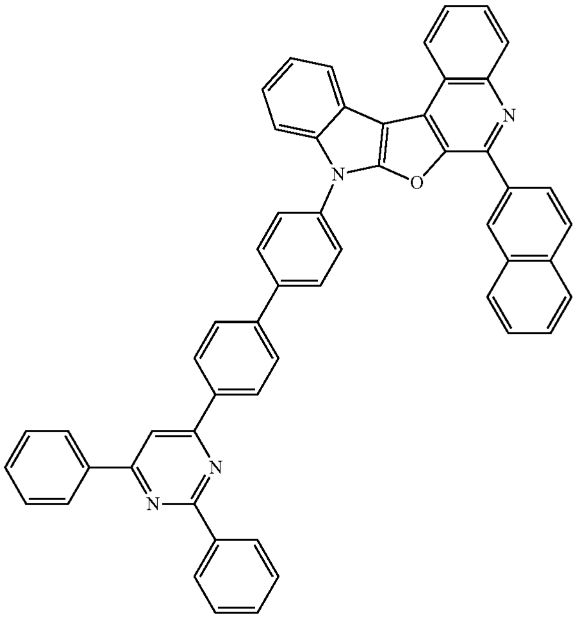
245
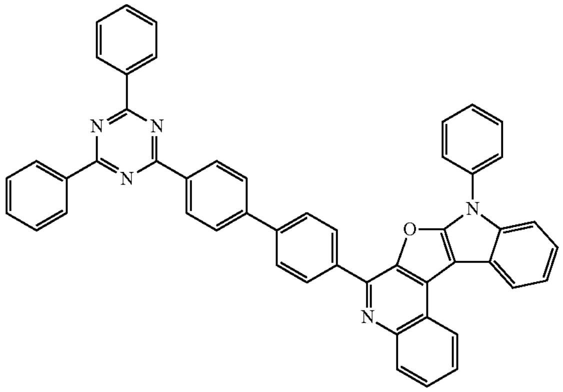
246
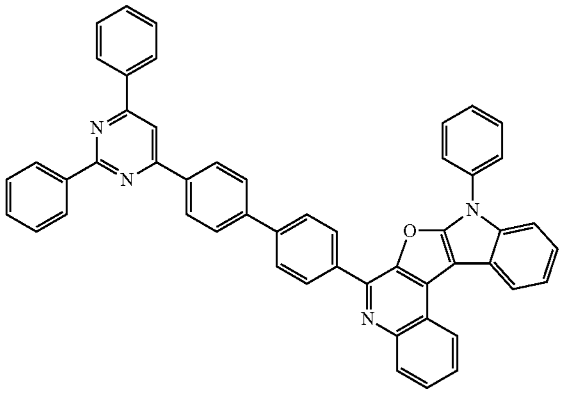
-continued
247
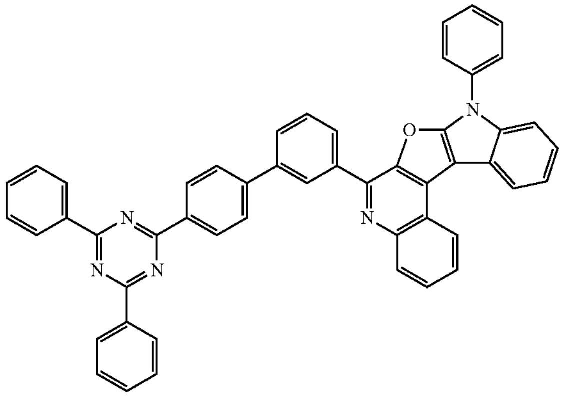
248
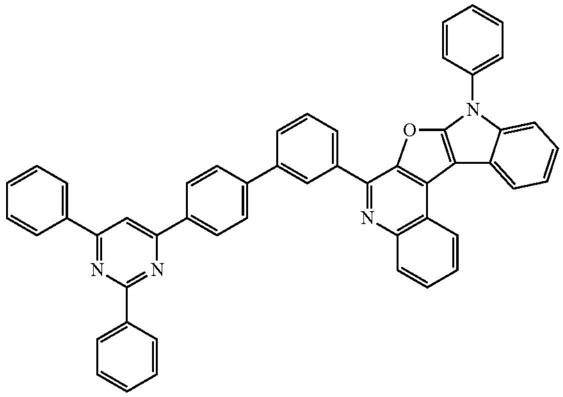
249
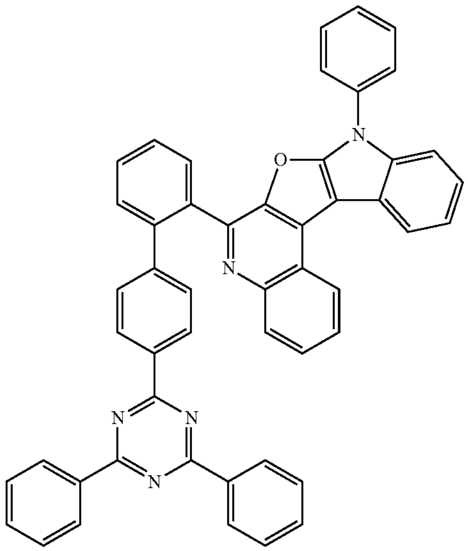

250
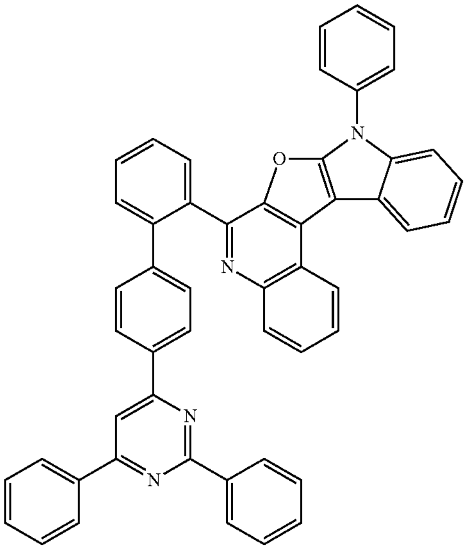
251
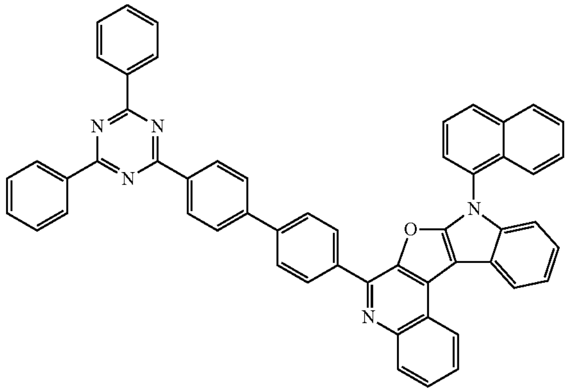
252
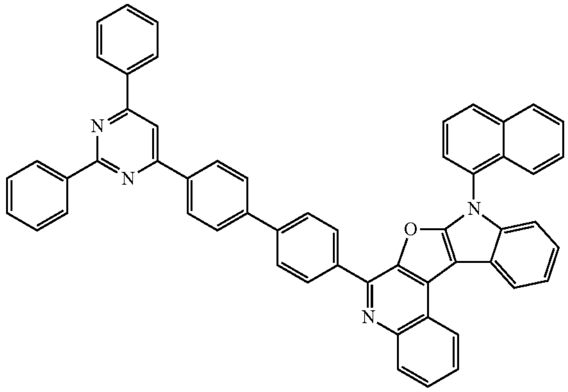
253
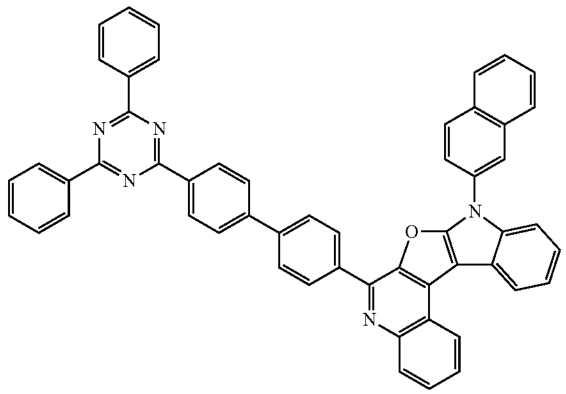
254
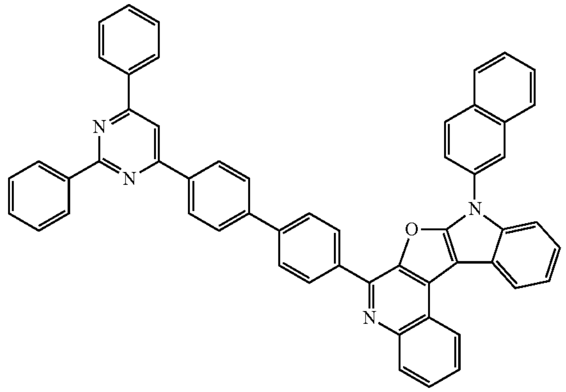
255
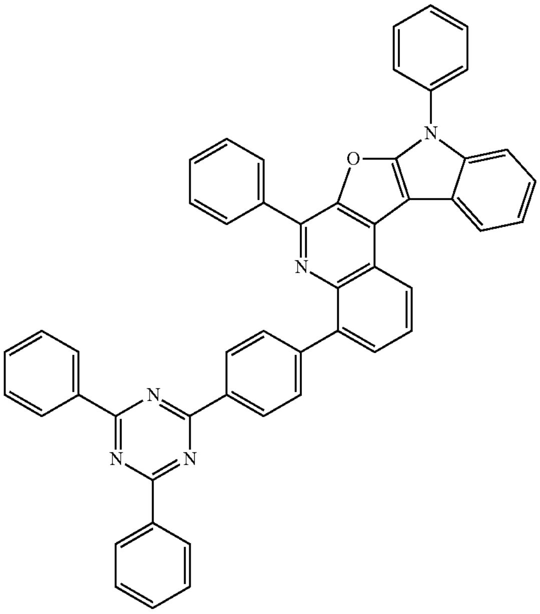

-continued
256
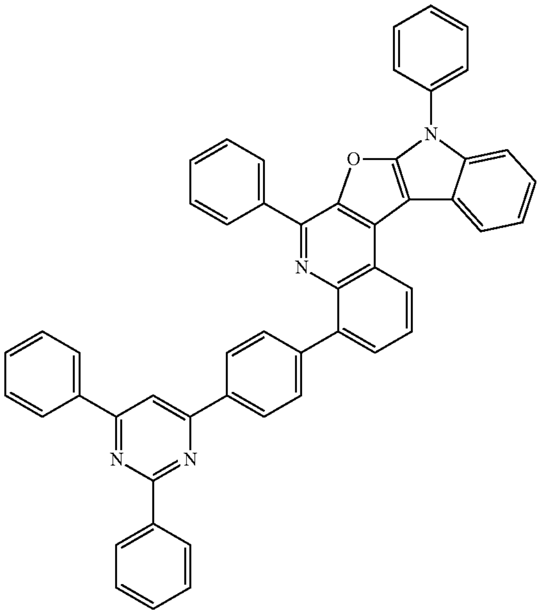
257
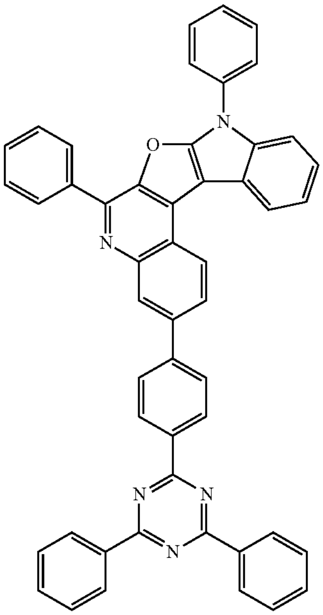
-continued
258
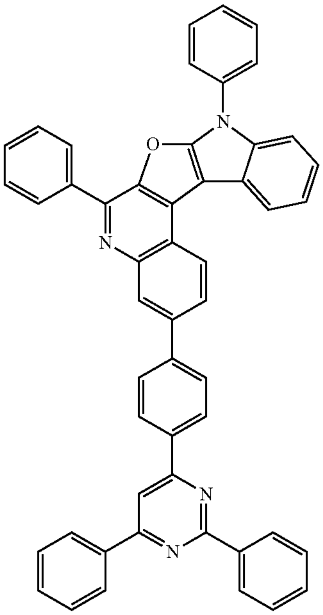
259
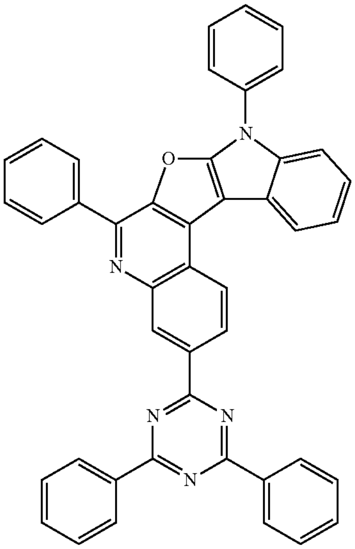

-continued
260
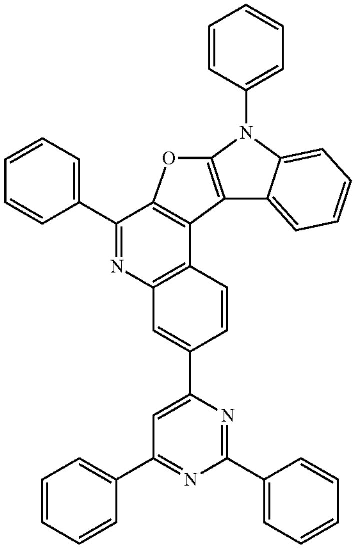
261
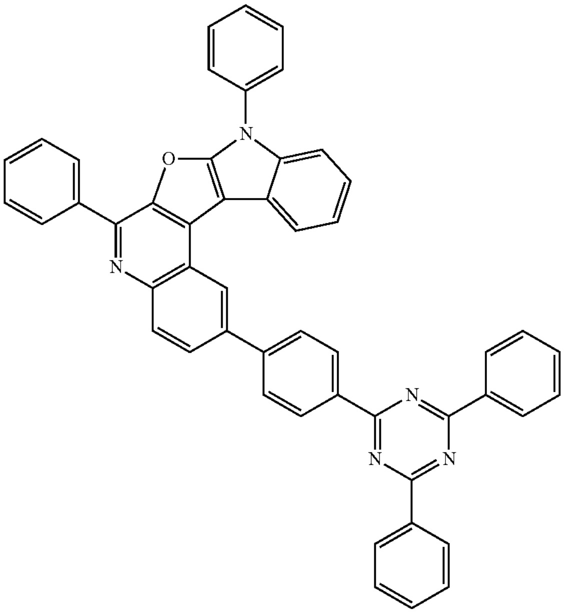
-continued
262
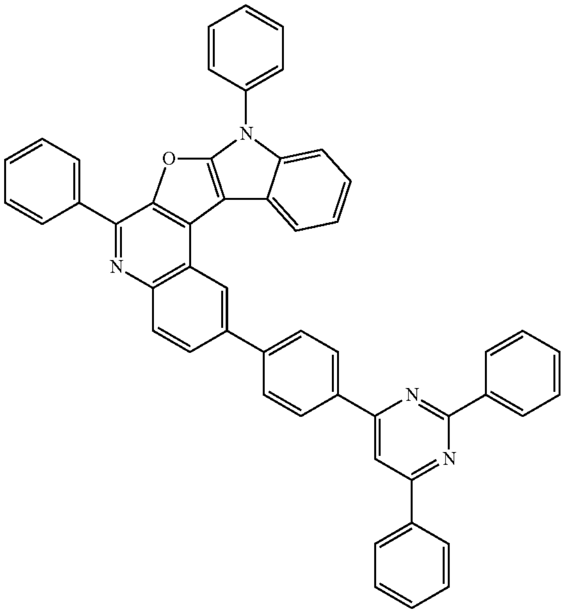
263
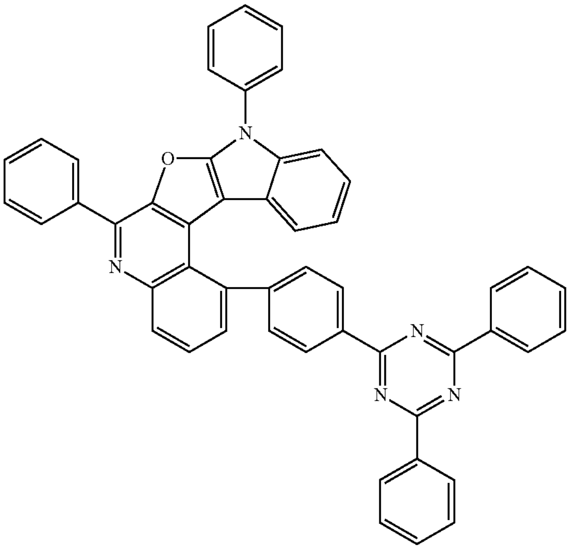

-continued
264
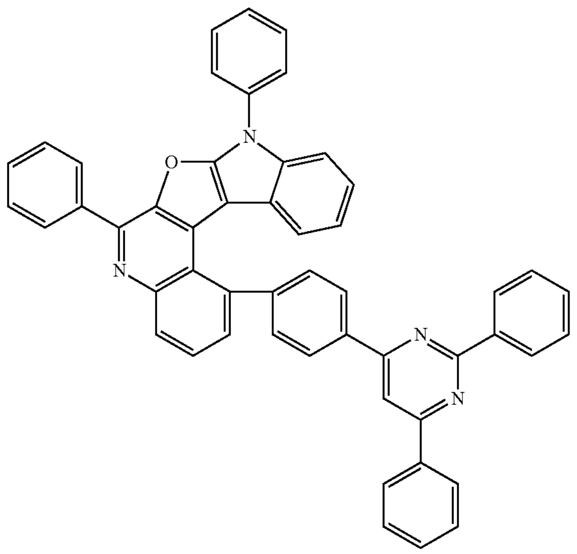
265
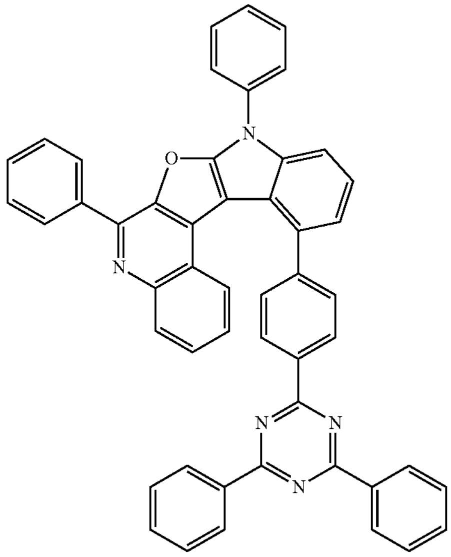
-continued
266
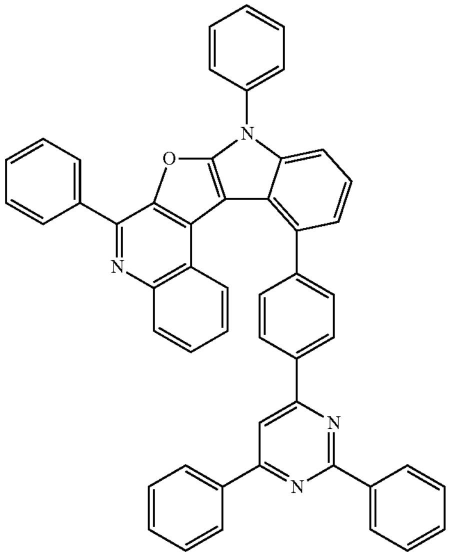
267
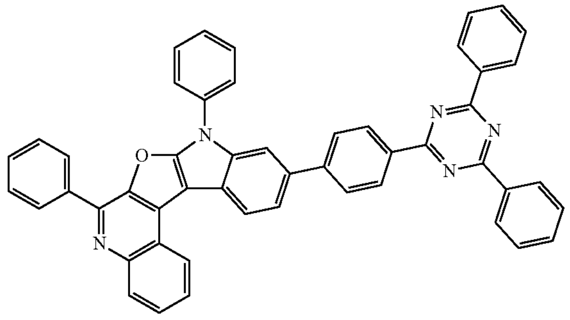
268
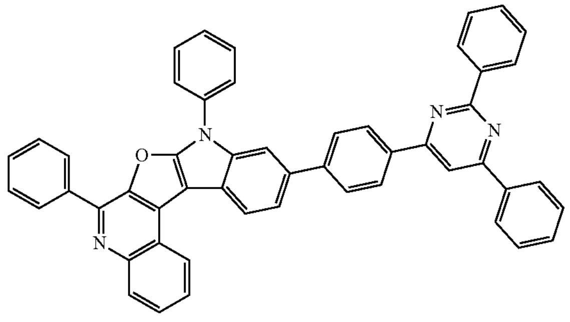

-continued

269

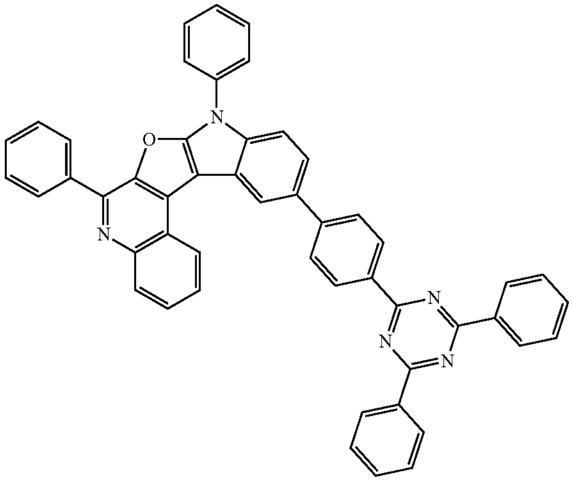

270

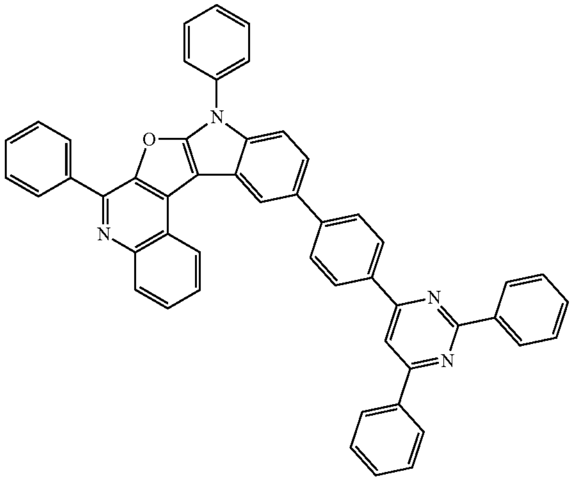

271

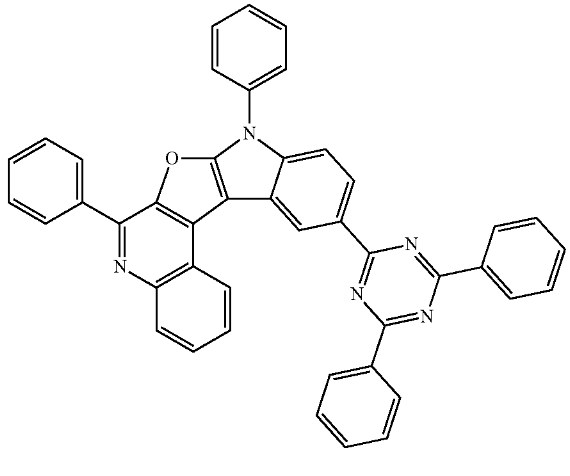

-continued

272

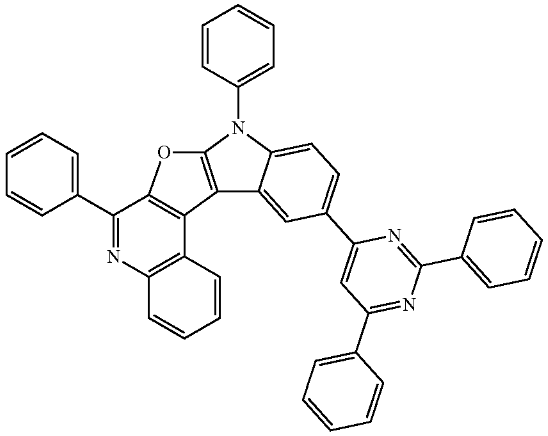

.

3. An organic light emitting device comprising:

a first electrode;

a second electrode provided opposite to the first electrode; and one or more organic material layers provided between the first electrode and the second electrode, wherein the organic material layer comprises electron transfer layer or the hole blocking layer and electron transfer layer or the hole blocking layer comprises the heterocyclic compound represented by the following Chemical Formula 2 or 4:

[Chemical Formula 2]

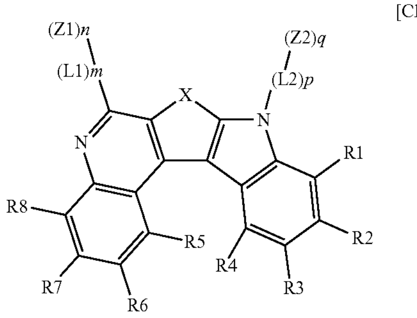

[Chemical Formula 4]

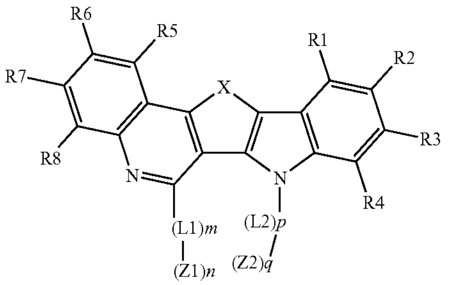

wherein, in Chemical Formulas 2 and 4,

X is O; or S;

R1 to R8 are the same as or different from each other, and each independently selected from the group consisting of hydrogen; deuterium; a substituted or unsubstituted C6 to C40 aryl group; and a substituted or unsubstituted C2 to C40 heteroaryl group, L1 and L2 are a C6 to C40 monocyclic arylene group; or a C10 to C40 polycyclic arylene group, Z1 and Z2 are hydrogen; a substituted or unsubstituted C1 to C40 alkyl group; a substituted or unsubstituted C6 to C40 aryl group; a substituted or unsubstituted C2 to C40 heteroaryl group; or —P(═O)RR'

R, and R' are the same as or different from each other, and each independently a substituted or unsubstituted C6 to C40 aryl group;

m and p are an integer of 1 to 4, and when m is 2 or greater, the two or more L1s are the same as or different from each other, and when p is 2 or greater, the two or more L2s are the same as or different from each other; and n and q are an integer of 1 to 6, and when n is 2 or greater, the two or more Z1s are the same as or different from each other, and when q is 2 or greater, the two or more Z2s are the same as or different from each other, "substituted or unsubstituted" means being substituted with one or more substituents selected from the group consisting of C1 to C60 linear or branched alkyl; C6 to C60 monocyclic or polycyclic aryl; C2 to C60 monocyclic or polycyclic heteroaryl; and —P(═O)RR'; or being unsubstituted, or being substituted with a substituent linking two or more substituents selected from among the substituents illustrated above, or being unsubstituted.

4. The organic light emitting device of claim 3, further comprising one, two or more layers selected from the group consisting of a light emitting layer, a hole injection layer, a hole transfer layer, an electron injection layer, an electron transfer layer, an electron blocking layer and a hole blocking layer.

5. An organic light emitting device, comprising:

a first electrode;

a first stack provided on the first electrode and comprising a first light emitting layer;

a charge generation layer provided on the first stack;

a second stack provided on the charge generation layer and comprising a second light emitting layer; and the second electrode provided on the second stack, wherein the charge generation layer comprises the heterocyclic compound represented by the following Chemical Formula 2 or 4:

[Chemical Formula 2]

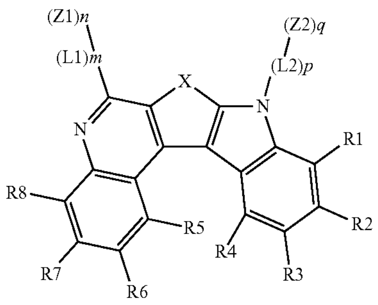

-continued

[Chemical Formula 4]

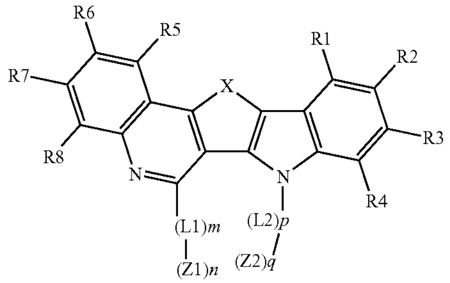

wherein, in Chemical Formulas 2 and 4,

X is O; or S;

R1 to R8 are the same as or different from each other, and each independently selected from the group consisting of hydrogen; deuterium; a substituted or unsubstituted C6 to C40 aryl group; and a substituted or unsubstituted C2 to C40 heteroaryl group, L1 and L2 are a C6 to C40 monocyclic arylene group; or a C10 to C40 polycyclic arylene group, Z1 and Z2 are hydrogen; a substituted or unsubstituted C1 to C40 alkyl group; a substituted or unsubstituted C6 to C40 aryl group; a substituted or unsubstituted C2 to C40 heteroaryl group; or —P(═O)RR'

R, and R' are the same as or different from each other, and each independently a substituted or unsubstituted C6 to C40 aryl group;

m and p are an integer of 1 to 4, and when m is 2 or greater, the two or more L1s are the same as or different from each other, and when p is 2 or greater, the two or more L2s are the same as or different from each other; and n and q are an integer of 1 to 6, and when n is 2 or greater, the two or more Z1s are the same as or different from each other, and when q is 2 or greater, the two or more Z2s are the same as or different from each other, "substituted or unsubstituted" means being substituted with one or more substituents selected from the group consisting of C1 to C60 linear or branched alkyl; C6 to C60 monocyclic or polycyclic aryl; C2 to C60 monocyclic or polycyclic heteroaryl; and —P(═O)RR'; or being unsubstituted, or being substituted with a substituent linking two or more substituents selected from among the substituents illustrated above, or being unsubstituted.

6. The organic light emitting device of claim 5, wherein the charge generation layer is an N-type charge generation layer, and the charge generation layer comprises the heterocyclic compound.

* * * * *